United States Patent
Kishi et al.

(10) Patent No.: US 10,633,392 B2
(45) Date of Patent: *Apr. 28, 2020

(54) CHROMIUM-MEDIATED COUPLING AND APPLICATION TO THE SYNTHESIS OF HALICHONDRINS

(71) Applicant: President and Fellows of Harvard College, Cambridge, MA (US)

(72) Inventors: Yoshito Kishi, Cambridge, MA (US); Wuming Yan, Wayne, NJ (US); Jingwei Li, Westfield, NJ (US); Zhanjie Li, Midland, MI (US); Kenzo Yahata, Osaka (JP)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/441,843

(22) Filed: Jun. 14, 2019

(65) Prior Publication Data

US 2020/0031843 A1    Jan. 30, 2020

Related U.S. Application Data

(63) Continuation of application No. 15/570,593, filed as application No. PCT/US2016/030064 on Apr. 29, 2016, now Pat. No. 10,344,038.

(60) Provisional application No. 62/155,067, filed on Apr. 30, 2015.

(51) Int. Cl.
    *C07D 493/22*    (2006.01)
    *C07D 493/14*    (2006.01)
    *C07D 493/04*    (2006.01)

(52) U.S. Cl.
    CPC ......... *C07D 493/22* (2013.01); *C07D 493/04* (2013.01); *C07D 493/14* (2013.01)

(58) Field of Classification Search
    CPC ... C07D 493/22; C07D 493/04; C07D 493/14
    See application file for complete search history.

(56) References Cited

U.S. PATENT DOCUMENTS

| | | | |
|---|---|---|---|
| 5,338,865 A | 8/1994 | Kishi et al. | |
| 5,436,238 A | 7/1995 | Kishi et al. | |
| 5,786,492 A | 7/1998 | Gravalos et al. | |
| 6,214,865 B1 | 4/2001 | Littlefield et al. | |
| 6,469,182 B1 | 10/2002 | Littlefield et al. | |
| 6,653,341 B1 | 11/2003 | Littlefield et al. | |
| 7,470,720 B2 | 12/2008 | Littlefield et al. | |
| 7,982,060 B2 | 7/2011 | Austad et al. | |
| 8,093,410 B2 | 1/2012 | Chase et al. | |
| 8,097,648 B2 | 1/2012 | Littlefield et al. | |
| 8,203,010 B2 | 6/2012 | Endo et al. | |
| 8,350,067 B2 | 1/2013 | Endo et al. | |
| 8,445,701 B2 | 5/2013 | Austad et al. | |
| 8,598,373 B2 | 12/2013 | Hu | |
| 8,618,313 B2 | 12/2013 | Benayoud et al. | |
| 8,884,031 B2 | 11/2014 | Chase et al. | |
| RE45,324 E | 1/2015 | Austad et al. | |
| 8,927,597 B2 | 1/2015 | Endo et al. | |
| 8,975,422 B2 | 3/2015 | Fang et al. | |
| 8,987,479 B2 | 3/2015 | Chase et al. | |
| 9,206,194 B2 | 12/2015 | Hu | |
| 9,278,979 B2 | 3/2016 | Souza et al. | |
| 9,303,039 B2 | 4/2016 | Zhang et al. | |
| 9,303,050 B2 | 4/2016 | Benayoud et al. | |
| 9,382,262 B2 | 7/2016 | Endo et al. | |
| 9,469,651 B2 | 10/2016 | Hu | |
| 9,938,288 B1 | 4/2018 | Kishi et al. | |
| 10,344,038 B2 | 7/2019 | Kishi et al. | |
| 2004/0198806 A1 | 10/2004 | Eisai et al. | |
| 2006/0104984 A1 | 5/2006 | Littlefield et al. | |
| 2006/0154312 A1 | 7/2006 | Agoulnik et al. | |
| 2007/0244187 A1 | 10/2007 | Austad et al. | |
| 2009/0198074 A1 | 8/2009 | Chase et al. | |
| 2009/0203771 A1 | 8/2009 | Inanaga et al. | |
| 2010/0254996 A1 | 10/2010 | Brantley-Sieders et al. | |

(Continued)

FOREIGN PATENT DOCUMENTS

| | | |
|---|---|---|
| JP | 6-122687 | 5/1994 |
| JP | 6-279450 | 10/1994 |

(Continued)

OTHER PUBLICATIONS

US 9,029,573 B2, 05/2015, Hu (withdrawn)
Extended European Search Report for EP 15814059.0, dated Nov. 24, 2017.
International Search Report and Written Opinion for PCT/US2015/038439, dated Sep. 29, 2015.
International Preliminary Report on Patentability for PCT/US2015/038439, dated Jan. 12, 2017.
International Search Report and Written Opinion for PCT/US2016/030064, dated Aug. 8, 2016.
International Preliminary Report on Patentability for PCT/US2016/030064, dated Nov. 9, 2017.
International Search Report and Written Opinion for PCT/US2018/025887, dated Jun. 21, 2018.

(Continued)

*Primary Examiner* — Timothy R Rozof
(74) *Attorney, Agent, or Firm* — Wolf, Greenfield & Sacks, P.C.

(57) ABSTRACT

The present invention provides unified synthesis of the CI-CI 9 building blocks of halichondrins and analogs thereof using selective coupling of poly-halogenated nucleophiles in chromium-mediated coupling reactions. The present invention also provides a practical and efficient synthesis of C20-C38 building blocks of halichondrins and analogs thereof. Also provided herein are general methods of selective activation and coupling of poly-halogenated analogs with an aldehyde. The provided coupling reactions are selective for halo-enone and halo-acetylenic ketal over vinyl halide and halide attached to a sp hydridized carbon. The provided efficient selective coupling reactions can allow easy access to the CI-CI 9 building blocks and C20-C38 building blocks of halichondrins and analogs thereof with limited or no purification or separation of the intermediates.

42 Claims, 30 Drawing Sheets

(56) References Cited

U.S. PATENT DOCUMENTS

| | | |
|---|---|---|
| 2011/0054194 A1 | 3/2011 | Hu et al. |
| 2011/0184190 A1 | 7/2011 | Endo et al. |
| 2013/0336974 A1 | 12/2013 | Collier et al. |
| 2014/0198806 A1 | 7/2014 | Pani et al. |
| 2017/0137437 A1 | 5/2017 | Kishi et al. |
| 2018/0155361 A1 | 6/2018 | Lee et al. |
| 2018/0230164 A1 | 8/2018 | Kishi et al. |

FOREIGN PATENT DOCUMENTS

| | | |
|---|---|---|
| JP | 6-279451 A | 10/1994 |
| JP | 2003-261447 A | 9/2003 |
| WO | WO 1993/017690 A1 | 9/1993 |
| WO | WO 1999/065894 A1 | 12/1999 |
| WO | WO 2005/118565 A1 | 12/2005 |
| WO | WO 2006/076100 A2 | 7/2006 |
| WO | WO 2007/139149 A1 | 12/2007 |
| WO | WO 2009/046308 A1 | 4/2009 |
| WO | WO 2009/064029 A1 | 5/2009 |
| WO | WO 2009/124237 A1 | 10/2009 |
| WO | WO 2011/094339 A1 | 8/2011 |
| WO | WO 2012/147900 A1 | 11/2012 |
| WO | WO 2013/097042 A1 | 4/2013 |
| WO | WO 2013/086634 A1 | 6/2013 |
| WO | WO 2013/142999 A1 | 10/2013 |
| WO | WO 2015/000070 A1 | 1/2015 |
| WO | WO 2015/066729 A1 | 5/2015 |
| WO | WO 2015/085193 A1 | 6/2015 |
| WO | WO 2016/003975 A1 | 1/2016 |
| WO | WO 2016/038624 A1 | 3/2016 |
| WO | WO 2016/176560 A1 | 11/2016 |
| WO | WO 2016/179607 A1 | 11/2016 |
| WO | WO 2018/187331 A1 | 10/2018 |
| WO | WO 2019/010363 A1 | 1/2019 |

OTHER PUBLICATIONS

International Preliminary Report on Patentability for Application No. PCT/US2018/025887 dated Oct. 17, 2019.
International Search Report and Written Opinion for PCT/US2018/031765, dated Jul. 2, 2018.
Invitation to Pay Additional Fees for PCT/US2018/041005, dated Sep. 14, 2018.
Invitation to Pay Additional Fees for PCT/US2018/061250, dated Feb. 26, 2019.
International Search Report and Written Opinion for PCT/US2018/061250, dated Apr. 16, 2019.
[No Author Listed] American Chemical Society. STN Database. Apr. 11, 2014. RN # 1583253-64-8.
[No Author Listed] Application for Product Designation Under the SAKIGAKE Designation System. Generic name E7130. Eisai Co., Ltd. Nov. 22, 2017.
[No Author Listed] Evidentiary Document for Applicability of E7130 to Designation Requirements. Eisai Co., Ltd. Nov. 22, 2017.
[No Author Listed] Overview Relating to the Suitability for Designation Requirements Under the SAKIGAKE Designation System. Generic name E7130. Eisai Co., Ltd.
Aicher et al., Synthetic studies towards halichondrins. Tetrahedron Lett. 1987;28(30):3463-66.
Aicher et al., Synthetic Studies towards Halichondrins: Synthesis of the C.27-C.38 Segment. Tetrahedron Lett. 1992;33(12):1549-52.
Aicher et al., Total synthesis of halichondrin B and norhalichondrin B. J. Am. Chem. Soc., 1992, 114 (8), pp. 3162-3164.
Austed et al., Commercial Manufacture of Halaven®: Chemoselective Transformations En Route to Structurally Complex Macrocyclic Ketones. Synlett 2013; 24(3): 333-337. doi: 10.1055/s-0032-1318026.
Berge et al., Pharmaceutical Salts. J. Pharmaceutical Sciences 1977;66(1):1-19.
Bringans, Studies on natural product derivatives : HIV therapies incorporating marine natural products. Dissertation. University of Canterbury, 2001.

Buszek et al., Synthetic Studies Towards Halichondrins: Synthesis of the Left Half of Halichondrins. Tetrahedron Lett. 1992;33:1553.
Chen et al., Ni(II)/Cr(II)-mediated coupling reaction: an asymmetric process. J. Org. Chem., 1995, 60 (17), pp. 5386-5387.
Choi et al., Asymmetric Ni(II)/Cr(II)-Mediated Coupling Reaction: Catalytic Process. Org. Lett., 2002, 4 (25), pp. 4435-4438. doi: 10.1021/ol026981x.
Choi et al., Synthetic studies on the marine natural product halichondrins. Pure Appl. Chem., 2003, vol. 75, No. 1, pp. 1-17.
Dong et al., New syntheses of E7389 C14-C35 and halichondrin C14-C38 building blocks: reductive cyclization and oxy-Michael cyclization approaches. J Am Chem Soc. Nov. 4, 2009;131(43):15642-6. doi: 10.1021/ja9058487.
Fang et al., Synthetic Studies Towards Halichondrins: Synthesis of the Left Halves of Norhalichondrins and Homohalichondrins. Tetrahedron Lett. 1992;33(12):1557-60.
Fukuyama et al., Application of a Rotor—Stator High-Shear System for Cr/Mn-Mediated Reactions in Eribulin Mesylate Synthesis. Org. Process Res. Dev., 2016, 20 (1), pp. 100-104. doi: 10.1021/acs.oprd.5b00383.
Fukuyama et al., Application of Continuous Flow for DIBAL-H Reduction and n-BuLi Mediated Coupling Reaction in the Synthesis of Eribulin Mesylate. Org. Process Res. Dev., 2016, 20 (2), pp. 503-509. doi: 10.1021/acs.oprd.5b00353.
Gould et al., Salt selection for basic drugs. International Journal of Pharmaceutics Nov. 1986;33(1-3):201-217. https://doi.org/10.1016/0378-5173(86)90055-4.
Guo et al., Toolbox approach to the search for effective ligands for catalytic asymmetric Cr-mediated coupling reactions. J Am Chem Soc. Oct. 28, 2009;131(42):15387-93. doi: 10.1021/ja905843e.
Hickford et al., Antitumour polyether macrolides: four new halichondrins from the New Zealand deep-water marine sponge Lissodendoryx sp. Bioorg Med Chem. Mar. 15, 2009;17(6):2199-203. doi: 10.1016/j.bmc.2008.10.093. Epub Nov. 19, 2008.
Hirata et al., Halichondrins—antitumor polyether macrolides from a marine sponge. Pure Appl. Chem., 1986, vol. 58, No. 5, pp. 701-710.
Jackson et al., A total synthesis of norhalichondrin B. Angew Chem Int Ed Engl. 2009;48(13):2346-50. doi: 10.1002/anie.200806111.
Kaburagi et al., Effective procedure for selective ammonolysis of monosubstituted oxiranes: application to E7389 synthesis. Tetrahedron Lett. 2007;48(51):8967-71.
Kim et al., New syntheses of E7389 C14-C35 and halichondrin C14-C38 building blocks: double-inversion approach. J Am Chem Soc. Nov. 4, 2009;131(43):15636-41. doi: 10.1021/ja9058475.
Kress et al., Investigations of the intramolecular Ni(II)/Cr(II)-mediated coupling reaction: Application to the taxane ring system. Tetrahedron Letters 1993;34(38);6003-6.
Kumar et al., Fe/Cu-Mediated One-Pot Ketone Synthesis. Org Lett. May 19, 2017;19(10):2766-2769. doi: 10.1021/acs.orglett.7b01128. Epub May 10, 2017.
Li et al., Unified Synthesis of C1-C19 Building Blocks of Halichondrins via Selective Activation/Coupling of Polyhalogenated Nucleophiles in (Ni)/Cr-Mediated Reactions. J Am Chem Soc. May 20, 2015;137(19):6226-31. doi: 10.1021/jacs.5b03499. Epub May 11, 2015.
Lill, Studies on New Zealand marine natural products. Dissertation. University of Canterbury, 1999.
Liu et al., Catalytic enantioselective Cr-mediated propargylation: application to halichondrin synthesis. Org Lett. Oct. 15, 2009;11(20):4520-3. doi: 10.1021/ol9016595.
Liu et al., Dramatic improvement in catalyst loadings and molar ratios of coupling partners for Ni/Cr-mediated coupling reactions: heterobimetallic catalysts. J Am Chem Soc. Nov. 25, 2009;131(46):16678-80. doi: 10.1021/ja9079308.
Liu et al., Synthesis of Alcohols from m-Fluorophenylsulfones and Dialkylboranes: Application to the C14-C35 Building Block of E7389. Org. Lett., 2012, 14 (9), pp. 2262-2265. doi: 10.1021/ol300672q.
Namba et al., New catalytic cycle for couplings of aldehydes with organochromium reagents. Org Lett. Dec. 23, 2004;6(26):5031-3.

(56) References Cited

OTHER PUBLICATIONS

Narayan et al., Novel second generation analogs of eribulin. Part I: Compounds containing a lipophilic C32 side chain overcome P-glycoprotein susceptibility. Bioorg Med Chem Lett, Mar. 15, 2011;21(6):1630-3.

Narayan et al., Novel second generation analogs of eribulin. Part II: Orally available and active against resistant tumors in vivo. Bioorg Med Chem Lett, Mar. 15, 2011;21(6):1634-8.

Narayan et al., Novel second generation analogs of eribulin. Part III: Blood-brain barrier permeability and in vivo activity in a brain tumor model. Bioorg Med Chem Lett, Mar. 15, 2011;21(6):1639-43.

Ortega et al., Potential clinical applications of halichondrins in breast cancer and other neoplasms. Breast Cancer (Dove Med Press). Feb. 8, 2012;4:9-19. doi: 10.2147/BCTT.S12423.

Seletsky et al., Structurally simplified macrolactone analogues of halichondrin B. Bioorg Med Chem Lett, Nov. 15, 2004;14(22):5547-50.

Shan et al., Concise and Highly Stereoselective Synthesis of the C20-C26 Building Block of Halichondrins and Eribulin. Org. Lett., 2012, 14 (2), pp. 660-663. doi: 10.1021/ol203373d.

Stamos et al., Ni(II)/Cr(II)-Mediated Coupling Reaction: Beneficial Effects of 4-tert-Butylpyridine as an Additive and Development of New and Improved Workup Procedures. Tetrahedron Lett. 1997;38(36):6355-8.

Stamos et al., Synthetic studies on halichondrins: A practical synthesis of the C.1–C.13 segment. Tetrahedron Letters Nov. 25, 1996;37(48):8643-8646.

Ueda et al., Total synthesis of halichondrin A, the missing member in the halichondrin class of natural products. J Am Chem Soc. Apr. 2, 2014;136(13):5171-6. doi: 10.1021/ja5013307. Epub Mar. 19, 2014.

Uemura et al., Norhalichondrin A: an antitumor polyether macrolide from a marine sponge. J. Am. Chem. Soc., 1985, 107 (16), pp. 4796-4798. doi: 10.1021/ja00302a042.

Uemura, Exploratory research on bioactive natural products with a focus on biological phenomena. Proc Jpn Acad Ser B Phys Biol Sci. 2010;86(3):190-201.

Wan et al., Asymmetric Ni(II)/Cr(II)-mediated coupling reaction: stoichiometric process. Org Lett. Dec. 12, 2002;4(25):4431-4.

Wang et al., Structure—activity relationships of Halichondrin B analogues: modifications at C.30-C.38. Bioorg Med Chem Lett, May 15, 2000;10(10):1029-32.

Xie et al., Synthesis of the C20-C26 Building Block of Halichondrins via a Regiospecific and Stereoselective SN2' Reaction. Org. Lett., 2002;4(25):4427-4429.DOI: 10.1021/ol026982p.

Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.

Yamamoto et al., Total synthesis of halichondrin C. J Am Chem Soc. Jan. 18, 2012;134(2):893-6. doi: 10.1021/ja2108307. Epub Dec. 23, 2011.

Yan et al., Selective Activation/Coupling of Polyhalogenated Nucleophiles in Ni/Cr-Mediated Reactions: Synthesis of C1-C19 Building Block of Halichondrin Bs. J. Am. Chem. Soc., 2015, 137 (19), pp. 6219-6225.

Zheng et al., Macrocyclic ketone analogues of halichondrin B. Bioorg Med Chem Lett. Nov. 15, 2004;14(22):5551-4.

a. Basic ion exchange resin b. Acidic ion exchange resin c. Dehydrating reagent
   (4Å molecular sieves)

X-A: Overall Transformation

X-B: Ni- and Cr-Catalytic Cycles

CHROMIUM-MEDIATED COUPLING AND APPLICATION TO THE SYNTHESIS OF HALICHONDRINS

RELATED APPLICATIONS

The present application is a continuation of U.S. patent application, U.S. Ser. No. 15/570,593, filed Oct. 30, 2017, which is a national stage filing under 35 U.S.C. § 371 of international PCT application, PCT/US2016/030064, filed Apr. 29, 2016, which claims priority under 35 U.S.C. § 119(e) to U.S. provisional patent application, U.S. Ser. No. 62/155,067, filed Apr. 30, 2015, the entire contents of each of which is incorporated herein by reference.

BACKGROUND OF THE INVENTION

The halichondrins are polyether macrolides, originally isolated from the marine sponge *Halichondria okadai* by Uemura, Hirata, and coworkers. Due to their intriguing structural architecture and extraordinary in vitro and in vivo anti-proliferative activity, the halichondrins have received much attention from the scientific community. Synthetic methods that streamline the preparation of these natural products or related derivatives are important given the structural complexity of the halichondrin backbone. A highly convergent approach has been adopted to synthesize halichondrins and analogs thereof. Because of its high degree of convergence, one can expect a high overall efficiency for the longest linear synthetic sequence. Interestingly, the key two couplings have been achieved efficiently with Ni/Cr-mediated reactions: one between the building blocks C20-C38 and C1-C19 to synthesize the macrolide; and another between a vinyl iodide and an aldehyde to synthesize the building block C1-C19. The structure of Halichondrin B is shown below, with carbon atoms numbered.

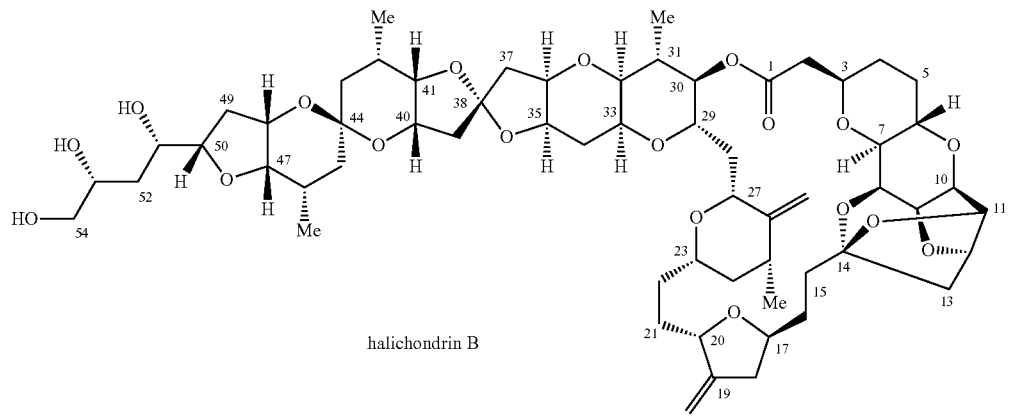 [SMILES: C=C1C[C@@H]2CC[C@@]34C[C@H]5O[C@H]6[C@@H](O3)[C@H]3O[C@H](CC[C@@H]3O[C@H]6C5O4)CC(=O)O[C@@H]3[C@@H](C)[C@@H]4O[C@@H]5C[C@]6(C[C@@H]7O[C@]8(C[C@H](C)[C@@H]9O[C@H]([C@@H](O)C[C@@H](O)CO)C[C@@H]9O8)C[C@H](C)[C@@H]7O6)O[C@@H]5C[C@@H]4O[C@H]3C[C@H]3O[C@@H](CC[C@@H]1O2)C[C@@H](C)C3=C]

halichondrin B

Chromium-mediated couplings of organic halides/triflates with aldehydes belong to a class of 1,2-carbonyl addition reactions. In this process, the active nucleophiles $RCrX_3$ are generated from halides/triflates in situ. Depending on the mode of activation, chromium-mediated couplings are divided into three sub-groups: (1) Ni/Cr-mediated alkenylation, alkynylation, and arylation, (2) Co or Fe/Cr-mediated alkylation, 2-haloallyl-ation and propargylation, and (3) Cr-mediated allylation and propargylation (See, e.g., Saccomano, N. A. in *Comprehensive Organic Synthesis*; Trost, B. M., Fleming, I., Eds.; Pergamon: Oxford, 1991; Vol. 1, p 173).

Ni/Cr-mediated couplings of alkenyl halides/triflates with aldehydes were originally reported by Takai, Hiyama, Nozaki, and coworkers in 1983. Since then, it has been shown that the coupling is initiated by a catalytic amount of $NiCl_2$ as a contaminant in the with $CrCl_2$. It is now generally accepted that this coupling involves: (1) oxidative addition of Ni(0), formed from $NiCl_2$ via reduction with $CrCl_2$ in situ, to an alkenyl halide/triflate to form an alkenyl Ni(II)-species, (2) transmetallation of the resultant Ni(II)-species to Cr(II) $Cl_2$ to form alkenyl Cr(III)-species, and (3) carbonyl addition of the resultant Cr(III)-species to an aldehyde to form the product Cr(III)-alkoxide (FIG. 5). Chemistry has been developed to achieve this coupling in a catalytic and asymmetric manner.

Due to the important biological activities of halichondrins, it is valuable to develop a unified and practical synthesis of the C1-C19 building block, as well as C20-C38 building blocks, to allow easy access to halichondrins (e.g., halichondrin A, B, C; norhalichondrin A, B, C; homohalichondrin A, B, C; eribulin), and analogs thereof.

SUMMARY OF THE INVENTION

As part of the ongoing research effort aimed at a unified total synthesis of members of the halichondrin class of marine natural products, an efficient synthesis of the C1-C19 building block has been developed (FIG. 4), and is provided herein. Furthermore, a practical and efficient synthesis of C20-C38 building blocks has also been developed and is provided herein. In the recently reported total synthesis of halichondrin A (Ueda et al., *J. Am. Chem. Soc.*, 2014, 136, 5171), the C1-C19 building block is joined with the C20-C38 building block to synthesize halichondrin A, B, and C, as well as their analogs (e.g., norhalichondrin A, B, C; homohalichondrin A, B, C; eribulin).

In one aspect, the present invention provides chromium-mediated coupling reactions which can be applied to the synthesis of halichondrins as well as other molecules. In one aspect, the present invention provides a method of preparing a compound of Formula (I):

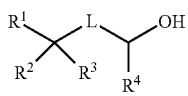

(I)

or a salt thereof, the method comprises coupling a compound of Formula (i):

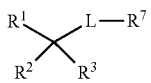

(i)

or a salt thereof, with an aldehyde of Formula (ii):

(ii)

in the presence of a chromium catalyst and optionally one or more catalysts (e.g., a nickel catalyst and a zirconium catalyst), wherein $R^1$, $R^2$, $R^3$, $R^4$, and $R^7$ are as defined herein. The provided coupling method effectively furnishes the coupling a wide range of halo-enone, halo-enone ketal, halo-acetylenic ketone, or halo-acetylenic ketal substrates and an aldehyde. Since a hydroxyl group is generated in the coupling product, an R- or S-isomer can be introduced in the chiral center. In some embodiments, the provided coupling method is a catalytic asymmetric coupling between the compound of Formula (i) and the aldehyde of Formula (ii). The chromium catalyst and one or more catalysts in the coupling can provide efficient asymmetric induction, geometrical isomerization, and coupling rate. In certain embodiments, the coupling reaction is catalyzed by a chromoium complex. In certain embodiments, the coupling reaction is catalyzed by a chromoium complex and one or more catalysts. In certain embodiments, the coupling reaction is catalyzed by a chromoium complex and a zirconium complex. In certain embodiments, the coupling reaction is catalyzed by a chromium complex and a nickel complex. In certain embodiments, the coupling reaction is catalyzed by a combination of a chromoium complex, a nickel complex, and a zirconium complex. In certain embodiments, the coupling reaction is catalyzed by a chromoium complex, wherein the chromoium complex comprises a chiral ligand. In certain embodiments, the coupling reaction is catalyzed by a chromoium complex and one or more catalysts, wherein the chromoium complex comprises a chiral ligand. In certain embodiments, the coupling reaction is catalyzed by a chromoium complex and a zirconium complex, wherein the chromoium complex comprises a chiral ligand. In certain embodiments, the coupling reaction is catalyzed by a chromium complex and a nickel complex, wherein the chromoium complex comprises a chiral ligand. In certain embodiments, the coupling reaction is catalyzed by a combination of a chromoium complex, a nickel complex, and a zirconium complex, wherein the chromoium complex comprises a chiral ligand.

In certain embodiments, the provided coupling method is stereoselective in installing a chiral center having a hydroxyl group. In certain embodiments, the compound of Formula (i) is a halo-enone or halo-enone ketal of Formula (i-a):

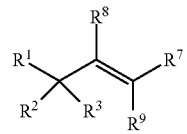

(i-a)

or a salt thereof, and the asymmetric coupling product is of Formula (I-a):

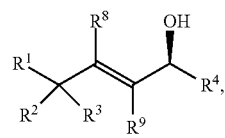

(I-a)

or salt thereof. In certain embodiments, the compound of Formula (i) is a halo-acetylenic ketone or halo-acetylenic ketal of Formula (i-b):

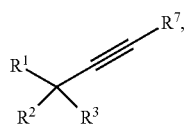

(i-b)

or a salt thereof, and the asymmetric coupling product is of Formula (I-b):

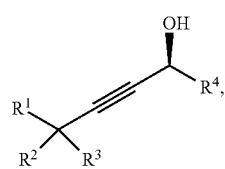

(I-b)

or a salt thereof.

In certain embodiments, the provided coupling method is selective for halo-enone, halo-enone ketal, halo-acetylenic enone, and halo-acetylenic ketal, over vinyl halide and a halide attached to a $sp^3$ hybridized carbon. A vinyl halide or a halide attached to a $sp^3$ hybridized carbon can remain intact during the coupling reaction between a halo-enone, halo-enone ketal, halo-acetylenic enone, or halo-acetylenic ketal, with an aldehyde of Formula (ii). The vinyl halide moiety can be a part of the compound of Formula (i), the aldehyde of Formula (ii), or another compound in the coupling reaction mixture. In certain embodiments, the provided coupling method is selective for halo-enone, halo-enone ketal, halo-acetylenic enone, and halo-acetylenic ketal, over vinyl iodide and chloride or iodide attached to a $sp^3$ hybridized carbon. In certain embodiments, the provided coupling method is selective for halo-acetylenic ketone or halo-acetylenic ketal over vinyl iodide or a iodide and chloride attached to a $sp^3$ hybridized carbon. The provided coupling methods are applicable to synthesizing the C1-C19 building block of halichondrins and analogs thereof as well as other compounds. The provided coupling methods are also applicable to the preparation of C20-C38 building blocks of halichondrins and analogs thereof. Furthermore, the provided coupling methods are useful in joining C1-C19 building blocks with C20-C38 building blocks, as well as joining the right half and left half of halichondrins and analogs thereof. For examples, see Schemes T1-T4.

In certain embodiments, the compound of Formula (i) is of Formula (i-a-3):

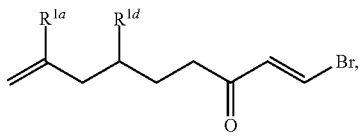
(i-a-3)

or a salt thereof;
and the aldehyde of Formula (ii) is of Formula (ii-a):

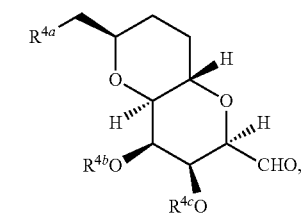
(ii-a)

or a salt thereof;
and the compound of Formula (I) is of Formula (I-a-3):

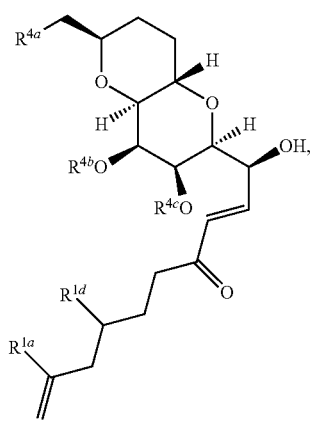
(I-a-3)

or a salt thereof,
wherein $R^{4a}$, $R^{4b}$, $R^{4c}$, $R^{1a}$, and $R^{1d}$ are as defined herein.

In certain embodiments, the compound of Formula (i) is of Formula (i-b-5):

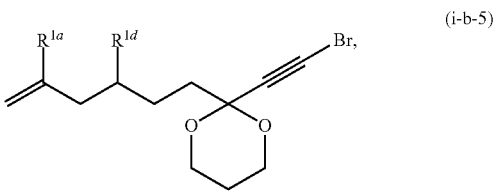
(i-b-5)

or a salt thereof, and
and the aldehyde of Formula (ii) is of Formula (ii-a):

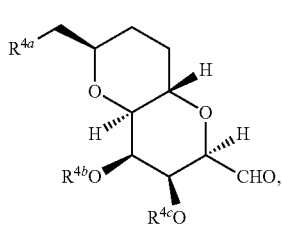
(ii-a)

or a salt thereof, and
the compound of Formula (I) is of Formula (I-b-5):

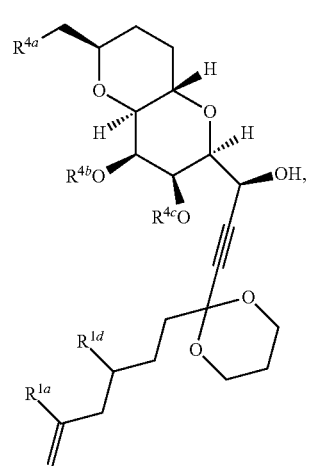
(I-b-5)

or a salt thereof,
wherein $R^{4a}$, $R^{4b}$, $R^{4c}$, $R^{1a}$, and $R^{1d}$ are as defined herein.

In another aspect, the present invention provides the synthesis of the C1-C19 building block of halichondrin A:

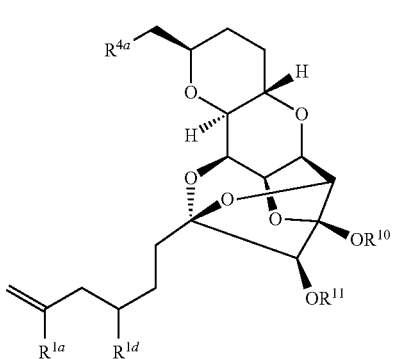

(I-b-13)

or a salt thereof, wherein $R^{4a}$, $R^{1a}$, $R^{1d}$, $R^{10}$, and $R^{11}$ are as defined herein.

In another aspect, the present invention provides the synthesis of the C1-C19 building block of halichondrin B:

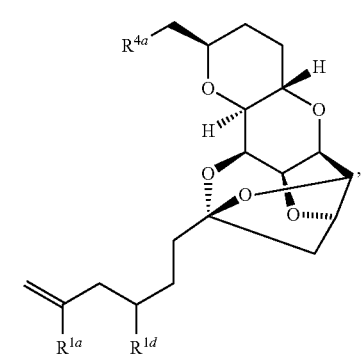

(I-a-4)

or a salt thereof, wherein $R^{4a}$, $R^{1a}$, and $R^{1d}$ are as defined herein.

In another aspect, the present invention provides the synthesis of the C1-C19 building block of halichondrin C:

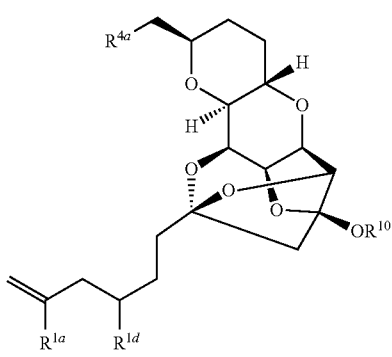

(I-b-6)

or a salt thereof, wherein $R^{4a}$, $R^{1a}$, $R^{1d}$, and $R^{10}$ are as defined herein.

In another aspect, the present invention provides methods of preparing C20-C38 building blocks of halichondrins (e.g., halichondrin A, B, C; norhalichondrin A, B, C; homohalichondrin A, B, C; eribulin), such as compounds of Formula (III-1):

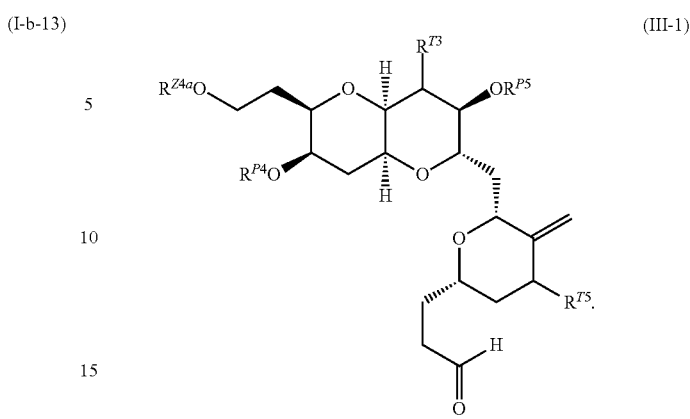

(III-1)

In certain embodiments, a C20-C38 building block is a compound of Formula (III-11). Provided herein are methods of preparing a compound of Formula (III-11):

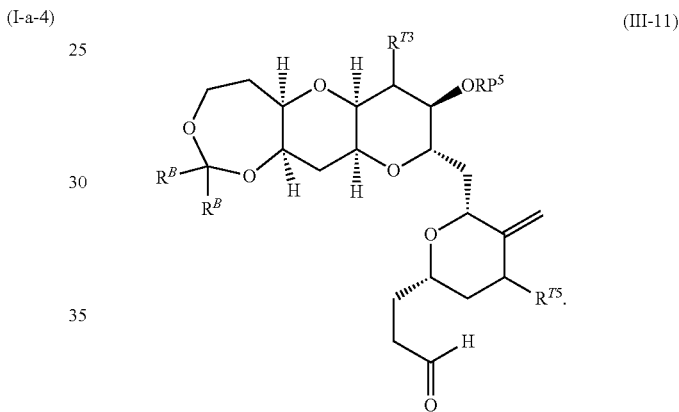

(III-11)

In another aspect, the prevent invention provides compounds which are useful intermediates in the preparation of halichondrins and building blocks described herein.

The details of certain embodiments of the invention are set forth in the Detailed Description of Certain Embodiments of the Invention, as described below. Other features, objects, and advantages of the invention will be apparent from the Claims.

BRIEF DESCRIPTION OF THE DRAWINGS

FIG. 5A: overall transformation; FIG. 5B: Ni- and Cr-catalytic cycles. $Zr(cp)_2Cl_2$ or TMS-Cl is used to dissociate the product from Cr-species, to regenerate the Cr-catalyst.

Chem. 1995, 60, 5386. (c) Namba, K.; Kishi, Y. *Org. Lett.* 2004, 6, 5031; Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387; Knochel, P.; Rao, C. J. *Tetrahedron*, 1993, 49, 29; Kress, M. H.; Ruel, R.; Miller, W. H.; Kishi, Y. *Tetrahedron Lett.* 1993, 34, 6003).

Figure 7:
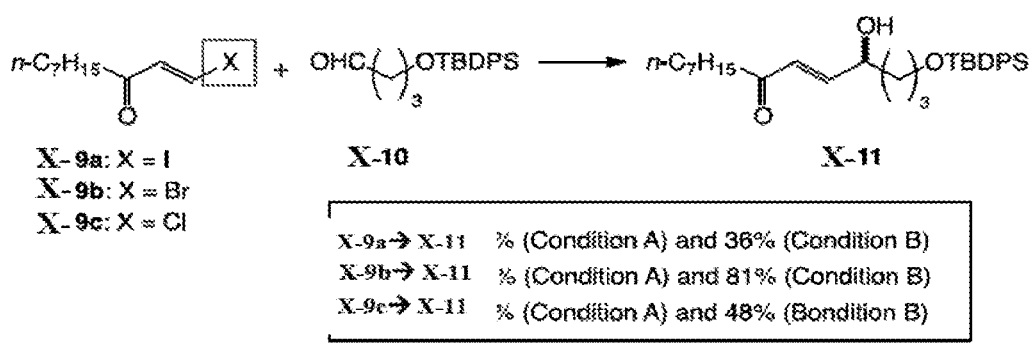
Figure 7:
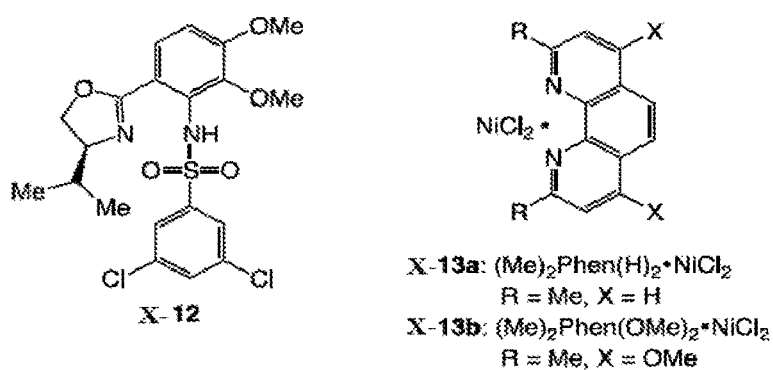

FIG. 7 shows model coupling reactions used to assess coupling efficiency. Coupling condition X-A: 10 mol % Cr-complex prepared from sulfonamide X-12 and 1 mol % nickel complex X-13a; Coupling condition X-B: 10 mol % Cr-complex prepared from sulfonamide X-12 and 0.05 mol % nickel complex X-13b; Yields are based on chromatographically isolated product.

Figure 8:
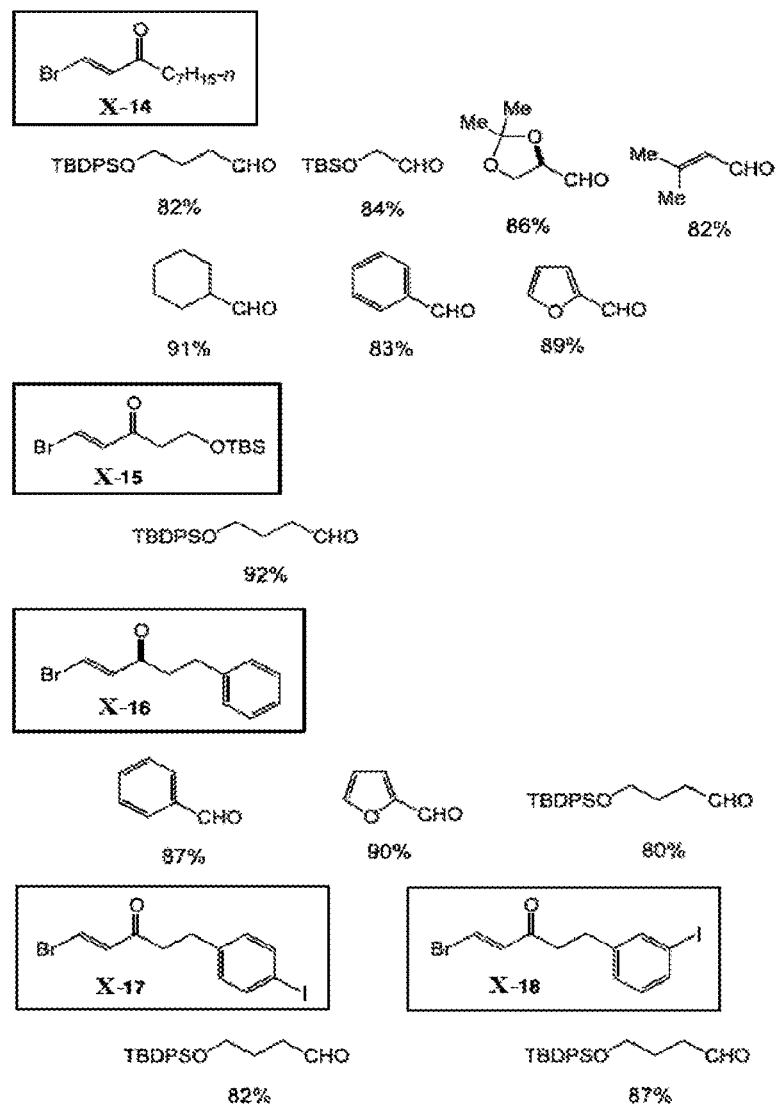

FIG. 8 shows examples tested for the coupling of di-substituted trans-β-bromoenones with aldehydes. Coupling condition: 10 mol % Cr-catalyst, prepared from sulfonamide X-12, 0.05 mol % Ni-complex X-13b, $Zr(cp)_2Cl_2$ (1.5 eq), LiCl (2 eq), and Mn (2 eq) in MeCN ([C] 0.4 M) at room temperature for 3 hours; Yield: based on chromatographically isolated products.

Figure 9:
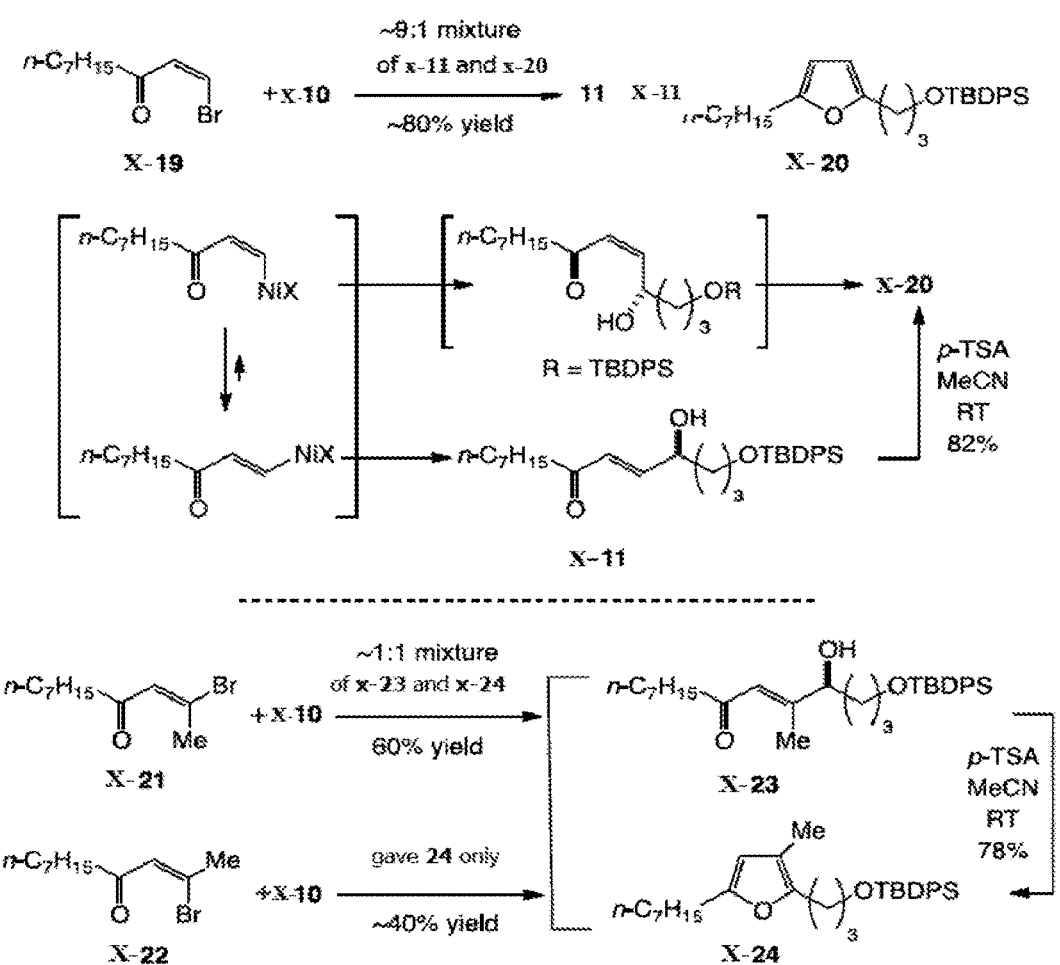

FIG. 9 shows attempted coupling with other types of β-bromo-enones. For coupling conditions, please see FIG. 8.

Figure 10:
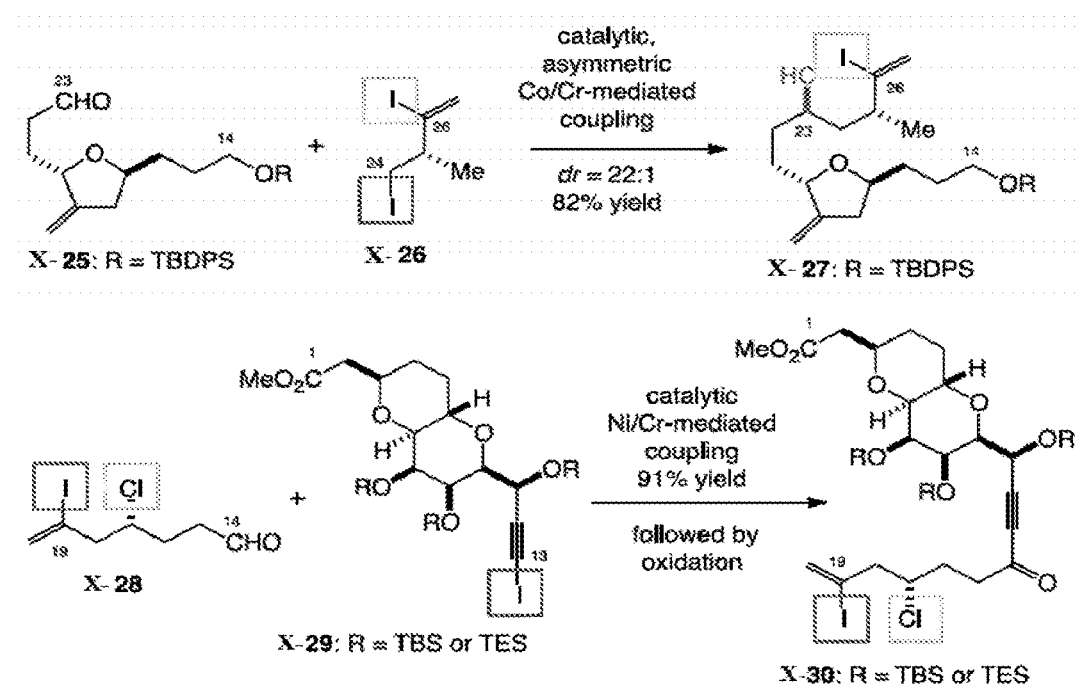

FIG. 10 shows two examples relevant to the synthesis of the C1-C19 building block of halichondrins. The first example shows that a selective activation/coupling is possible with the use of a selective activator in the Cr-mediated coupling; namely, cobalt- and iron-salts are known to activate saturated halides, but not vinyl halides (Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387; Takai, K.; Nitta, K.; Fujimura, O.; Utimoto, K. *J. Org. Chem.* 1989, 54, 4732; Wan, Z.-K.; Choi, H.-w.; Kang, F.-A.; Nakajima, K.; Demeke, D.; Kishi, Y. *Org. Lett.* 2002, 4, 4431). The second example shows that selective activation of iodoacetylene in the Ni/Cr-mediated reaction is possible without disturbing the vinyl iodide present in the electrophile (Ueda, A.; Yamamoto, A.; Kato, D.; Kishi, Y. *J. Am. Chem. Soc.* 2014, 136, 5171).

Figure 11:
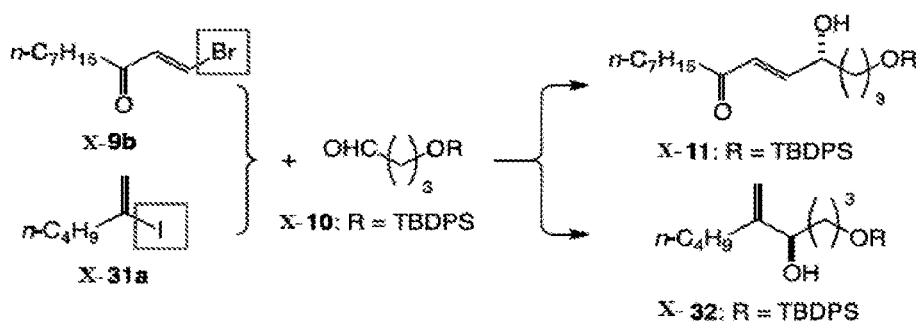

FIG. 11 shows a competition experiment of trans-β-bromoenone X-9b over vinyl iodides X-31a~c. Coupling condition: nucleophile: a 1:1 mixture of X-9b and X-31a, b, or c. Reagents: 10 mol % Cr-catalyst, prepared from sulfonamide X-12, 0.05 mol % Ni-complex X-13a or X-13b, $Zr(cp)_2Cl_2$ (1.5 eq), LiCl (2 eq), and Mn (2 eq) in MeCN ([C] 0.4 M) at room temperature for 3 hours. The product ratio was estimated from $^1$H NMR analysis of crude coupling products.

Figure 12:
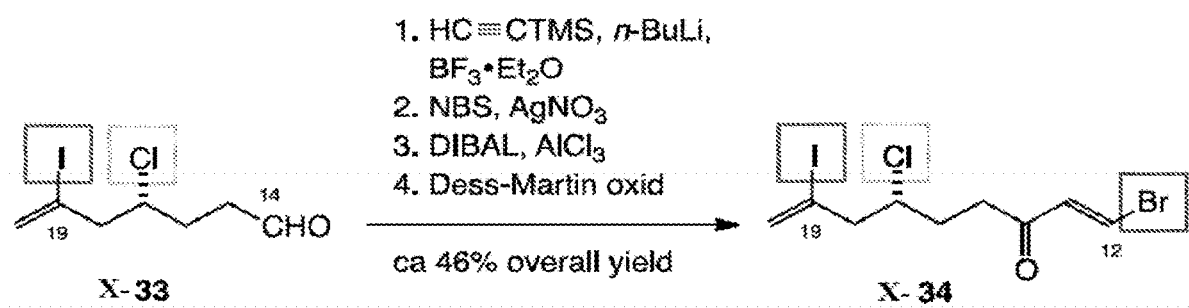

FIG. 12 shows an exemplary synthesis of poly-halogenated nucleophile X-34.

Figure 13:
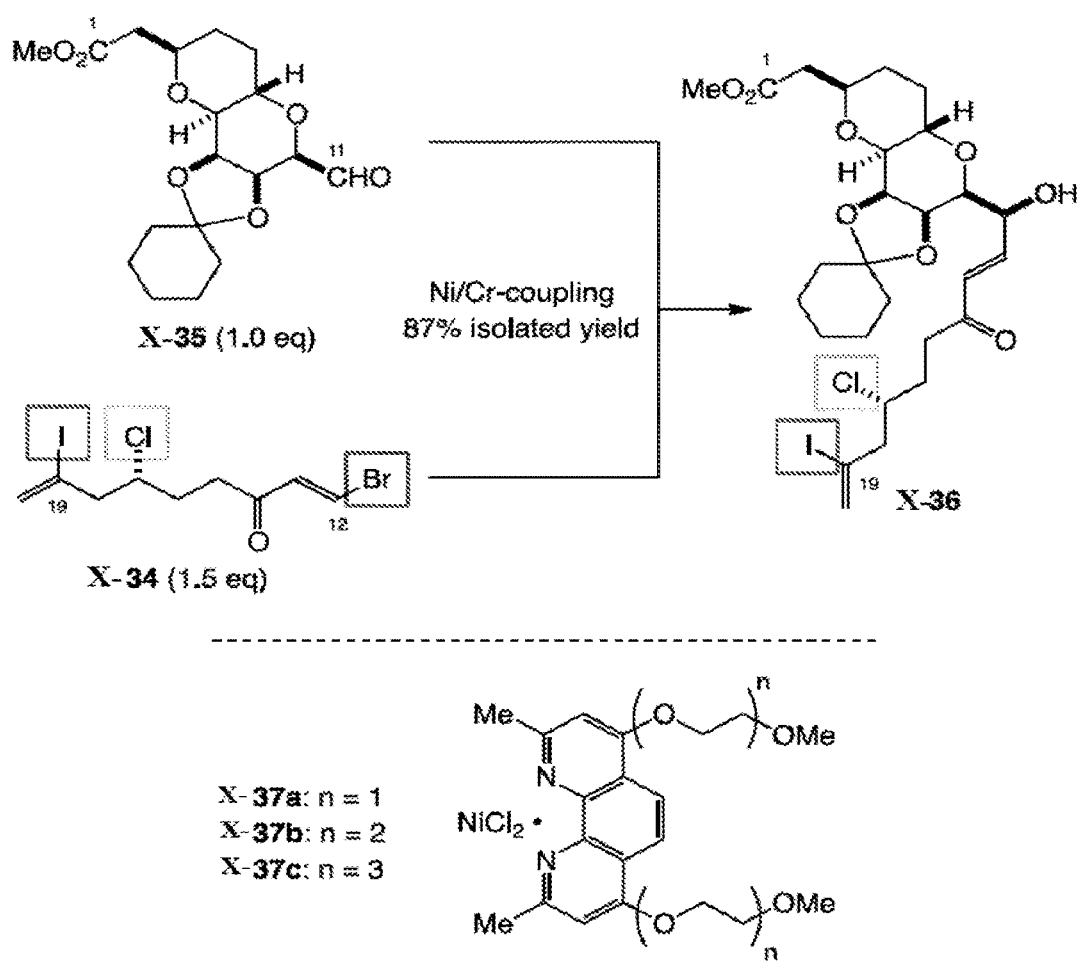

FIG. 13 shows Ni/Cr-mediated coupling of X-34 with X-35, with use of polyether-type phenanthrene.$NiCl_2$ complex X-37c. Coupling condition: 10 mol % Cr-catalyst, prepared from sulfonamide X-12, 0.05 mol % Ni-complex X-37c, $Zr(cp)_2Cl_2$ (1.5 eq), LiCl (2 eq), and Mn (2 eq) in MeCN ([C] 0.4 M) at room temperature for 3 hours. Yield: chromatographically isolated yield in 7.1 g aldehyde scale.

Figure 14:
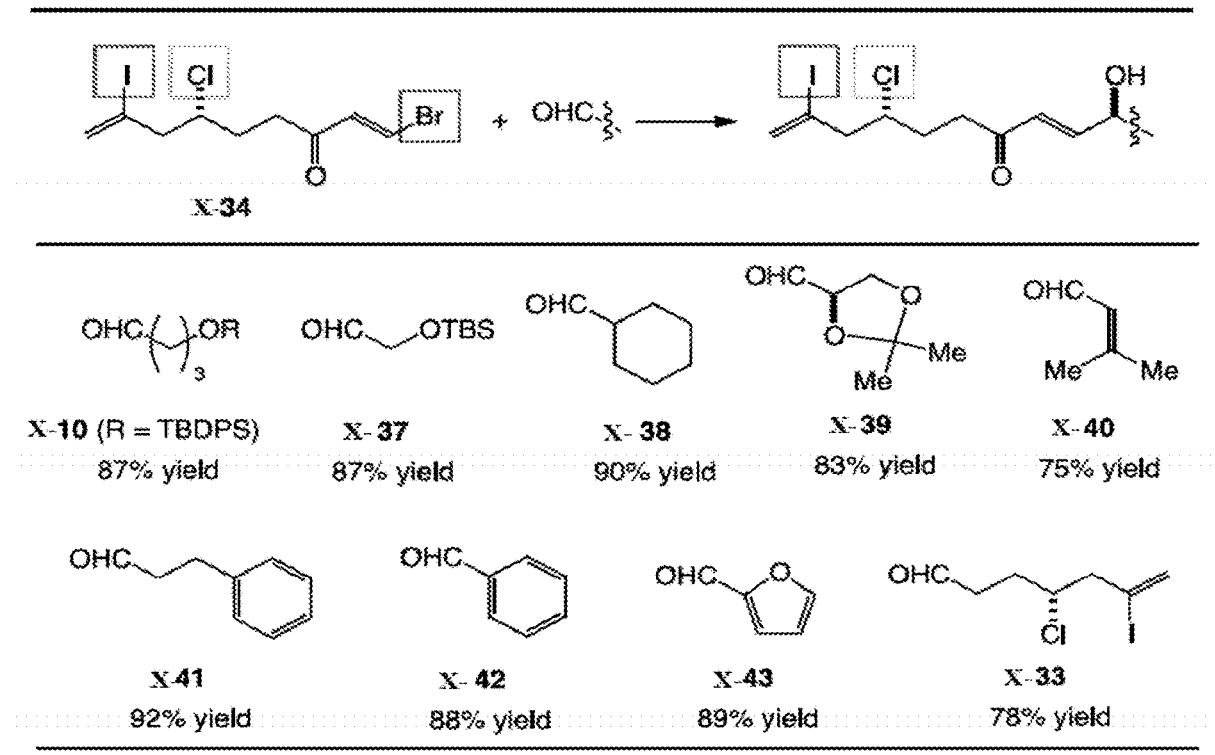

FIG. 14 shows examples tested for the coupling of poly-halogenated nucleophile X-34 with various aldehydes. Coupling condition: 10 mol % Cr-catalyst, prepared from sulfonamide X-12, 0.05 mol % Ni-complex X-37c, $Zr(cp)_2Cl_2$ (1.5 eq), LiCl (2 eq), and Mn (2 eq) in MeCN ([C] 0.4 M) at room temperature for 3 hours; Yield: based on chromatographically isolated products.

Figure 15:
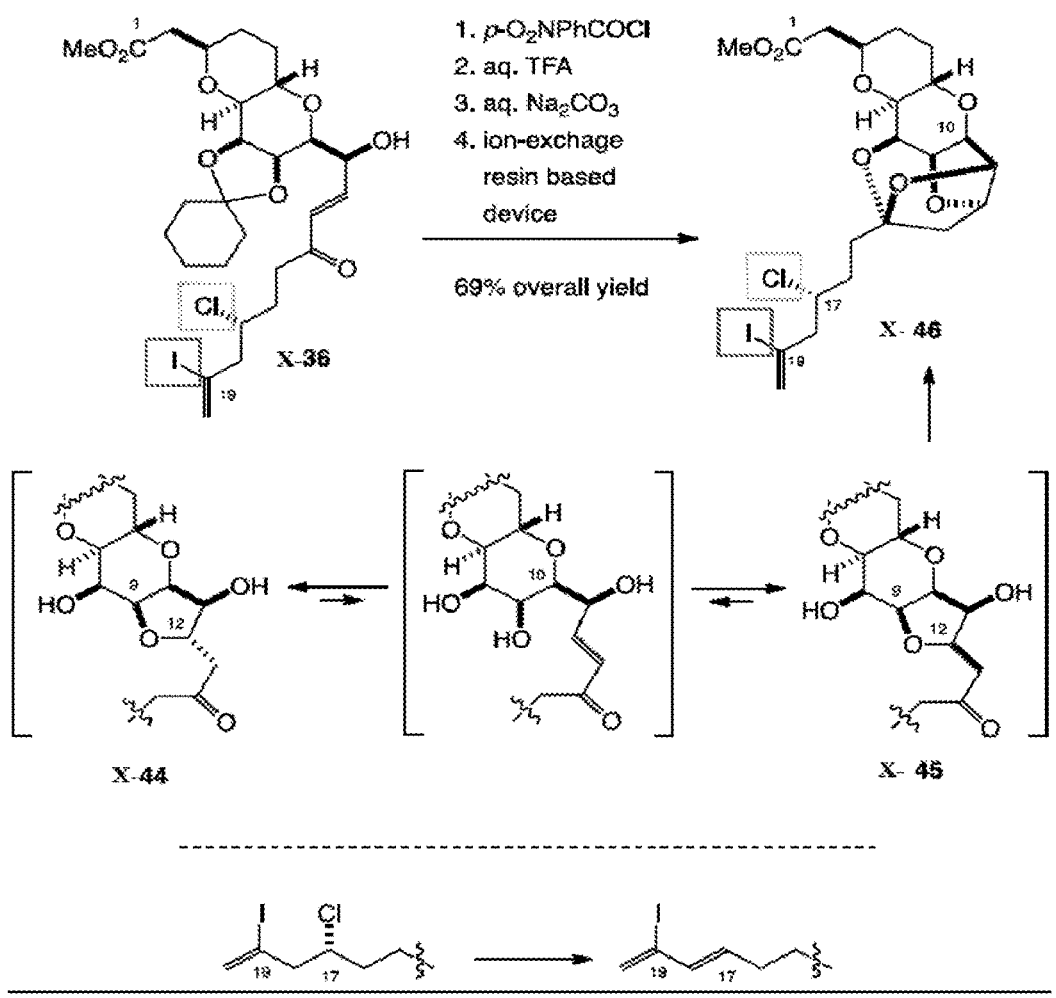

FIG. 15 shows the completion of synthesis of the C1-C19 building block X-46 of halichondrin Bs. Yield: chromatographically isolated yield in 11.4 g scale of coupling product X-36.

Figure 16:
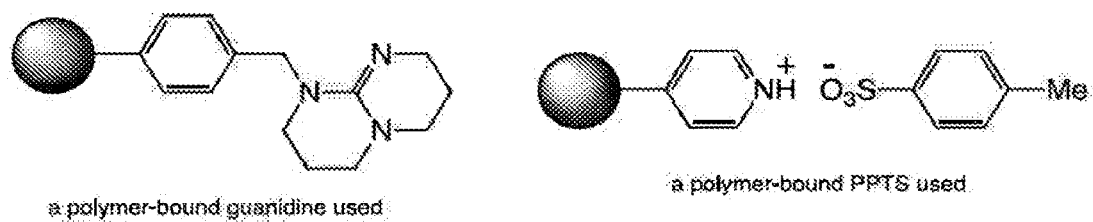

FIG. 16 shows polymer-bound guanidine and PPTS used for ion-exchange-resin based device.

Figure 17:
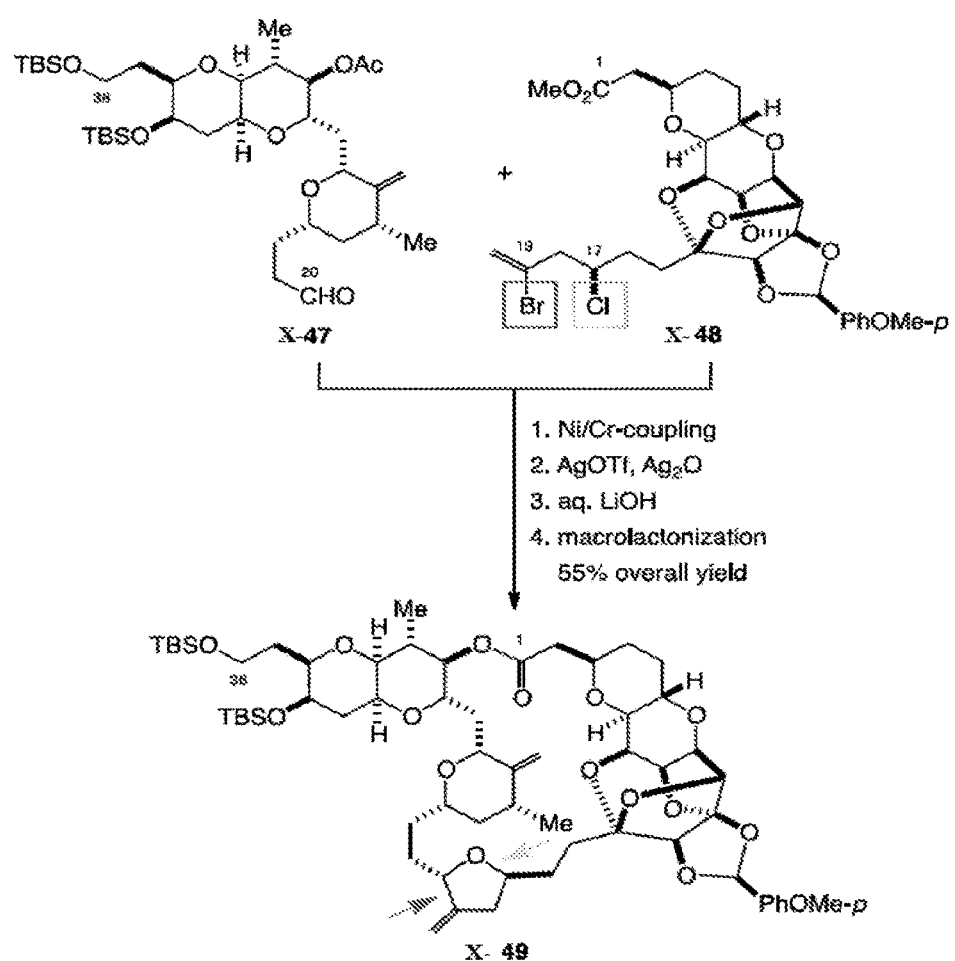

FIG. 17 shows a summary of the exemplary synthesis of the right-half of halichondrin A.

Figure 18:
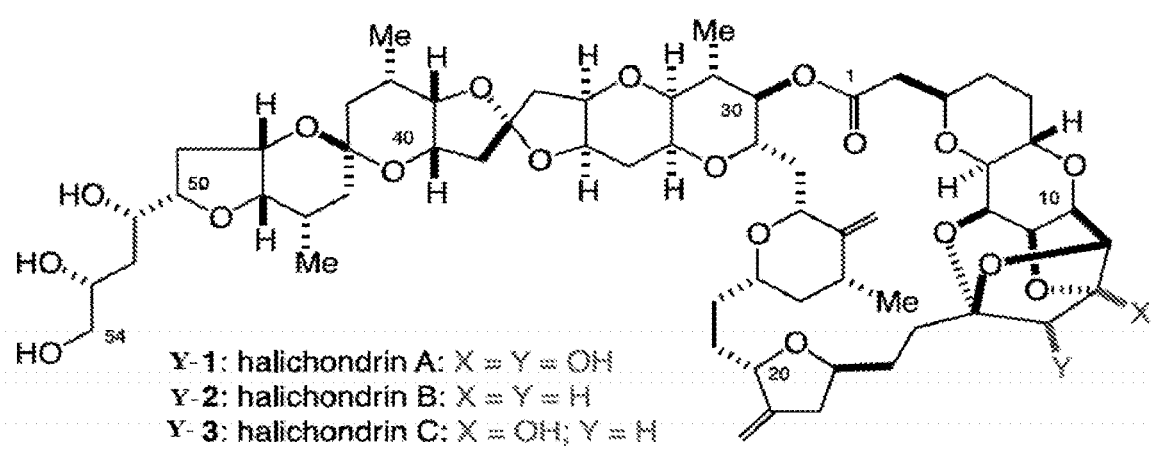

FIG. 18 shows structures of halichondrins A, B, and C.

Figure 19:
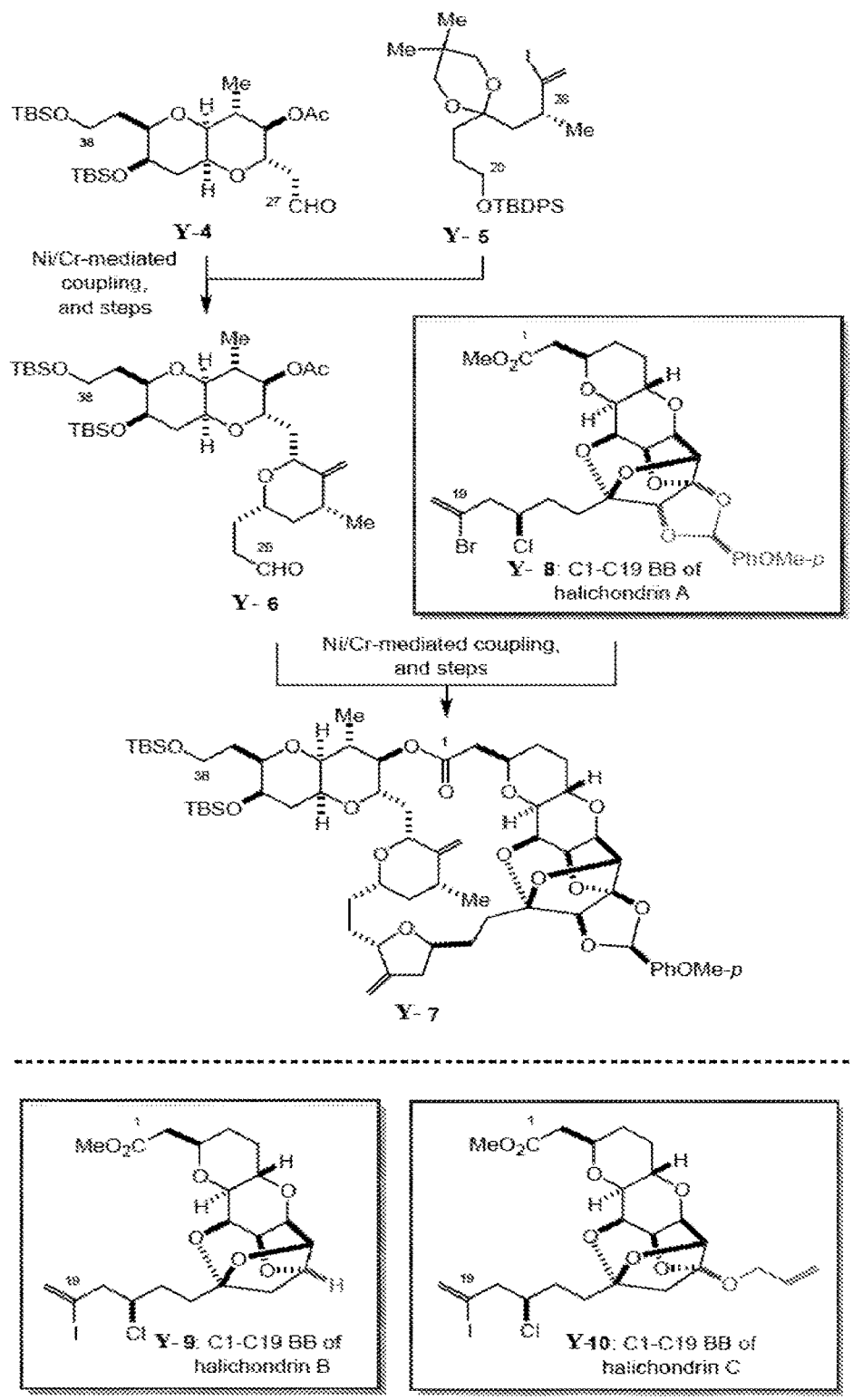

FIG. 19 shows a summary of the synthesis of the right half of halichondrin A and requisite C1-C19 building blocks (BBs) of halichondrins A-C.

Figure 20:
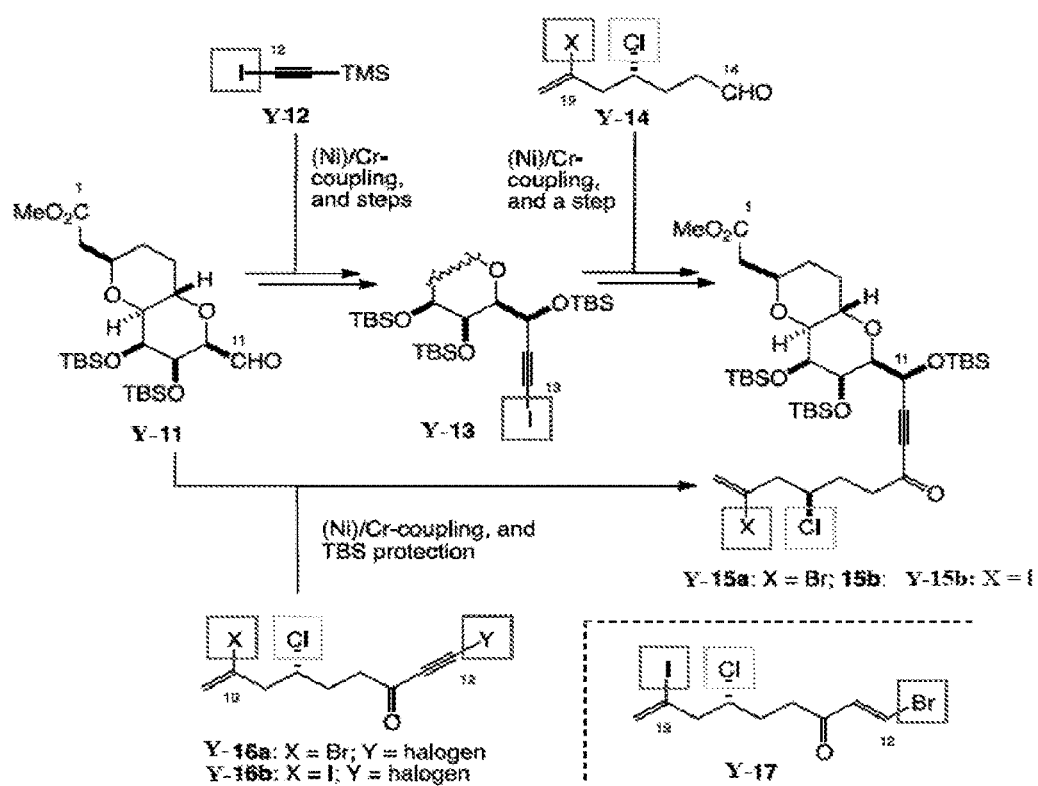

FIG. 20 shows a proposed one-step synthesis of acetylenic ketones Y-15a,b via selective activation/coupling of halo-acetylenic ketones Y-16a,b.

Figure 21:
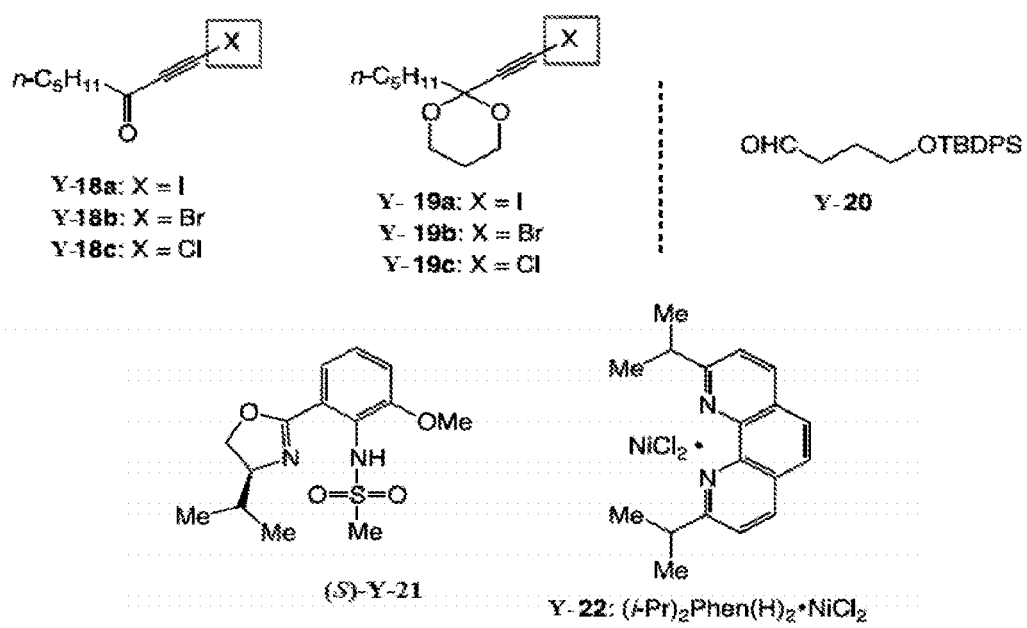

FIG. 21 shows substrates, sulfonamide, and Ni-catalyst used for the model study.

Figure 22:
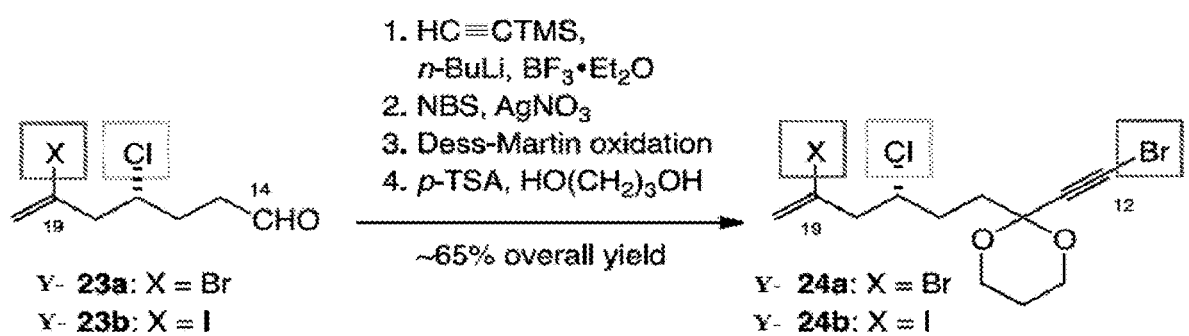

FIG. 22 shows an exemplary synthesis of nucleophiles Y-24a,b.

Figure 23:
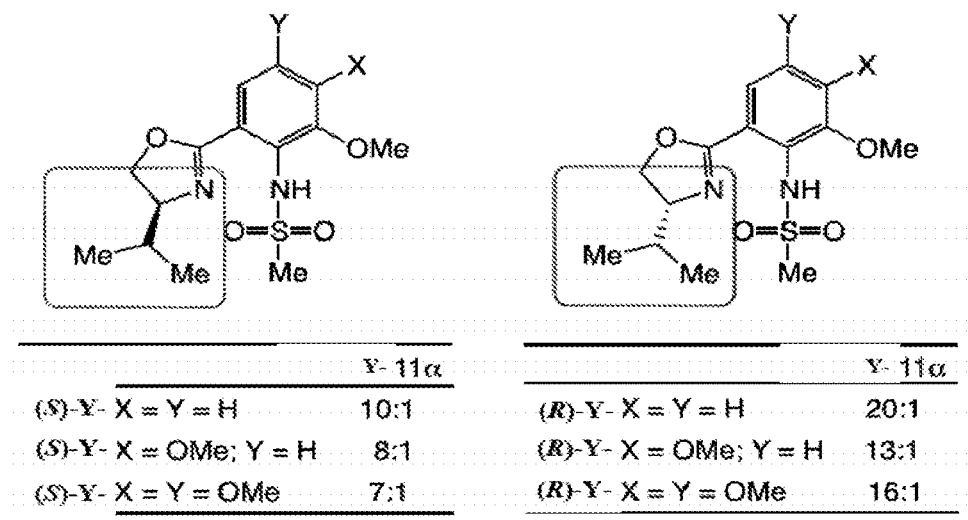

FIG. 23 shows exemplary sufonamides.

Figure 24:
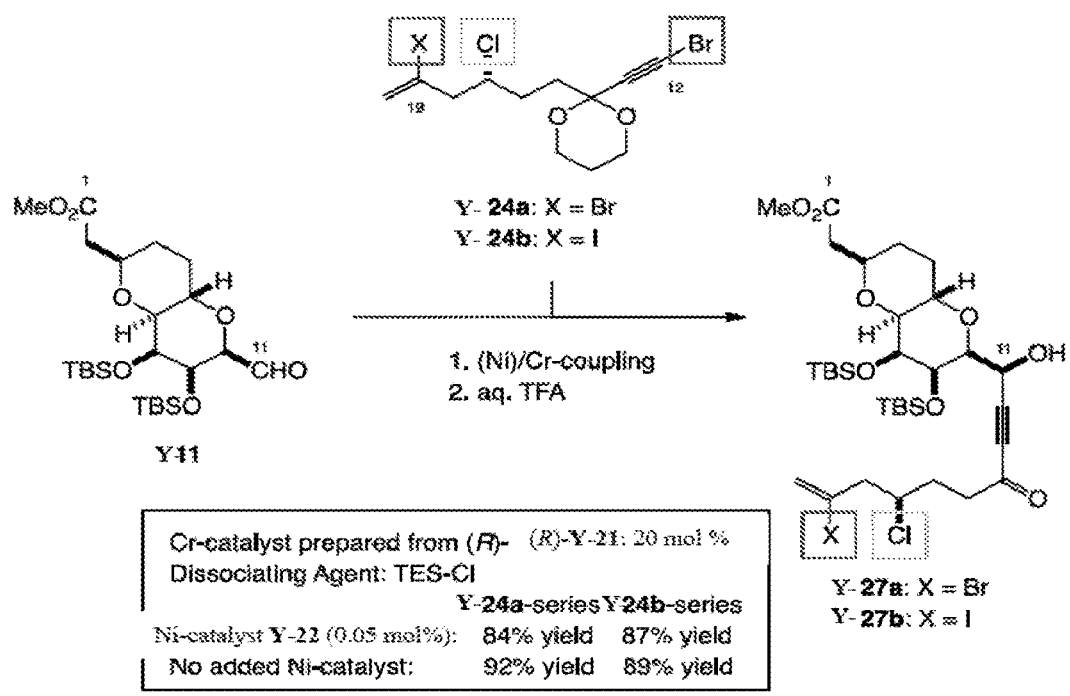

FIG. 24 shows (Ni)/Cr-Mediated couplings. Coupling condition: Cr-catalyst prepared from (R)-Y-21: 20 mol %; Ni-catalyst Y-22b (0.05 mol %) or no added Ni-catalyst; TES-Cl (2.5 eq); LiCl (4 eq); Mn (4 eq); EtCN ([C] 0.4 M); RT; Yields are based on chromatographically isolated product.

Figure 25:
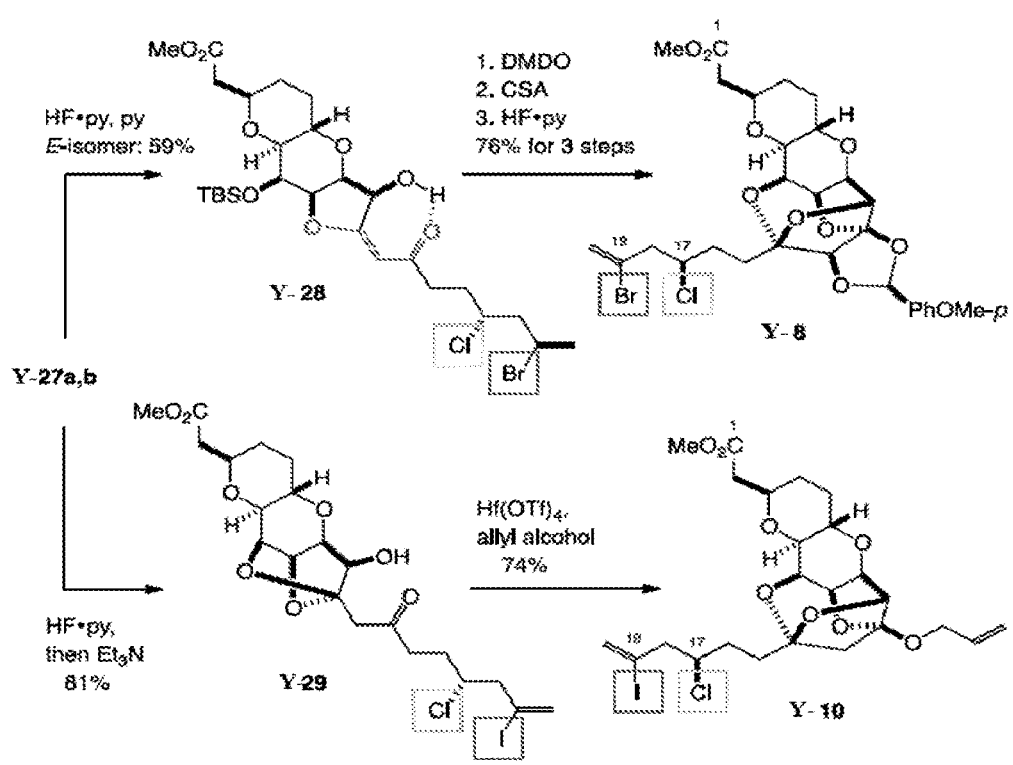

FIG. 25 shows an exemplary synthesis of C1-C19 building blocks (BBs) in the halichondrin A and C series.

Figure 26:
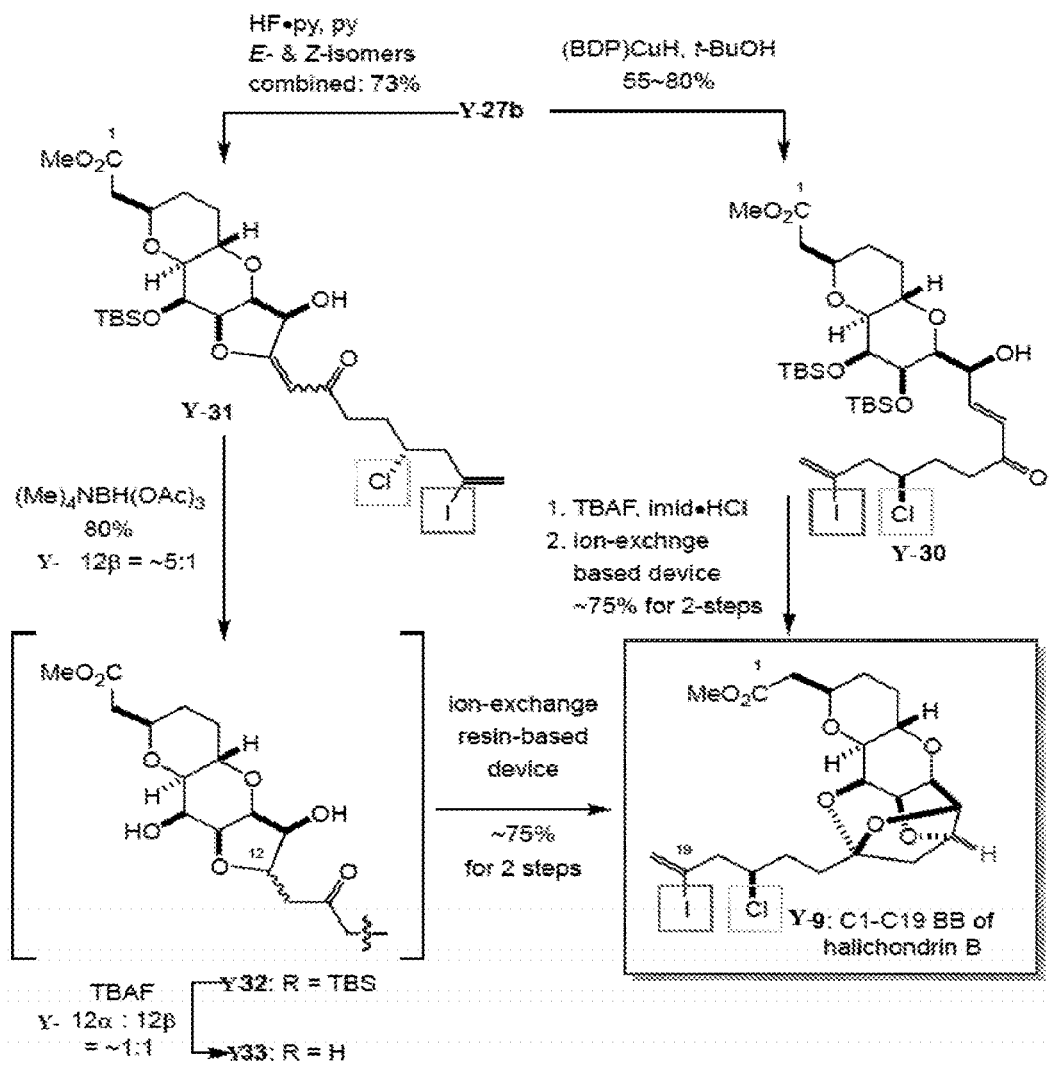

FIG. 26 shows an exemplary synthesis of C1-C19 BBs in the halichondrin B series.

Figure 27:
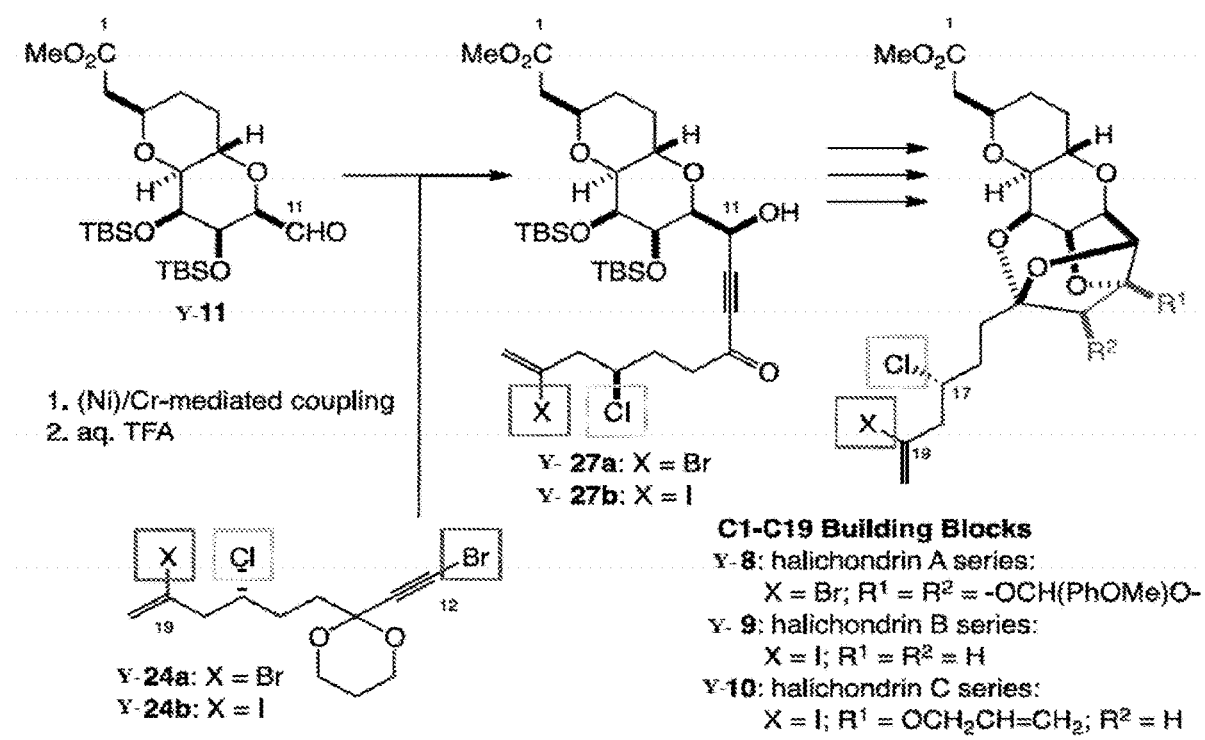

FIG. 27 shows an exemplary synthesis of C1-C19 building blocks from compound Y-11.

Figure 28:
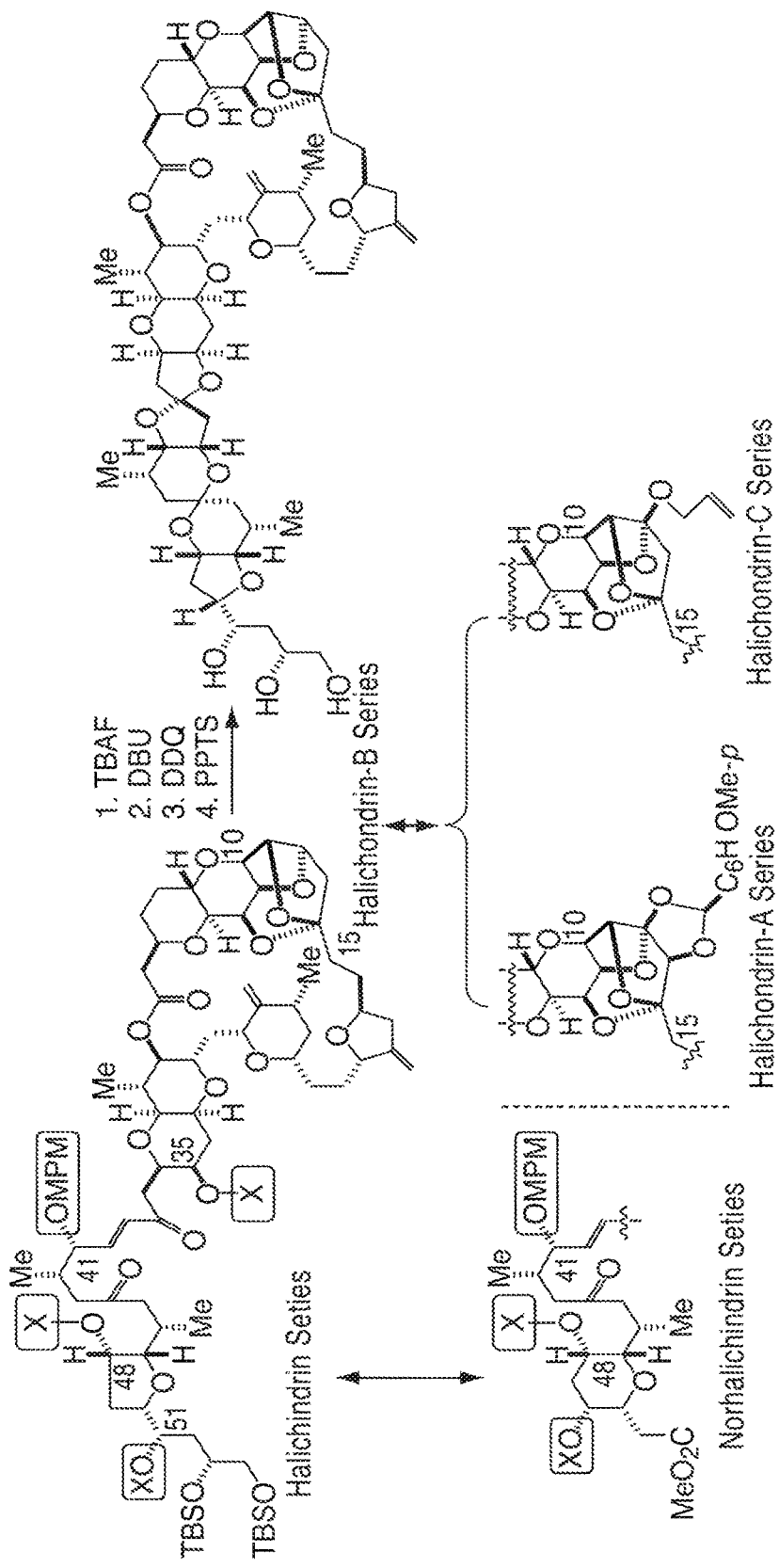

FIG. 28 shows an example of a transformation that can be used to prepare halichondrins A-C and norhalichondrins A-C. This transformation is achieved in four steps (i.e., 1. TBAF, 2. DBU, 3. DDQ, and PPTS). In the halichondrin-A and -C series, after this transformation, the protecting groups at C11 at C12 can be removed to yield the natural product. The enone-to-halichondrin transformation can be carried out with several combinations of the protecting groups for the hydroxyl groups, including, for example, C35-TES (triethylsilyl), C41-MPM (4-methyoxybenzyl), C48-TES, C51-TES, C53-TBS (tert-butyl dimethylsilyl), and C54-TBS in the halichondrin-B series; C35-TES, C41-MPM, C48-TES, and C50-TES in the norhalichondrin-B series. In FIG. 28, X is an oxygen protecting group.

Figure 29:
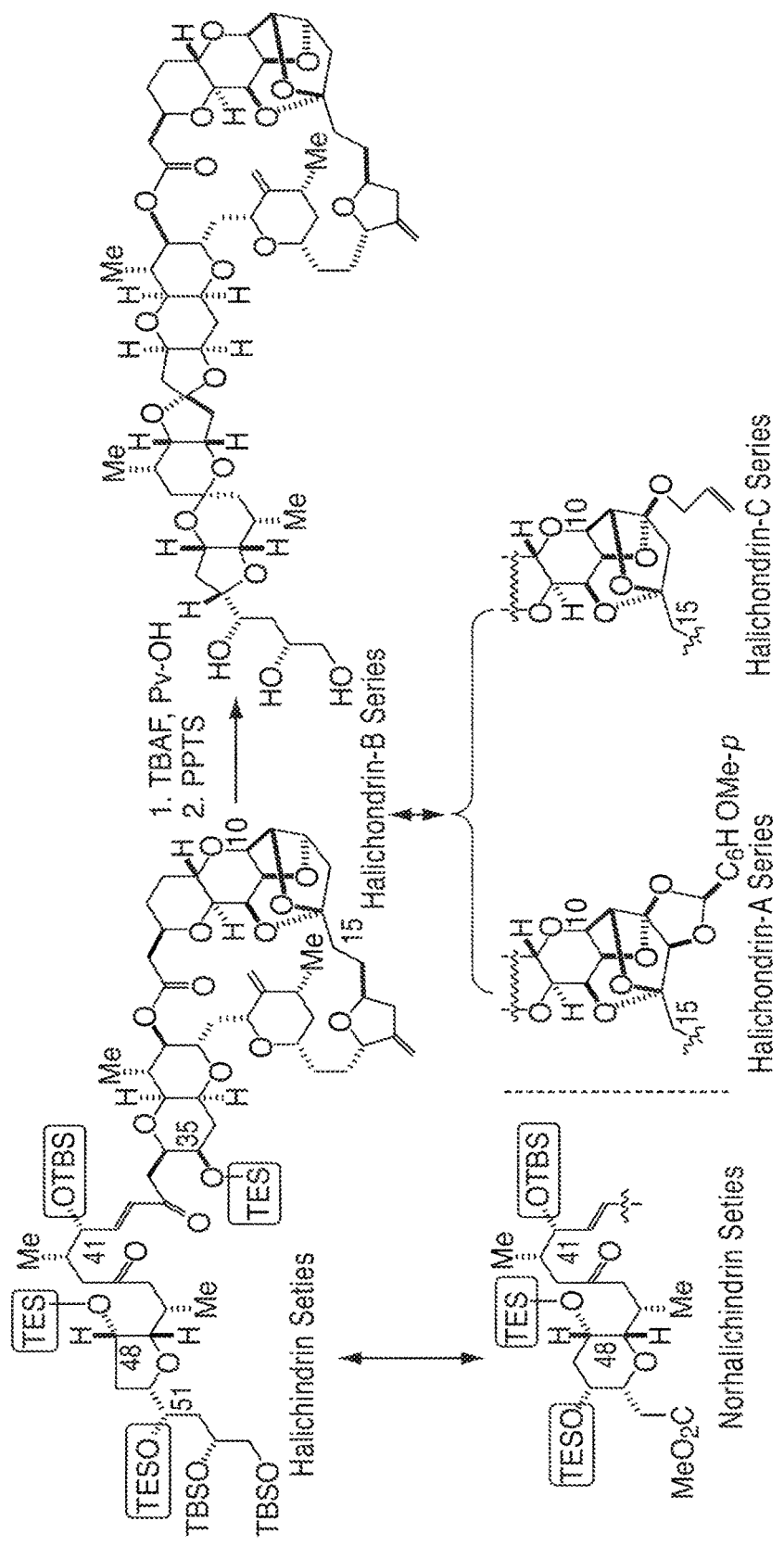

FIG. 29 shows an improved protecting group strategy for the enone-to-halichondrin transformation and enone-to-norhalichondrin transformations in FIG. 28. Use of a TES-protecting group for the C35- and C48-hydroxyl groups allows the use of a TBS-protecting group for the C41-hydroxyl group. With this change, the enone-to-halichondrin transformation can be completed in two steps, instead of four steps. Improved combinations of protecting groups for this synthetic sequence include: C35-TES, C41-TBS, C48-TES, C51-TES, C53-TBS, and C54-TBS in the halichondrin-B series; C35-TES, C41-TBS, C48-TES, and C50-TES in the norhalichondrin-B series. This combination of protecting groups can be used to prepare halichondrins A-C as well as norhalichondrins A-C.

Figure 30:
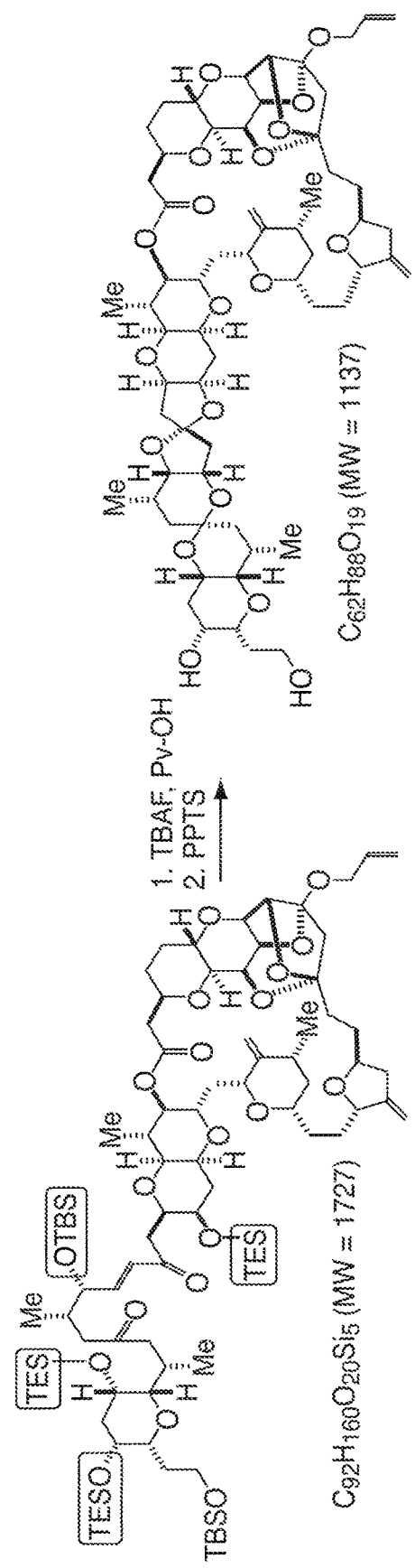

FIG. 30 shows how the two-step enone-to-halichondrin transformation can be applied to the synthesis of the norhalichondrin series (e.g., norhalicondrin C as shown).

DEFINITIONS

Chemical Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —CHF2, —CH2F, —$CF_3$, —CH2CF3, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C2 alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C═C double bond for which the stereochemistry is unspecified (e.g., —CH═CHCH$_3$ or 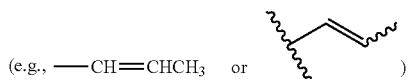 )

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C3), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl").

In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C4), cyclobutenyl (C$_4$), cyclopentyl (C$_5$), cyclopentenyl (C$_5$), cyclohexyl (C$_6$), cyclohexenyl (C$_6$), cyclohexadienyl (C6), and the like. Exemplary C$_3$-s carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C8), and the like. Exemplary C$_{3-10}$ carbocyclyl groups include, without limitation, the aforementioned C$_{3-8}$ carbocyclyl groups as well as cyclononyl (C9), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-14}$ cycloalkyl. In certain embodiments, the cycloalkyl group is a substituted C$_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$Pz(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3^+$X$^-$, —P(OR$^{cc}$)$_3^+$X$^-$, —P(R$^{cc}$)$_4$, —P(OR$^{cc}$)$_4$, —OP(R$^{cc}$)$_2$, —OP(R$^{cc}$)$_3^+$X$^-$, —OP(OR$^{cc}$)$_2$, —OP(OR$^{cc}$)$_3^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{aa}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$groups, or two geminal R$^{dd}$ substituents can be joined to form =O or =S; wherein X$^-$ is a counterion;

each instance of R$^{ff}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(=NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$X$^-$, wherein $R^{bb}$ and X$^-$ are as defined herein.

The term "sulfonyl" refers to a group selected from —SO$_2$N($R^{bb}$)$_2$, —SO$_2$R$^{aa}$, and —SO$_2$OR$^{aa}$, wherein $R^{aa}$ and $R^{bb}$ are as defined herein.

The term "sulfinyl" refers to the group —S(=O)R$^{aa}$, wherein $R^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{bb}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein $R^{aa}$ and $R^{bb}$ are as defined herein.

The term "silyl" refers to the group —Si(R$^{aa}$)$_3$, wherein $R^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$Re, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{aa}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{aa}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{aa}$)$_2$, —P(R$^{cc}$)$_3$$^+$X$^-$, —P(OR$^{aa}$)$_2$, —P(OR$^{aa}$)$_3$$^+$X$^-$, —P(=O)(R$^{aa}$)$_2$, —P(=O)(OR$^{aa}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —$C^AH(C^BH_2{}^CCH_3)$— includes one chain atom $C^A$, one hydrogen atom on $C^A$, and non-chain substituent —$(C^BH_2{}^CCH_3)$. The term "$C_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —$CH(C_2H_5)$— is a $C_1$ hydrocarbon chain, and

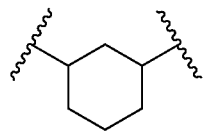 [SMILES: *C1CCCC(*)C1]

is a $C_3$ hydrocarbon chain. When a range of values is used, the meaning of the range is as described herein. For example, a $C_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —$(CH_2)_4$—). A hydrocarbon chain may also be unsaturated and include one or more C=C and/or C≡C bonds anywhere in the hydrocarbon chain. For instance, —CH=CH—$(CH_2)_2$—, —$CH_2$—C≡C—$CH_2$-, and —C≡C—CH=CH— are all examples of a unsubstituted and unsaturated hydrocarbon chain. In certain embodiments, the hydrocarbon chain is unsubstituted (e.g., —C≡C— or —$(CH_2)_4$—). In certain embodiments, the hydrocarbon chain is substituted (e.g., —$CH(C_2H_5)$— and —$CF_2$—). Any two substituents on the hydrocarbon chain may be joined to form an optionally substituted carbocyclyl, optionally substituted heterocyclyl, optionally substituted aryl, or optionally substituted heteroaryl ring. For instance,

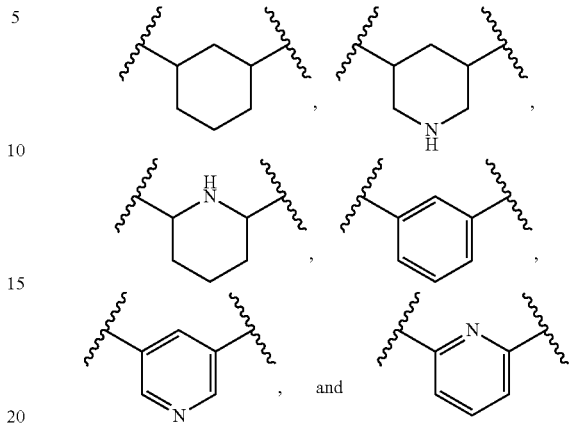

are all examples of a hydrocarbon chain. In contrast, in certain embodiments,

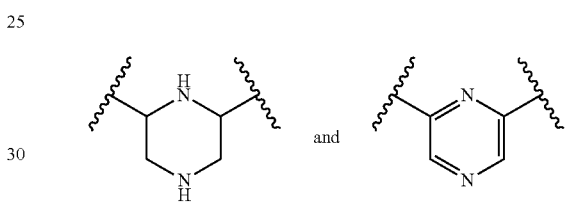

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

is a $C_3$ hydrocarbon chain wherein one chain atom is replaced with an oxygen atom.

The term "acyl" refers a group wherein the carbon directly attached to the parent molecule is $sp^2$ hybridized, and is substituted with an oxygen, nitrogen, or sulfur atom, e.g., a group selected from ketones (—$C(=O)R^{aa}$), carboxylic acids (—$CO_2H$), aldehydes (—CHO), esters (—$CO_2R^{aa}$, —$C(=O)SR^{aa}$, —$C(=S)SR^{aa}$), amides (—$C(=O)N(R^{bb})_2$, —$C(=O)NR^{bb}SO_2R^{aa}$, —$C(=S)N(R^{bb})_2$), and imines (—$C(=NR^{bb})R^{aa}$, —$C(=NR^{bb})OR^{aa}$, $C(=NR^{bb})N(R^{bb})_2$), wherein $R^{aa}$ and $R^{bb}$ are as defined herein.

The term "Lewis acid" refers to a species as defined by IUPAC, that is "a molecular entity (and the corresponding chemical species) that is an electron-pair acceptor and therefore able to react with a Lewis base to form a Lewis adduct, by sharing the electron pair furnished by the Lewis base." Exemplary Lewis acids include, without limitation, boron trifluoride, aluminum trichloride, tin tetrachloride, titanium tetrachloride, and iron tribromide.

The term "Brønsted acid" refers to a protic or proton-donating species. Exemplary Brønsted acids include, without limitation, acetic acid, triflic acid, hydrochloric acid, and barbituric acid.

The term "salt" refers to those salts which are derived from suitable inorganic and organic acids and bases. Examples of acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other exemplary salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5\ H_2O$)), and polyhydrates (x is a number greater than 1, e.g., dihydrates ($R.2\ H_2O$) and hexahydrates ($R.6\ H_2O$)).

The term "tautomers" or "tautomeric" refers to two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F-, Cl-, Br-, I—), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March Advanced Organic Chemistry 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

DETAILED DESCRIPTION OF CERTAIN EMBODIMENTS OF THE INVENTION

Cr-mediated couplings of organic halides/triflates with aldehydes are valuable tools to generate compounds with multi-functional groups. Cr-mediated couplings are used in synthesis of complicated macrolides such as halichondrin A and B. Depending on the mode of activation, Cr-mediated couplings are divided into three sub-groups: (1) Ni/Cr-mediated alkenylation, alkynylation, and arylation, (2) Co or Fe/Cr-mediated alkylation, 2-haloallylation and (propargylation), and (3) Cr-mediated allylation and propargylation (see, e.g., Saccomano, N. A. in *Comprehensive Organic Synthesis*; Trost, B. M., Fleming, I., Eds.; Pergamon: Oxford, 1991; Vol. 1, p 173).

This Cr-mediated coupling process is a Grignard-type carbonyl addition reaction. It displays selectivity towards aldehydes over other carbonyl compounds. Activation of halides or triflates in the presence of aldehydes provides not only an experimental convenience, but also an opportunity to achieve chemical transformations in an unconventional manner, e.g., cyclization. The most valuable feature of this coupling is its compatibility with a wide range of functional groups. This unique potential is especially important when applied to polyfunctional molecules, especially in the late-stages of a multi-step synthesis. Provided herein are chromium-mediated coupling reactions which are applicable to the preparation of halichondrins (e.g., halichondrin A, B, C; norhalichondrin A, B, C; homohalichondrin A, B, C; eribulin) and intermediates in the synthesis thereof.

In one aspect, the present invention provides a method of preparing a compound of Formula (I):

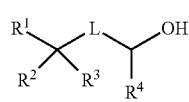

(I)

or a salt thereof,
the method comprising coupling a compound of Formula (i):

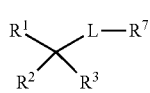

(i)

or a salt thereof,
with an aldehyde of Formula (ii):

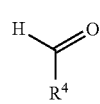

(ii)

in the presence of a chromium catalyst and optionally one or more catalysts;
wherein
$R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl;
$R^2$ is $-OR^5$;
$R^5$ is optionally substituted alkyl, or an oxygen protecting group;
$R^3$ is $-OR^6$;
$R^6$ is optionally substituted alkyl, or an oxygen protecting group;
or $R^2$ and $R^3$ are taken together to form =O;
or $R^5$ and $R^6$ are taken together with the intervening atoms to form an optionally substituted heterocyclic ring;
$R^4$ is optionally substituted alkyl, optionally substituted alkenyl, optionally substituted alkynyl, optionally substituted carbocyclyl, optionally substituted heterocyclyl, optionally substituted aryl, or optionally substituted heteroaryl;
$R^7$ is halogen; and
L is optionally substituted ethenylene or ethynylene.

Since a hydroxyl group is generated in the coupling product of Formula (I), a chiral center can be introduced in the process. In some embodiments, the provided coupling method is a catalytic asymmetric coupling between a compound of Formula (i) and an aldehyde of Formula (ii) to provide a compound of Formula (I$^a$):

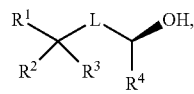

or a salt thereof. In some embodiments, the provided coupling method is a catalytic asymmetric coupling between a compound of Formula (i) and an aldehyde of Formula (ii) to provide a compound of Formula (I$^a$):

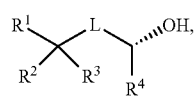

or a salt thereof.

In certain embodiments, the provided coupling reaction between the compound of Formula (i) and the aldehyde of Formula (ii) is selective for halo-enone, halo-enone ketal, halo-acetylenic ketone, or halo-acetylenic ketal, over a halide attached to a sp$^3$ hybridized carbon. A vinyl halide or a halide attached to a sp$^3$ hybridized carbon can remain intact during the coupling reaction between a halo-enone, halo-enone ketal, halo-acetylenic enone, or halo-acetylenic ketal, with an aldehyde of Formula (ii). The vinyl halide moiety can be a portion of the compound of Formula (i), the aldehyde of Formula (ii), or another compound in the coupling reaction mixture. In certain embodiments, the provided coupling reaction between the compound of Formula (i) and the aldehyde of Formula (ii) is selective for the halo-enone or halo-acetylenic ketal over a halide attached to a sp$^3$ hybridized carbon. In certain embodiments, the halide attached to a sp$^3$ hybridized carbon is chloride. In certain embodiments, the halide attached to a sp$^3$ hybridized carbon is bromide. In certain embodiments, the halide attached to a sp$^3$ hybridized carbon is iodide. In certain embodiments, the compound of Formula (i) comprises a halide attached to a sp³ hybridized carbon, for example, in $R^1$. In certain embodiments, the step of coupling is performed in the presence of another compound other than the compounds of Formulae (i) and (ii), wherein the another compound comprises a halide attached to a sp3 hybridized carbon.

In certain embodiments, the provided coupling reaction between the compound of Formula (i) and the aldehyde of Formula (ii) is selective for halo-enone, halo-enone ketal, halo-acetylenic ketone, or halo-acetylenic ketal over a vinyl halide. In certain embodiments, the provided coupling reaction between the compound of Formula (i) and the aldehyde of Formula (ii) is selective for the halo-enone or halo-acetylenic ketal over a vinyl halide. In certain embodiments, the compound of Formula (i) comprises a vinyl halide moiety, for example, as part of $R^1$. In certain embodiments, the step of coupling is performed in the presence of another compound other than the compounds of Formulae (i) and (ii), wherein the other compound includes a vinyl halide moiety. In certain embodiments, the vinyl halide moiety is a vinyl iodide moiety. In certain embodiments, the vinyl halide is a vinyl bromide moiety. In certain embodiments, the vinyl halide is a vinyl chloride moiety. In certain embodiments, the vinyl halide moiety is a vinyl iodide moiety in the compound of Formula (i). In certain embodiments, the vinyl halide is a vinyl bromide moiety in the compound of Formula (i). In certain embodiments, the vinyl halide is a vinyl chloride moiety in the compound of Formula (i). In certain embodiments, the vinyl halide moiety is a vinyl iodide moiety in $R^1$ of the compound of Formula (i). In certain embodiments, the vinyl halide is a vinyl bromide moiety in $R^1$ of the compound of Formula (i). In certain embodiments, the vinyl halide is a vinyl chloride moiety in $R^1$ of the compound of Formula (i). In certain embodiments, the vinyl halide moiety is a vinyl iodide moiety in the aldehyde of Formula (ii). In certain embodiments, the vinyl halide is a vinyl bromide moiety in the aldehyde of Formula (ii). In certain embodiments, the vinyl halide is a vinyl chloride moiety in the aldehyde of Formula (ii). In certain embodiments, the vinyl halide moiety is a vinyl iodide moiety in another compound other than the compounds of Formulae (i) and (ii) in the coupling reaction mixture. In certain embodiments, the vinyl halide is a vinyl bromide moiety in another compound other than the compounds of Formulae (i) and (ii) in the coupling reaction mixture. In certain embodiments, the vinyl halide is a vinyl chloride moiety in another compound other than the compounds of Formulae (i) and (ii) in the coupling reaction mixture.

As generally defined herein, $R^1$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^1$ is optionally substituted alkyl. In certain embodiments, $R^1$ is unsubstituted alkyl. In certain embodiments, $R^1$ is methyl or ethyl. In certain embodiments, $R^1$ is n-$C_7H_{15}$. In certain embodiments, $R^1$ is substituted alkyl. In certain embodiments, $R^1$ is optionally substituted alkoxyalkyl. In certain embodiments, $R^1$ is optionally substituted alkenylalkyl. In certain embodiments, $R^1$ is unsubstituted alkenylalkyl. In certain embodiments, $R^1$ is substituted alkenylalkyl. In certain embodiments, $R^1$ is optionally substituted arylalkyl. In certain embodiments, $R^1$ is optionally substituted phenylalkyl. In certain embodiments, $R^1$ is unsubstituted phenylalkyl. In certain embodiments, $R^1$ is substituted phenylalkyl. In certain embodiments, $R^1$ is iodo-phenylalkyl. In certain embodiments, $R^1$ is p-iodo-phenylalkyl. In certain embodiments, $R^1$ is m-iodo-phenylalkyl. In certain embodiments, $R^1$ is o-iodo-phenylalkyl.

In certain embodiments, $R^1$ comprises a halide attached to a sp³ hybridized carbon. In certain embodiments, $R^1$ comprises a chloride attached to a sp³ hybridized carbon. In certain embodiments, $R^1$ comprises a bromide attached to a sp³ hybridized carbon. In certain embodiments, $R^1$ comprises an iodide attached to a sp³ hybridized carbon.

In certain embodiments, $R^1$ comprises a vinyl halide moiety. In certain embodiments, $R^1$ comprises a vinyl iodide moiety. In certain embodiments, $R^1$ comprises a vinyl bromide moiety. In certain embodiments, $R^1$ comprises a vinyl chloride moiety.

As generally used herein, a vinyl halide is a compound of Formula (VY):

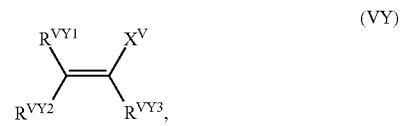

or a salt thereof,
wherein
each of $R^{VY1}$, $R^{VY2}$, and $R^{VY3}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and
$X^V$ is halogen.

As generally used herein, a vinyl halide is a vinyl iodide of Formula (VY-1):

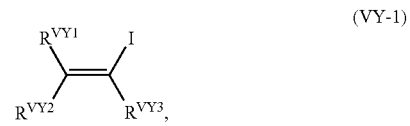

or a salt thereof, wherein $R^{VY1}$, $R^{VY2}$, and $R^{VY3}$ are as defined herein.

In certain embodiments, $R^1$ comprises a vinyl halide moiety and is of Formula (F-1):

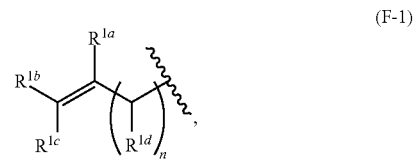

wherein
each of $R^{1a}$, $R^{1b}$, and $R^{1c}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each instance of $R^{1d}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and n is an integer between 1 to 10, inclusive.

As generally defined herein, $R^{1a}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{1a}$ is hydrogen. In certain embodiments, $R^{1a}$ is halogen. In certain embodiments, $R^{1a}$ is iodide. In certain embodiments, $R^{1a}$ is bromide. In certain embodiments, $R^{1a}$ is chloride. In certain embodiments, $R^{1a}$ is optionally substituted alkyl. In certain embodiments, $R^{1a}$ is unsubstituted alkyl. In certain embodiments, $R^{1a}$ is methyl or ethyl. In certain embodiments, $R^{1a}$ is substituted alkyl.

As generally defined herein, $R^{1b}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{1b}$ is hydrogen. In certain embodiments, $R^{1b}$ is halogen. In certain embodiments, $R^{1b}$ is iodide. In certain embodiments, $R^{1b}$ is bromide. In certain embodiments, $R^{1b}$ is chloride. In certain embodiments, $R^{1b}$ is optionally substituted alkyl. In certain embodiments, $R^{1b}$ is unsubstituted alkyl. In certain embodiments, $R^{1b}$ is methyl or ethyl. In certain embodiments, $R^{1b}$ is substituted alkyl.

As generally defined herein, $R^{1c}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{1c}$ is hydrogen. In certain embodiments, $R^{1c}$ is halogen. In certain embodiments, $R^{1c}$ is iodide. In certain embodiments, $R^{1c}$ is bromide. In certain embodiments, $R^{1c}$ is chloride. In certain embodiments, $R^{1c}$ is optionally substituted alkyl. In certain embodiments, $R^{1c}$ is unsubstituted alkyl. In certain embodiments, $R^{1c}$ is methyl or ethyl. In certain embodiments, $R^{1c}$ is substituted alkyl.

In certain embodiments, $R^{1a}$ is halogen; and $R^{1b}$ and $R^{1c}$ are hydrogen. In certain embodiments, $R^{1a}$ is iodide; and $R^{1b}$ and $R^{1c}$ are hydrogen. In certain embodiments, $R^{1a}$ is bromide; and $R^{1b}$ and $R^{1c}$ are hydrogen.

As generally defined herein, each instance of $R^{1d}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, at least one instance of $R^{1d}$ is hydrogen. In certain embodiments, each instance of $R^{1d}$ is hydrogen. In certain embodiments, at least one instance of $R^{1d}$ is halogen. In certain embodiments, at least one instance of $R^{1d}$ is iodide. In certain embodiments, at least one instance of $R^{1d}$ is bromide. In certain embodiments, at least one instance of $R^{1d}$ is chloride. In certain embodiments, at least one instance of $R^{1d}$ is optionally substituted alkyl. In certain embodiments, at least one instance of $R^{1d}$ is unsubstituted alkyl. In certain embodiments, at least one instance of $R^{1d}$ is methyl or ethyl. In certain embodiments, at least one instance of $R^{1d}$ is substituted alkyl.

In certain embodiments, n is 1. In certain embodiments, n is 2. In certain embodiments, n is 3. In certain embodiments, n is 4. In certain embodiments, n is 5. In certain embodiments, n is 6.

In certain embodiments, n is 4, and at least one instance of $R^{1d}$ is halogen. In certain embodiments, n is 4, and one instance of $R^{1d}$ is halogen. In certain embodiments, n is 4, and one instance of $R^{1d}$ is chloride.

As generally defined herein, $R^2$ is —$OR^5$, wherein $R^5$ is optionally substituted alkyl or an oxygen protecting group. In certain embodiments, $R^5$ is optionally substituted alkyl. In certain embodiments, $R^5$ is unsubstituted alkyl (e.g. methyl or ethyl). In certain embodiments, $R^5$ is substituted alkyl. In certain embodiments, $R^5$ is an oxygen protecting group.

As generally defined herein, $R^3$ is —$OR^6$, wherein $R^6$ is optionally substituted alkyl or an oxygen protecting group. In certain embodiments, $R^6$ is optionally substituted alkyl. In certain embodiments, $R^6$ is unsubstituted alkyl (e.g. methyl or ethyl). In certain embodiments, $R^6$ is substituted alkyl. In certain embodiments, $R^6$ is an oxygen protecting group.

In certain embodiments, $R^2$ and $R^3$ are taken together to form =O. In certain embodiments, the compound of Formula (I) is of one of the formulae:

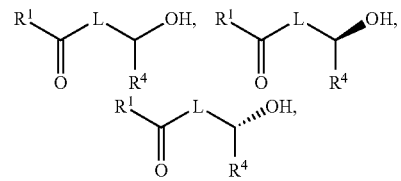

or a salt thereof; and the compound of Formula (i) is of the formula:

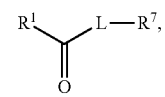

or a salt thereof.

In certain embodiments, $R^2$ is —$OR^5$; $R^3$ is —$OR^6$; and $R^5$ and $R^6$ are each independently oxygen protecting groups. In certain embodiments, the compound of Formula (I) is of the formula:

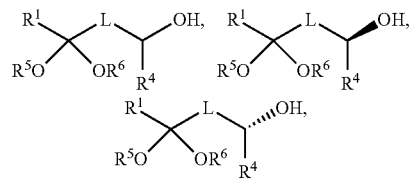

or a salt thereof; and the compound of Formula (i) is of the formula:

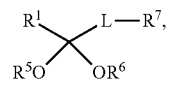

or a salt thereof.

As generally defined herein, $R^4$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^4$ is optionally substituted alkyl. In certain embodiments, $R^4$ is unsubstituted alkyl. In certain embodiments, $R^4$ is methyl or ethyl. In certain embodiments, $R^4$ is substituted alkyl. In certain embodiments, $R^4$ is optionally substituted alkoxylalkyl. In certain embodiments, $R^4$ is optionally substituted alkenylalkyl. In certain embodiments, $R^4$ is unsubstituted alkenylalkyl. In certain embodiments, $R^4$ is substituted alkenylalkyl. In certain embodiments, $R^4$ is optionally substituted arylalkyl. In certain embodiments, $R^4$ is optionally substituted phenylalkyl. In certain embodiments, $R^4$ is unsubstituted phenylalkyl. In certain embodiments, $R^4$ is substituted phenylalkyl. In certain embodiments, $R^4$ is optionally substituted heteroarylalkyl. In certain embodiments, $R^4$ is optionally substituted heterocyclylalkyl. In certain embodiments, $R^4$ is optionally substituted carbocyclylalkyl. In certain embodiments, $R^4$ is optionally substituted carbocyclyl. In certain embodiments, $R^4$ is optionally substituted heterocyclyl. In certain embodiments, $R^4$ is optionally substituted aryl. In certain embodiments, $R^4$ is optionally substituted phenyl. In certain embodiments, $R^4$ is optionally substituted heteroaryl. In certain embodiments, $R^4$ is optionally substituted furanyl, thiophenyl, or pyrrolyl.

As generally defined herein, L is optionally substituted ethenylene or ethynylene. In certain embodiments, L is optionally substituted ethenylene. In certain embodiments, L is unsubstituted ethenylene. In certain embodiments, L is substituted ethenylene. In certain embodiments, L is optionally substituted trans-ethenylene. In certain embodiments, L is unsubstituted trans-ethenylene. In certain embodiments, L is substituted trans-ethenylene. In certain embodiments, L is optionally substituted cis-ethenylene. In certain embodiments, L is unsubstituted cis-ethenylene. In certain embodiments, L is substituted cis-ethenylene. In certain embodiments, L is ethynylene.

L being Optionally Substituted Ethenylene

In certain embodiments of the provided coupling method between a compound of Formula (i) and the aldehyde of Formula (ii), the compound of Formula (i) is of Formula (i-a):

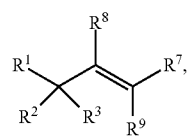

(i-a)

or a salt thereof, wherein $R^1$, $R^2$, $R^3$, and $R^7$ are as defined herein, and each of $R^8$ and $R^9$ is independently hydrogen or optionally substituted alkyl.

In certain embodiments of the provided coupling method between a compound of Formula (i) and the aldehyde of Formula (ii), the compound of Formula (i) is of Formula (i-a):

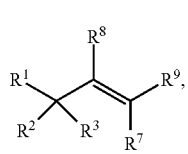

(i-a')

or a salt thereof, wherein $R^1$, $R^2$, $R^3$, and $R^7$ are as defined herein, and each of $R^8$ and $R^9$ is independently hydrogen or optionally substituted alkyl.

In certain embodiments, $R^8$ is hydrogen. In certain embodiments, $R^8$ is optionally substituted alkyl. In certain embodiments, $R^8$ is unsubstituted alkyl. In certain embodiments, $R^8$ is methyl or ethyl. In certain embodiments, $R^8$ is substituted alkyl.

In certain embodiments, $R^9$ is hydrogen. In certain embodiments, $R^9$ is optionally substituted alkyl. In certain embodiments, $R^9$ is unsubstituted alkyl. In certain embodiments, $R^9$ is methyl or ethyl. In certain embodiments, $R^9$ is substituted alkyl.

In certain embodiments, the coupling step is between a compound of Formula (i-a) and an aldehyde of Formula (ii) to yield a compound of one of the following formulae:

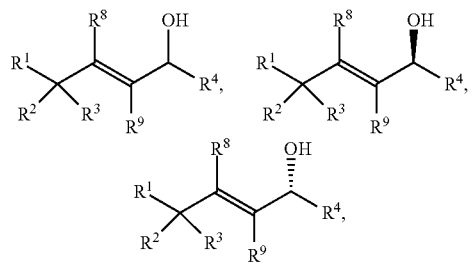

and salts thereof. In certain embodiments, the compound of Formula (I) is of Formula (I-a):

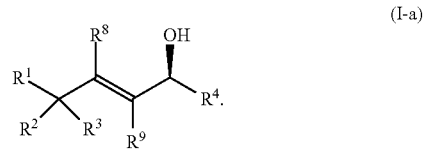

(I-a)

In certain embodiments, the compound of Formula (I) is of Formula (I-a-2):

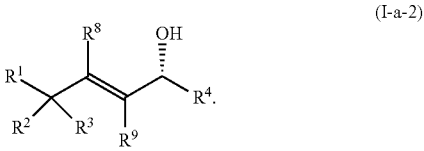

(I-a-2)

In certain embodiments, the coupling step is between a compound of Formula (i-a') and an aldehyde of Formula (ii) to yield a compound of one of the following formulae:

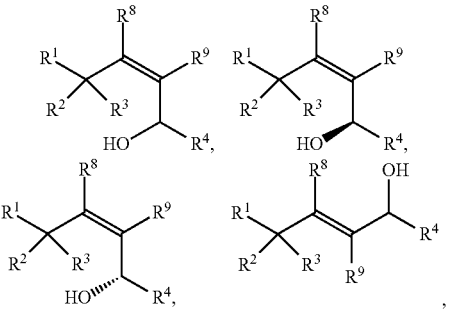

-continued

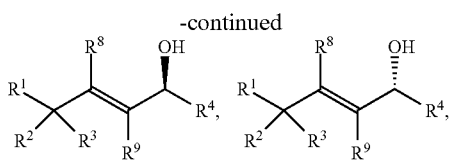

and salts thereof. In certain embodiments, the coupling step is between a compound of Formula (i-a') and an aldehyde of Formula (ii) to yield a compound of one of the following formulae:

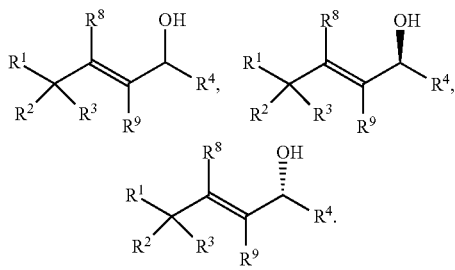

In certain embodiments, the compound of Formula (i) is of Formula (i-a-1):

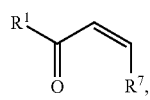

(i-a-1')

or a salt thereof; and the compound of Formula (I) is of Formula (I-a-1):

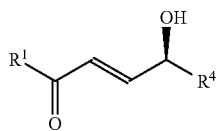

(I-a-1)

or a salt thereof; wherein $R^1$, $R^7$, and $R^4$ are as defined herein.

In some embodiments, the coupling product of Formulae (I)-(I-a-1) are stable enough to isolate and characterize. In some embodiments, the coupling product of Formula (I)-(I-a-1) cyclizes to form an optionally substituted furan of Formula (FU-1):

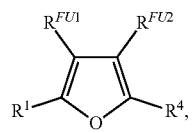

(FU-1)

or a salt thereof,
wherein $R^1$ and $R^4$ are as defined herein; and
each of $R^{FU1}$ and $R^{FU2}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, the step of cyclizing occurs in situ (i.e. in the reaction mixture without isolation). In certain embodiments, the step of cyclizing occurs upon addition of an acid. In certain embodiments, the acid is a Lewis acid. In certain embodiments, the acid is a Brønsted acid. In certain embodiments, the acid is one or more selected from the group consisting of p-toluenesulfonic acid (PTSA), p-toluenesulfonic acid (p-TSA), or camphorsulfonic acid (CSA), pyridinium p-toluenesulfonate (PPTS), or sulfonic acid exchange resin (Amberlyst, Dowex). In certain embodiments, the acid is p-toluenesulfonic acid (p-TSA) or camphorsulfonic acid (CSA).

In certain embodiments, the provided coupling method is applied to synthesis of the C1-C19 building block of halichondrins and analogs thereof. In certain embodiments, the provided coupling method is applied to the synthesis of the C1-C19 building block of halichondrin B.

In certain embodiments, the compound of Formula (i-a-1) is of Formula (i-a-3):

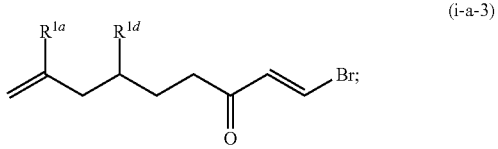

(i-a-3)

or a salt thereof; the aldehyde of Formula (ii) is of Formula (ii-a):

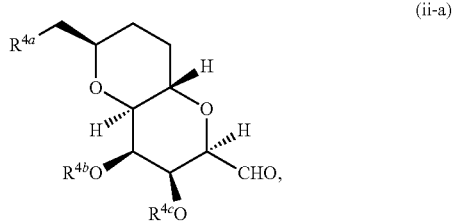

(ii-a)

or a salt thereof; and the compound of Formula (I) is of Formula (I-a-3):

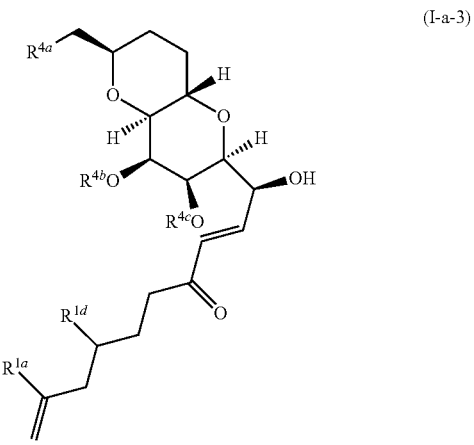

(I-a-3)

or a salt thereof, wherein $R^{1a}$ and $R^{1d}$ are as defined herein, $R^{4a}$ is $-CO_2R^{4d}$, wherein $R^{4d}$ is hydrogen, optionally substituted alkyl, or an oxygen protecting group; and $R^{4b}$ and $R^{4c}$ are each independently substituted or unsubstituted alkyl, or an oxygen protecting group; or $R^{4b}$ and $R^{4c}$ are taken with the intervening oxygen atoms to form an optionally substituted heterocyclic ring.

As generally defined herein, $R^{4a}$ is $-CO_2R^{4d}$, wherein $R^{4d}$ is hydrogen, optionally substituted alkyl, or an oxygen protecting group. In certain embodiments, $R^{4d}$ is hydrogen. In certain embodiments, $R^{4d}$ is optionally substituted alkyl. In certain embodiments, $R^{4d}$ is unsubstituted alkyl. In certain embodiments, $R^{4d}$ is methyl or ethyl. In certain embodiments, $R^{4d}$ is substituted alkyl. In certain embodiments, $R^{4d}$ is an oxygen protecting group.

In certain embodiments, $R^{4b}$ is optionally substituted alkyl. In certain embodiments, $R^{4b}$ is unsubstituted alkyl. In certain embodiments, $R^{4b}$ is methyl or ethyl. In certain embodiments, $R^{4b}$ is an oxygen protecting group. In certain embodiments, $R^{4b}$ is a silyl protecting group. In certain embodiments, $R^{4b}$ is a trialkyl silyl protecting group. In certain embodiments, $R^{4b}$ is a t-butyldimethylsilyl protecting group. In certain embodiments, $R^{4b}$ is a trimethylsilyl protecting group. In certain embodiments, $R^{4b}$ is a triethylsilyl protecting group. In certain embodiments, $R^{4b}$ is a t-butyldiphenylsilyl protecting group. In certain embodiments, $R^{4b}$ is a triisopropylsilyl protecting group. In certain embodiments, $R^{4b}$ is a benzylic protecting group. In certain embodiments, $R^{4b}$ is a p-methoxybenzyl protecting group. In certain embodiments, $R^{4b}$ is an acyl protecting group. In certain embodiments, $R^{4b}$ is an acetyl protecting group. In certain embodiments, $R^{4b}$ is a benzoyl protecting group. In certain embodiments, $R^{4b}$ is a p-nitro benzoyl protecting group. In certain embodiments, $R^{4b}$ is a pivaloyl protecting group. In certain embodiments, $R^{4b}$ is a t-butyl carbonate (BOC) protecting group. In certain embodiments, $R^{4b}$ is an acetal protecting group. In certain embodiments, $R^{4b}$ is a tetrahydropyranyl protecting group. In certain embodiments, $R^{4b}$ is an alkoxyalkyl protecting group. In certain embodiments, $R^{4b}$ is an ethoxyethyl protecting group.

In certain embodiments, $R^{4c}$ is optionally substituted alkyl. In certain embodiments, $R^{4c}$ is unsubstituted alkyl. In certain embodiments, $R^{4c}$ is methyl or ethyl. In certain embodiments, $R^{4c}$ is an oxygen protecting group. In certain embodiments, $R^{4c}$ is a silyl protecting group. In certain embodiments, $R^{4c}$ is a trialkyl silyl protecting group. In certain embodiments, $R^{4c}$ is a t-butyldimethylsilyl (TBS) protecting group. In certain embodiments, $R^{4c}$ is a trimethylsilyl protecting group. In certain embodiments, $R^{4c}$ is a triethylsilyl protecting group. In certain embodiments, $R^{4c}$ is a t-butyldiphenylsilyl protecting group. In certain embodiments, $R^{4c}$ is a triisopropylsilyl protecting group. In certain embodiments, $R^{4c}$ is a benzylic protecting group. In certain embodiments, $R^{4c}$ is a p-methoxybenzyl protecting group. In certain embodiments, $R^{4c}$ is an acyl protecting group. In certain embodiments, $R^{4c}$ is an acetyl protecting group. In certain embodiments, $R^{4c}$ is a benzoyl protecting group. In certain embodiments, $R^{4c}$ is a p-nitro benzoyl protecting group. In certain embodiments, $R^{4c}$ is a pivaloyl protecting group. In certain embodiments, $R^{4c}$ is a t-butyl carbonate (BOC) protecting group. In certain embodiments, $R^{4c}$ is an acetal protecting group. In certain embodiments, $R^{4c}$ is a tetrahydropyranyl protecting group. In certain embodiments, $R^{4c}$ is an alkoxyalkyl protecting group. In certain embodiments, $R^{4c}$ is an ethoxyethyl protecting group.

In certain embodiments, $R^{4b}$ and $R^{4c}$ are independently an oxygen protecting group. In certain embodiments, $R^{4b}$ and $R^{4c}$ are the same. In certain embodiments, $R^{4b}$ and $R^{4c}$ are different. In certain embodiments, $R^{4b}$ and $R^{4c}$ are independently a silyl protecting group. In certain embodiments, $R^{4b}$ and $R^{4c}$ are a t-butyldimethylsilyl protecting group.

In certain embodiments, $R^{4b}$ and $R^{4c}$ are taken with the intervening oxygen atoms to form an optionally substituted heterocyclic ring. In certain embodiments, $R^{4b}$ and $R^{4c}$ are taken with the intervening oxygen atoms to form an optionally substituted monocyclic heterocyclic ring. In certain embodiments, $R^{4b}$ and $R^{4c}$ are taken with the intervening oxygen atoms to form an optionally substituted bicyclic heterocyclic ring. In certain embodiments, $R^{4b}$ and $R^{4c}$ are taken with the intervening oxygen atoms to form an optionally substituted bicyclic heterocyclic ring of formula:

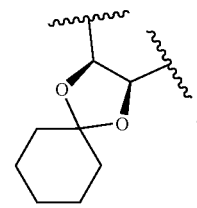

In certain embodiments, the compound of Formula (ii-a) is of Formula (ii-a-1):

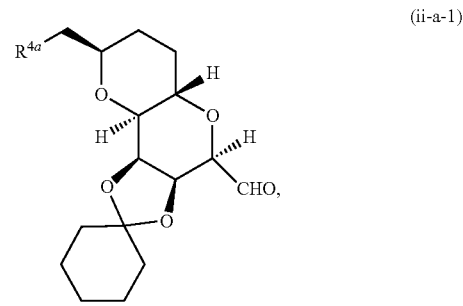

(ii-a-1)

or a salt thereof. In certain embodiments, the compound of Formula (I-a-3) is of the Formula (I-a-3-i):

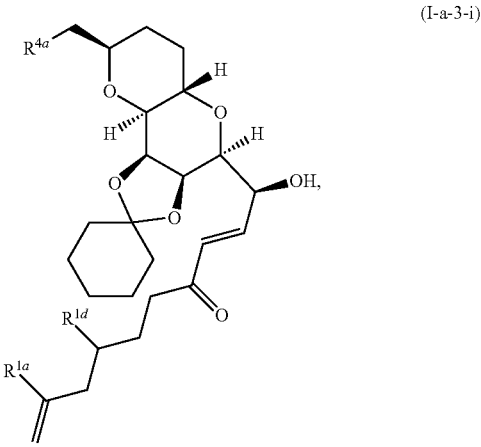

(I-a-3-i)

or a salt thereof.

In certain embodiments, the coupling reaction between the compounds of Formula (i-a-3) and Formula (ii-a) is achieved with high regioselectivity of the bromo-enone over $R^{1a}$ and high stereoselectivity with one or more chiral catalyst ligands (see the Catalystic Condition Section). The compounds of Formulae (I-a-3) and (I-a-3-i) provide an efficient synthesis of the C1-C19 building block of halichodrin B.

In one aspect, provided herein is a method of preparing a compound of Formula (I-a-4):

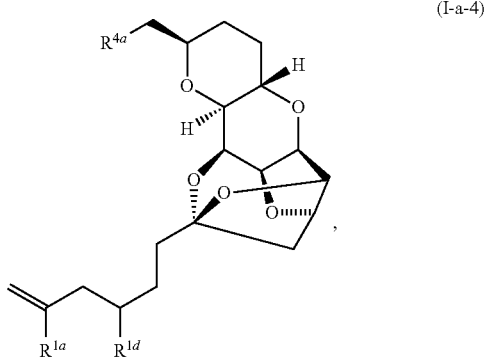

(I-a-4)

or a salt thereof, comprising cyclizing a compound of Formula (I-a-5):

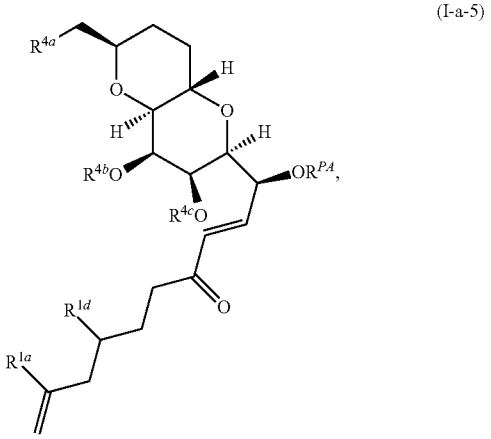

(I-a-5)

or a salt thereof, wherein $R^{1a}$, $R^{1d}$, $R^{4a}$, $R^{4b}$, and $R^{4c}$ are as defined herein; and $R^{PA}$ is optionally substituted alkyl or an oxygen protecting group.

In certain embodiments, the step of cyclizing comprises deprotecting the compound of Formula (I-a-5), i.e., converting $R^{4b}$ and $R^{4c}$ to hydrogen.

In certain embodiments, the steps of cyclizing further comprising equilibrating the deprotected compound of Formula (I-a-5) with one or more bases. The equilibrating step isomerizes the C12 chiral center (see FIG. 15). It is to be understood that any organic and inorgance base is applicable as long as the base does not interfere with any functional groups of the deprotected compound of Formula (I-a-5). In certain embodiments, the base is one or more organic or inorganic bases. In certain embodiments, the base is one organic or inorganic base. In certain embodiments, the base is sodium carbonate, 1,8-diazabicyclo[5.4.0]undec-7-ene (DBU), or tetramethylguanidine In certain embodiments, the base is a combination of two or more organic or inorganic bases. In certain embodiments, the bases are 1,8-diazabicyclo[5.4.0]undec-7-ene (DBU) and tetramethylguanidine.

In certain embodiments, the step of cyclizing further comprising contacting the equilibrating reaction mixture with an acid. In certain embodiments, the acid is a Lewis acid. In certain embodiments, the acid is a Brønsted acid. In certain embodiments, the acid is one or more selected from the group consisting of p-toluenesulfonic acid (PTSA), p-toluenesulfonic acid (p-TSA), camphorsulfonic acid (CSA), pyridinium p-toluenesulfonate (PPTS), and sulfonic acid exchange resin (Amberlyst, Dowex). In certain embodiments, the acid is pyridinium p-toluenesulfonate (PPTS).

In certain embodiments, the steps of cyclizing further comprises contacting the equilibration reaction mixture with one or more ion-exchange resins. In certain embodiments, the ion-exchange resins are polymer-bound guanidine and polymer-bound pyridinium p-toluenesulfonate (PPTS).

Figure 2:
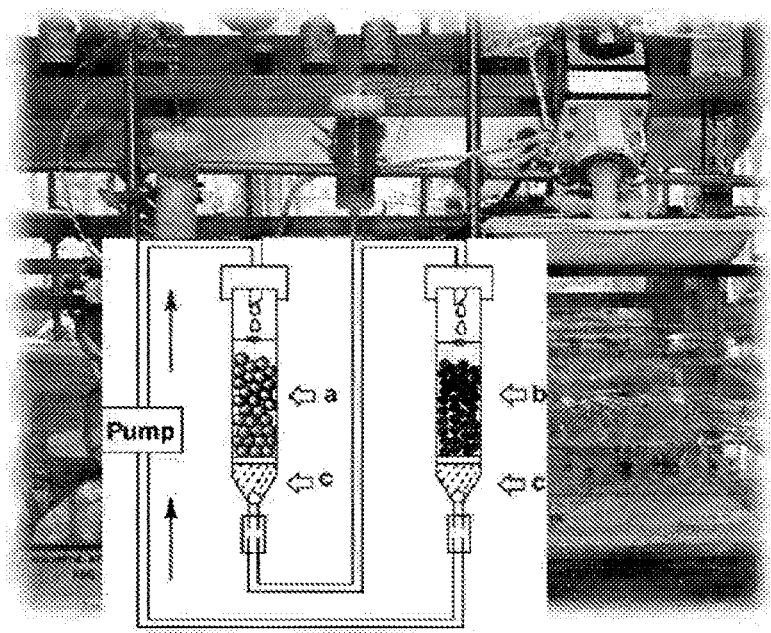
FIG. 2 shows an exemplary ion-exchange resin device consisting of a pump, reaction flask, and ion-exchange columns.
Figure 2:
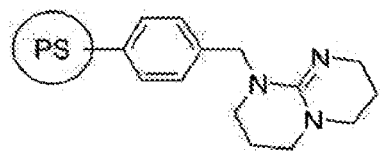
Figure 2:
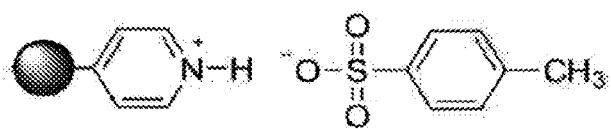

In certain embodiments, the step of cyclizing further comprising contacting the equilibrating reaction mixture with an acid in an ion-exchange resin device. In certain embodiments, the ion-exchange resin device comprises a first column with basic ion exchange resins and a second column with acidic ion exchange resins. In certain embodiments, the ion-exchange resin device comprises a first column with basic ion exchange resins and a dehydrating reagent (e.g., 4 Å molecular sieves); and a second column with acidic ion exchange resins and a dehydrating reagent (e.g., 4 Å molecular sieves). In certain embodiments, the ion-exchange resin device is as shown in FIG. 2.

In certain embodiments, the provided method of synthesizing the C1-C19 building block of halichodrin B further comprises the step of protecting a compound of Formula (I-a-3):

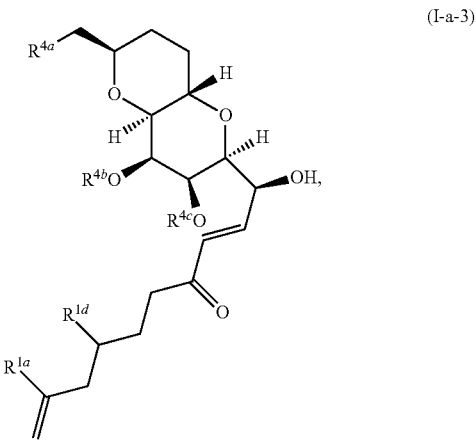

(I-a-3)

or a salt thereof, to yield a compound of Formula (I-a-5):

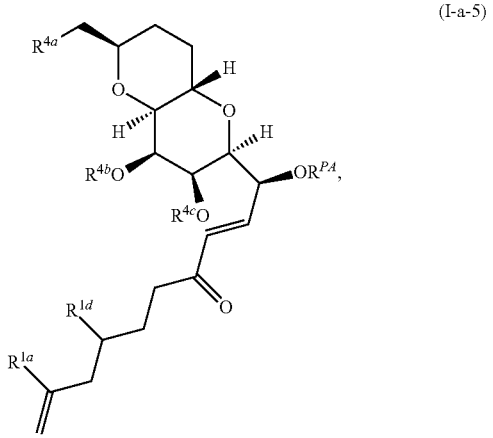

(I-a-5)

or a salt thereof, wherein $R^{1a}$, $R^{1d}$, $R^{4a}$, $R^{4b}$, $R^{4c}$, and $R^{P1}$ are as defined herein.

In certain embodiments, $R^{PA}$ is optionally substituted alkyl. In certain embodiments, $R^{PA}$ is unsubstituted alkyl. In certain embodiments, $R^{PA}$ is methyl or ethyl. In certain embodiments, $R^{PA}$ is an oxygen protecting group. In certain embodiments, $R^{PA}$ is a silyl protecting group. In certain embodiments, $R^{PA}$ is a trialkyl silyl protecting group. In certain embodiments, $R^{PA}$ is a t-butyldimethylsilyl (TBS) protecting group. In certain embodiments, $R^{PA}$ is a trimethylsilyl protecting group. In certain embodiments, $R^{PA}$ is a triethylsilyl protecting group. In certain embodiments, $R^{PA}$ is a t-butyldiphenylsilyl protecting group. In certain embodiments, $R^{PA}$ is a triisopropylsilyl protecting group. In certain embodiments, $R^{PA}$ is a benzylic protecting group. In certain embodiments, $R^{PA}$ is a p-methoxybenzyl protecting group. In certain embodiments, $R^{PA}$ is an acyl protecting group. In certain embodiments, $R^{PA}$ is an acetyl protecting group. In certain embodiments, $R^{PA}$ is a benzoyl protecting group. In certain embodiments, $R^{PA}$ is a p-nitro benzoyl protecting group. In certain embodiments, $R^{PA}$ is a pivaloyl protecting group. In certain embodiments, $R^{PA}$ is a t-butyl carbonate (BOC) protecting group. In certain embodiments, $R^{PA}$ is an acetal protecting group. In certain embodiments, $R^{PA}$ is a tetrahydropyranyl protecting group. In certain embodiments, $R^{PA}$ is an alkoxyalkyl protecting group. In certain embodiments, $R^{PA}$ is an ethoxyethyl protecting group.

In certain embodiments, $R^{4b}$ and $R^{4c}$ are independently a silyl protecting group; and $R^{PA}$ is an acyl protecting group. In certain embodiments, $R^{4b}$ and $R^{4c}$ are a t-butyldimethylsilyl protecting group; and $R^{PA}$ is an acyl protecting group. In certain embodiments, $R^{4b}$ and $R^{4c}$ are a t-butyldimethylsilyl protecting group; and $R^{PA}$ is an optionally substituted benzoylic protecting group. In certain embodiments, $R^{4b}$ and $R^{4c}$ are t-butyldimethylsilyl protecting groups; and $R^{PA}$ is an optionally substituted p-NO$_2$-benzoylic protecting group.

In certain embodiments, $R^{4b}$ and $R^{4c}$ are taken with the intervening oxygen atoms to form an optionally substituted heterocyclic ring and $R^{PA}$ is an acyl protecting group an acyl protecting group. In certain embodiments, $R^{4b}$ and $R^{4c}$ are taken with the intervening oxygen atoms to form an optionally substituted monocyclic heterocyclic ring and $R^{PA}$ is an acyl protecting group an acyl protecting group. In certain embodiments, $R^{4b}$ and $R^{4c}$ are taken with the intervening oxygen atoms to form an optionally substituted bicyclic heterocyclic ring of the formula:

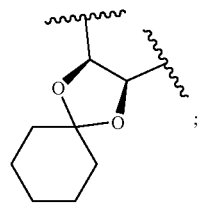 [SMILES: *[C@@H]1OC2(CCCCC2)O[C@@H]1*]

and $R^{PA}$ is an optionally substituted benzoylic protecting group. In certain embodiments, $R^{4b}$ and $R^{4c}$ are taken with the intervening oxygen atoms to form an optionally substituted bicyclic heterocyclic ring of the formula:

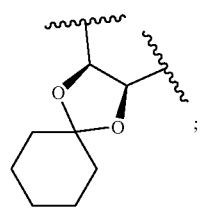 [SMILES: *[C@@H]1OC2(CCCCC2)O[C@@H]1*]

and $R^{PA}$ is an optionally substituted p-NO$_2$-benzoylic protecting group.

L being Ethynylene

In certain embodiments of the provided coupling method between the compound of Formula (i) and the aldehyde of Formula (ii), the compound of Formula (i) is of Formula (i-b):

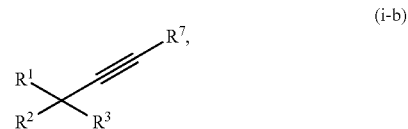

(i-b)

or a salt thereof, and the compound of Formula (I) is of Formula (I-b):

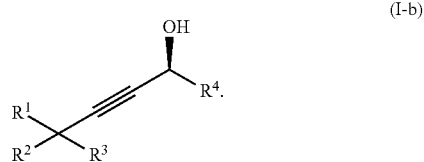

(I-b)

or a salt thereof, wherein $R^1$, $R^2$, $R^3$, $R^4$, and $R^7$ are as defined herein.

In certain embodiments, the compound of Formula (i) is of Formula (i-b-1):

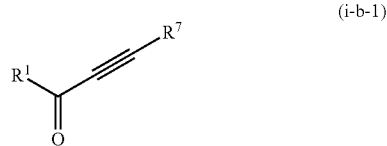

(i-b-1)

or a salt thereof, and the compound of Formula (I) is of Formula (I-b-1)

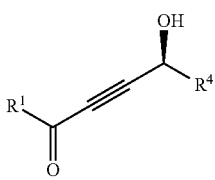
(I-b-1)

or a salt thereof, wherein $R^1$, $R^4$, and $R^7$ are as defined herein.

In certain embodiments, the compound of Formula (i) is of Formula (i-b-2):

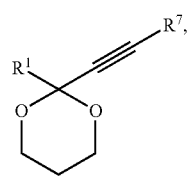
(i-b-2)

or a salt thereof, and the compound of Formula (I) is of Formula (I-b-2):

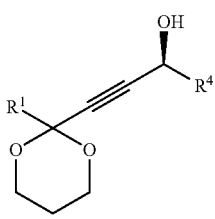
(I-b-2)

or a salt thereof, wherein $R^1$, $R^4$, and $R^7$ are as defined herein.

In certain embodiments, the compound of Formula (i) is of Formula (i-b-3):

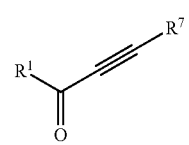
(i-b-3)

or a salt thereof, and the compound of Formula (I) is of Formula (I-b-3)

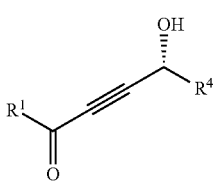
(I-b-3)

or a salt thereof, wherein $R^1$, $R^4$, and $R^7$ are as defined herein.

In certain embodiments, the compound of Formula (i) is of Formula (i-b-4):

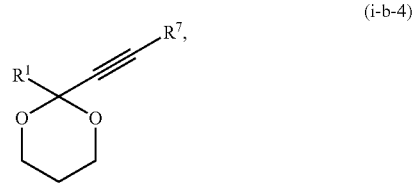
(i-b-4)

or a salt thereof, and the compound of Formula (I) is of Formula (I-b-4):

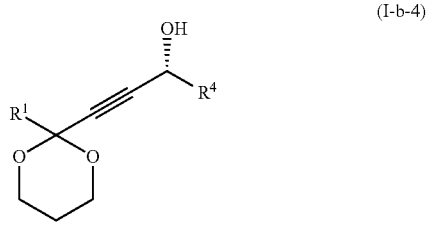
(I-b-4)

or a salt thereof, wherein $R^1$, $R^4$, and $R^7$ are as defined herein.

Methods for Preparing C1-C19 Building Block of Halichondrins

In certain embodiments, the provided coupling method can be applied to synthesizing the C1-C19 building blocks of halichodrin A, B, and C, and analogs thereof (e.g., norhalichondrin A, B, C; homohalichondrin A, B, C). The synthesis involves formation of an intermediate of Formula (I-b-5). In certain embodiments, the compound of Formula (i) is of Formula (i-b-5):

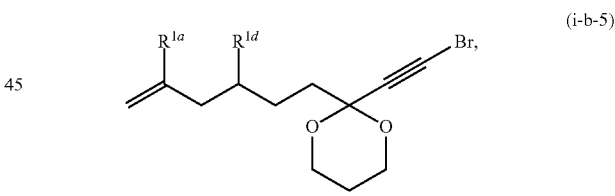
(i-b-5)

or a salt thereof, and the aldehyde of Formula (ii) is of Formula (ii-a):

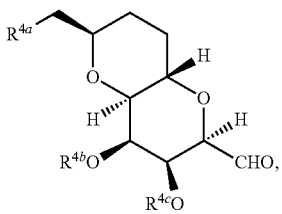
(ii-a)

or a salt thereof, and the compound of Formula (I) is of Formula (I-b-5):

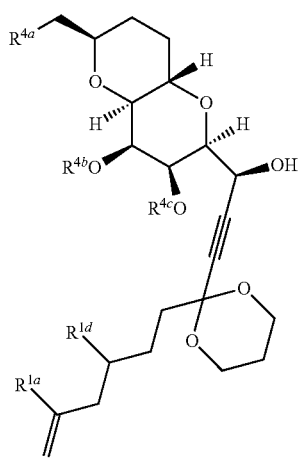

(I-b-5)

or a salt thereof, wherein $R^{1a}$, $R^{1d}$, $R^{4a}$, $R^{4b}$, and $R^{4c}$ are as defined herein.

In another aspect of the present invention, provided herein is a method of synthesizing the C1-C19 building block of halichodrin C and analogs (e.g., norhalichondrin C, homohalichondrin C). In certain embodiments, provided herein is a method of preparing a compound of Formula (I-b-6):

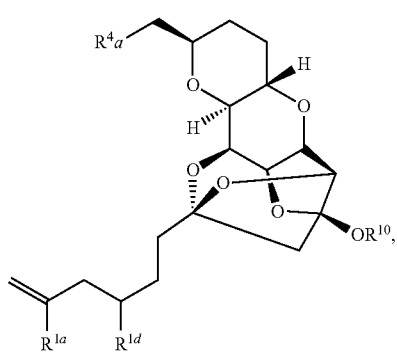

(I-b-6)

or a salt thereof, comprising contacting a compound of Formula (I-b-7):

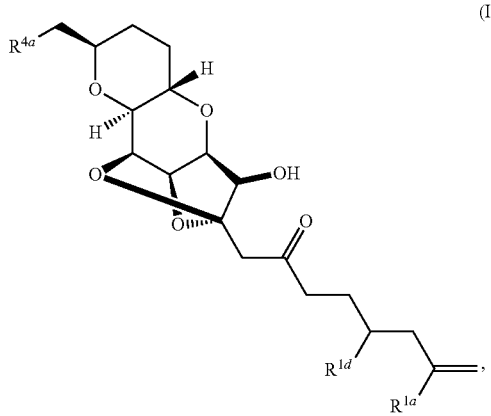

(I-b-7)

or a salt thereof, with a Lewis acid and an alcohol, wherein $R^{1a}$, $R^{1d}$, $R^{4a}$, $R^{4b}$, and $R^{4c}$ are as defined herein, and $R^{10}$ is hydrogen, optionally substituted alkyl, or an oxygen protecting group.

In certain embodiments, $R^{10}$ is hydrogen. In certain embodiments, $R^{10}$ is optionally substituted alkyl. In certain embodiments, $R^{10}$ is unsubstituted alkyl. In certain embodiments, $R^{10}$ is methyl or ethyl. In certain embodiments, $R^{10}$ is substituted alkyl. In certain embodiments, $R^{10}$ is optionally substituted alkenylalkyl. In certain embodiments, $R^{10}$ is unsubstituted alkenylalkyl. In certain embodiments, $R^{10}$ is $CH_2=CHCH_2-$. In certain embodiments, $R^{10}$ is an oxygen protecting group. In certain embodiments, $R^{10}$ is a silyl protecting group. In certain embodiments, $R^{10}$ is an acetyl protecting group.

As generally defined herein, the Lewis acid is a chemical species that reacts with a Lewis base to form a Lewis adduct. In certain embodiments, the Lewis acid is a metal salt that can accept a pair of electrons. In certain embodiments, the Lewis acid is a metal halide. In certain embodiments, the Lewis acid is a metal acetate. In certain embodiments, the Lewis acid is a metal triflate. In certain embodiments, the Lewis acid is a transition metal halide. In certain embodiments, the Lewis acid is a transition metal acetate. In certain embodiments, the Lewis acid is a transition metal triflate. In certain embodiments, the Lewis acid is $Sc(OTf)_3$, $Ln(OTf)_3$, $Yb(OTf)_3$, $Lu(OTf)_3$, $Hf(OTf)_4$, CuOTf. In certain embodiments, the Lewis acid is a hafnium(IV) salt. In certain embodiments, the Lewis acid is $Hf(OTf)_4$.

In certain embodiments, the alcohol is an optionally substituted alkyl alcohol. In certain embodiments, the alcohol is an optionally substituted alkenylalkyl alcohol. In certain embodiments, the alcohol is an unsubstituted alkenylalkyl alcohol. In certain embodiments, the alcohol is $CH_2=CHCH_2OH$.

In certain embodiments of synthesizing the C1-C19 building block of halichodrin C and analogs, the step of contacting the compound of Formula (I-b-7) with a Lewis acid and an alcohol further comprising the step of deprotecting a compound of Formula (I-b-8):

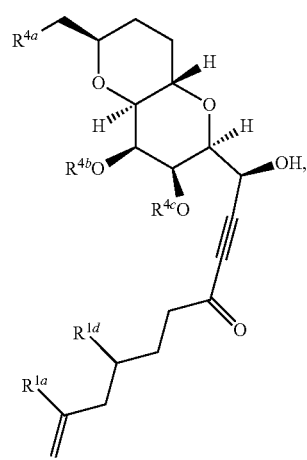

(I-b-8)

or a salt thereof, to yield a compound of Formula (I-b-7):

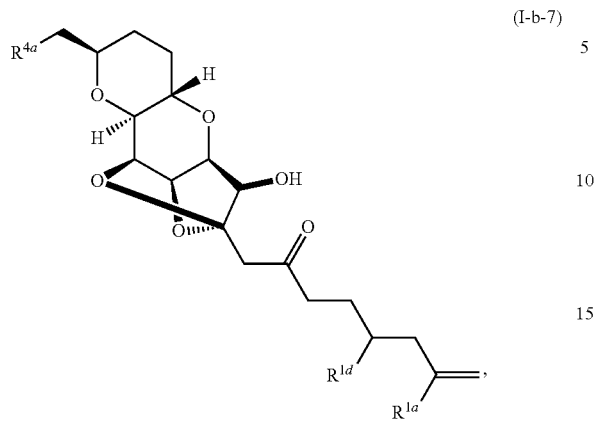

(I-b-7)

or a salt thereof, wherein $R^{1a}$, $R^{1d}$, $R^{4a}$, $R^{4b}$, and $R^{4c}$ are as defined herein. In certain embodiments, this step of deprotecting comprises converting the protecting groups at $R^{4b}$ and $R^{4c}$ to hydrogen. In certain embodiments, the protecting groups at $R^{4b}$ and $R^{4c}$ are silyl protecting groups. In certain embodiments, this step of deprotecting is performed in the presence of a source of fluoride. In certain embodiments, the step of deprotecting is performed in the presence of HF. pyridine. In certain embodiments, the step of deprotecting is performed in the presence of HF. pyridine followed by treatment with a base. In certain embodiments, the step of deprotecting is performed in the presence of HF.pyridine followed by treatment with an organic base. In certain embodiments, the step of deprotecting is performed in the presence of HF-pyridine followed by treatment with Et$_3$N.

In certain embodiments of synthesizing the C1-C19 building block of halichodrin C and analogs, the method further comprises the step of deprotecting a compound of Formula (I-b-5):

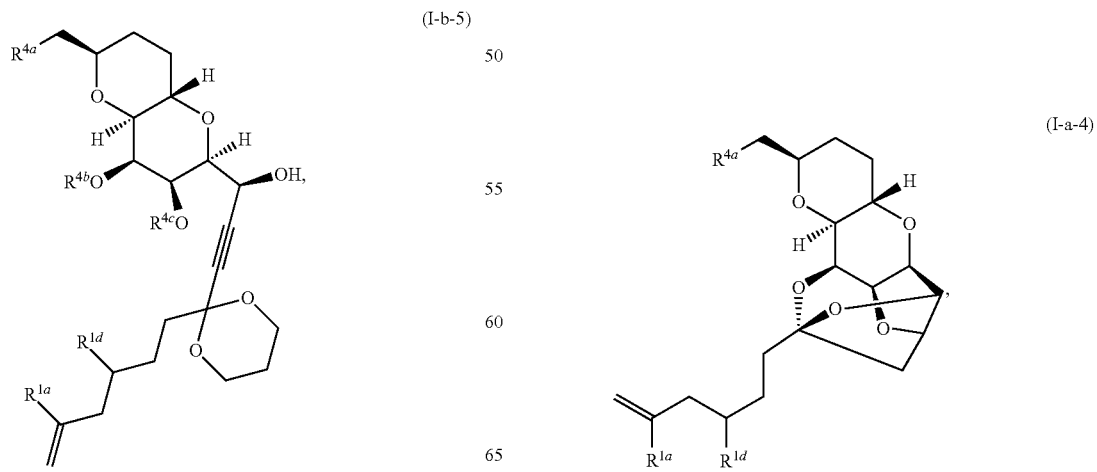

(I-b-5)

or a salt thereof, to yield a compound of Formula (I-b-8):

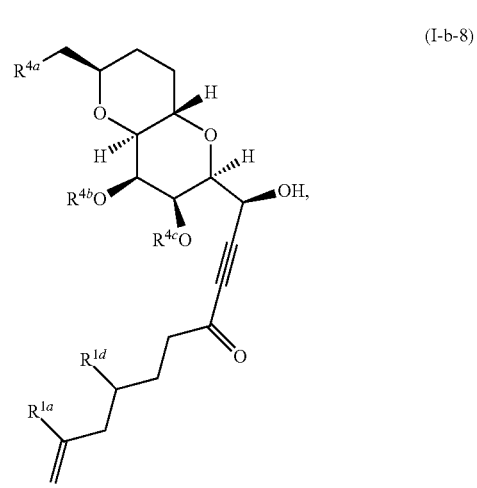

(I-b-8)

or a salt thereof, wherein $R^{1a}$, $R^{1d}$, $R^{4a}$, $R^{4b}$, and $R^{4c}$ are as defined herein. In certain embodiments, this step of deprotecting comprises converting the ketal of the compound of Formula (I-b-5) to a ketone of the compound of Formula (I-b-8). In certain embodiments, the step of deprotecting is performed in the presence of an acid. In certain embodiments, this step of deprotecting is performed in the presence of a Brønsted acid (i.e., a source of H+).

In another aspect of the present invention, provided herein is a method of synthesizing the C1-C19 building block of halichodrin B and analogs (e.g., norhalichondrin B, homohalichondrin B). In certain embodiments, provided herein is a method of preparing a compound of Formula (I-a-4):

(I-a-4)

or a salt thereof, comprising the steps of deprotecting a compound of Formula (I-b-10):

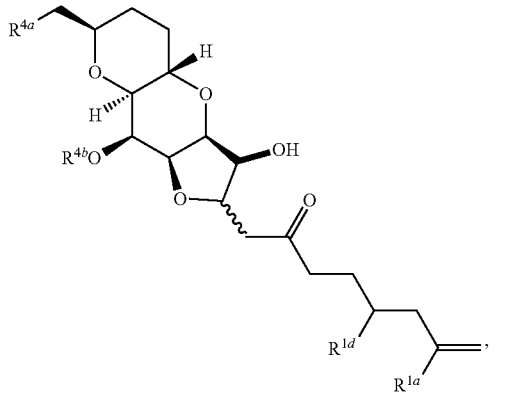

or a salt thereof, followed by cyclizing the deprotected compound, wherein $R^{1a}$, $R^{1d}$, $R^{4a}$, and $R^{4b}$ are as defined herein. In certain embodiments, the step of cyclizing comprises contacting the compound of Formula (I-b-10) with an acid. In certain embodiments, the acid in the step of cyclizing is a Lewis acid. In certain embodiments, the acid in the step of cyclizing is a Brønsted acid. In certain embodiments, the acid in the step of cyclizing is an organic acid. In certain embodiments, the acid is one or more selected from the group consisting of p-toluenesulfonic acid (PTSA), p-toluenesulfonic acid (p-TSA), or camphorsulfonic acid (CSA), pyridinium p-toluenesulfonate (PPTS), or sulfonic acid exchange resin (Amberlyst, Dowex). In certain embodiments, the acid is p-toluenesulfonic acid (p-TSA) or camphorsulfonic acid (CSA). In certain embodiments, the acid in the step of cyclizing is pyridinium p-toluenesulfonate (PPTS) or p-toluenesulfonic acid (p-TSA). In certain embodiments, the step of cyclizing comprises contacting the compound of Formula (I-b-10) with an ion-exchange resin. In certain embodiments, the ion-exchange resin is an acidic polymer-bound resin. In certain embodiments, the ion-exchange resin is a polymer-bound PPTS.

In certain embodiments, the step of cyclizing further comprising contacting the equilibrating reaction mixture with an acid in an ion-exchange resin device. In certain embodiments, the ion-exchange resin device comprises a first column with basic ion exchange resins and a second column with acidic ion exchange resins. In certain embodiments, the ion-exchange resin device comprises a first column with basic ion exchange resins and a dehydrating reagent (e.g., 4 Å molecular sieves); and a second column with acidic ion exchange resins and a dehydrating reagent (e.g., 4 Å molecular sieves). In certain embodiments, the ion-exchange resin device is as shown in FIG. 2.

In certain embodiments of synthesizing the C1-C19 building block of halichodrin B and analogs, the method further comprises the step of reducing a compound of Formula (I-b-11):

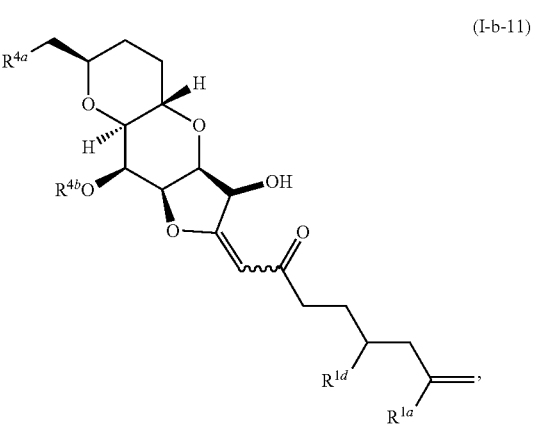

or a salt thereof, to yield a compound of Formula (I-b-10):

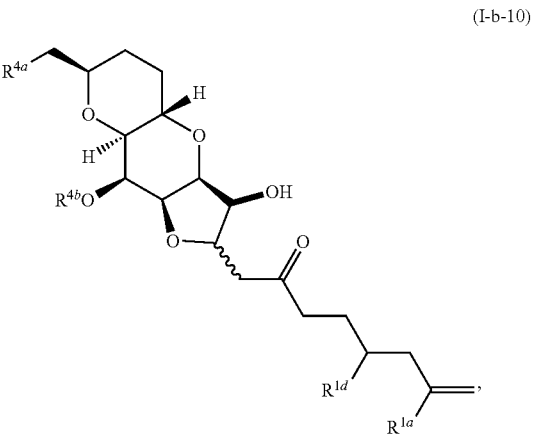

or a salt thereof, wherein $R^{1a}$, $R^{1d}$, $R^{4a}$, and $R^{4b}$ are as defined herein. In certain embodiments, the step of reducing is performed in the presence of a source of hydride. In certain embodiments, the source of hydride is one or more reagents selected from the group of consisting of lithium hydrides, copper hydrides, and boron hydrides. In certain embodiments, the source of hydride is a boron hydride. In certain embodiments, the source of hydride is (Me)$_4$NBH(OAc).

In certain embodiments of synthesizing the C1-C19 building block of halichodrin B and analogs, the method further comprises the step of deprotecting a compound of Formula (I-b-8):

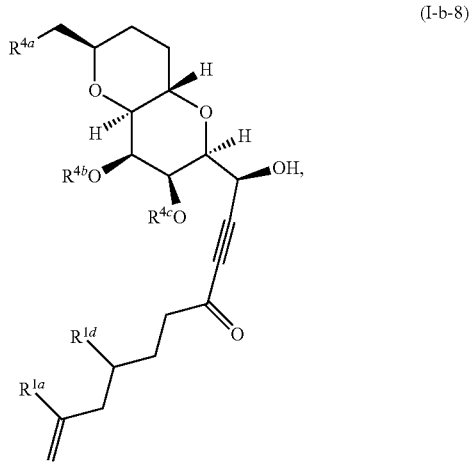

(I-b-8)

or a salt thereof, to yield a compound of Formula (I-b-11):

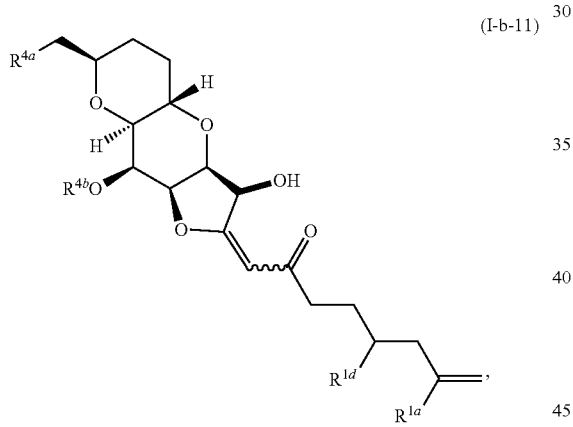

(I-b-11)

or a salt thereof, wherein $R^{1a}$, $R^{1d}$, $R^{4a}$, $R^{4b}$, and $R^{4c}$ are as defined herein. In certain embodiments, the step of deprotecting is to convert the protecting group at $R^{4c}$ to hydrogen. In certain embodiments, the step of deprotecting is to convert the protecting group at $R^{4c}$ to hydrogen, wherein both $R^{4b}$ and $R^{4c}$ are independently silyl protecting groups. In certain embodiments, this step of deprotecting is performed in the presence of a source of fluoride. In certain embodiments, the step of deprotecting is performed in the presence of HF.pyridine.

In another aspect of the present invention, provided herein is a method of synthesizing the C1-C19 building block of halichodrin B and analogs. In certain embodiments, provided herein is a method of preparing a compound of Formula (I-a-4):

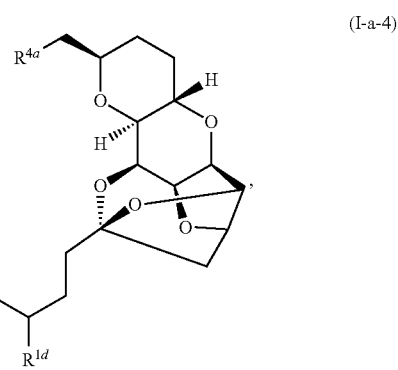

(I-a-4)

or a salt thereof, comprising the step of deprotecting a compound of Formula (I-b-12):

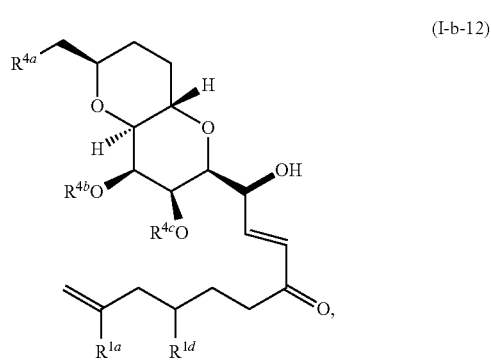

(I-b-12)

or a salt thereof; and cyclizing the deprotected compound, wherein $R^{1a}$, $R^{1d}$, $R^{4a}$, $R^{4b}$, and $R^{4c}$ are as defined herein. In certain embodiments, the step of deprotecting is to convert the protecting group at $R^{4c}$ to hydrogen. In certain embodiments, the step of deprotecting is to convert the protecting group at $R^{4c}$ to hydrogen, wherein both $R^{4b}$ and $R^{4c}$ are independently silyl protecting groups. In certain embodiments, this step of deprotecting is performed in the presence of a source of fluoride. In certain embodiments, the step of deprotecting is performed in the presence of TBAF. In certain embodiments, the step of cyclizing comprises contacting the reduced compound of Formula (I-b-12) with an organic acid. In certain embodiments, the step of cyclizing comprises contacting the compound of Formula (I-b-12) with an acid. In certain embodiments, the acid in the step of cyclizing is a Lewis acid. In certain embodiments, the acid in the step of cyclizing is a Brønsted acid. In certain embodiments, the acid in the step of cyclizing is pyridinium p-toluenesulfonate (PPTS) or p-toluenesulfonic acid (p-TSA). In certain embodiments, the step of cyclizing comprises contacting the compound of Formula (I-b-12) with an ion-exchange resin. In certain embodiments, the ion-exchange resin is an acidic polymer-bound resin. In certain embodiments, the ion-exchange resin is a polymer-bound PPTS.

In certain embodiments, the step of cyclizing further comprising contacting the equilibrating reaction mixture with an acid in an ion-exchange resin device. In certain embodiments, the ion-exchange resin device comprises a first column with basic ion exchange resins and a second column with acidic ion exchange resins. In certain embodiments, the ion-exchange resin device comprises a first column with basic ion exchange resins and a dehydrating reagent (e.g., 4 Å molecular sieves); and a second column with acidic ion exchange resins and a dehydrating reagent (e.g., 4 Å molecular sieves). In certain embodiments, the ion-exchange resin device is as shown in FIG. 2.

In certain embodiments of synthesizing the C1-C19 building block of halichodrin B and analogs, the method further comprises the step of reducing a compound of Formula (I-b-8):

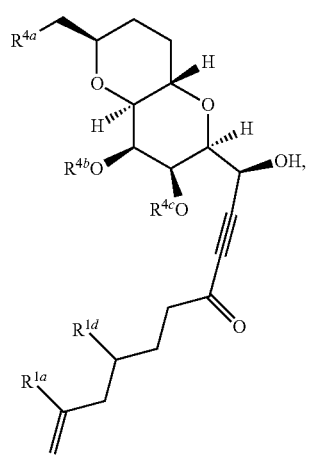

(I-b-8)

or a salt thereof, to yield a compound of Formula (I-b-12):

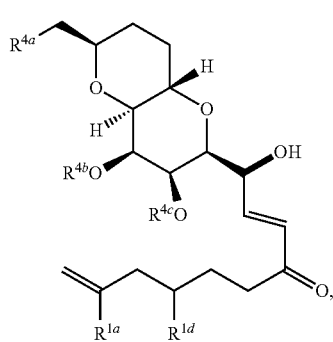

(I-b-12)

or a salt thereof, wherein $R^{1a}$, $R^{1d}$, $R^{4a}$, $R^{4b}$, and $R^{4c}$ are as defined herein. In certain embodiments, the step of reducing is performed in the presence of a source of hydride. In certain embodiments, the source of hydride is one or more selected from the group of consisting of lithium hydrides, copper hydrides, and boron hydrides. In certain embodiments, the soured of hydride is a copper hydride. In certain embodiments, the soured of hydride is 1,2-bis(diphenylphosphino)benzenecopper hydride ((BDP)CuH).

In anther aspect of the present invention, provided herein is a method of synthesizing the C1-C19 building block of halichodrin A and analogs (e.g., norhalichondrin A, homohalichondrin A). In certain embodiments, provided herein is a method of preparing a compound of Formula (I-b-13):

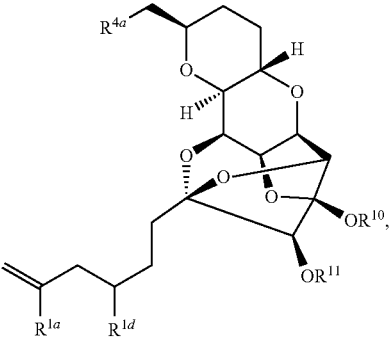

(I-b-13)

or a salt thereof, comprising cyclizing a compound of Formula (I-b-14):

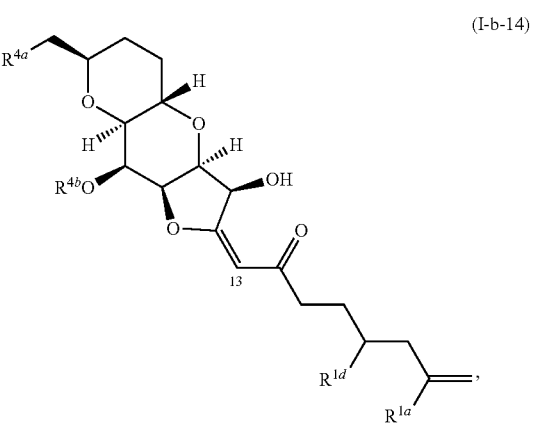

(I-b-14)

or a salt thereof, wherein $R^{1a}$, $R^{1d}$, $R^{4a}$, $R^{4b}$, and 10 are as defined herein, and $R^{11}$ is hydrogen, optionally substituted alkyl, or an oxygen protecting group. In certain embodiments, the step of cyclizing comprises oxidizing the compound of Formula (I-b-14). In certain embodiment, the step of oxidizing is to introduce the C13 hydroxyl group. In certain embodiments, the step of oxidizing is performed in the presence of an organic peroxide (e.g. a compound comprising an O-O bond). In certain embodiments, the step of oxidizing is performed in the presence of dimethyldioxirane (DMDO). In certain embodiments, the step of oxidizing further comprises contacting the oxidized compound of Formula (I-b-14) with an acid. In certain embodiments, the acid is a Lewis acid. In certain embodiments, the acid is a Brønsted acid. In certain embodiments, the acid in the step of cyclizing is an organic acid. In certain embodiments, the acid is one or more selected from the group consisting of p-toluenesulfonic acid (PTSA), p-toluenesulfonic acid (p-TSA), or camphorsulfonic acid (CSA), pyridinium p-toluenesulfonate (PPTS), or sulfonic acid exchange resin (Amberlyst, Dowex). In certain embodiments, the acid is p-toluenesulfonic acid (p-TSA) or camphorsulfonic acid (CSA). In certain embodiments, the acid in the step of cyclizing is pyridinium p-toluenesulfonate (PPTS) or p-toluenesulfonic acid (p-TSA).

In certain embodiments, the step of cyclizing comprises contacting the oxidized compound of Formula (I-b-14) with PPTS. In certain embodiments, the step of cyclizing comprises contacting the oxidized compound of Formula (I-b-

14) with an ion-exchange resin. In certain embodiments, the ion-exchange resin is an acidic polymer-bound resin. In certain embodiments, the ion-exchange resin is a polymer-bound PPTS.

In certain embodiments, the step of cyclizing further comprising contacting the equilibrating reaction mixture with an acid in an ion-exchange resin device. In certain embodiments, the ion-exchange resin device comprises a first column with basic ion exchange resins and a second column with acidic ion exchange resins. In certain embodiments, the ion-exchange resin device comprises a first column with basic ion exchange resins and a dehydrating reagent (e.g., 4 Å molecular sieves); and a second column with acidic ion exchange resins and a dehydrating reagent (e.g., 4 Å molecular sieves). In certain embodiments, the ion-exchange resin device is as shown in FIG. 2.

In certain embodiments of synthesizing the C1-C19 building block of halichodrin A and analogs, the method further comprises the step of deprotecting a compound of Formula (I-b-8):

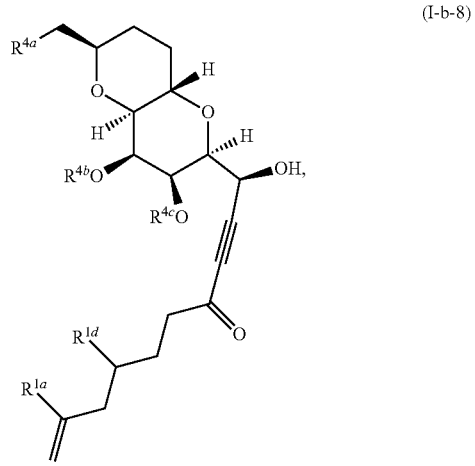

(I-b-8)

or a salt thereof,
to give a compound of Formula (I-b-14):

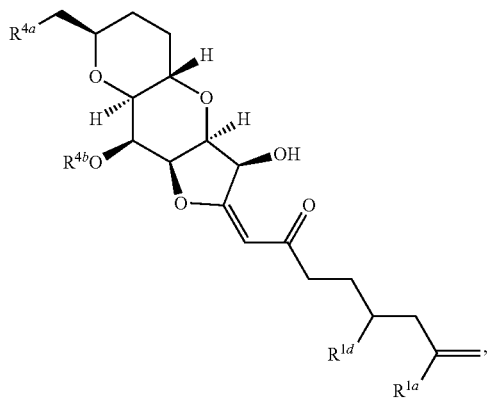

(I-b-14)

or a salt thereof,
wherein $R^{1a}$, $R^{1d}$, $R^{4a}$, $R^{4b}$, and 10 are as defined herein. In certain embodiments, the step of deprotecting is to convert the protecting group at $R^{4c}$ to hydrogen. In certain embodiments, the step of deprotecting is to convert the protecting group at $R^{4c}$ to hydrogen, wherein both $R^{4b}$ and $R^{4c}$ are independently silyl protecting groups. In certain embodiments, this step of deprotecting is performed in the presence of a source of fluoride. In certain embodiments, the step of deprotecting is performed in the presence of HF.pyridine.

Methods for Preparing C20-C38 Building Block of Halichondrins

Provided herein are methods for preparing C20-C38 building blocks of halichondrins and analogs thereof (e.g., halichondrins A, B, C; homohalichondrin A, B, C; norhalichindrin A, B, C; eribulin). In certain embodiments, C20-C38 building blocks of the halichondrins are compounds of Formula (TJ-1):

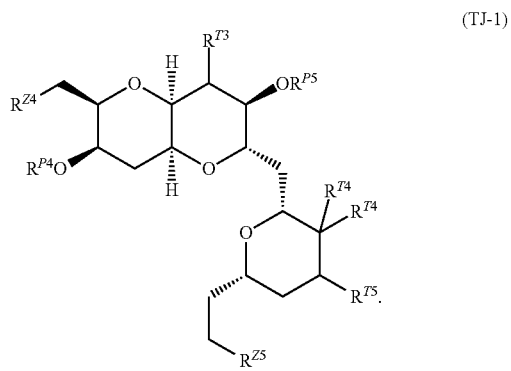

(TJ-1)

In certain embodiments, a compound of Formula (TJ-1) is a compound of Formula (III-1). Compounds of Formula (III-1) can be prepared as shown in Scheme A.

Scheme A

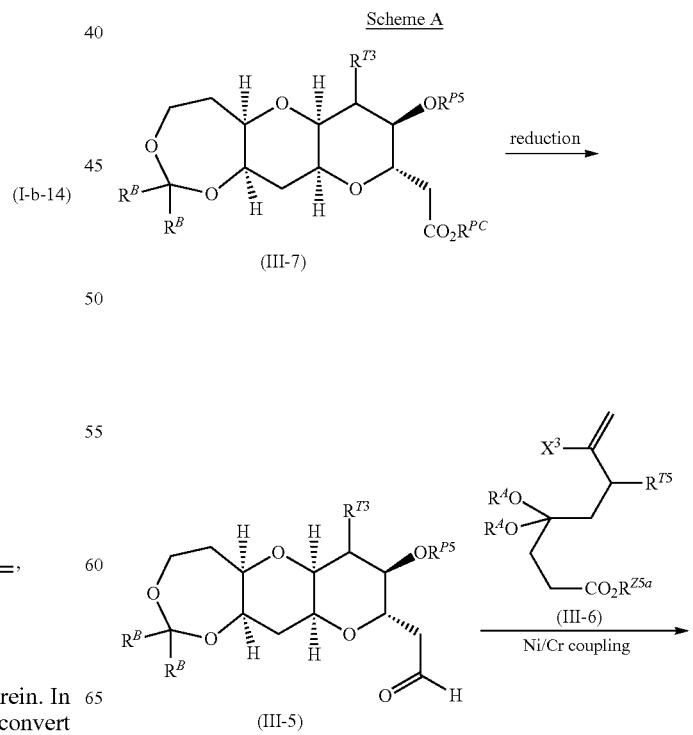

-continued

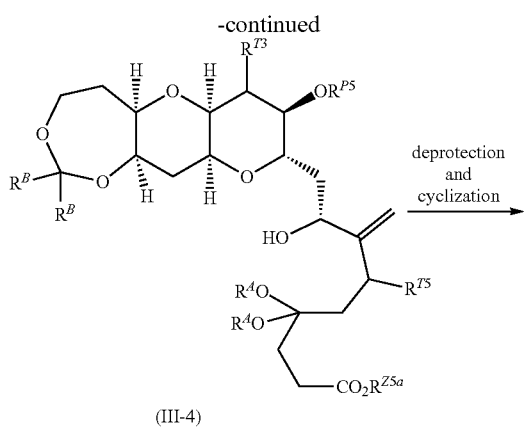

(III-4)

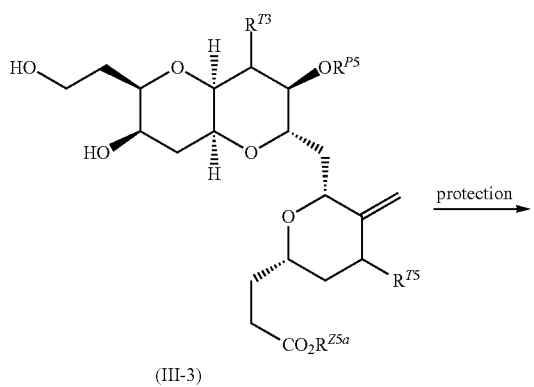

(III-3)

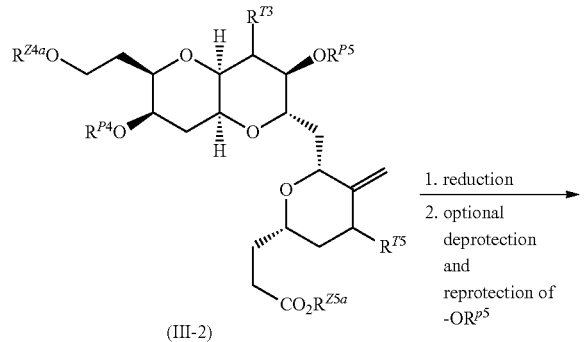

(III-2)

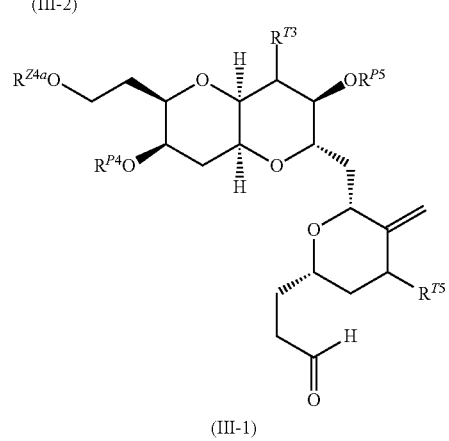

(III-1)

Provided herein is a method of preparing a compound of Formula (III-1):

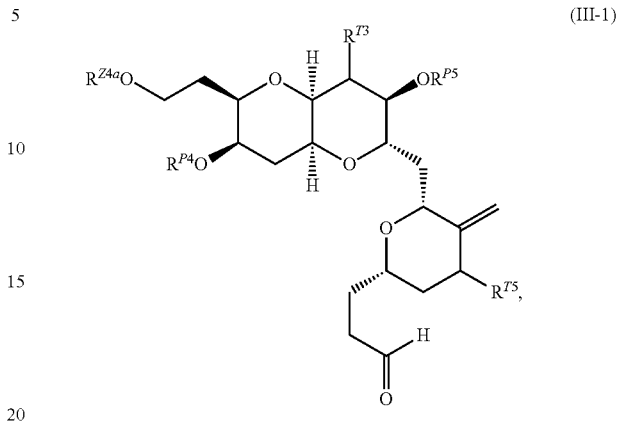

(III-1)

or a salt thereof, the method comprising a step of reducing a compound of Formula (III-2):

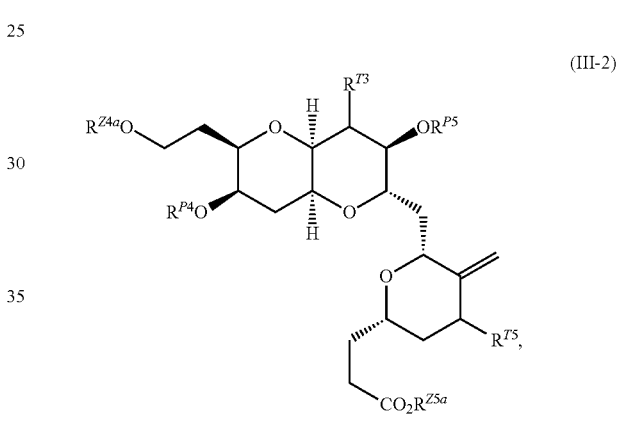

(III-2)

or a salt thereof. The step of reducing converts the —$CO_2R^{Z5a}$ moiety to an aldehyde moiety. In certain embodiments, the step of reducing is carried out in the presence of a hydride (i.e., H⁻) source. Any hydride source known in the art may be used in this transformation. Examples of hydride sources include, but are not limited to, lithium aluminum hydride, sodium borohydride, and diisobutylaluminum hydride. In certain embodiments, the hydride source is diisobutylaluminum hydride (DIBAL). The step of reducing may optionally comprise reducing the —$CO_2R^{Z5a}$ moiety to an alcohol, followed by oxidation of the resulting alcohol to an aldehyde to yield a compound of Formula (III-1).

As shown in Scheme A, the method of preparing a compound of Formula (III-1) optionally comprises steps of deprotecting and reprotecting the moiety corresponding to —$OR^{P5}$. The steps of deprotection and reprotection serve to change the group $R^{P5}$ from one protecting group to another. For example, in certain embodiments, the group $R^{P5}$ can be changed from a para-methoxyphenyl (MPM) group to an acyl group via deprotection and reprotection.

In certain embodiments, the method of preparing a C20-C38 building block comprises a step of deprotecting a compound of Formula (III-1), or a salt thereof, to yield a compound of Formula (III-1-a):

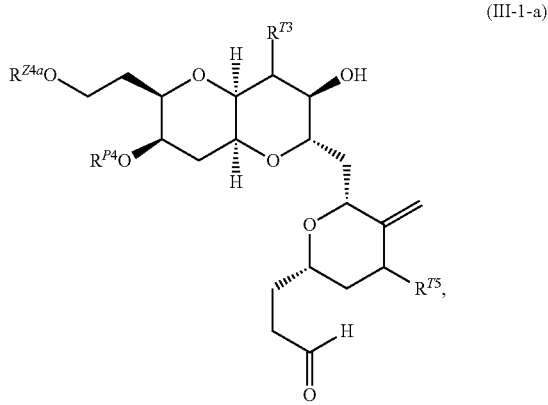

(III-1-a)

or a salt thereof, wherein $R^{P5}$ of Formula (III-1) is an oxygen protecting group. In certain embodiments, the step of deprotecting comprises reacting a compound of Formula (III-1) in the presence of a reagent for deprotection. For example, in certain embodiments, $R^{P5}$ is a para-methoxyphenyl protecting group (MPM), and the reagent for deprotection is an oxidant. In certain embodiments, $R^{P5}$ is a para-methoxyphenyl protecting group (MPM), and the reagent for deprotection is 2,3-dichloro-5,6-dicyano-1,4-benzoquinone (DDQ). In certain embodiments, $R^{P5}$ is a para-methoxyphenyl protecting group (MPM), and the reagent for deprotection is an oxidant. In certain embodiments, the reagent for deprotection is dimethylboron bromide, magnesium bromide-dimethyl sulfide, ceric ammonium nitrate (CAN), or an acid. The MPM protecting group may also be removed via hydrogenolysis using hydrogen gas.

As described herein, a compound of Formula (III-a) may be reprotected to yield a compound of Formula (III-1). Therefore, in certain embodiments, the method of preparing a C20-C38 building block comprises a step of protecting a compound of Formula (III-1-a), or a salt thereof, to yield a compound of Formula (III-1), or a salt thereof. In certain embodiments, the step of protecting involves acylating the free alcohol (e.g., installing $R^{P5}$ as an acyl protecting group). In certain embodiments, the step of protecting is carried out in the presence of an acylating agent (e.g., an acyl halide or acyl anhydride). In certain embodiments, the step of protecting is carried out in the presence of acetyl chloride or acetyl anhydride (e.g., to install $R^{P5}$ as —C(=O)CH$_3$). In certain embodiments, the step of protecting is carried out in the presence of acetyl anhydride. In certain embodiments, the step of protecting is carried out in the presence of a coupling reagent and/or a base. In certain embodiments, the step of protecting is carried out in the presence of an amine base (e.g., a trialkylamine such as triethylamine or N,N-diisoproylethylamine). In certain embodiments, the step of protecting is carried out in the presence of a pyridine base or coupling reagent. In certain embodiments, the step of coupling is carried out in the presence of pyridine. In certain embodiments, the step of coupling is carried out in the presence of 4-dimethylaminopyridine (DMAP).

In certain embodiments, the method of preparing a C20-C38 building block comprises a step of protecting a compound of Formula (III-3):

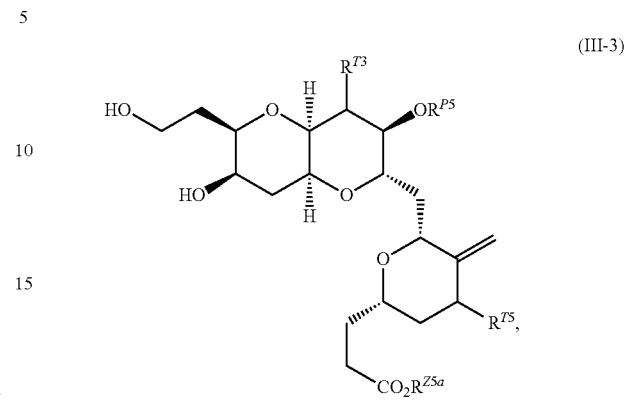

(III-3)

or a salt thereof, to yield a compound of Formula (III-2):

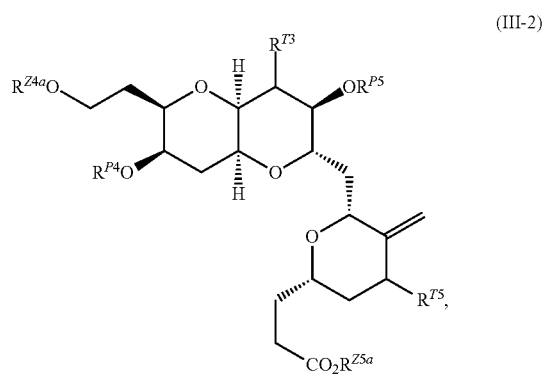

(III-2)

or a salt thereof. The step of protecting involves protecting the primary and secondary free alcohols of a compound of Formula (III-3) to introduce the groups $R^{Z4a}$ and $R^{P4}$. The two alcohols may be protected in separate steps or the same step, and may be protected with the same or different protecting groups (e.g., $R^{Z4a}$ and $R^{P4}$ are the same or different). In certain embodiments, the step of protecting is carried out in the presence of a protecting reagent. For example, in certain embodiments, $R^{Z4a}$ and $R^{P4}$ are trialkylsilyl groups, and the step of protecting is carried out in the presence of a trialkylsilyl halide or a trialkylsilyl sulfonate. For example, in certain embodiments, $R^{Z4a}$ and $R^{P4}$ are tert-butyldimethylsilyl (TBS), and the step of protecting is carried out in the presence of tert-butyldimethylsilyl trifluoromethanesulfonate ("TBS-triflate" or "TBSOTf"). The step of protecting may optionally be carried out in the presence of a base.

In certain embodiments, the method of preparing a C20-C38 building block comprises a step of deprotecting and cyclizing a compound of Formula (III-4):

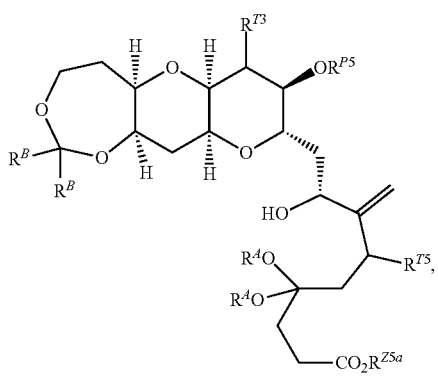

(III-4)

or a salt thereof, to yield a compound of Formula (III-3):

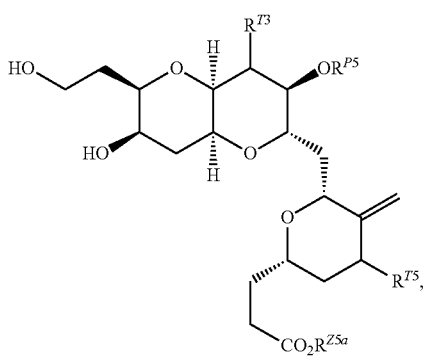

(III-3)

or a salt thereof. The step of deprotecting and cyclizing involves deprotecting the two ketals of a compound of Formula (III-4), followed by a cyclization reaction to provide the new six-membered ring of the compound of Formula (III-3). The deprotecting and cyclizing may be done in the same step, or in separate steps, and in either order. In certain embodiments, the step of deprotecting and cyclizing is carried out in the presence of an acid (e.g., Lewis acid, Bronsted acid). In certain embodiments, the step of deprotecting and cyclizing is carried out in the presence of a hydride source. In certain embodiments, the step of deprotecting and cyclizing is carried out in the presence of a trialkylsilyl sulfonate or trialkylsilyl halide. In certain embodiments, the step of deprotecting and cyclizing is carried out in the presence of a trialkylsilane. In certain embodiments, the step of deprotecting and cyclizing is carried out in the presence of triethylsilyl trifluoromethylsulfonate ("TES-triflate" or "TESOTf"). In certain embodiments, the step of deprotecting and cyclizing is carried out in the presence of triethylsilane. In certain embodiments, the step of deprotecting and cyclizing is carried out in the presence of TESOTf and triethylsilane.

In certain embodiments, the method of preparing a C20-C38 building block comprises a step of coupling a compound of Formula (III-5):

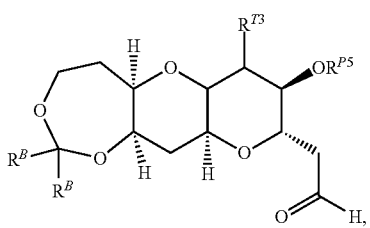

(III-5)

or a salt thereof, with a compound of Formula (III-6):

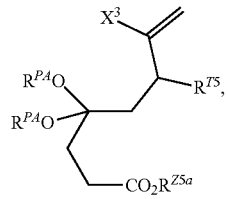

(III-6)

or a salt thereof, in the presence of a chromium catalyst and optionally one or more catalysts, to yield a compound of Formula (III-4):

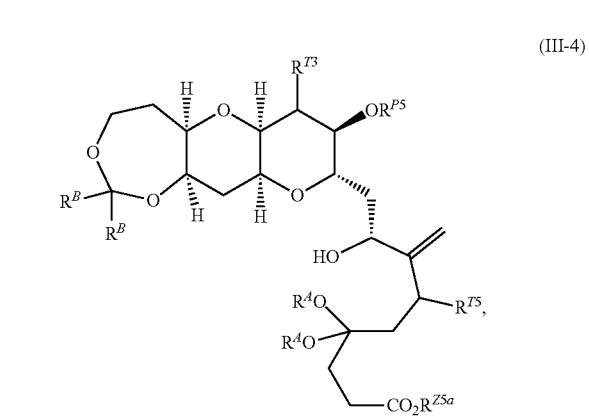

(III-4)

or a salt thereof. The coupling may be any chromium-mediated coupling reaction known in the art or described herein, and involve any catalysts or reagents known in the art or described herein. In certain embodiments, the chromium catalyst is a chromium complex (i.e., comprising a ligand). In certain embodiments, the chromium catalyst is chromium sulfonamide (see, e.g., Namba K et al., *Org. Lett.*, 2004, 6(26), 5031-5033; Ueda et al. *J. Am. Chem. Soc.* 2014, 136, 5171-5176). In certain embodiments, the chromium sulfonamide is of Formula (S-1), described herein. In certain embodiments, the chromium sulfonamide is of the following formula:

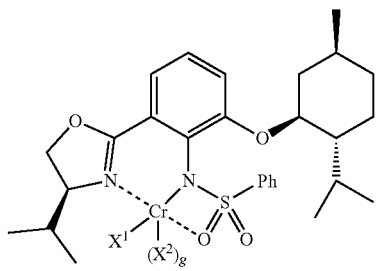

In certain embodiments, the chromium sulfonamde is formed by contacting a chromium salt (e.g., $CrCl_2$) with a sulfonamide. In certain embodiments, the sulfonamide is of Formula (S-2), as described herein. In certain embodiments, the sulfonamide is of the formula:

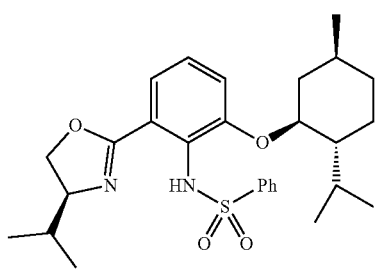

In certain embodiments, the step of coupling is carried out in the presence of a nickel catalyst. Any nickel catalyst known in art or described herein may be used. In certain embodiments, the nickel catalyst is a catalyst of Formula (N-1), described herein. In certain embodiments, the nickel catalyst is of the following formula:

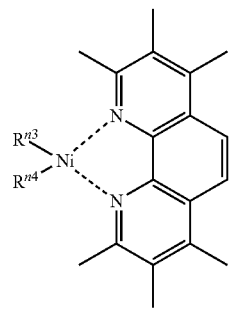

In certain embodiments, the nickel catalyst is $(Me)_6Phen$-$NiCl_2$, of the formula:

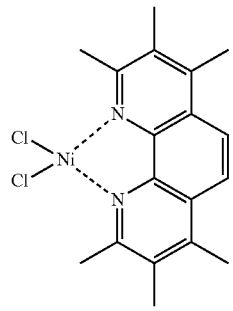

In certain embodiments, the step of coupling may be carried out in the presence of one or more additional reagents (e.g., salts, bases, metals). In certain embodiments, the step of coupling may be carried out in the presence of one or more additional agents selected from the group consisting of lithium salts (e.g., LiCl), transition metals (e.g., Mn), and zirconium complexes (e.g., $Cp_2ZrCl_2$). In certain embodiments, the step of coupling is be carried out in the presence of LiCl, Mn, and $Cp_2ZrCl_2$. In certain embodiments, the step of coupling is carried out in the presence of a proton sponge.

In certain embodiments, the method of preparing C20-C38 building block comprises a step of reducing a compound of Formula (III-7):

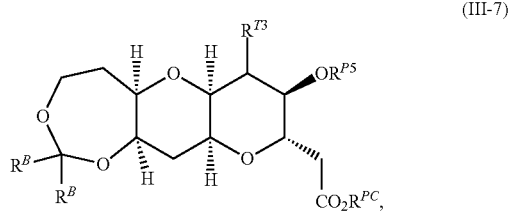

or a salt thereof, to yield a compound of Formula (III-5):

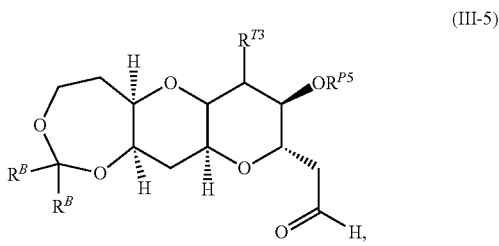

or a salt thereof. The step of reducing is to convert the $-CO_2R^{Z5a}$ moiety to an aldehyde moiety. In certain embodiments, the step of reducing is carried out in the presence of a hydride (i.e., $H^-$) source. Any hydride source known in the art may be used in this transformation. Examples of hydride sources include, but are not limited to, lithium aluminum hydride, sodium borohydride, and diisobutylaluminum hydride. In certain embodiments, the hydride source is diisobutylaluminum hydride (DIBAL). The step of reducing may optionally comprise reducing the $-CO_2R^{Z5a}$ moiety to an alcohol, followed by oxidation of the alcohol to an aldehyde to yield a compound of Formula (III-5).

C20-C38 building blocks of halichondrins (e.g., halichondrin A, B, C; homohalichondrin A, B, C; norhalichondrin A, B, C) and analogs thereof may be of Formula (III-11):

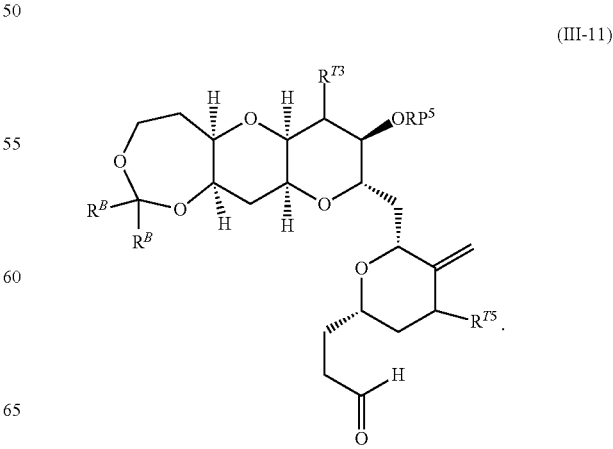

The present invention provides methods of preparing C20-C38 building blocks of halichondrins, including compounds of Formula (III-11). Compounds of Formula (III-11) can be coupled with C1-C19 building blocks described herein (e.g., compounds of Formula (TC-1) in order to prepare the macrocyclic right halves of the halichondrins. Compounds of Formula (III-11) may be prepared as shown in Scheme B.

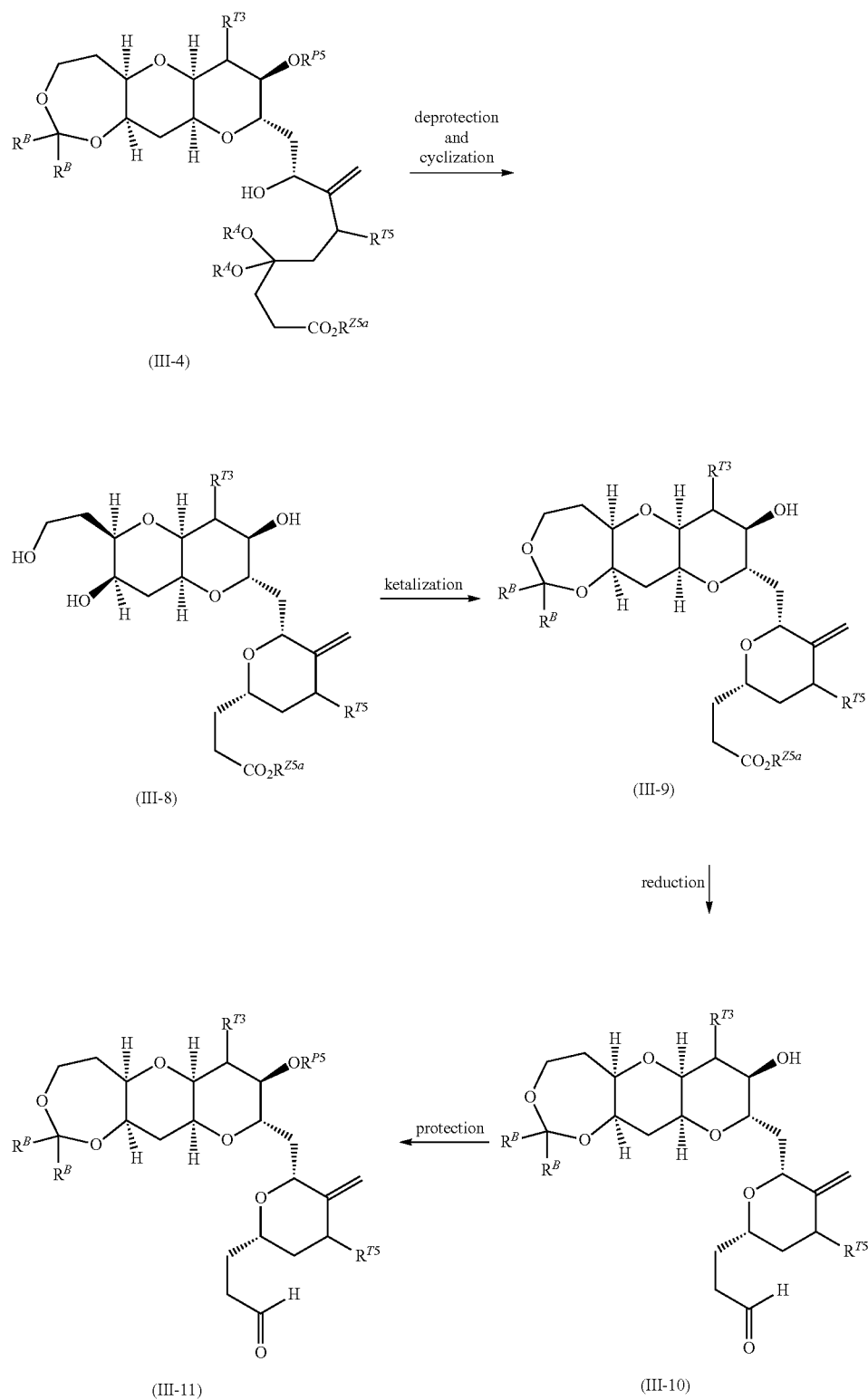

Scheme B

In certain embodiments, the method of preparing a compound of Formula (III-11) comprises a step of protecting a compound of Formula (III-10):

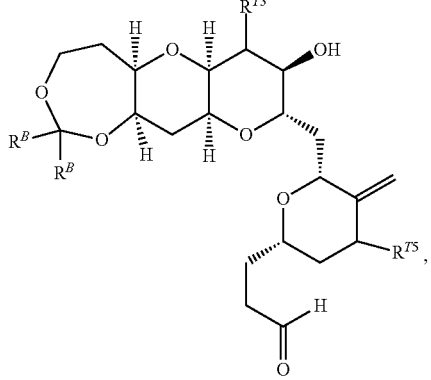

(III-10)

or a salt thereof, to yield a compound of Formula (III-11). The step of protecting serves to protect the free secondary alcohol of a compound of Formula (III-10) and install the group $R^{P5}$. In certain embodiments, the step of protecting involves acylating the free alcohol (e.g., installing $R^{P5}$ as an acyl protecting group). In certain embodiments, the step of protecting is carried out in the presence of an acylating agent (e.g., an acyl halide or acyl anhydride). In certain embodiments, the step of protecting is carried out in the presence of acetyl chloride or acetyl anhydride (e.g., to install $R^{P5}$ as —C(=O)CH$_3$). In certain embodiments, the step of protecting is carried out in the presence of acetyl anhydride. In certain embodiments, the step of protecting is carried out in the presence of an amine base (e.g., a trialkylamine such as triethylamine or N,N-diisoproylethylamine). In certain embodiments, the step of protecting is carried out in the presence of a pyridine base or coupling reagent. In certain embodiments, the step of coupling is carried out in the presence of pyridine. In certain embodiments, the step of protecting is carried out in the presence of a coupling reagent and/or a base. In certain embodiments, the step of coupling is carried out in the presence of 4-dimethylaminopyridine (DMAP).

In certain embodiments, the method of preparing a C20-C38 building block comprises a step of reducing a compound of Formula (III-9):

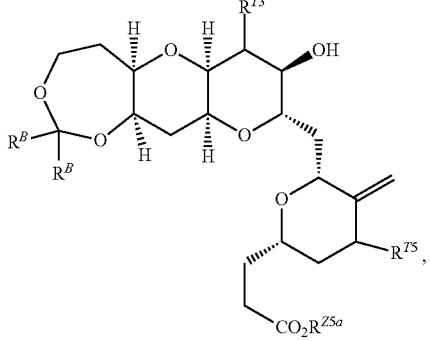

(III-9)

or a salt thereof, to yield a compound of Formula (I-10):

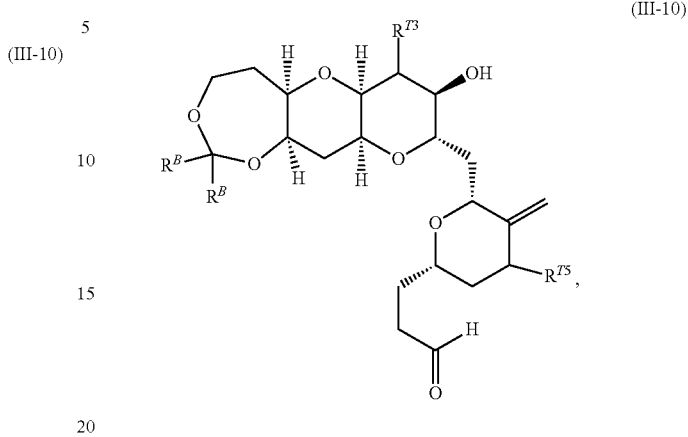

(III-10)

or a salt thereof. The step of reducing is to convert the —CO$_2$R$^{Z5a}$ moiety to an aldehyde. In certain embodiments, the step of reducing is carried out in the presence of a hydride (i.e., H$^-$) source. Any hydride source known in the art may be used in this transformation. Examples of hydride sources include, but are not limited to, lithium aluminum hydride, sodium borohydride, and diisobutylaluminum hydride. In certain embodiments, the hydride source is diisobutylaluminum hydride (DIBAL). The step of reducing may optionally comprise reducing the —CO$_2$R$^{Z5a}$ moiety to an alcohol, followed by oxidation of the resulting alcohol to an aldehyde to yield a compound of Formula (III-10).

In certain embodiments, the method of preparing a C20-C38 building block comprises a step of ketalizing a compound of Formula (III-8), or a salt thereof, to yield a compound of Formula (III-9), or a salt thereof. For example, in certain embodiments, the method of preparing a C20-C38 building block comprises a step of contacting a compound of Formula (III-8):

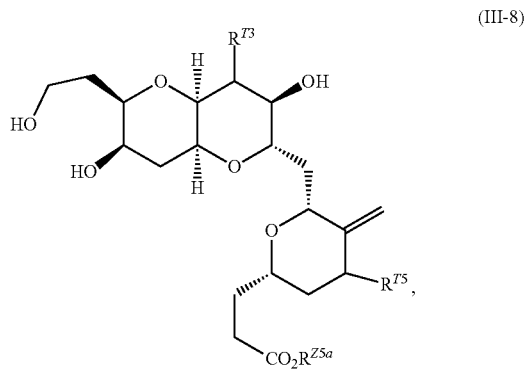

(III-8)

or a salt thereof, with a compound of the formula:

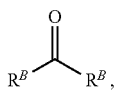

or a salt thereof, in the presence of an acid to yield a compound of Formula (III-9):

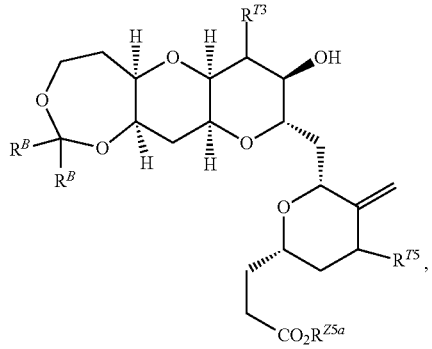

or a salt thereof. The acid used in this transformation may be a Lewis acid or a Bronsted acid. The acid may be used in a catalytic, stoichiometric, or excess amount. In certain embodiments, the acid is a Bronsted acid. In certain embodiments, the acid is a sulfonic acid. In certain embodiments, the acid is a pyridinium salt. In certain embodiments, the acid is a pyridinium salt of a sulfonic acid. In certain embodiments, the acid is pyridinium p-toluenesulfonate (PPTS). In certain embodiments, the step of ketalizing is carried out in the presence of one or more additional reagents (e.g., ketals). In certain embodiments, the reaction is carried out in the presence of an additional ketal (e.g., 2,2-dimethoxypropane). In certain embodiments, the reaction is carried out in the presence of 2,2-dimethoxypropane.

In certain embodiments, the method of preparing a C20-C38 building block comprises steps of deprotecting and cyclizing a compound of Formula (III-4):

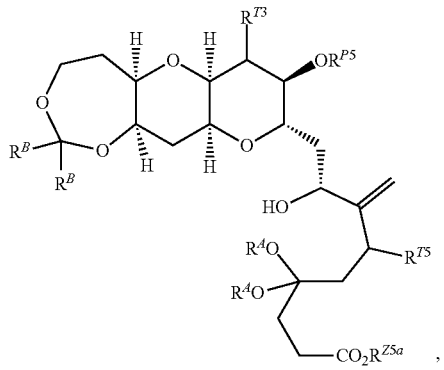

or a salt thereof, to yield a compound of Formula (III-8):

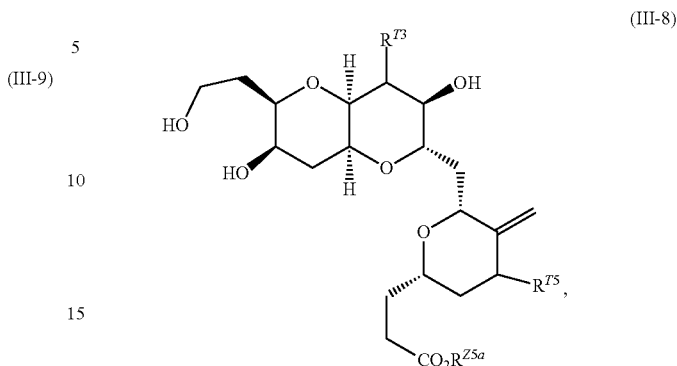

or a salt thereof. The steps of deprotecting and cyclizing may be carried out in separate steps and in either order; or optionally in the same step. In certain embodiments, the deprotecting and cyclizing are carried out in the same step. In certain embodiments, the step of deprotecting and cyclizing is carried out in the presence of an acid (e.g., Lewis acid, Bronsted acid). In certain embodiments, the step of deprotecting and cyclizing is carried out in the presence of a hydride source. In certain embodiments, the step of deprotecting and cyclizing is carried out in the presence of a trialkylsilyl sulfonate or trialkylsilyl halide. In certain embodiments, the step of deprotecting and cyclizing is carried out in the presence of a trialkylsilane. In certain embodiments, the step of deprotecting and cyclizing is carried out in the presence of triethylsilyl trifluoromethylsulfonate ("TES-triflate" or "TESOTf"). In certain embodiments, the step of deprotecting and cyclizing is carried out in the presence of triethylsilane. In certain embodiments, the step of deprotecting and cyclizing is carried out in the presence of TESOTf and triethylsilane.

Catalytic Coupling Reaction Condition

The provided coupling method between the compound of Formula (i) and the aldehyde of Formula (ii) is a catalytic chromium-mediated coupling reaction.

In certain embodiments, the provided coupling method is a catalytic asymmetric Cr-mediated coupling reaction. In certain embodiments, the chromium catalyst is a chromium complex (i.e., comprising a ligand). In certain embodiments, the chromium catalyst is chromium sulfonamide (see, e.g., Namba K et al., *Org. Lett.*, 2004, 6(26), 5031-5033).

In certain embodiments, the chromium sulfonamide is of Formula (S-1):

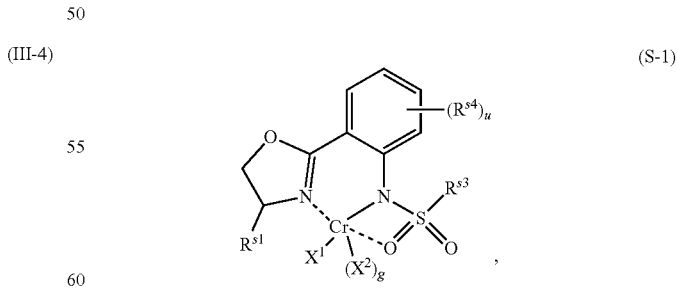

wherein $R^{s1}$ is halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, or optionally substituted heteroaryl;

$R^{s2}$ is hydrogen, optionally substituted alkyl, or a nitrogen protecting group;

$R^{s3}$ is optionally substituted alkyl, optionally substituted aryl, or optionally substituted heteroaryl;

each instance of $R^{s4}$ is independently hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkoxy, an optionally substituted amino group, or optionally substituted acyl;

$X^1$ is halogen;

each instance of $X^2$ is independently halogen or a solvent;

u is 0 or an integer between 1 and 4, inclusive; and g is 0, 1, 2, 3, or 4.

In certain embodiments, the chromium sulfonamide is of Formula (S-1-a) or (S-1-a'):

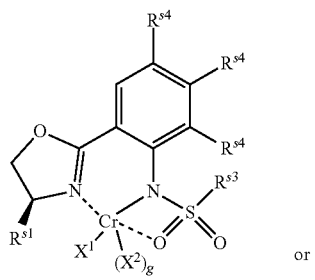

(S-1-a)

or (S-1-a')

In certain embodiments, the chromium sulfonamide is of Formula (S-1-a):

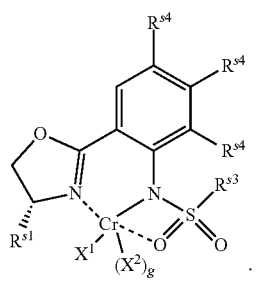

(S-1-a)

In certain embodiments, the chromium sulfonamide is of Formula (S-1-b):

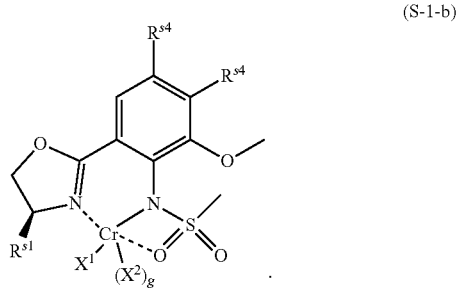

(S-1-b)

In certain embodiments, the chromium sulfonamide is of Formula (S-1-c):

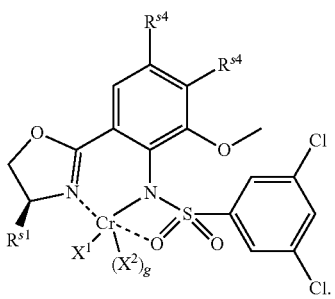

(S-1-c)

In certain embodiments, the chromium sulfonamide is prepared by contacting a chromium salt with a ligand of Formula (S-2):

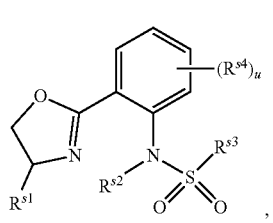

(S-2)

wherein $R^{s1}$, $R^{s2}$, $R^{s3}$, $R^{s4}$, and u are as defined herein.

In certain embodiments, the ligand of Formula (S-2) is of Formula (S-2-a)

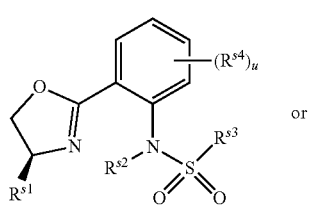

(S-2-a)

or

-continued

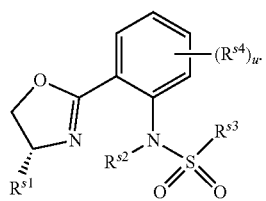
(S-2-a′)

In certain embodiments, the ligand of Formula (S-2) is of Formula (S-2-b):

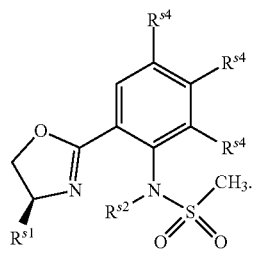
(S-2-b)

In certain embodiments, the ligand of Formula (S-2) is of Formula (S-2-b-i):

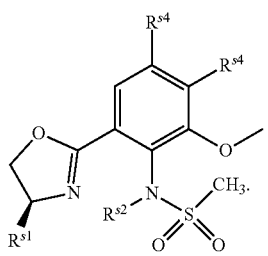
(S-2-b-i)

In certain embodiments, the ligand of Formula (S-2) is of Formula (S-2-c):

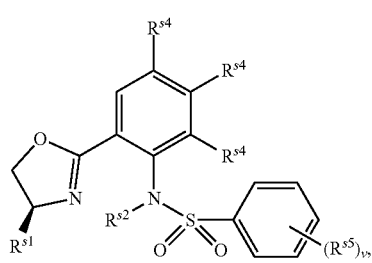
(S-2-c)

wherein $R^{s1}$, $R^{s2}$, $R^{s3}$, $R^{s4}$, and v are as defined herein.

In certain embodiments, the ligand of Formula (S-2) is of Formula (S-2-c-i):

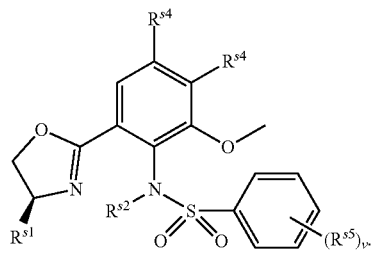
(S-2-c-i)

In certain embodiments, the ligand of Formula (S-2) is of Formula (S-2-c-iii):

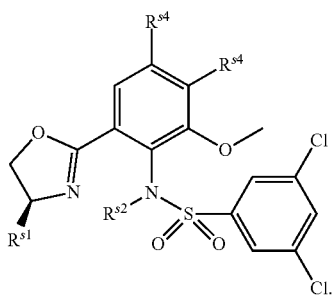
(S-2-c-iii)

In certain embodiments, $X^1$ is chloride. In certain embodiments, $X^1$ is bromide.

In certain embodiments, $X^2$ is a halogen. In certain embodiments, $X^2$ is Cl. In certain embodiments, $X^2$ is Br. In certain embodiments, $X^2$ is I. In certain embodiments, $X^2$ is a solvent. In certain embodiments, the solvent comprises N, O, and/or S. In certain embodiments, the solvent for generating the chromium sulfonamide is THF. In certain embodiments, the solvent for generating the chromium sulfonamide is pyridine.

In certain embodiments, g is 1. In certain embodiments, g is 2. In certain embodiments, g is 3.

In certain embodiments, u is 0. In certain embodiments, u is 1. In certain embodiments, u is 2. In certain embodiments, u is 3.

In certain embodiments, $X^1$ is chloride; $X^2$ is pyridine; g is 1 or 2; and u is 1, 2, or 3. In certain embodiments, $X^1$ is chloride; $X^2$ is pyridine; g is 1; and u is 1, 2, or 3. In certain embodiments, $X^1$ is chloride; $X^2$ is pyridine; g is 2; and u is 1, 2, or 3.

In certain embodiments, $R^{s1}$ is optionally substituted alkyl. In certain embodiments, $R^{s1}$ is unsubstituted alkyl. In certain embodiments, $R^{s1}$ is methyl, ethyl, n-propyl, i-propyl, n-butyl, s-butyl, t-butyl. In certain embodiments, $R^1$ is i-propyl. In certain embodiments, $R^1$ is t-butyl. In certain embodiments, $R^{s1}$ is substituted alkyl.

In certain embodiments, $R^{s2}$ is hydrogen.

In certain embodiments, $R^{s3}$ is optionally substituted alkyl. In certain embodiments, $R^{s3}$ is unsubstituted alkyl. In certain embodiments, $R^{s3}$ is methyl or ethyl. In certain embodiments, $R^{s3}$ is substituted alkyl. In certain embodiments, $R^{s3}$ is optionally substituted aryl. In certain embodiments, $R^{s3}$ is optionally substituted phenyl. In certain embodiments, $R^{s3}$ is unsubstituted phenyl. In certain embodiments, $R^{s3}$ is substituted phenyl. In certain embodiments, $R^3$ is halogenated phenyl. In certain embodiments, $R^{s3}$ is optionally substituted naphthyl. In certain embodiments, $R^{s3}$ is unsubstituted naphthyl.

In certain embodiments, each instance of $R^{s4}$ is independently hydrogen, halogen, optionally substituted alkyl, optionally substituted aryl, optionally substituted heteroaryl, or optionally substituted alkoxy. In certain embodiments, at least one instance of $R^{s4}$ is hydrogen. In certain embodiments, at least one instance of $R^{s4}$ is optionally substituted alkyl. In certain embodiments, one instance of $R^{s4}$ is optionally substituted alkyl. In certain embodiments, one instance of $R^{s4}$ is unsubstituted alkyl (e.g., methyl or ethyl). In certain embodiments, two instances of $R^{s4}$ are optionally substituted alkyl. In certain embodiments, two instances of $R^{s4}$ are unsubstituted alkyl (e.g., methyl or ethyl). In certain embodiments, at least once instance of $R^{s4}$ is optionally substituted alkoxy. In certain embodiments, two instances of $R^{s4}$ are optionally substituted alkoxy. In certain embodiments, two instances of $R^{s4}$ are unsubstituted alkoxy (e.g. —$OCH_3$).

In certain embodiments, each instance of $R^{s5}$ is independently hydrogen, halogen, optionally substituted alkyl, optionally substituted aryl, or optionally substituted heteroaryl. In certain embodiments, at least one instance of $R^{s5}$ is hydrogen. In certain embodiments, at least one instance of $R^{s5}$ is halogen. In certain embodiments, two instances of $R^{s5}$ are halogen.

In certain embodiments, v is 1. In certain embodiments, v is 2.

In certain embodiments, the ligand of Formula (S-2) is of the following formula:

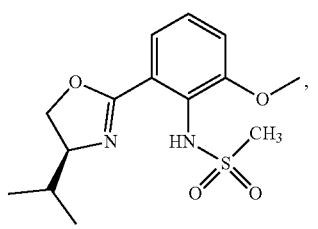

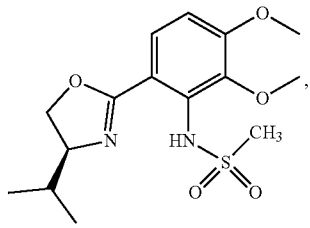

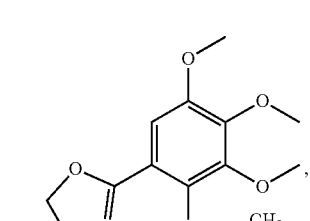

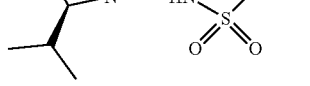

-continued

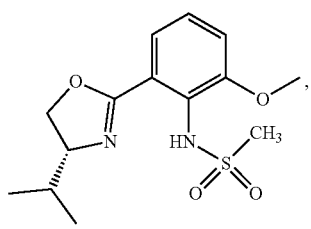

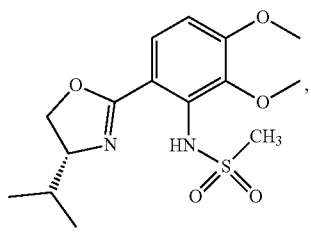

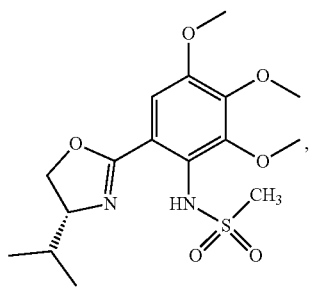

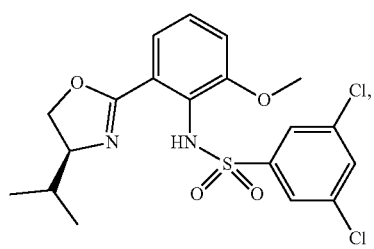

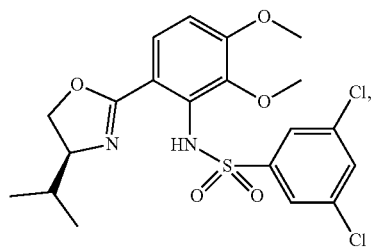

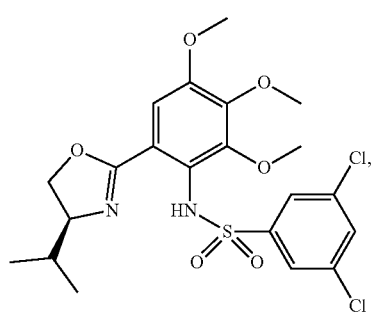

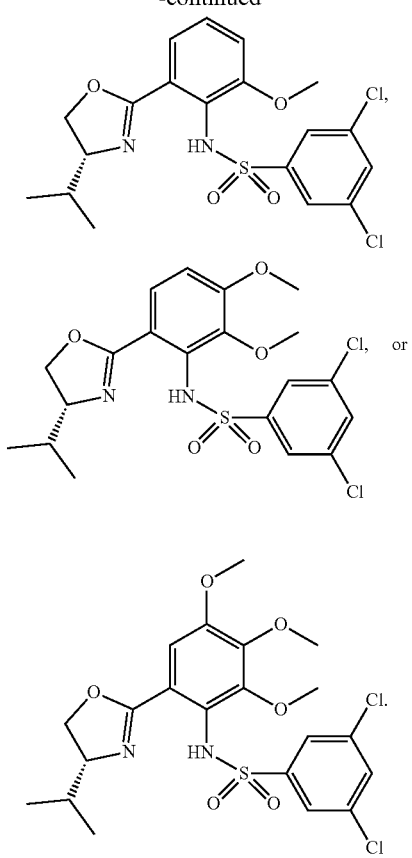

In certain embodiments, the chromium salt used to prepare the chromium complex is chromium halide. In certain embodiments, the chromium salt is a chromium (II) salt. In certain embodiments, the chromium salt is CrCl$_2$. In certain embodiments, the chromium salt is CrBr$_2$. In certain embodiments, the chromium salt is a chromium (III) salt. In certain embodiments, the chromium salt is CrCl$_3$. In certain embodiments, the chromium salt is CrBr$_3$.

In certain embodiments, the amount of chromium or chromium complex is catalytic. In certain embodiments, the chromium catalyst is at a concentration of about 1 mol % to about 30 mol % of the compound of Formula (i) or Formula (ii). In certain embodiments, the chromium catalyst is at a concentration of about 1 mol % to about 25 mol % of the compound of Formula (i) or Formula (ii). In certain embodiments, the chromium catalyst is at a concentration of about 1 mol % to about 20 mol % of the compound of Formula (i) or Formula (ii). In certain embodiments, the chromium catalyst is at a concentration of about 1 mol % to about 15 mol % of the compound of Formula (i) or Formula (ii). In certain embodiments, the chromium catalyst is at a concentration of about 5 mol % to about 15 mol % of the compound of Formula (i) or Formula (ii). In certain embodiments, the chromium catalyst is at a concentration of about 10 mol % of the compound of Formula (i) or Formula (ii).

In certain embodiments, the provided coupling method comprises a second catalyst. In certain embodiments, the second catalyst is a transition metal or transition metal complex. In certain embodiments, the second catalyst is a nickel complex.

In certain embodiments, the nickel complex is of Formula (N-1):

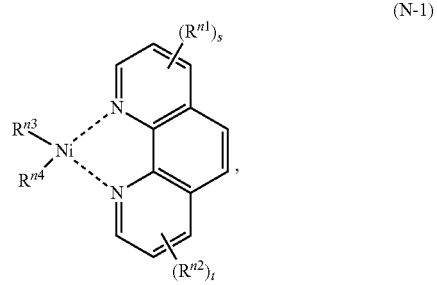

wherein each instance of $R^{a1}$ and $R^{a2}$ is independently hydrogen, halogen, —CN, —NO$_2$, —N$_3$, optionally substituted alkyl, optionally substituted alkenyl, optionally substituted alkynyl, optionally substituted carbocyclyl, optionally substituted aryl, optionally substituted heterocyclyl, optionally substituted heteroaryl, optionally substituted alkoxy, an optionally substituted amino group, or optionally substituted acyl;

each of $R^{a3}$ and $R^{a4}$ is independently halogen, —CN, —NO$_2$, optionally substituted alkoxy, or an optionally substituted amino group;

s is an integer between 1 and 3, inclusive; and t is an integer between 1 and 3, inclusive.

In certain embodiments, the nickel complex of Formula (N-1) is of Formula (N-1-a):

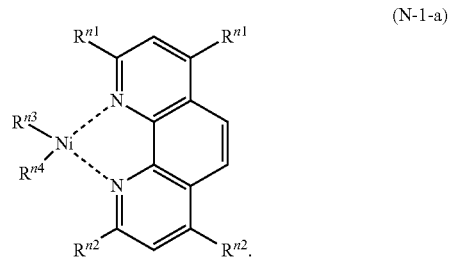

In certain embodiments, the nickel complex of Formula (N-1) is of Formula (N-1-a):

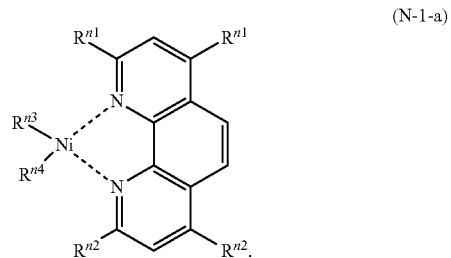

In certain embodiments, the nickel complex of Formula (N-1) is of Formula (N-1-b):

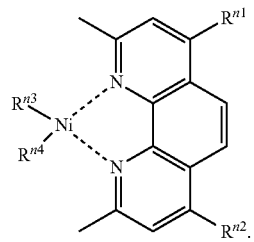
(N-1-b)

In certain embodiments, the nickel complex of Formula (N-1) is of Formula (N-1-c):

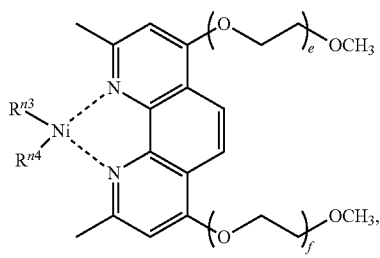
(N-1-c)

wherein e is 0, 1, 2, 3, 4, 5, or 6; and f is 0, 1, 2, 3, 4, 5, or 6.

In certain embodiments, the nickel complex of Formula (N-1) is of one of the following formulae:

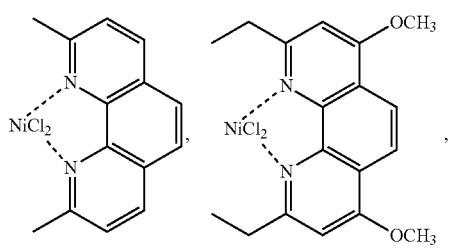

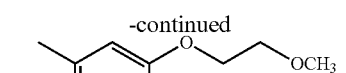
-continued

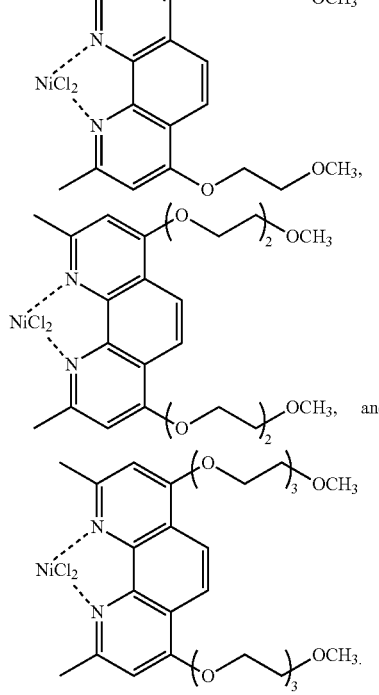

In certain embodiments, each instance of $R^{n1}$ is independently hydrogen, halogen, optionally substituted alkyl, optionally substituted aryl, optionally substituted heteroaryl, or optionally substituted alkoxy. In certain embodiments, at least one instance of $R^{n1}$ is hydrogen. In certain embodiments, at least one instance of $R^{n1}$ is optionally substituted alkyl. In certain embodiments, one instance of $R^{n1}$ is optionally substituted alkyl. In certain embodiments, one instance of $R^{n1}$ is unsubstituted alkyl (e.g. methyl or ethyl). In certain embodiments, two instances of $R^{n1}$ are optionally substituted alkyl. In certain embodiments, two instances of $R^{n1}$ are unsubstituted alkyl (e.g. methyl or ethyl). In certain embodiments, at least one instance of $R^{n1}$ is optionally substituted. In certain embodiments, two instances of $R^{n1}$ are optionally substituted alkoxy. In certain embodiments, two instances of $R^{n1}$ are unsubstituted alkoxy (e.g. —$OCH_3$). In certain embodiments, two instances of $R^{n1}$ are substituted alkoxy.

In certain embodiments, each instance of $R^{n2}$ is independently hydrogen, halogen, optionally substituted alkyl, optionally substituted aryl, optionally substituted heteroaryl, or optionally substituted alkoxy. In certain embodiments, at least one instance of $R^{n2}$ is hydrogen. In certain embodiments, at least one instance of $R^{n2}$ is optionally substituted alkyl. In certain embodiments, one instance of $R^{n2}$ is optionally substituted alkyl. In certain embodiments, one instance of $R^{n2}$ is unsubstituted alkyl (e.g. methyl or ethyl). In certain embodiments, two instances of $R^{n2}$ are optionally substituted alkyl. In certain embodiments, two instances of $R^{n2}$ are unsubstituted alkyl (e.g. methyl or ethyl). In certain embodiments, at least one instance of $R^{n2}$ is optionally substituted. In certain embodiments, two instances of $R^{n2}$ are optionally substituted alkoxy. In certain embodiments, two instances of $R^{n2}$ are unsubstituted alkoxy (e.g. —$OCH_3$). In certain embodiments, two instances of $R^{n2}$ are substituted alkoxy.

In certain embodiments, at least one instance of $R^{n1}$ and $R^{n2}$ are the same. In certain embodiments, two instances of $R^{n1}$ and $R^{n2}$ are the same.

In certain embodiments, the amount of nickel or nickel complex is catalytic. In certain embodiments, the nickel catalyst is at a concentration of about 0.001 mol % to about 30 mol % of the compound of Formula (i) or Formula (ii). In certain embodiments, the nickel catalyst is at a concentration of about 0.001 mol % to about 20 mol % of the compound of Formula (i) or Formula (ii). In certain embodiments, the nickel catalyst is at a concentration of about 0.001 mol % to about 10 mol % of the compound of Formula (i) or Formula (ii). In certain embodiments, the nickel catalyst is at a concentration of about 0.001 mol % to about 5 mol % of the compound of Formula (i) or Formula (ii). In certain embodiments, the nickel catalyst is at a concentration of about 0.001 mol % to about 1 mol % of the compound of Formula (i) or Formula (ii). In certain embodiments, the nickel catalyst is at a concentration of about 0.01 mol % to about 0.5 mol % of the compound of Formula (i) or Formula (ii). In certain embodiments, the nickel catalyst is at a concentration of about 0.05 mol % to about 0.1 mol % of the compound of Formula (i) or Formula (ii). In certain embodiments, the nickelcatalyst is at a concentration of about 0.1 mol % of the compound of Formula (i) or Formula (ii). In certain embodiments, the nickel catalyst is at a concentration of about 0.01 mol % to about 0.05 mol % of the compound of Formula (i) or Formula (ii). In certain embodiments, the nickel catalyst is at a concentration of about 0.05 mol % of the compound of Formula (i) or Formula (ii).

In certain embodiments, the chromium catalyst is at a concentration of about 1 mol % to about 20 mol % of the compound of Formula (i) or Formula (ii) and the nickel catalyst is at a concentration of about 0.01 mol % to about 0.5 mol % of the compound of Formula (i) or Formula (ii). In certain embodiments, the chromium catalyst is at a concentration of about 1 mol % to about 20 mol % of the compound of Formula (i) or Formula (ii) and the nickel catalyst is at a concentration of about 0.01 mol % to about 0.1 mol % of the compound of Formula (i) or Formula (ii). In certain embodiments, the chromium catalyst is at a concentration of about 10 mol % of the compound of Formula (i) or Formula (ii) and the nickel catalyst is at a concentration of about 0.1 mol % of the compound of Formula (i) or Formula (ii). In certain embodiments, the chromium catalyst is at a concentration of about 10 mol % of the compound of Formula (i) or Formula (ii) and the nickel catalyst is at a concentration of about 0.05 mol % of the compound of Formula (i) or Formula (ii).

In certain embodiments, an additional catalyst is present in the step of coupling. In certain embodiments, the additional catalyst is a transition metal or transitional metal complex. In certain embodiments, the additional catalyst is a silyl complex. In certain embodiments, the additional catalyst is TES-Cl. In certain embodiments, the additional catalyst is a zirconium catalyst. In certain embodiments, the zirconium catalyst is a zirconium complex. In certain embodiments, the zirconium catalyst is $Zr(Cp)_2Cl_2$.

In certain embodiments, the catalysts in the step of coupling are a chromium catalyst, a nickel complex, and a zirconium catalyst. In certain embodiments, the catalysts in the step of coupling are a chromium catalyst and a zirconium catalyst. In certain embodiments, the zirconium catalyst is a zirconium complex. In certain embodiments, the zirconium catalyst is $Zr(Cp)_2Cl_2$.

In certain embodiments, the amount of the additional catalyst is stoichiometric. In certain embodiments, the amount of zirconium complex is stoichiometric. In certain embodiments, the zirconium complex is at a concentration of about 0.1 eq to about 5.0 eq of the compound of Formula (i) or Formula (ii). In certain embodiments, the zirconium complex is at a concentration of about 1.0 eq to about 4.0 eq of the compound of Formula (i) or Formula (ii). In certain embodiments, the zirconium complex is at a concentration of about 1.0 eq to about 3.0 eq of the compound of Formula (i) or Formula (ii). In certain embodiments, the zirconium complex is at a concentration of about 1.0 eq to about 2.0 eq of the compound of Formula (i) or Formula (ii). In certain embodiments, the zirconium complex is at a concentration of about 1.5 eq of the compound of Formula (i) or Formula (ii).

In certain embodiments, the step of coupling is performed in the presence of a reducing agent. The reducing agent can reduce chromium in the catalytic cycle. In certain embodiments, the reducing agent is a transition metal. In certain embodiments, the reducing agent is manganese (Mn).

In certain embodiments, the reducing agent is at a concentration of about 1.0 eq to about 10.0 eq of the compound of Formula (i) or Formula (ii). In certain embodiments, the reducing agent is at a concentration of about 1.0 eq to about 8.0 eq of the compound of Formula (i) or Formula (ii). In certain embodiments, the reducing agent is at a concentration of about 1.0 eq to about 6.0 eq of the compound of Formula (i) or Formula (ii). In certain embodiments, the reducing agent is at a concentration of about 1.0 eq to about 4.0 eq of the compound of Formula (i) or Formula (ii). In certain embodiments, the reducing agent is at a concentration of about 4.0 eq of the compound of Formula (i) or Formula (ii).

In certain embodiments, the step of coupling is performed in the presence of an inorganic salt. In certain embodiments, the inorganic salt is an IA group salt. In certain embodiments, the inorganic salt is LiCl.

In certain embodiments, the inorganic salt is at a concentration of about 1.0 eq to about 10.0 eq of the compound of Formula (i) or Formula (ii). In certain embodiments, the inorganic salt is at a concentration of about 1.0 eq to about 8.0 eq of the compound of Formula (i) or Formula (ii). In certain embodiments, the inorganic salt is at a concentration of about 1.0 eq to about 6.0 eq of the compound of Formula (i) or Formula (ii). In certain embodiments, the inorganic salt is at a concentration of about 1.0 eq to about 4.0 eq of the compound of Formula (i) or Formula (ii). In certain embodiments, the inorganic salt is at a concentration of about 4.0 eq of the compound of Formula (i) or Formula (ii).

In certain embodiments, the provided coupling reaction can be carried out in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are $CH_2Cl_2$, MeCN, EtCN, toluene, DMF, diglyme, THF, and DMSO. In certain embodiments, the solvent is EtCN.

In certain embodiments, the compound of Formula (i) or Formula (ii) is at the concentration of about 0.05 to about 5.0 M. In certain embodiments, the compound of Formula (i) or Formula (ii) is at the concentration of about 0.05 to about 3.0 M. In certain embodiments, the compound of Formula (i) or Formula (ii) is at the concentration of about 0.05 to about 1.0 M. In certain embodiments, the compound of Formula (i) or Formula (ii) is at the concentration of about 0.1 to about 1.0 M. In certain embodiments, the compound of Formula (i) or Formula (ii) is at the concentration of about 0.1 to about 0.5

M. In certain embodiments, the compound of Formula (i) or Formula (ii) is at the concentration of about 0.4 M.

Synthesis of Halichondrins

In another aspect, provided herein are methods of synthesizing halichondrin A, B, and C, and analogs thereof (e.g., homohalichondrin A, B, C; norhalichondrin A, B, C), from the C1-C19 building blocks and the C20-C38 building blocks of halichondrins provided herein. The synthetic routes presented herein include: (1) synthesis of the macrocyclic core via an asymmetric nickel/chromium-mediated coupling, followed by base-induced furan formation, and macrolactonization (Scheme TI); (2) synthesis of an unsaturated ketone intermediate via nickel/chromium-mediated coupling, followed by Dess-Martin oxidation (Schemes T2-T4); and (3) a selective acid-mediated equilibration of C38-epi-halichondrins (Schemes T2-T4).

In Scheme T1, compounds of Formula (TJ-1) are C20-C38 building blocks, and compounds of Formula (TC-1) are C1-C19 building blocks of halichondrins. These building blocks can be joined via the process shown in Scheme T1 to form right halves of halichondrins (e.g., compounds of Formula (TE-1)). Once the right half of a halichondrin is assembled, the right half can be coupled to a left halves (e.g., compounds of Formulae (TI-1), (TK-1), and (TK-1)) via the processes shown in Schemes T2-T4.

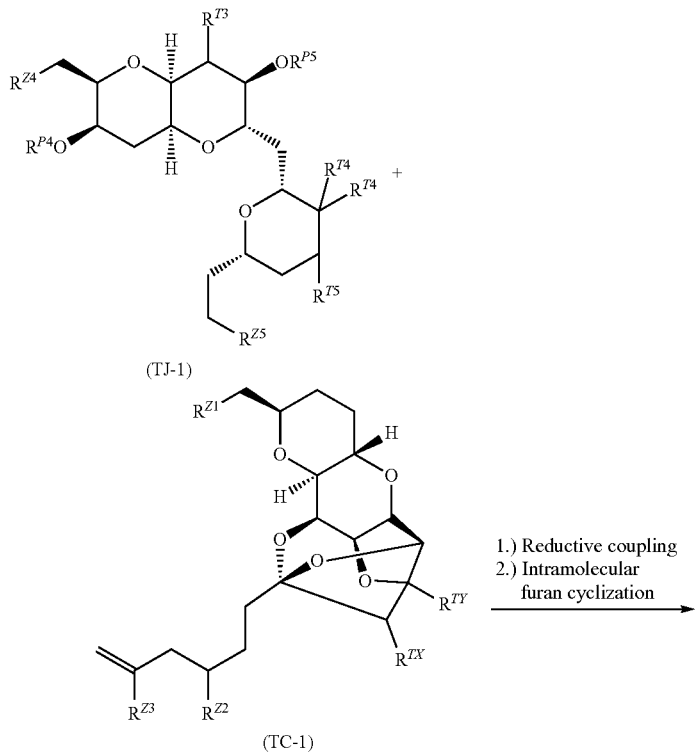

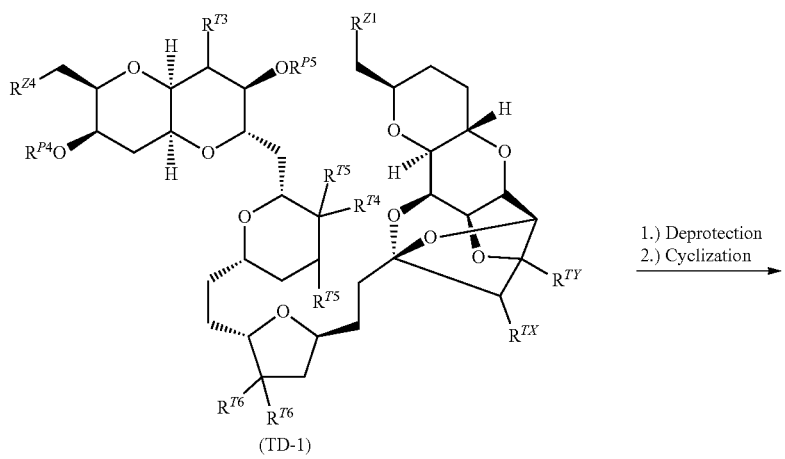

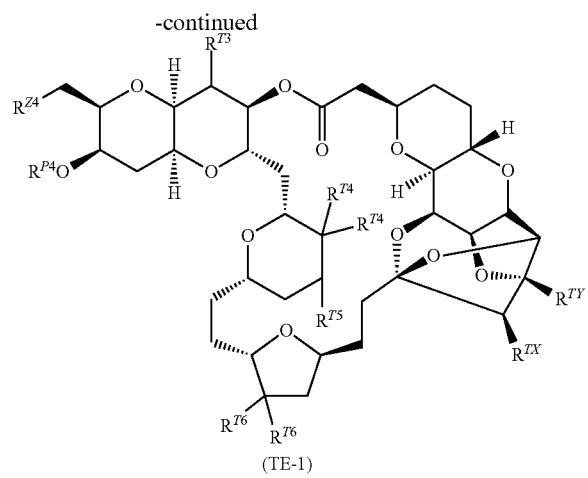
(TE-1)
Scheme T2
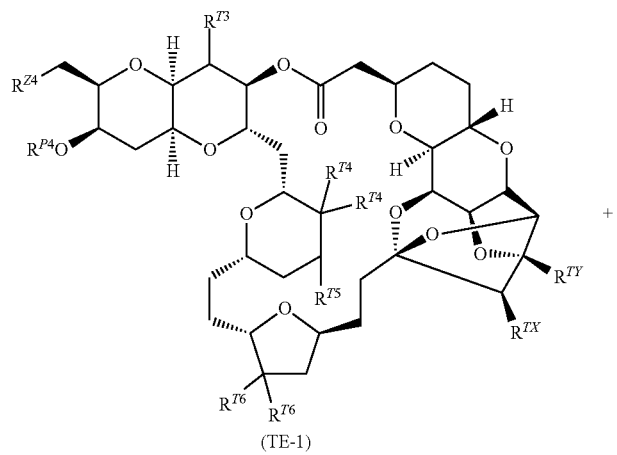
(TE-1)    +
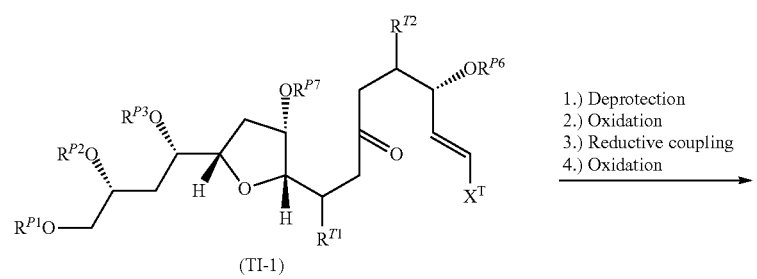
(TI-1)
1.) Deprotection
2.) Oxidation
3.) Reductive coupling
4.) Oxidation -continued
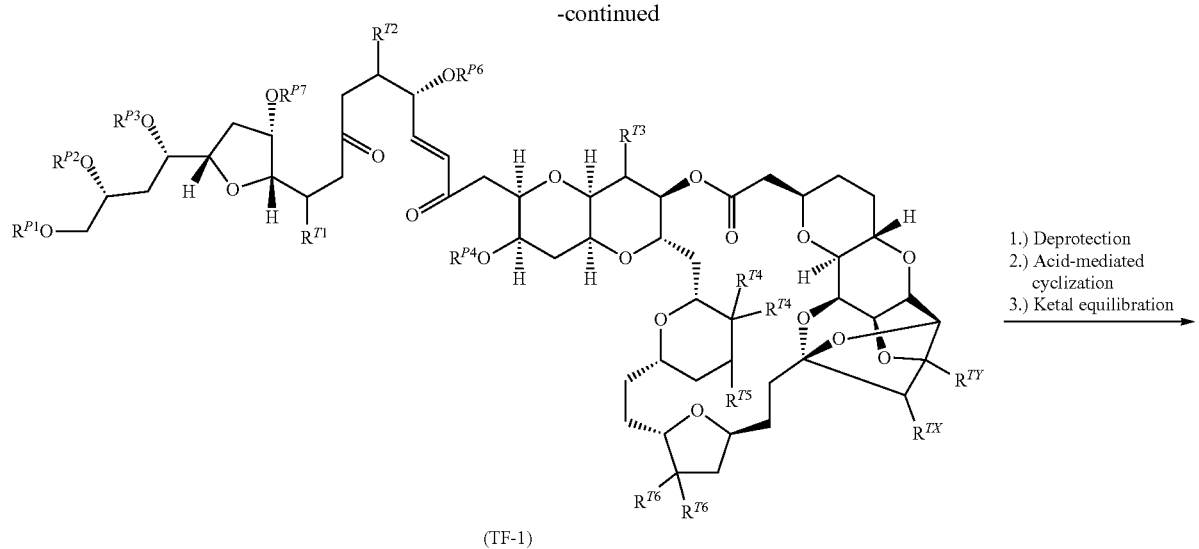
(TF-1)
1.) Deprotection
2.) Acid-mediated cyclization
3.) Ketal equilibration
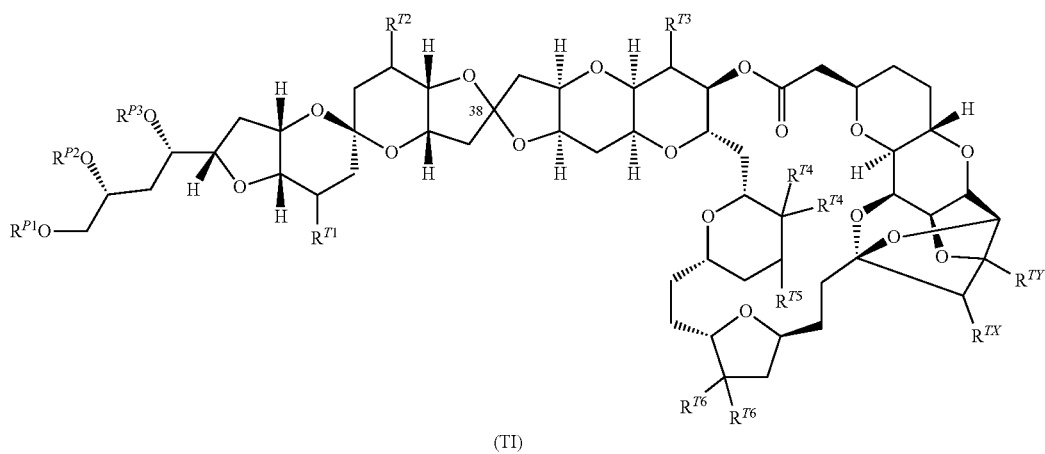
(TI)
Scheme T3
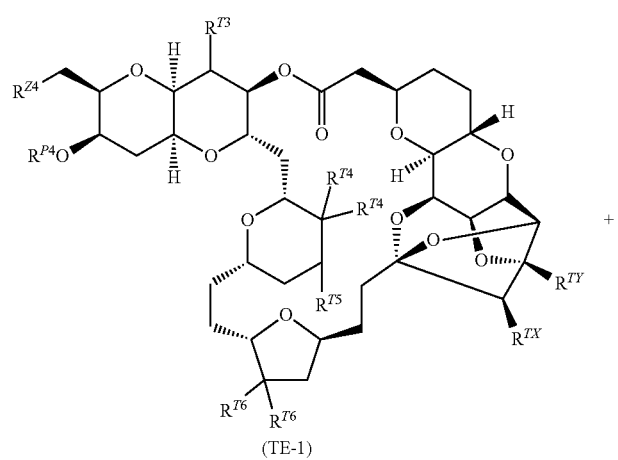
(TE-1)
+

-continued
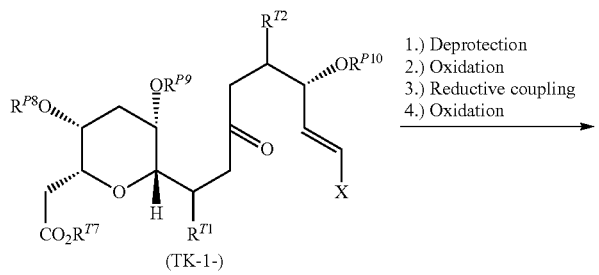
(TK-1-)
1.) Deprotection
2.) Oxidation
3.) Reductive coupling
4.) Oxidation
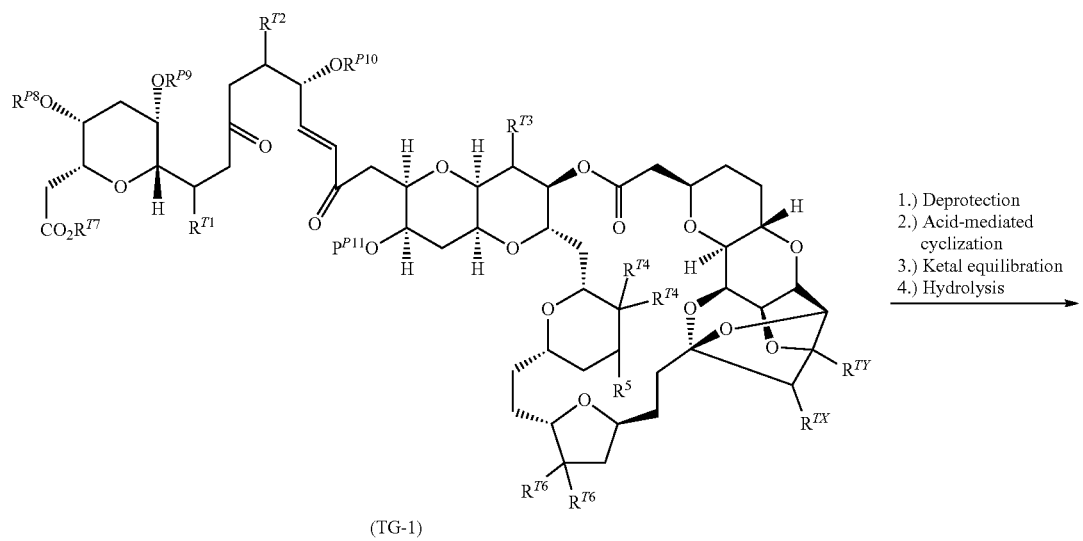
(TG-1)
1.) Deprotection
2.) Acid-mediated cyclization
3.) Ketal equilibration
4.) Hydrolysis
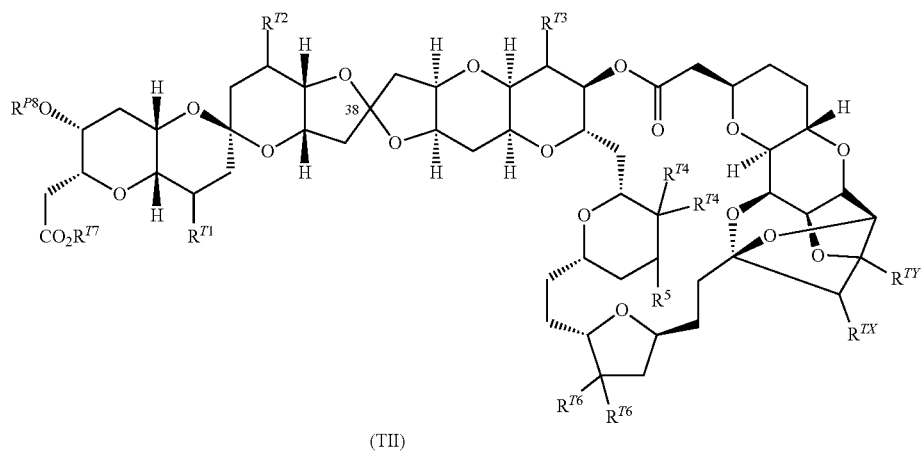
(TII)

Scheme T4
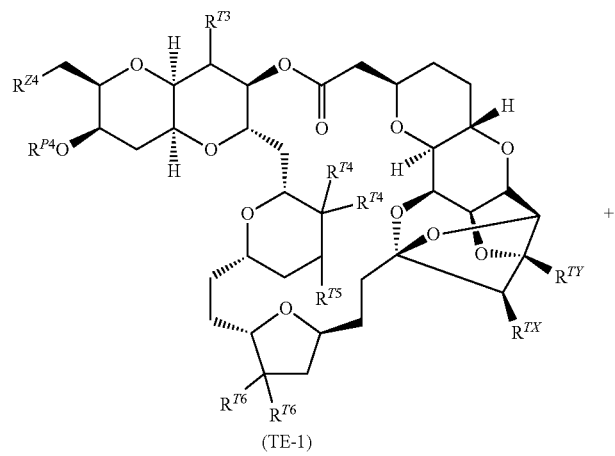
(TE-1)
+
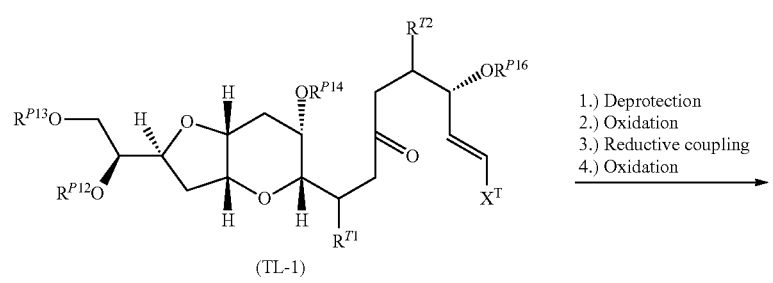
(TL-1)
1.) Deprotection
2.) Oxidation
3.) Reductive coupling
4.) Oxidation

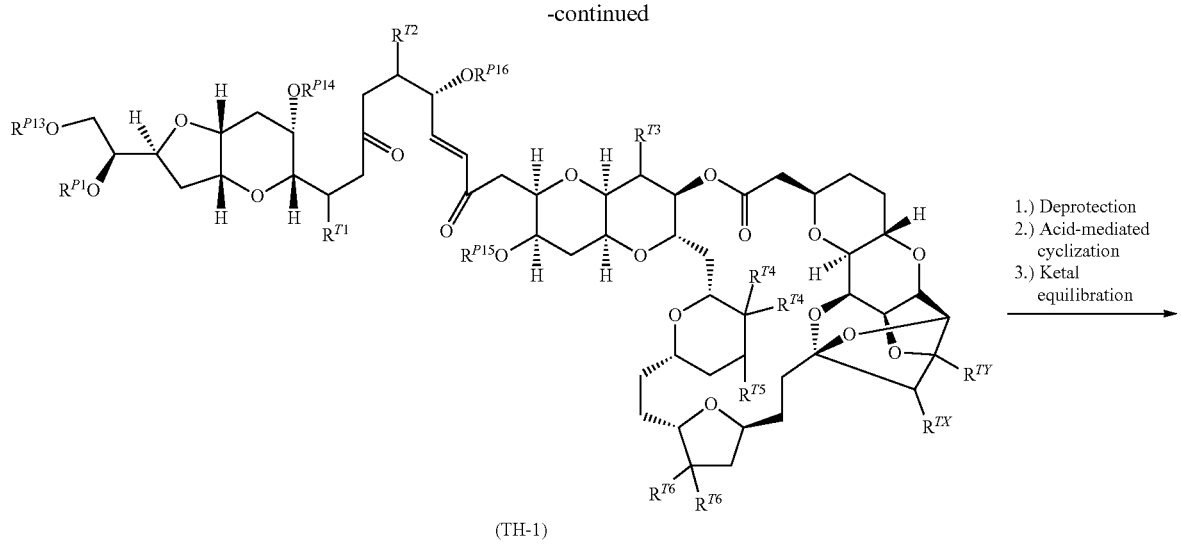

(TH-1)

1.) Deprotection
2.) Acid-mediated cyclization
3.) Ketal equilibration

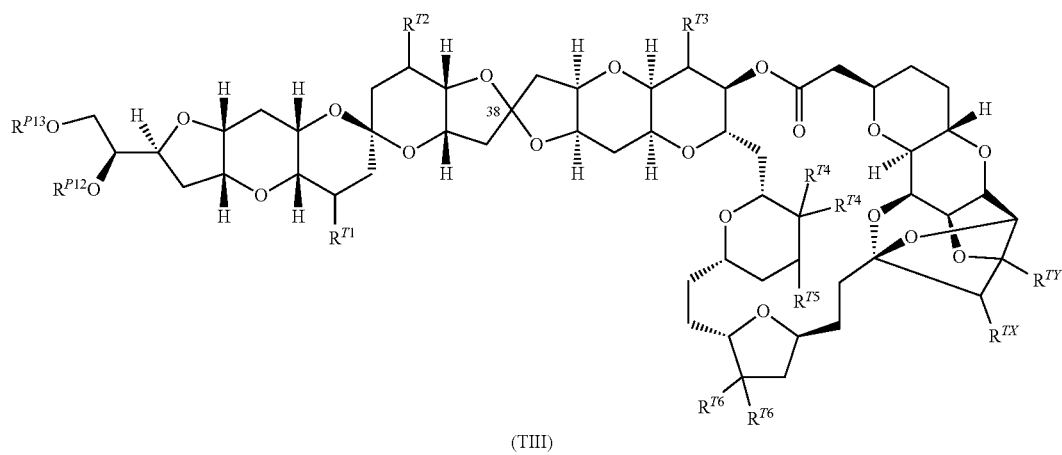

(TIII)

As shown in Schemes T1-T4, the C1-C19 building block of halichondrins and analogs thereof are of Formula (TC-1). In certain embodiments, the compound of Formula (TC-1) is of Formula (I-a-4) or a salt thereof. In certain embodiments, the compound of Formula (TC-1) is of Formula (I-b-6) or a salt thereof. In certain embodiments, the compound of Formula (TC-1) is of Formula (I-b-9) or a salt thereof. In certain embodiments, the compound of Formula (TC-1) is of Formula (I-b-13) or a salt thereof.

In certain embodiments, as shown in Scheme T2, the halichondrins and analogs synthesized from the C1-C19 building blocks and C20-C38 building blocks are of Formula (TI). In certain embodiments, the compound of Formula (TI) is of the formula:

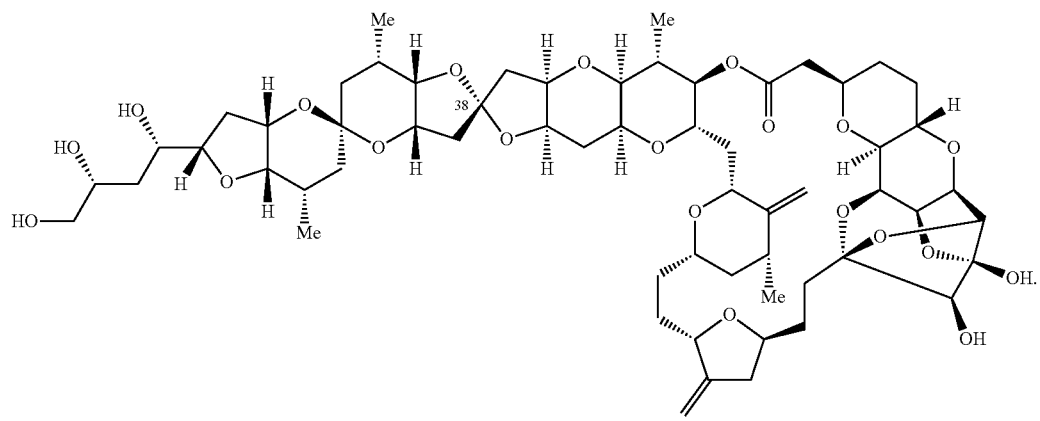
halichondrin A
In certain embodiments, the compound of Formula (TI) is of the formula:
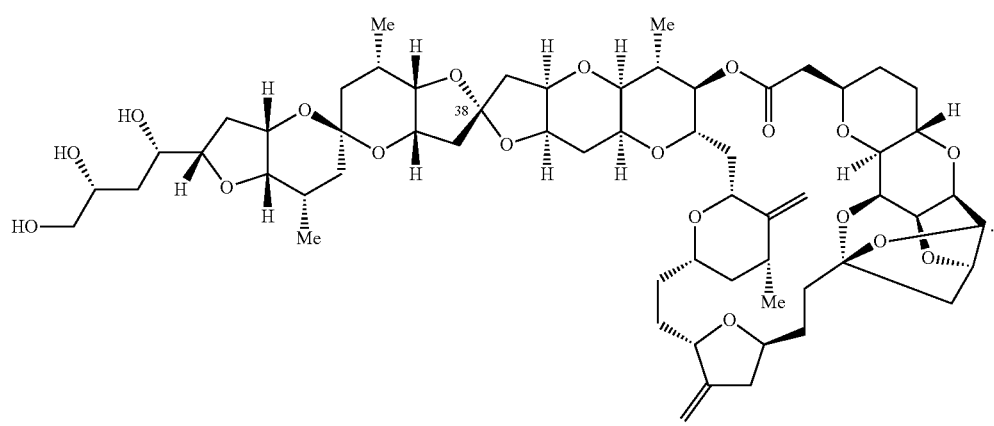
halichondrin B
In certain embodiments, the compound of Formula (TI) is of the formula:
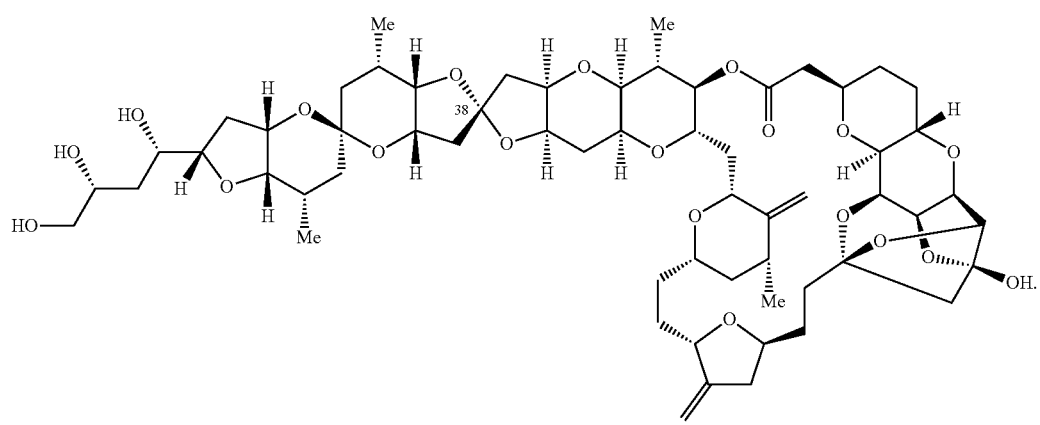
halichondrin C In certain embodiments, preparation of compounds of Formula (TI) and salts thereof comprises cyclizing an intermediate compound of Formula (TF-1) or a salt thereof (see Scheme T2). In certain embodiments, when a compound of Formula (TF-1) is protected (e.g., with silyl or benzylic protecting groups), the synthetic route comprises a deprotection step prior to cyclization. In certain embodiments, deprotection of a compound of Formula (TF-1) comprises a source of fluoride (e.g., TBAF, HF.pyridine). In certain embodiments, deprotection of a compound of Formula (TF-1) comprises a hydrogenolysis (e.g., a palladium or nickel catalyst and $H_2$) or oxidation (e.g., DDQ) step. In certain embodiments, the cyclization conditions comprise an acid. In certain embodiments, the cyclization conditions comprise a Brønsted acid (i.e., a source of $H^+$). In certain embodiments, the cyclization conditions comprise an organic acid (e.g., PPTS). In certain embodiments, the cyclization conditions provide a compound of Formula (TI) as a single diastereomer. In certain embodiments, the cyclization conditions provide a diastereomeric mixture that is enriched in one of two epimeric C38 ketals. In certain embodiments, the synthetic route comprises an equilibration step to enrich a compound of Formula (TI) in one of two epimeric C38 ketals. In certain embodiments, the equilibration step enriches a compound of Formula (TI) in the (R)-epimer. In certain embodiments, the equilibration step enriches a compound of Formula (TI) in the (R)-epimer in a range of 2:1, 3:1, 4:1, 5:1, or >5:1. In certain embodiments, the equilibration step enriches a compound of Formula (TI) in the (S)-epimer. In certain embodiments, the equilibration step enriches a compound of Formula (TI) in the (S)-epimer in a range of 2:1, 3:1, 4:1, 5:1, 10:1, or >10:1. In certain embodiments, the equilibration step comprises a Lewis acid. In certain embodiments, the equilibration step comprises a silyl Lewis acid (e.g., a silicon tetrahalide or and organosilicon halide or triflate). In certain embodiments, the equilibration step comprises trimethylsilyl triflate. In certain embodiments, the equilibration step comprises a solvent. In certain embodiments, the equilibration step comprises a halogenated (e.g., dichloromethane) or ethereal (e.g., diethyl ether) solvent.

As described herein, the deprotection, cyclization, and equilibration of a compound of Formula (TF-1) to yield a compound of Formula (TI) can be performed in two steps when particular protecting groups are utilized on the intermediate (TF-1). For example, when $R^{P1}$, $R^{P2}$, and $R^{P8}$ are TBS, and $R^{P3}$, $R^{P7}$, and $R^{P4}$ are TES, the deprotection, cyclization, and equilibration can be performed in two steps by treating a compound of Formula (TF-1) with a fluoride source, followed by an acid. Any fluoride source known in the art may be used. Examples of fluoride sources include, but are not limited to, HF-pyridine, KF, CsF, AgF, ammonium fluoride, and tetraalkylammonium fluorides. In certain embodiments, the fluoride source is a tetraalkylammonium fluoride (e.g., tetramethylammonium fluoride, tetraethylammonium fluoride, tetrabutylammonium fluoride, benzyltrimethylammonium fluoride). In certain embodiments, the acid is a Brønsted acid. In certain embodiments, the acid is an inorganic acid (e.g., HCl, HF, HBr). In certain embodiments, the acid is an organic acid (e.g., carboxylic acid, sulfinic acid, sulfonic acid, phosphoric acid). In certain embodiments, the acid is a carboxylic acid (e.g., acetic acid, trfluoroacetic acid (TFA), pivalic acid). For example, in certain embodiments wherein $R^{P1}$, $R^{P2}$, and $R^{P8}$ are TBS, and $R^{P3}$, $R^{P7}$, and $R^{P4}$ are TES, a compound of Formula (TF-1) can be convered to a compound of Formula (TI) by treatment with TBAF and pivalic acid, followed by treatment with PPTS (see, e.g., FIG. 29).

In certain embodiments, preparation of C38 epi-halichondrin A comprises an acid-mediated equilibration of the C38 ketal stereocenter of halichondrin A. In certain embodiments, preparation of halichondrin A comprises an acid-mediated equilibration of the C38 ketal stereocenter of C38 epi-halichondrin A.

In certain embodiments, preparation of C38 epi-halichondrin B comprises an acid-mediated equilibration of the C38 ketal stereocenter of halichondrin B. In certain embodiments, preparation of halichondrin B comprises an acid-mediated equilibration of the C38 ketal stereocenter of C38 epi-halichondrin B.

In certain embodiments, preparation of C38 epi-halichondrin C comprises an acid-mediated equilibration of the C38 ketal stereocenter of halichondrin C. In certain embodiments, preparation of halichondrin C comprises an acid-mediated equilibration of the C38 ketal stereocenter of C38 epi-halichondrin C.

In certain embodiments, as shown in Scheme T3, the halichondrins and analogs synthesized from the C1-C19 building blocks and C20-C38 building blocks are of Formula (TII). In certain embodiments, the compound of Formula (TII) is of one of the following formulae:

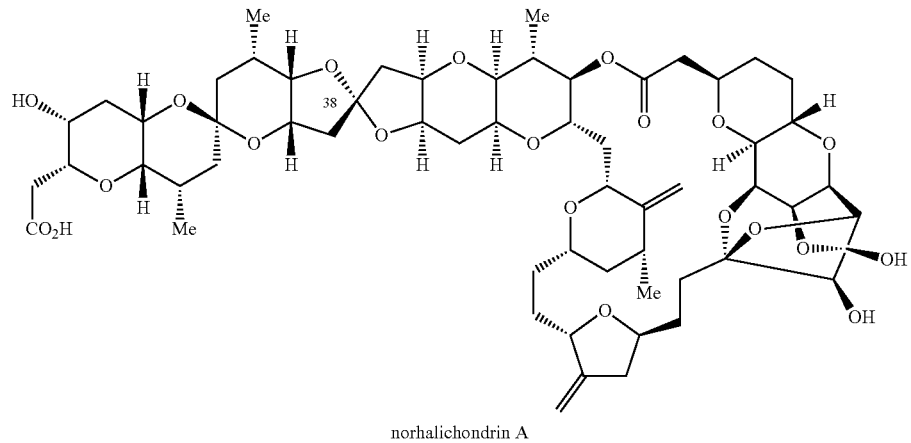

norhalichondrin A

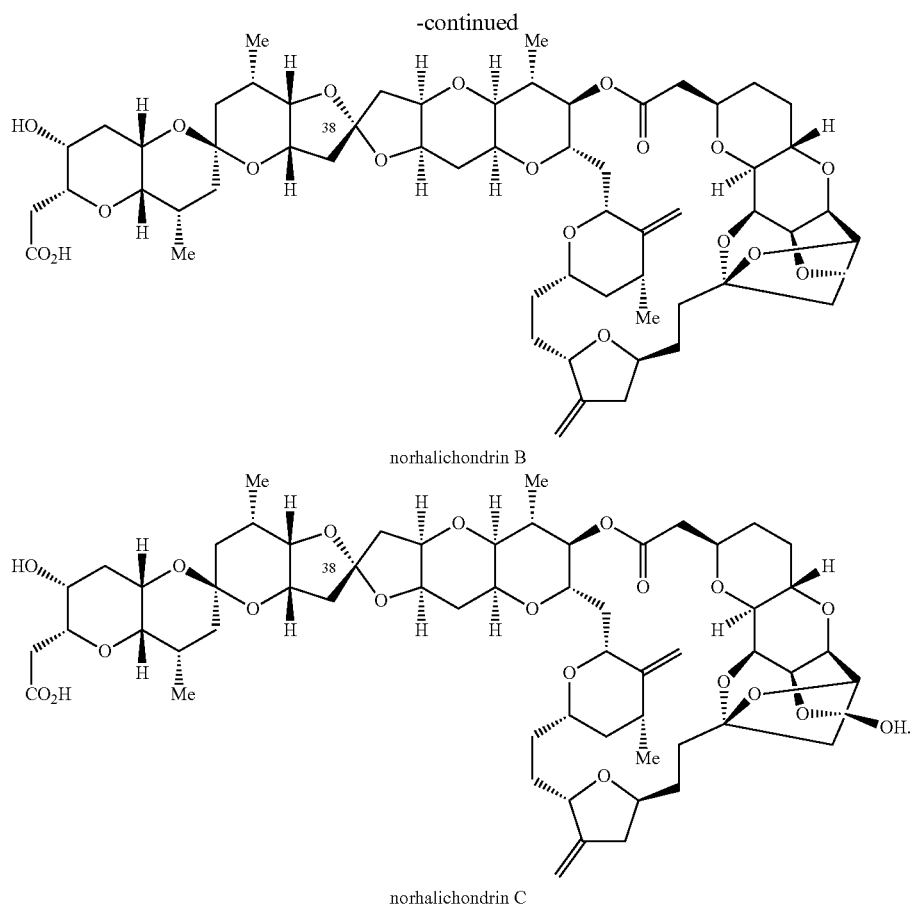

norhalichondrin B norhalichondrin C

In certain embodiments, preparation of compounds of Formula (TII) and salts thereof comprises cyclizing an intermediate compound of Formula (TG-1) or a salt thereof (see Scheme T3). In certain embodiments, when a compound of Formula (TG-1) is protected (e.g., with silyl or benzylic protecting groups), the synthetic route comprises a deprotection step prior to cyclization. In certain embodiments, deprotection of a compound of Formula (TG-1) comprises a source of fluoride (e.g., TBAF, HF.pyridine). In certain embodiments, deprotection of a compound of Formula (TG-1) comprises a hydrogenolysis (e.g., a palladium or nickel catalyst and $H_2$) or oxidation (e.g., DDQ) step. In certain embodiments, the cyclization conditions comprise an acid. In certain embodiments, the cyclization conditions comprise a Brønsted acid (i.e., a source of H+). In certain embodiments, the cyclization conditions comprise an organic acid (e.g., PPTS). In certain embodiments, the cyclization conditions provide a compound of Formula (TII) as a single diastereomer. In certain embodiments, the cyclization conditions provide a diastereomeric mixture that is enriched in one of two epimeric C38 ketals. In certain embodiments, the synthetic route comprises an equilibration step to enrich a compound of Formula (TII) in one of two epimeric C38 ketals. In certain embodiments, the equilibration step enriches a compound of Formula (TII) in the (R)-epimer. In certain embodiments, the equilibration step enriches a aldehyde of Formula (ii) in the (R)-epimer in a range of 2:1, 3:1, 4:1, 5:1, or >5:1. In certain embodiments, the equilibration step enriches a aldehyde of Formula (ii) in the (S)-epimer. In certain embodiments, the equilibration step enriches a aldehyde of Formula (ii) in the (S)-epimer in a range of 2:1, 3:1, 4:1, 5:1, 10:1, or >10:1. In certain embodiments, the equilibration step comprises a Lewis acid. In certain embodiments, the equilibration step comprises a silyl Lewis acid (e.g., a silicon tetrahalide or and organosilicon halide or triflate). In certain embodiments, the equilibration step comprises trimethylsilyl triflate. In certain embodiments, the equilibration step comprises a solvent. In certain embodiments, the equilibration step comprises a halogenated (e.g., dichloromethane) or ethereal (e.g., diethylether) solvent. In certain embodiments, when $R^{77}$ is not hydrogen, the synthetic route comprises a hydrolysis step comprising a base (e.g., lithium, sodium, or potassium hydroxide).

As described herein, the deprotection, cyclization, and equilibration of a compound of Formula (TG-1) to yield a compound of Formula (TII) can be performed in two synthetic steps when particular protecting groups are utilized for the intermediate (TG-1). For example, when $R^{P10}$ is TBS, and $R^{P8}$ and $R^{P9}$ are TES, the deprotection, cyclization, and equilibration can be performed in two steps by treating a compound of Formula (TG-1) with a fluoride source, followed by an acid. Any fluoride source known in the art may be used. Examples of fluoride sources include, but are not limited to, HF-pyridine, KF, CsF, AgF, ammonium fluoride, and tetraalkylammonium fluorides. In certain embodiments, the fluoride source is a tetraalkylammonium fluoride (e.g., tetramethylammonium fluoride, tetraethylammonium fluoride, tetrabutylammonium fluoride, benzyltrimethylammonium fluoride). In certain embodiments, the acid is a Brøn- sted acid. In certain embodiments, the acid is an inorganic acid (e.g., HCl, HF, HBr). In certain embodiments, the acid is an organic acid (e.g., carboxylic acid, sulfinic acid, sulfonic acid, phosphoric acid). In certain embodiments, the acid is a carboxylic acid (e.g., acetic acid, trfluoroacetic acid (TFA), pivalic acid). For example, in certain embodiments wherein $R^{P10}$ is TBS, and $R^{P8}$ and $R^{P9}$ are TES, a compound of Formula (TG-1) can be convered to a compound of Formula (TII) by treatment with TBAF and pivalic acid, followed by treatment with PPTS (see, e.g., FIG. 29).

In certain embodiments, preparation of a compound of Formula (TG-1) or salt thereof comprises joining an intermediate compound of Formula (TE-1) or salt thereof and an intermediate of Formula (TK-1) or salt thereof (see Scheme T3). In certain embodiments, when $R^{TZ4}$ is —$CH_2OR^{TZ4a}$ and $R^{TZ4a}$ is a protecting group, the synthetic route comprises a deprotection step. In certain embodiments, when $R^{TZ4a}$ is a silyl protecting group (e.g., t-butyldimethylsilyl), selective deprotection of $R^{TZ4a}$ comprises a mild source of fluoride (e.g., TBAF, HF.pyridine). In certain embodiments, when $R^{TZ4}$ is —$CH_2OH$, the synthetic route comprises an oxidation step. In certain embodiments, $R^{TZ4}$ is oxidized into an aldehyde (—CHO) under mild and selective conditions (e.g., Dess-Martin periodinane, $SO_3$.pyridine, or Swern oxidation). Compounds of Formula (TE-1) are joined with a compound of Formula (TK-1) under reductive coupling conditions. In certain embodiments, the conditions used to join a compound of Formula (TE-1) with a compound of Formula (TK-1) comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 1-3 equivalents). In certain embodiments, the coupling comprises a ligand or ligated transition metal complex. The reaction used to join a compound of Formula (TE-1) and Formula (TK-1) provides an intermediate hydroxy group that must be oxidized to provide a compound of Formula (TG-1). In certain embodiments, the oxidation is carried out under mild and selective conditions (e.g., Dess-Martin periodinane, $SO_3$.pyridine, or Swern oxidation).

In certain embodiments, as shown in Scheme T4, the halichondrins and analogs synthesized from the C1-C19 building blocks and C20-C38 building blocks are of Formula (TIII). In certain embodiments, the compound of Formula (TIII) is of one of the following formulae:

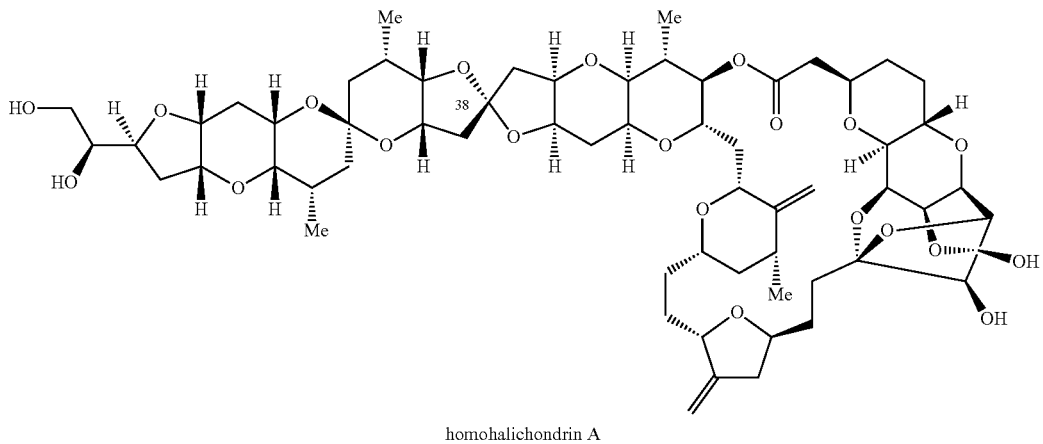

homohalichondrin A

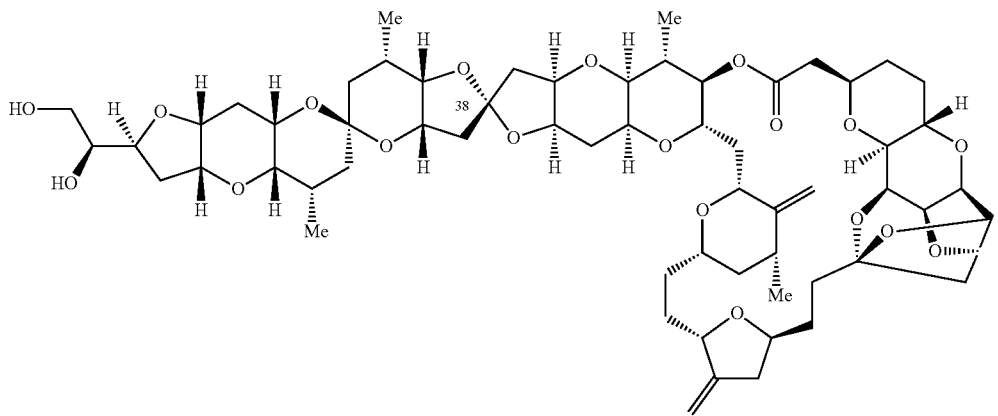

homohalichondrin B

-continued

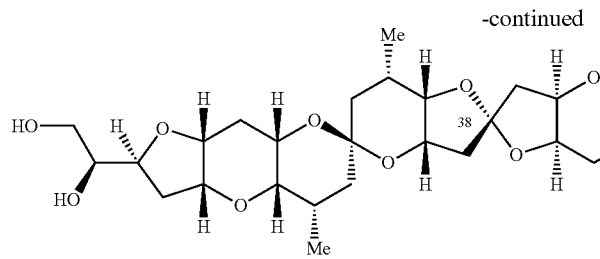
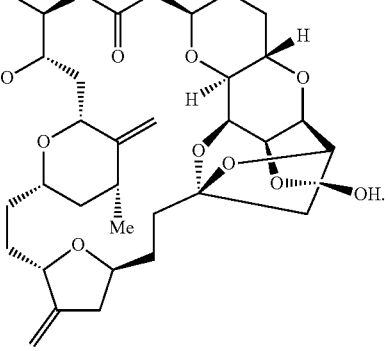

homohalichondrin C

In certain embodiments, preparation of compounds of Formula (TIII) and salts thereof comprises cyclizing an intermediate compound of Formula (TH-1) or a salt thereof (see Scheme T4). In certain embodiments, when a compound of Formula (TH-1) is protected (e.g., with silyl or benzylic protecting groups), the synthetic route comprises a deprotection step prior to cyclization. In certain embodiments, deprotection of a compound of Formula (TG-1) comprises a source of fluoride (e.g., TBAF, HF.pyridine). In certain embodiments, deprotection of a compound of Formula (TH-1) comprises a hydrogenolysis (e.g., a palladium or nickel catalyst and $H_2$) or oxidation (e.g., DDQ) step. In certain embodiments, the cyclization conditions comprise an acid. In certain embodiments, the cyclization conditions comprise a Brønsted acid (i.e., a source of H+). In certain embodiments, the cyclization conditions comprise an organic acid (e.g., PPTS). In certain embodiments, the cyclization conditions provide a compound of Formula (TIII) as a single diastereomer. In certain embodiments, the cyclization conditions provide a diastereomeric mixture that is enriched in one of two epimeric C38 ketals. In certain embodiments, the synthetic route comprises an equilibration step to enrich a compound of Formula (TIII) in one of two epimeric C38 ketals. In certain embodiments, the equilibration step enriches a compound of Formula (TIII) in the (R)-epimer. In certain embodiments, the equilibration step enriches a compound of Formula (TIII) in the (R)-epimer in a range of 2:1, 3:1, 4:1, 5:1, or >5:1. In certain embodiments, the equilibration step enriches a compound of Formula (TIII) in the (S)-epimer. In certain embodiments, the equilibration step enriches a compound of Formula (TIII) in the (S)-epimer in a range of 2:1, 3:1, 4:1, 5:1, 10:1, or >10:1. In certain embodiments, the equilibration step comprises a Lewis acid. In certain embodiments, the equilibration step comprises a silyl Lewis acid (e.g., a silicon tetrahalide or and organosilicon halide or triflate). In certain embodiments, the equilibration step comprises trimethylsilyl triflate. In certain embodiments, the equilibration step comprises a solvent. In certain embodiments, the equilibration step comprises a halogenated (e.g., dichloromethane) or ethereal (e.g., diethylether) solvent.

In certain embodiments, preparation of a compound of Formula (TH-1) or a salt thereof comprises joining an intermediate compound of Formula (TE-1) or a salt thereof and an intermediate of Formula (TL-1) or a salt thereof. In certain embodiments, when $R^{TZ4}$ is —$CH_2OR^{TZ4a}$ and $R^{TZ4a}$ is a protecting group, the synthetic route comprises a deprotection step. In certain embodiments, when $R^{TZ4a}$ is a silyl protecting group (e.g., t-butyldimethylsilyl), selective deprotection of $R^{TZ4a}$ comprises a mild source of fluoride (e.g., TBAF, HF.pyridine). In certain embodiments, when $R^{TZ4}$ is —$CH_2OH$, the synthetic route comprises an oxidation step. In certain embodiments, $R^{TZ4}$ is oxidized into an aldehyde (—CHO) under mild and selective conditions (e.g., Dess-Martin periodinane, $SO_3$.pyridine, or Swern oxidation). Compounds of Formula (TE-1) are joined with a compound of Formula (TL-1) under reductive coupling conditions. In certain embodiments, the conditions used to join a compound of Formula (TE-1) with a compound of Formula (TL-1) comprise a transition metal (e.g., nickel or chromium). In certain embodiments, the coupling reaction is catalytic in transition metal (e.g., 2-40 mol %). In certain embodiments, the coupling reaction is stoichiometric in transition metal (e.g., 1-3 equivalents). In certain embodiments, the coupling comprises a ligand or ligated transition metal complex. The reaction used to join a compound of Formula (TE-1) and Formula (TL-1) provides an intermediate hydroxy group that must be oxidized to provide a compound of Formula (TH-1). In certain embodiments, the oxidation is carried out under mild and selective conditions (e.g., Dess-Martin periodinane, $SO_3$.pyridine, or Swern oxidation).

Groups $R^{P1-P19}$

As generally described herein, $R^{P1}$, $R^{P2}$, $R^{P3}$, $R^{P4}$, $R^{P5}$, $R^{P6}$, $R^{P7}$, $R^{P8}$, $R^{P9}$, $R^{P10}$, $R^{P11}$, $R^{P12}$, $R^{P13}$, $R^{P14}$, $R^{P15}$, $R^{P16}$, $R^{P17}$, $R^{P18}$, and $R^{P19}$ are each independently hydrogen, substituted or unsubstituted alkyl, optionally substituted acyl, or an oxygen protecting group.

In certain embodiments, $R^{P1}$ is hydrogen. In certain embodiments, $R^{P1}$ is substituted or unsubstituted alkyl. In certain embodiments, $R^{P1}$ is substituted or unsubstituted $C_{1-6}$ alkyl. In certain embodiments, $R^{P1}$ is substituted or unsubstituted, branched $C_{1-6}$ alkyl. In certain embodiments, $R^{P1}$ is unsubstituted $C_{1-6}$ alkyl. In certain embodiments, $R^{P1}$ is methyl. In certain embodiments, $R^{P1}$ is ethyl. In certain embodiments, $R^{P1}$ is propyl. In certain embodiments, $R^{P1}$ is iso-propyl. In certain embodiments, $R^{P1}$ is t-butyl. In certain embodiments, $R^{P1}$ is an oxygen protecting group. In certain embodiments, $R^{P1}$ is a silyl protecting group. In certain embodiments, $R^{P1}$ is a trialkyl silyl protecting group. In certain embodiments, $R^{P1}$ is a t-butyldimethylsilyl protecting group. In certain embodiments, $R^{P1}$ is a trimethylsilyl protecting group. In certain embodiments, $R^{P1}$ is a triethylsilyl protecting group. In certain embodiments, $R^{P1}$ is a t-butyldiphenylsilyl protecting group. In certain embodiments, $R^{P1}$ is a triisopropylsilyl protecting group. In certain embodiments, $R^{P1}$ is a benzylic protecting group. In certain embodiments, $R^{P1}$ is a p-methoxybenzyl protecting group. In certain embodiments, $R^{P1}$ is an acyl protecting group. In certain embodiments, $R^{P1}$ is an acetyl protecting group. In certain embodiments, $R^{P1}$ is a benzoyl protecting group. In certain embodiments, $R^{P1}$ is a p-nitro benzoyl protecting group. In certain embodiments, $R^{P1}$ is a pivaloyl protecting group. In certain embodiments, $R^{P1}$ is a t-butyl carbonate (BOC) protecting group. In certain embodiments, $R^P$ is an acetal protecting group. In certain embodiments, $R^{P1}$ is a tetrahydropyranyl protecting group. In certain embodiments, $R^{P1}$ is an alkoxyalkyl protecting group. In certain embodiments, $R^{P1}$ is an ethoxyethyl protecting group.

In certain embodiments, $R^{P2}$ is hydrogen. In certain embodiments, $R^{P2}$ is substituted or unsubstituted alkyl. In certain embodiments, $R^{P2}$ is substituted or unsubstituted $C_{1-6}$ alkyl. In certain embodiments, $R^{P2}$ is substituted or unsubstituted, branched $C_{1-6}$ alkyl. In certain embodiments, $R^{P2}$ is unsubstituted $C_{1-6}$ alkyl. In certain embodiments, $R^{P2}$ is methyl. In certain embodiments, $R^{P2}$ is ethyl. In certain embodiments, $R^{P2}$ is propyl. In certain embodiments, $R^{P2}$ is iso-propyl. In certain embodiments, $R^{P2}$ is t-butyl. In certain embodiments, $R^{P2}$ is an oxygen protecting group. In certain embodiments, $R^{P2}$ is a silyl protecting group. In certain embodiments, RP is a trialkyl silyl protecting group. In certain embodiments, $R^{P2}$ is a t-butyldimethylsilyl protecting group. In certain embodiments, $R^{P2}$ is a trimethylsilyl protecting group. In certain embodiments, $R^{P2}$ is a triethylsilyl protecting group. In certain embodiments, $R^{P2}$ is a t-butyldiphenylsilyl protecting group. In certain embodiments, $R^{P2}$ is a triisopropylsilyl protecting group. In certain embodiments, $R^{P2}$ is a benzylic protecting group. In certain embodiments, RP is a p-methoxybenzyl protecting group. In certain embodiments, $R^{P2}$ is an acyl protecting group. In certain embodiments, $R^{P2}$ is an acetyl protecting group. In certain embodiments, $R^{P2}$ is a benzoyl protecting group. In certain embodiments, $R^{P2}$ is a p-nitro benzoyl protecting group. In certain embodiments, $R^{P2}$ is a pivaloyl protecting group. In certain embodiments, $R^{P2}$ is a t-butyl carbonate (BOC) protecting group. In certain embodiments, $R^{P2}$ is an acetal protecting group. In certain embodiments, $R^{P2}$ is a tetrahydropyranyl protecting group. In certain embodiments, $R^{P2}$ is an alkoxyalkyl protecting group. In certain embodiments, RP is an ethoxyethyl protecting group.

In certain embodiments, $R^{P3}$ is hydrogen. In certain embodiments, $R^{P3}$ is substituted or unsubstituted alkyl. In certain embodiments, $R^{P3}$ is substituted or unsubstituted $C_{1-6}$ alkyl. In certain embodiments, $R^{P3}$ is substituted or unsubstituted, branched $C_{1-6}$ alkyl. In certain embodiments, $R^{P3}$ is unsubstituted $C_{1-6}$ alkyl. In certain embodiments, $R^{P3}$ is methyl. In certain embodiments, $R^{P3}$ is ethyl. In certain embodiments, $R^{P3}$ is propyl. In certain embodiments, $R^{P3}$ is iso-propyl. In certain embodiments, $R^{P3}$ is t-butyl. In certain embodiments, $R^{P3}$ is an oxygen protecting group. In certain embodiments, $R^{P3}$ is a silyl protecting group. In certain embodiments, $R^{P3}$ is a trialkyl silyl protecting group. In certain embodiments, $R^{P3}$ is a t-butyldimethylsilyl protecting group. In certain embodiments, $R^{P3}$ is a trimethylsilyl protecting group. In certain embodiments, $R^{P3}$ is a triethylsilyl protecting group. In certain embodiments, $R^{P3}$ is a t-butyldiphenylsilyl protecting group. In certain embodiments, $R^{P3}$ is a triisopropylsilyl protecting group. In certain embodiments, $R^{P3}$ is a benzylic protecting group. In certain embodiments, $R^{P3}$ is a p-methoxybenzyl protecting group. In certain embodiments, $R^{P3}$ is an acyl protecting group. In certain embodiments, $R^{P3}$ is an acetyl protecting group. In certain embodiments, $R^{P3}$ is a benzoyl protecting group. In certain embodiments, $R^{P3}$ is a p-nitro benzoyl protecting group. In certain embodiments, $R^{P3}$ is a pivaloyl protecting group. In certain embodiments, $R^{P3}$ is a t-butyl carbonate (BOC) protecting group. In certain embodiments, $R^{P3}$ is an acetal protecting group. In certain embodiments, $R^{P3}$ is a tetrahydropyranyl protecting group. In certain embodiments, $R^{P3}$ is an alkoxyalkyl protecting group. In certain embodiments, $R^{P3}$ is an ethoxyethyl protecting group.

In certain embodiments, $R^{P4}$ is hydrogen. In certain embodiments, $R^{P4}$ is substituted or unsubstituted alkyl. In certain embodiments, $R^{P4}$ is substituted or unsubstituted $C_{1-6}$ alkyl. In certain embodiments, $R^{P4}$ is substituted or unsubstituted, branched $C_{1-6}$ alkyl. In certain embodiments, $R^{P4}$ is unsubstituted $C_{1-6}$ alkyl. In certain embodiments, $R^{P4}$ is methyl. In certain embodiments, $R^{P4}$ is ethyl. In certain embodiments, $R^{P4}$ is propyl. In certain embodiments, $R^{P4}$ is iso-propyl. In certain embodiments, $R^{P4}$ is t-butyl. In certain embodiments, $R^{P4}$ is an oxygen protecting group. In certain embodiments, $R^{P4}$ is a silyl protecting group. In certain embodiments, $R^{P4}$ is a trialkyl silyl protecting group. In certain embodiments, $R^{P4}$ is a t-butyldimethylsilyl protecting group. In certain embodiments, $R^{P4}$ is a trimethylsilyl protecting group. In certain embodiments, $R^{P4}$ is a triethylsilyl protecting group. In certain embodiments, $R^{P4}$ is a t-butyldiphenylsilyl protecting group. In certain embodiments, $R^{P4}$ is a triisopropylsilyl protecting group. In certain embodiments, $R^{P4}$ is a benzylic protecting group. In certain embodiments, $R^{P4}$ is a p-methoxybenzyl protecting group. In certain embodiments, $R^{P4}$ is an acyl protecting group. In certain embodiments, $R^{P4}$ is an acetyl protecting group. In certain embodiments, $R^{P4}$ is a benzoyl protecting group. In certain embodiments, $R^{P4}$ is a p-nitro benzoyl protecting group. In certain embodiments, $R^{P4}$ is a pivaloyl protecting group. In certain embodiments, $R^{P4}$ is a t-butyl carbonate (BOC) protecting group. In certain embodiments, $R^{P4}$ is an acetal protecting group. In certain embodiments, $R^{P4}$ is a tetrahydropyranyl protecting group. In certain embodiments, $R^{P4}$ is an alkoxyalkyl protecting group. In certain embodiments, $R^{P4}$ is an ethoxyethyl protecting group.

In certain embodiments, $R^{P5}$ is hydrogen. In certain embodiments, $R^{P5}$ is substituted or unsubstituted alkyl. In certain embodiments, $R^{P5}$ is substituted or unsubstituted $C_{1-6}$ alkyl. In certain embodiments, $R^{P5}$ is substituted or unsubstituted, branched $C_{1-6}$ alkyl. In certain embodiments, $R^{P5}$ is unsubstituted $C_{1-6}$ alkyl. In certain embodiments, $R^{P5}$ is methyl. In certain embodiments, $R^{P5}$ is ethyl. In certain embodiments, $R^{P5}$ is propyl. In certain embodiments, $R^{P5}$ is iso-propyl. In certain embodiments, $R^{P5}$ is t-butyl. In certain embodiments, $R^{P5}$ is an oxygen protecting group. In certain embodiments, $R^{P5}$ is a silyl protecting group. In certain embodiments, $R^{P5}$ is a trialkyl silyl protecting group. In certain embodiments, $R^{P5}$ is a t-butyldimethylsilyl protecting group. In certain embodiments, $R^{P5}$ is a trimethylsilyl protecting group. In certain embodiments, $R^{P5}$ is a triethylsilyl protecting group. In certain embodiments, $R^{P5}$ is a t-butyldiphenylsilyl protecting group. In certain embodiments, $R^{P5}$ is a triisopropylsilyl protecting group. In certain embodiments, $R^{P5}$ is a benzylic protecting group. In certain embodiments, $R^{P5}$ is a p-methoxybenzyl protecting group. In certain embodiments, $R^{P5}$ is optionally substituted acyl. In certain embodiments, $R^{P5}$ is unsubstituted acyl. In certain embodiments, $R^{P5}$ is an acyl protecting group. In certain embodiments, $R^{P5}$ is an acetyl protecting group. In certain embodiments, $R^{P5}$ is a benzoyl protecting group. In certain embodiments, $R^{P5}$ is a p-nitro benzoyl protecting group. In certain embodiments, $R^{P5}$ is a pivaloyl protecting group. In certain embodiments, $R^{P5}$ is a t-butyl carbonate (BOC) protecting group. In certain embodiments, $R^{P5}$ is an acetal protecting group. In certain embodiments, $R^{P5}$ is a tetrahydropyranyl protecting group. In certain embodiments, $R^{P5}$ is an alkoxyalkyl protecting group. In certain embodiments, $R^{P5}$ is an ethoxyethyl protecting group.

In certain embodiments, $R^{P6}$ is hydrogen. In certain embodiments, $R^{P6}$ is substituted or unsubstituted alkyl. In certain embodiments, $R^{P6}$ is substituted or unsubstituted $C_{1-6}$ alkyl. In certain embodiments, $R^{P6}$ is substituted or unsubstituted, branched $C_{1-6}$ alkyl. In certain embodiments, $R^{P6}$ is unsubstituted $C_{1-6}$ alkyl. In certain embodiments, $R^{P6}$ is methyl. In certain embodiments, $R^{P6}$ is ethyl. In certain embodiments, $R^{P6}$ is propyl. In certain embodiments, $R^{P6}$ is iso-propyl. In certain embodiments, $R^{P6}$ is t-butyl. In certain embodiments, $R^{P6}$ is an oxygen protecting group. In certain embodiments, $R^{P6}$ is a silyl protecting group. In certain embodiments, $R^{P6}$ is a trialkyl silyl protecting group. In certain embodiments, $R^{P6}$ is a t-butyldimethylsilyl protecting group. In certain embodiments, $R^{P6}$ is a trimethylsilyl protecting group. In certain embodiments, $R^{P6}$ is a triethylsilyl protecting group. In certain embodiments, $R^{P6}$ is a t-butyldiphenylsilyl protecting group. In certain embodiments, $R^{P6}$ is a triisopropylsilyl protecting group. In certain embodiments, $R^{P6}$ is a benzylic protecting group. In certain embodiments, $R^{P6}$ is a p-methoxybenzyl protecting group. In certain embodiments, $R^{P6}$ is an acyl protecting group. In certain embodiments, $RP$ is an acetyl protecting group. In certain embodiments, $R^{P6}$ is a benzoyl protecting group. In certain embodiments, $R^{P6}$ is a p-nitro benzoyl protecting group. In certain embodiments, $R^{P6}$ is a pivaloyl protecting group. In certain embodiments, $R^{P6}$ is a t-butyl carbonate (BOC) protecting group. In certain embodiments, $R^{P6}$ is an acetal protecting group. In certain embodiments, $R^{P6}$ is a tetrahydropyranyl protecting group. In certain embodiments, $R^{P6}$ is an alkoxyalkyl protecting group. In certain embodiments, $R^{P6}$ is an ethoxyethyl protecting group.

In certain embodiments, $R^{P7}$ is hydrogen. In certain embodiments, $R^{P7}$ is substituted or unsubstituted alkyl. In certain embodiments, $R^{P7}$ is substituted or unsubstituted $C_{1-6}$ alkyl. In certain embodiments, $R^{P7}$ is substituted or unsubstituted, branched $C_{1-6}$ alkyl. In certain embodiments, $R^{P7}$ is unsubstituted $C_{1-6}$ alkyl. In certain embodiments, $R^{P7}$ is methyl. In certain embodiments, $R^{P7}$ is ethyl. In certain embodiments, $R^{P7}$ is propyl. In certain embodiments, $R^{P}$ is iso-propyl. In certain embodiments, $R^{P7}$ is t-butyl. In certain embodiments, $R^{P7}$ is an oxygen protecting group. In certain embodiments, $R^{P7}$ is a silyl protecting group. In certain embodiments, $R^{P7}$ is a trialkyl silyl protecting group. In certain embodiments, $R^{P7}$ is a t-butyldimethylsilyl protecting group. In certain embodiments, $R^{P7}$ is a trimethylsilyl protecting group. In certain embodiments, $R^{P7}$ is a triethylsilyl protecting group. In certain embodiments, $R^{P7}$ is a t-butyldiphenylsilyl protecting group. In certain embodiments, $R^{P7}$ is a triisopropylsilyl protecting group. In certain embodiments, $R^{P7}$ is a benzylic protecting group. In certain embodiments, $R^{P7}$ is a p-methoxybenzyl protecting group. In certain embodiments, $R^{P7}$ is an acyl protecting group. In certain embodiments, $R^{P7}$ is an acetyl protecting group. In certain embodiments, $R^{P7}$ is a benzoyl protecting group. In certain embodiments, $R^{P7}$ is a p-nitro benzoyl protecting group. In certain embodiments, $R^{P7}$ is a pivaloyl protecting group. In certain embodiments, $R^{P7}$ is a t-butyl carbonate (BOC) protecting group. In certain embodiments, $R^{P7}$ is an acetal protecting group. In certain embodiments, $R^{P7}$ is a tetrahydropyranyl protecting group. In certain embodiments, $R^{P7}$ is an alkoxyalkyl protecting group. In certain embodiments, $R^{P7}$ is an ethoxyethyl protecting group.

In certain embodiments, $R^{P8}$ is hydrogen. In certain embodiments, $R^{P8}$ is substituted or unsubstituted alkyl. In certain embodiments, $R^{P8}$ is substituted or unsubstituted $C_{1-6}$ alkyl. In certain embodiments, $R^{P5}$ is substituted or unsubstituted, branched $C_{1-6}$ alkyl. In certain embodiments, $R^{P8}$ is unsubstituted $C_{1-6}$ alkyl. In certain embodiments, $R^{P8}$ is methyl. In certain embodiments, $R^{P8}$ is ethyl. In certain embodiments, $R^{P8}$ is propyl. In certain embodiments, $R^{P8}$ is iso-propyl. In certain embodiments, $R^{P8}$ is t-butyl. In certain embodiments, $R^{P8}$ is an oxygen protecting group. In certain embodiments, $R^{P8}$ is a silyl protecting group. In certain embodiments, $R^{P8}$ is a trialkyl silyl protecting group. In certain embodiments, $R^{P8}$ is a t-butyldimethylsilyl protecting group. In certain embodiments, $R^{P8}$ is a trimethylsilyl protecting group. In certain embodiments, $R^{P8}$ is a triethylsilyl protecting group. In certain embodiments, $R^{P8}$ is a t-butyldiphenylsilyl protecting group. In certain embodiments, $R^{P8}$ is a triisopropylsilyl protecting group. In certain embodiments, $R^{P8}$ is a benzylic protecting group. In certain embodiments, $R^{P8}$ is a p-methoxybenzyl protecting group. In certain embodiments, $R^{P8}$ is an acyl protecting group. In certain embodiments, $R^{P8}$ is an acetyl protecting group. In certain embodiments, $R^{P8}$ is a benzoyl protecting group. In certain embodiments, $R^{P8}$ is a p-nitro benzoyl protecting group. In certain embodiments, $R^{P8}$ is a pivaloyl protecting group. In certain embodiments, $R^{P8}$ is a t-butyl carbonate (BOC) protecting group. In certain embodiments, $R^{P8}$ is an acetal protecting group. In certain embodiments, $R^{P8}$ is a tetrahydropyranyl protecting group. In certain embodiments, $R^{8s}$ is an alkoxyalkyl protecting group. In certain embodiments, $R^{P8}$ is an ethoxyethyl protecting group.

In certain embodiments, $R^{P9}$ is hydrogen. In certain embodiments, $R^{P9}$ is substituted or unsubstituted alkyl. In certain embodiments, $R^{P9}$ is substituted or unsubstituted $C_{1-6}$ alkyl. In certain embodiments, $R^{P9}$ is substituted or unsubstituted, branched $C_{1-6}$ alkyl. In certain embodiments, $R^{P9}$ is unsubstituted $C_{1-6}$ alkyl. In certain embodiments, $R^{P9}$ is methyl. In certain embodiments, $R^{P9}$ is ethyl. In certain embodiments, $R^{P9}$ is propyl. In certain embodiments, $R^{P9}$ is iso-propyl. In certain embodiments, $R^{P9}$ is t-butyl. In certain embodiments, $R^{P9}$ is an oxygen protecting group. In certain embodiments, $R^{P9}$ is a silyl protecting group. In certain embodiments, $R^{P9}$ is a trialkyl silyl protecting group. In certain embodiments, $R^{P9}$ is a t-butyldimethylsilyl protecting group. In certain embodiments, $R^{P9}$ is a trimethylsilyl protecting group. In certain embodiments, $R^{P9}$ is a triethylsilyl protecting group. In certain embodiments, $R^{P9}$ is a t-butyldiphenylsilyl protecting group. In certain embodiments, $R^{P9}$ is a triisopropylsilyl protecting group. In certain embodiments, $R^{P9}$ is a benzylic protecting group. In certain embodiments, $R^{P9}$ is a p-methoxybenzyl protecting group. In certain embodiments, $R^{P9}$ is an acyl protecting group. In certain embodiments, $R^{P9}$ is an acetyl protecting group. In certain embodiments, $R^{P9}$ is a benzoyl protecting group. In certain embodiments, $R^{P9}$ is a p-nitro benzoyl protecting group. In certain embodiments, $R^{P9}$ is a pivaloyl protecting group. In certain embodiments, $R^{P9}$ is a t-butyl carbonate (BOC) protecting group. In certain embodiments, $R^{P9}$ is an acetal protecting group. In certain embodiments, $R^{P9}$ is a tetrahydropyranyl protecting group. In certain embodiments, $R^{P9}$ is an alkoxyalkyl protecting group. In certain embodiments, $R^{P9}$ is an ethoxyethyl protecting group.

In certain embodiments, $R^{P10}$ is hydrogen. In certain embodiments, $R^{P10}$ is substituted or unsubstituted alkyl. In certain embodiments, $R^{P10}$ is substituted or unsubstituted $C_{1-6}$ alkyl. In certain embodiments, $R^{P10}$ is substituted or unsubstituted, branched $C_{1-6}$ alkyl. In certain embodiments, $R^{P10}$ is unsubstituted $C_{1-6}$ alkyl. In certain embodiments, $R^{P10}$ is methyl. In certain embodiments, $R^{P10}$ is ethyl. In certain embodiments, $R^{P10}$ is propyl. In certain embodiments, $R^{P10}$ is iso-propyl. In certain embodiments, $R^{P10}$ is t-butyl. In certain embodiments, $R^{P10}$ is an oxygen protecting group. In certain embodiments, $R^{P10}$ is a silyl protecting group. In certain embodiments, $R^{P10}$ is a trialkyl silyl protecting group. In certain embodiments, $R^{P10}$ is a t-butyldimethylsilyl protecting group. In certain embodiments, $R^{P10}$ is a trimethylsilyl protecting group. In certain embodiments, $R^{P10}$ is a triethylsilyl protecting group. In certain embodiments, $R^{P10}$ is a t-butyldiphenylsilyl protecting group. In certain embodiments, $R^{P10}$ is a triisopropylsilyl protecting group. In certain embodiments, $R^{P10}$ is a benzylic protecting group. In certain embodiments, $R^{P10}$ is a p-methoxybenzyl protecting group. In certain embodiments, $R^{P1}$ is an acyl protecting group. In certain embodiments, $R^{P10}$ is an acetyl protecting group. In certain embodiments, $R^{P10}$ is a benzoyl protecting group. In certain embodiments, $R^{P10}$ is a p-nitro benzoyl protecting group. In certain embodiments, $R^{P10}$ is a pivaloyl protecting group. In certain embodiments, $R^{P10}$ is a t-butyl carbonate (BOC) protecting group. In certain embodiments, $R^{P10}$ is an acetal protecting group. In certain embodiments, $R^{P10}$ is a tetrahydropyranyl protecting group. In certain embodiments, $R^{P10}$ is an alkoxyalkyl protecting group. In certain embodiments, $R^{P10}$ is an ethoxyethyl protecting group.

In certain embodiments, $R^{P11}$ is hydrogen. In certain embodiments, $R^{P11}$ is substituted or unsubstituted alkyl. In certain embodiments, $R^{P11}$ is substituted or unsubstituted $C_{1-6}$ alkyl. In certain embodiments, $R^{P11}$ is substituted or unsubstituted, branched $C_{1-6}$ alkyl. In certain embodiments, $R^{P11}$ is unsubstituted $C_{1-6}$ alkyl. In certain embodiments, $R^{P11}$ is methyl. In certain embodiments, $R^{P11}$ is ethyl. In certain embodiments, $R^{P11}$ is propyl. In certain embodiments, $R^{P11}$ is iso-propyl. In certain embodiments, $R^{P11}$ is t-butyl. In certain embodiments, $R^{P11}$ is an oxygen protecting group. In certain embodiments, $R^{P11}$ is a silyl protecting group. In certain embodiments, $R^{P11}$ is a trialkyl silyl protecting group. In certain embodiments, $R^{P11}$ is a t-butyldimethylsilyl protecting group. In certain embodiments, $R^{P11}$ is a trimethylsilyl protecting group. In certain embodiments, $R^{P11}$ is a triethylsilyl protecting group. In certain embodiments, $R^{P11}$ is a t-butyldiphenylsilyl protecting group. In certain embodiments, $R^{P11}$ is a triisopropylsilyl protecting group. In certain embodiments, $R^{P11}$ is a benzylic protecting group. In certain embodiments, $R^{P11}$ is a p-methoxybenzyl protecting group. In certain embodiments, $R^{P11}$ is an acyl protecting group. In certain embodiments, $R^{P11}$ is an acetyl protecting group. In certain embodiments, $R^{P11}$ is a benzoyl protecting group. In certain embodiments, $R^{P11}$ is a p-nitro benzoyl protecting group. In certain embodiments, $R^{P11}$ is a pivaloyl protecting group. In certain embodiments, $R^{P11}$ is a t-butyl carbonate (BOC) protecting group. In certain embodiments, $R^{P11}$ is an acetal protecting group. In certain embodiments, $R^{P11}$ is a tetrahydropyranyl protecting group. In certain embodiments, $R^{P11}$ is an alkoxyalkyl protecting group. In certain embodiments, $R^{P11}$ is an ethoxyethyl protecting group.

In certain embodiments, $R^{P12}$ is hydrogen. In certain embodiments, $R^{P12}$ is substituted or unsubstituted alkyl. In certain embodiments, $R^{P12}$ is substituted or unsubstituted $C_{1-6}$ alkyl. In certain embodiments, $R^{P12}$ is substituted or unsubstituted, branched $C_{1-6}$ alkyl. In certain embodiments, $R^{P12}$ is unsubstituted $C_{1-6}$ alkyl. In certain embodiments, $R^{P12}$ is methyl. In certain embodiments, $R^{P12}$ is ethyl. In certain embodiments, $R^{P12}$ is propyl. In certain embodiments, $R^{P12}$ is iso-propyl. In certain embodiments, $R^{P12}$ is t-butyl. In certain embodiments, $R^{P12}$ is an oxygen protecting group. In certain embodiments, $R^{P12}$ is a silyl protecting group. In certain embodiments, $R^{P12}$ is a trialkyl silyl protecting group. In certain embodiments, $R^{P12}$ is a t-butyldimethylsilyl protecting group. $R^{P12}$ is a trimethylsilyl protecting group. In certain embodiments, $R^{P12}$ is a triethylsilyl protecting group. In certain embodiments, $R^{P12}$ is a t-butyldiphenylsilyl protecting group. In certain embodiments, $R^{P12}$ is a triisopropylsilyl protecting group. In certain embodiments, $R^{P12}$ is a benzylic protecting group. In certain embodiments, $R^{P12}$ is a p-methoxybenzyl protecting group. In certain embodiments, $R^{P12}$ is an acyl protecting group. In certain embodiments, $R^{P12}$ is an acetyl protecting group. In certain embodiments, $R^{P12}$ is a benzoyl protecting group. In certain embodiments, $R^{P12}$ is a p-nitro benzoyl protecting group. In certain embodiments, $R^{P12}$ is a pivaloyl protecting group. In certain embodiments, $R^{P12}$ is a t-butyl carbonate (BOC) protecting group. In certain embodiments, $R^{P12}$ is an acetal protecting group. In certain embodiments, $R^{P12}$ is a tetrahydropyranyl protecting group. In certain embodiments, $R^{P12}$ is an alkoxyalkyl protecting group. In certain embodiments, $R^{P12}$ is an ethoxyethyl protecting group.

In certain embodiments, $R^{P13}$ is hydrogen. In certain embodiments, $R^{P13}$ is substituted or unsubstituted alkyl. In certain embodiments, $R^{P13}$ is substituted or unsubstituted $C_{1-6}$ alkyl. In certain embodiments, $R^{P13}$ is substituted or unsubstituted, branched $C_{1-6}$ alkyl. In certain embodiments, $R^{P13}$ is unsubstituted $C_{1-6}$ alkyl. In certain embodiments, $R^{P13}$ is methyl. In certain embodiments, $R^{P13}$ is ethyl. In certain embodiments, $R^{P13}$ is propyl. In certain embodiments, $R^{P13}$ is iso-propyl. In certain embodiments, $R^{P13}$ is t-butyl. In certain embodiments, $R^{P13}$ is an oxygen protecting group. In certain embodiments, $R^{P13}$ is a silyl protecting group. In certain embodiments, $R^{P13}$ is a trialkyl silyl protecting group. In certain embodiments, $R^{P13}$ is a t-butyldimethylsilyl protecting group. In certain embodiments, $R^{P13}$ is a trimethylsilyl protecting group. In certain embodiments, $R^{P13}$ is a triethylsilyl protecting group. In certain embodiments, $R^{P13}$ is a t-butyldiphenylsilyl protecting group. In certain embodiments, $R^{P13}$ is a triisopropylsilyl protecting group. In certain embodiments, $R^{P13}$ is a benzylic protecting group. In certain embodiments, $R^{P13}$ is a p-methoxybenzyl protecting group. In certain embodiments, $R^{P13}$ is an acyl protecting group. In certain embodiments, $R^{P13}$ is an acetyl protecting group. In certain embodiments, $R^{P13}$ is a benzoyl protecting group. In certain embodiments, $R^{P13}$ is a p-nitro benzoyl protecting group. In certain embodiments, $R^{P13}$ is a pivaloyl protecting group. In certain embodiments, $R^{P13}$ is a t-butyl carbonate (BOC) protecting group. In certain embodiments, $R^{P13}$ is an acetal protecting group. In certain embodiments, $R^{P13}$ is a tetrahydropyranyl protecting group. In certain embodiments, $R^{P13}$ is an alkoxyalkyl protecting group. In certain embodiments, $R^{P13}$ is an ethoxyethyl protecting group.

In certain embodiments, $R^{P14}$ is hydrogen. In certain embodiments, $R^{P14}$ is substituted or unsubstituted alkyl. In certain embodiments, $R^{P14}$ is substituted or unsubstituted $C_{1-6}$ alkyl. In certain embodiments, $R^{P14}$ is substituted or unsubstituted, branched $C_{1-6}$ alkyl. In certain embodiments, $R^{P14}$ is unsubstituted $C_{1-6}$ alkyl. In certain embodiments, $R^{P14}$ is methyl. In certain embodiments, $R^{P14}$ is ethyl. In certain embodiments, $R^{P14}$ is propyl. In certain embodiments, $R^{P14}$ is iso-propyl. In certain embodiments, $R^{P14}$ is t-butyl. In certain embodiments, $R^{P14}$ is an oxygen protecting group. In certain embodiments, $R^{P14}$ is a silyl protecting group. In certain embodiments, $R^{P14}$ is a trialkyl silyl protecting group. In certain embodiments, $R^{P14}$ is a t-butyldimethylsilyl protecting group. In certain embodiments, $R^{P14}$ is a trimethylsilyl protecting group. In certain embodiments, $R^{P14}$ is a triethylsilyl protecting group. In certain embodiments, $R^{P14}$ is a t-butyldiphenylsilyl protecting group. In certain embodiments, $R^{P14}$ is a triisopropylsilyl protecting group. In certain embodiments, $R^{P14}$ is a benzylic protecting group. In certain embodiments, $R^{P14}$ is a p-methoxybenzyl protecting group. In certain embodiments, $R^{P14}$ is an acyl protecting group. In certain embodiments, $R^{P14}$ is an acetyl protecting group. In certain embodiments, $R^{P14}$ is a benzoyl protecting group. In certain embodiments, $R^{P14}$ is a p-nitro benzoyl protecting group. In certain embodiments, $R^{P14}$ is a pivaloyl protecting group. In certain embodiments, $R^{P14}$ is a t-butyl carbonate (BOC) protecting group. In certain embodiments, $R^{P14}$ is an acetal protecting group. In certain embodiments, $R^{P14}$ is a tetrahydropyranyl protecting group. In certain embodiments, $R^{P14}$ is an alkoxyalkyl protecting group. In certain embodiments, $R^{P14}$ is an ethoxyethyl protecting group.

In certain embodiments, $R^{P15}$ is hydrogen. In certain embodiments, $R^{P15}$ is substituted or unsubstituted alkyl. In certain embodiments, $R^{P15}$ is substituted or unsubstituted $C_{1-6}$ alkyl. In certain embodiments, $R^{P15}$ is substituted or unsubstituted, branched $C_{1-6}$ alkyl. In certain embodiments, $R^{P15}$ is unsubstituted $C_{1-6}$ alkyl. In certain embodiments, $R^{P15}$ is methyl. In certain embodiments, $R^{P15}$ is ethyl. In certain embodiments, $R^{P15}$ is propyl. In certain embodiments, $R^{P15}$ is iso-propyl. In certain embodiments, $R^{P15}$ is t-butyl. In certain embodiments, $R^{P15}$ is an oxygen protecting group. In certain embodiments, $R^{P15}$ is a silyl protecting group. In certain embodiments, $R^{P15}$ is a trialkyl silyl protecting group. In certain embodiments, $R^{P15}$ is a t-butyldimethylsilyl protecting group. In certain embodiments, $R^{P15}$ is a trimethylsilyl protecting group. In certain embodiments, $R^{P15}$ is a triethylsilyl protecting group. In certain embodiments, $R^{P15}$ is a t-butyldiphenylsilyl protecting group. In certain embodiments, $R^{P15}$ is a triisopropylsilyl protecting group. In certain embodiments, $R^{P15}$ is a benzylic protecting group. In certain embodiments, $R^{P15}$ is a p-methoxybenzyl protecting group. In certain embodiments, $R^{P15}$ is an acyl protecting group. In certain embodiments, $R^{P15}$ is an acetyl protecting group. In certain embodiments, $R^{P15}$ is a benzoyl protecting group. In certain embodiments, $R^{P15}$ is a p-nitro benzoyl protecting group. In certain embodiments, $R^{P15}$ is a pivaloyl protecting group. In certain embodiments, $R^{P15}$ is a t-butyl carbonate (BOC) protecting group. In certain embodiments, $R^{P15}$ is an acetal protecting group. In certain embodiments, $R^{P15}$ is a tetrahydropyranyl protecting group. In certain embodiments, $R^{P15}$ is an alkoxyalkyl protecting group. In certain embodiments, $R^{P15}$ is an ethoxyethyl protecting group.

In certain embodiments, $R^{P16}$ is hydrogen. In certain embodiments, $R^{P16}$ is substituted or unsubstituted alkyl. In certain embodiments, $R^{P16}$ is substituted or unsubstituted $C_{1-6}$ alkyl. In certain embodiments, $R^{P16}$ is substituted or unsubstituted, branched $C_{1-6}$ alkyl. In certain embodiments, $R^{P16}$ is unsubstituted $C_{1-6}$ alkyl. In certain embodiments, $R^{P16}$ is methyl. In certain embodiments, $R^{P16}$ is ethyl. In certain embodiments, $R^{P16}$ is propyl. In certain embodiments, $R^{P16}$ is iso-propyl. In certain embodiments, $R^{P16}$ is t-butyl. In certain embodiments, $R^{P16}$ is an oxygen protecting group. In certain embodiments, $R^{P16}$ is a silyl protecting group. In certain embodiments, $R^{P16}$ is a trialkyl silyl protecting group. In certain embodiments, $R^{P16}$ is a t-butyldimethylsilyl protecting group. In certain embodiments, $R^{P16}$ is a trimethylsilyl protecting group. In certain embodiments, $R^{P16}$ is a triethylsilyl protecting group. In certain embodiments, $R^{P16}$ is a t-butyldiphenylsilyl protecting group. In certain embodiments, $R^{P16}$ is a triisopropylsilyl protecting group. In certain embodiments, $R^{P16}$ is a benzylic protecting group. In certain embodiments, $R^{P16}$ is a p-methoxybenzyl protecting group. In certain embodiments, $R^{P16}$ is an acyl protecting group. In certain embodiments, $R^{P16}$ is an acetyl protecting group. In certain embodiments, $R^{P16}$ is a benzoyl protecting group. In certain embodiments, $R^{P16}$ is a p-nitro benzoyl protecting group. In certain embodiments, $R^{P16}$ is a pivaloyl protecting group. In certain embodiments, $R^{P16}$ is a t-butyl carbonate (BOC) protecting group. In certain embodiments, $R^{P16}$ is an acetal protecting group. In certain embodiments, $R^{P16}$ is a tetrahydropyranyl protecting group. In certain embodiments, $R^{P16}$ is an alkoxyalkyl protecting group. In certain embodiments, $R^{P16}$ is an ethoxyethyl protecting group.

Groups $R^{T1}$, $R^{T2}$, $R^{T3}$, and $R^{T5}$

As generally described herein, $R^{T1}$, $R^{T2}$, $R^{T3}$, and $R^{T5}$ are each independently hydrogen, halogen, or substituted or unsubstituted alkyl.

In certain embodiments, $R^{T1}$ is hydrogen. In certain embodiments, $R^{T1}$ is halogen (e.g., —F, —Cl, —Br, or —I). In certain embodiments, $R^{T1}$ is fluorine. In certain embodiments, $R^{T1}$ is chlorine. In certain embodiments, $R^{T1}$ is substituted or unsubstituted alkyl. In certain embodiments, $R^{T1}$ is substituted or unsubstituted $C_{1-6}$ alkyl. In certain embodiments, $R^{T1}$ is substituted or unsubstituted, branched $C_{1-6}$ alkyl. In certain embodiments, $R^{T1}$ is unsubstituted $C_{1-6}$ alkyl. In certain embodiments, $R^{T1}$ is methyl. In certain embodiments, $R^{T1}$ is methyl; and the carbon to which the methyl group is attached is in the (S)-configuration. In certain embodiments, $R^1$ is methyl; and the carbon to which the methyl group is attached is in the (R)-configuration. In certain embodiments, $R^{T1}$ is ethyl. In certain embodiments, $R^{T1}$ is propyl. In certain embodiments, $R^{T1}$ is iso-propyl. In certain embodiments, $R^{T1}$ is butyl. In certain embodiments, $R^{T1}$ is t-butyl.

In certain embodiments, the stereochemical configuration of the carbon atom to which $R^{T1}$ is attached is (S). In certain embodiments, the stereochemical configuration of the carbon atom to which $R^{T1}$ is attached is (R).

In certain embodiments, $R^{T2}$ is hydrogen. In certain embodiments, $R^{T1}$ is halogen (e.g., —F, —Cl, —Br, or —I). In certain embodiments, $R^{T2}$ is fluorine. In certain embodiments, $R^{T2}$ is chlorine. In certain embodiments, $R^{T2}$ is substituted or unsubstituted alkyl. In certain embodiments, $R^{T2}$ is substituted or unsubstituted $C_{1-6}$ alkyl. In certain embodiments, $R^{T2}$ is substituted or unsubstituted, branched $C_{1-6}$ alkyl. In certain embodiments, $R^{T2}$ is unsubstituted $C_{1-6}$ alkyl. In certain embodiments, $R^{T2}$ is methyl. In certain embodiments, $R^{T2}$ is methyl; and the carbon to which the methyl group is attached is in the (S)-configuration. In certain embodiments, $R^{T2}$ is methyl; and the carbon to which the methyl group is attached is in the (R)-configuration. In certain embodiments, $R^{T2}$ is ethyl. In certain embodiments, $R^{T2}$ is propyl. In certain embodiments, $R^{T2}$ is iso-propyl. In certain embodiments, $R^{T2}$ is butyl. In certain embodiments, $R^{T2}$ is t-butyl.

In certain embodiments, the stereochemical configuration of the carbon atom to which $R^{T2}$ is attached is (S). In certain embodiments, the stereochemical configuration of the carbon atom to which $R^{T2}$ is attached is (R).

In certain embodiments, $R^{T3}$ is hydrogen. In certain embodiments, $R^{T3}$ is halogen (e.g., —F, —Cl, —Br, or —I). In certain embodiments, $R^{T3}$ is fluorine. In certain embodiments, $R^{T3}$ is chlorine. In certain embodiments, $R^{T3}$ is substituted or unsubstituted alkyl. In certain embodiments, $R^{T3}$ is substituted or unsubstituted $C_{1-6}$ alkyl. In certain embodiments, $R^{T3}$ is substituted or unsubstituted, branched $C_{1-6}$ alkyl. In certain embodiments, RT is unsubstituted $C_{1-6}$ alkyl. In certain embodiments, $R^{T3}$ is methyl. In certain embodiments, $R^{T3}$ is methyl; and the carbon to which the methyl group is attached is in the (S)-configuration. In certain embodiments, $R^{T3}$ is methyl; and the carbon to which the methyl group is attached is in the (R)-configuration. In certain embodiments, $R^{T3}$ is ethyl. In certain embodiments, $R^{T3}$ is propyl. In certain embodiments, $R^{T3}$ is iso-propyl. In certain embodiments, $R^{T3}$ is butyl. In certain embodiments, $R^{T3}$ is t-butyl.

In certain embodiments, the stereochemical configuration of the carbon atom to which $R^{T3}$ is attached is (S). In certain embodiments, the stereochemical configuration of the carbon atom to which $R^{T3}$ is attached is (R).

In certain embodiments, $R^{T5}$ is hydrogen. In certain embodiments, $R^{T5}$ is halogen (e.g., —F, —Cl, —Br, or —I). In certain embodiments, $R^{T5}$ is fluorine. In certain embodiments, $R^{T5}$ is chlorine. In certain embodiments, $R^{T5}$ is substituted or unsubstituted alkyl. In certain embodiments, $R^{T5}$ is substituted or unsubstituted $C_{1-6}$ alkyl. In certain embodiments, $R^{T5}$ is substituted or unsubstituted, branched $C_{1-6}$ alkyl. In certain embodiments, $R^{T5}$ is unsubstituted $C_{1-6}$ alkyl. In certain embodiments, $R^{T5}$ is methyl. In certain embodiments, $R^{T5}$ is methyl; and the carbon to which the methyl group is attached is in the (S)-configuration. In certain embodiments, $R^{T5}$ is methyl; and the carbon to which the methyl group is attached is in the (R)-configuration. In certain embodiments, $R^{T5}$ is ethyl. In certain embodiments, $R^{T5}$ is propyl. In certain embodiments, $R^{T5}$ is iso-propyl. In certain embodiments, $R^{T5}$ is butyl. In certain embodiments, $R^{T5}$ is t-butyl.

In certain embodiments, the stereochemical configuration of the carbon atom to which $R^{T5}$ is attached is (S). In certain embodiments, the stereochemical configuration of the carbon atom to which $R^{T5}$ is attached is (R).

In certain embodiments, all of $R^{T1}$, $R^{T2}$, $R^{T3}$, and $R^{T5}$ are independently substituted or unsubstituted alkyl. In certain embodiments, all of $R^{T1}$, $R^{T2}$, $R^{T3}$, and $R^{T5}$ are independently substituted or unsubstituted $C_{1-6}$ alkyl. In certain embodiments, all of $R^{T1}$, $R^{T2}$, $R^{T3}$, and $R^{T5}$ are independently substituted or unsubstituted, branched $C_{1-6}$ alkyl. In certain embodiments, all of $R^{T1}$, $R^{T2}$, $R^{T3}$, and $R^{T5}$ are independently unsubstituted $C_{1-6}$ alkyl. In certain embodiments, all of $R^{T1}$, $R^{T2}$, $R^{T3}$, and $R^{T5}$ are methyl. In certain embodiments, the stereochemical configuration of the carbon atom to which each of $R^{T1}$, $R^{T2}$, and $R^{T3}$ is attached is (S); and the stereochemical configuration of the carbon atom to which $R^{T5}$ is attached is (R). In certain embodiments, the stereochemical configuration of the carbon atom to which each of $R^{T1}$, $R^{T2}$, and $R^{T3}$ is attached is (S); the stereochemical configuration of the carbon atom to which $R^{T5}$ is attached is (R); and all of $R^{T1}$, $R^{T2}$, $R^{T3}$, and $R^{T5}$ are methyl.

Groups $R^{T4}$ and $R^{T6}$

As generally described herein, $R^{T4}$ and $R^{T6}$ are each independently hydrogen, halogen, or substituted or unsubstituted alkyl, or two $R^{T4}$ groups can be taken together to form a

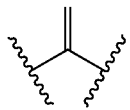 [SMILES: *C(*)=C]

group. In certain embodiments, at least one $R^{T4}$ is hydrogen. In certain embodiments, both of $R^{T4}$ are hydrogen. In certain embodiments, at least one $R^{T4}$ is halogen (e.g., —F, —Cl, —Br, or —I). In certain embodiments, at least one $R^{T4}$ is fluorine. In certain embodiments, at least one $R^{T4}$ is chlorine. In certain embodiments, at least one $R^{T4}$ is substituted or unsubstituted alkyl. In certain embodiments, at least one $R^{T4}$ is substituted or unsubstituted $C_{1-6}$ alkyl. In certain embodiments, at least one $R^{T4}$ is substituted or unsubstituted, branched $C_{1-6}$ alkyl. In certain embodiments, at least one $R^{T4}$ is unsubstituted $C_{1-6}$ alkyl. In certain embodiments, at least one $R^{T4}$ is methyl. In certain embodiments, at least one $R^{T4}$ is methyl; and the carbon to which the methyl group is attached is in the (S)-configuration. In certain embodiments, at least one $R^{T4}$ is methyl; and the carbon to which the methyl group is attached is in the (R)-configuration. In certain embodiments, both of $R^{T4}$ are methyl. In certain embodiments, at least one $R^{T4}$ is ethyl. In certain embodiments, at least one $R^{T4}$ is propyl. In certain embodiments, at least one $R^{T4}$ is butyl. In certain embodiments, at least one $R^{T4}$ is t-butyl. In certain embodiments, the stereochemical configuration of the carbon atom to which $R^{T4}$ is attached is (S). In certain embodiments, the stereochemical configuration of the carbon atom to which $R^{T4}$ is attached is (R). In certain embodiments, two $R^{T4}$ groups are taken together to form a

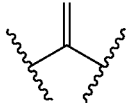 [SMILES: *C(*)=C]

group.

In certain embodiments, at least one $R^{T6}$ is hydrogen. In certain embodiments, both of $R^{T6}$ are hydrogen. In certain embodiments, at least one $R^{T6}$ is halogen (e.g., —F, —Cl, —Br, or —I). In certain embodiments, at least one $R^{T6}$ is fluorine. In certain embodiments, at least one $R^{T6}$ is chlorine. In certain embodiments, at least one $R^{T6}$ is substituted or unsubstituted alkyl. In certain embodiments, at least one $R^{T6}$ is substituted or unsubstituted $C_{1-6}$ alkyl. In certain embodiments, at least one $R^{T6}$ is substituted or unsubstituted, branched $C_{1-6}$ alkyl. In certain embodiments, at least one $R^{T6}$ is unsubstituted $C_{1-6}$ alkyl. In certain embodiments, at least one $R^{T6}$ is methyl. In certain embodiments, at least one $R^{T6}$ is methyl; and the carbon to which the methyl group is attached is in the (S)-configuration. In certain embodiments, at least one $R^{T6}$ is methyl; and the carbon to which the methyl group is attached is in the (R)-configuration. In certain embodiments, both of $R^{T6}$ are methyl. In certain embodiments, at least one $R^{T6}$ is ethyl. In certain embodiments, at least one $R^{T6}$ is propyl. In certain embodiments, at least one $R^{T6}$ is butyl. In certain embodiments, at least one $R^{T6}$ is t-butyl. In certain embodiments, the stereochemical configuration of the carbon atom to which $R^{T6}$ is attached is (S). In certain embodiments, the stereochemical configuration of the carbon atom to which $R^{T6}$ is attached is (R). In certain embodiments, two $R^{T6}$ groups are taken together to form a

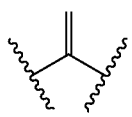

group.

In certain embodiments, two $R^{T4}$ groups are taken together to form a

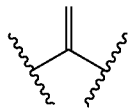

group;
and two $R^{T6}$ groups are taken together to form a

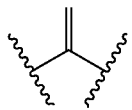 [SMILES: *C(*)=C]

group.

Groups $R^{TX}$, $R^{TY}$, $R^{TX1}$, $R^{TY1}$, and $R^{TXY}$

As generally described herein, $R^{TX}$ is hydrogen or —$OR^{TX1}$, wherein $R^{TX1}$ is hydrogen, substituted or unsubstituted alkyl, or an oxygen protecting group; $R^{TY}$ is hydrogen or —$OR^{TY1}$, wherein $R^{TY1}$ is hydrogen, substituted or unsubstituted alkyl, or an oxygen protecting group; and $R^{TX}$ and $R^{TY}$ can be taken with their intervening atoms to form a substituted or unsubstituted heterocyclic ring.

In certain embodiments, the stereochemical configuration of the carbon atom to which $R^{TX}$ is attached is (S). In certain embodiments, the stereochemical configuration of the carbon atom to which $R^{TX}$ is attached is (R).

In certain embodiments, the stereochemical configuration of $R^{TY}$ is (S). In certain embodiments, the stereochemical configuration of $R^{Y}$ is (R).

In certain embodiments, $R^{TX}$ is hydrogen. In certain embodiments, $R^{TX}$ is —$OR^{TX1}$. In certain embodiments, $R^{TY}$ is hydrogen. In certain embodiments, $R^{TY}$ is —$OR^{TY1}$. In certain embodiments, $R^{TX}$ and $R^{TY}$ are hydrogen. In certain embodiments, one of $R^{TX}$ and $R^{TY}$ is hydrogen. In certain embodiments, $R^{TX}$ is hydrogen, and $R^{TY}$ is —$OR^{TY1}$. In certain embodiments, $R^{TY}$ is hydrogen, and $R^{TX}$ is —$OR^{TX1}$. In certain embodiments, each of $R^{TX}$ is —$OR^{TX1}$; and $R^{TY}$ is —$OR^{TY1}$. In certain embodiments, $R^{TX}$ is —$OR^{TX1}$; $R^{TY}$ is —$OR^{TY1}$; and $R^{TX1}$ and $R^{TX1}$ are taken together with the intervening atoms to form an optionally substituted heterocyclic ring. In certain embodiments, $R^{TX}$ is —$OR^{TX1}$; $R^{TY}$ is —$OR^{TY1}$; and $R^{TX1}$ and $R^{TX1}$ are taken together with the intervening atoms to form an optionally substituted dioxane.

In certain embodiments, $R^{TX1}$ is hydrogen. In certain embodiments, $R^{TX1}$ is substituted or unsubstituted alkyl. In certain embodiments, $R^{TX1}$ is substituted or unsubstituted $C_{1-6}$ alkyl. In certain embodiments, $R^{TX1}$ is substituted or unsubstituted, branched $C_{1-6}$ alkyl. In certain embodiments, $R^{TX1}$ is unsubstituted $C_{1-6}$ alkyl. In certain embodiments, $R^{TX1}$ is methyl. In certain embodiments, $R^{TX1}$ is ethyl. In certain embodiments, $R^{TX1}$ is propyl. In certain embodiments, $R^{TX1}$ is iso-propyl. In certain embodiments, $R^{TX1}$ is t-butyl. In certain embodiments, $R^{TX1}$ is an oxygen protecting group. In certain embodiments, $R^{TX1}$ is a silyl protecting group. In certain embodiments, $R^{TX1}$ is a trialkyl silyl protecting group. In certain embodiments, $R^{TX1}$ is a t-butyldimethylsilyl protecting group. In certain embodiments, $R^{TX1}$ is a trimethylsilyl protecting group. In certain embodiments, $R^{TX1}$ is a triethylsilyl protecting group. In certain embodiments, $R^{TX1}$ is a t-butyldiphenylsilyl protecting group. In certain embodiments, $R^{TX1}$ is a triisopropylsilyl protecting group. In certain embodiments, $R^{TX1}$ is a benzylic protecting group. In certain embodiments, $R^{TX1}$ is a p-methoxybenzyl protecting group. In certain embodiments, $R^{TX1}$ is an acyl protecting group. In certain embodiments, $R^{TX1}$ is an acetyl protecting group. In certain embodiments, $R^{TX1}$ is a benzoyl protecting group. In certain embodiments, $R^{TX1}$ is a p-nitro benzoyl protecting group. In certain embodiments, $R^{TX1}$ is a pivaloyl protecting group. In certain embodiments, $R^{TX1}$ is a t-butyl carbonate (BOC) protecting group. In certain embodiments, $R^{TX1}$ is an acetal protecting group. In certain embodiments, $R^{TX1}$ is a tetrahydropyranyl protecting group. In certain embodiments, $R^{TX1}$ is an alkoxyalkyl protecting group. In certain embodiments, $R^{TX1}$ is an ethoxyethyl protecting group.

In certain embodiments, $R^{TY1}$ is hydrogen. In certain embodiments, $R^{TY1}$ is substituted or unsubstituted alkyl. In certain embodiments, $R^{TY1}$ is substituted or unsubstituted $C_{1-6}$ alkyl. In certain embodiments, $R^{TY1}$ is substituted or unsubstituted, branched $C_{1-6}$ alkyl. In certain embodiments, $R^{TY1}$ is unsubstituted $C_{1-6}$ alkyl. In certain embodiments, $R^{TY1}$ is methyl. In certain embodiments, $R^{TY1}$ is ethyl. In certain embodiments, $R^{TY1}$ is propyl. In certain embodiments, $R^{TY1}$ is iso-propyl. In certain embodiments, $R^{TY1}$ is t-butyl. In certain embodiments, $R^{TY1}$ is an oxygen protecting group. In certain embodiments, $R^{TY1}$ is a silyl protecting group. In certain embodiments, $R^{TY1}$ is a trialkyl silyl protecting group. In certain embodiments, $R^{TY1}$ is a t-butyldimethylsilyl protecting group. In certain embodiments, $R^{TY1}$ is a trimethylsilyl protecting group. In certain embodiments, $R^{TY1}$ is a triethylsilyl protecting group. In certain embodiments, $R^{TY1}$ is a t-butyldiphenylsilyl protecting group. In certain embodiments, $R^{TY1}$ is a triisopropylsilyl protecting group. In certain embodiments, $R^{TY1}$ is a benzylic protecting group. In certain embodiments, $R^{TY1}$ is a p-methoxybenzyl protecting group. In certain embodiments, $R^{TY1}$ is an acyl protecting group. In certain embodiments, $R^{TY1}$ is an acetyl protecting group. In certain embodiments, $R^{TY1}$ is a benzoyl protecting group. In certain embodiments, $R^{TY1}$ is a p-nitro benzoyl protecting group. In certain embodiments, $R^{TY1}$ is a pivaloyl protecting group. In certain embodiments, $R^{TY1}$ is a t-butyl carbonate (BOC) protecting group. In certain embodiments, $R^{TY1}$ is an acetal protecting group. In certain embodiments, $R^{TY1}$ is a tetrahydropyranyl protecting group. In certain embodiments, $R^{TY1}$ is an alkoxyalkyl protecting group. In certain embodiments, $R^{TY1}$ is an ethoxyethyl protecting group.

In certain embodiments, both $R^{TX1}$ and $R^{TY1}$ are hydrogen.

In certain embodiments, the stereochemical configuration of the carbon atom to which $R^{TX}$ is attached is (S). In certain embodiments, the stereochemical configuration of the carbon atom to which $R^{TX}$ is attached is (R). In certain embodiments, the stereochemical configuration of the carbon atom to which $R^{TY}$ is attached is (S). In certain embodiments, the stereochemical configuration of the carbon atom to which $R^{TY}$ is attached is (R).

In certain embodiments, the stereochemical configuration of the carbon atom to which $R^{TX}$ is attached is (S); and the stereochemical configuration of the carbon atom to which $R^{TY}$ is attached is (S). In certain embodiments, the stereochemical configuration of the carbon atom to which $R^{TX}$ is attached is (R); and the stereochemical configuration of the carbon atom to which $R^{TY}$ is attached is (R). In certain embodiments, the stereochemical configuration of the carbon atom to which $R^{TX}$ is attached is (S); and the stereochemical configuration of the carbon atom to which $R^{TY}$ is attached is (R). In certain embodiments, the stereochemical configuration of the carbon atom to which $R^{TX}$ is attached is (R); and the stereochemical configuration of the carbon atom to which $R^{TY}$ is attached is (S).

In certain embodiments, $R^{TX}$ and $R^{TY}$ are taken with their intervening atoms to form a substituted or unsubstituted heterocyclic ring. In certain embodiments, $R^{TX}$ and $R^{TY}$ form a substituted or unsubstituted, 5-membered heterocyclic ring. In certain embodiments, $R^{X}$ and $R^{TY}$ form a substituted or unsubstituted, 6-membered heterocyclic ring. In certain embodiments, $R^{TX}$ and $R^{TY}$ form a substituted or unsubstituted dioxolane. In certain embodiments, $R^{TX}$ and $R^{TY}$ form a mono-substituted dioxolane. In certain embodiments, $R^{TX}$ and $R^{TY}$ form a dioxolane substituted with one instance of a substituted or unsubstituted phenyl ring. In certain embodiments, $R^{TX}$ and $R^{TY}$ form a dioxolane substituted with one instance of a mono-substituted phenyl ring. In certain embodiments, $R^{TX}$ and $R^{TY}$ form a substituted or unsubstituted dioxane.

Group $R^{T7}$

In certain embodiments, $R^{T7}$ is hydrogen. In certain embodiments, $R^{T7}$ is substituted or unsubstituted alkyl. In certain embodiments, $R^{T7}$ is substituted or unsubstituted $C_{1-6}$ alkyl. In certain embodiments, $R^{T7}$ is substituted or unsubstituted, branched $C_{1-6}$ alkyl. In certain embodiments, $R^{T7}$ is unsubstituted $C_{1-6}$ alkyl. In certain embodiments, $R^{T7}$ is methyl. In certain embodiments, $R^{T7}$ is ethyl. In certain embodiments, $R^{T7}$ is propyl. In certain embodiments, $R^{T7}$ is iso-propyl. In certain embodiments, $R^{T7}$ is t-butyl. In certain embodiments, $R^{T7}$ is an oxygen protecting group. In certain embodiments, $R^{T7}$ is a silyl protecting group. In certain embodiments, $R^{T7}$ is a trialkyl silyl protecting group. In certain embodiments, $R^{T7}$ is a t-butyldimethylsilyl protecting group. In certain embodiments, $R^{T7}$ is a trimethylsilyl protecting group. In certain embodiments, $R^{T1}$ is a triethylsilyl protecting group. In certain embodiments, $R^{T7}$ is a t-butyldiphenylsilyl protecting group. In certain embodiments, $R^{T7}$ is a triisopropylsilyl protecting group. In certain embodiments, $R^{T7}$ is a benzylic protecting group. In certain embodiments, $R^{T7}$ is a p-methoxybenzyl protecting group. In certain embodiments, $R^{T7}$ is an acyl protecting group. In certain embodiments, $R^{T7}$ is an acetyl protecting group. In certain embodiments, $R^{T7}$ is a benzoyl protecting group. In certain embodiments, $R^{T7}$ is a p-nitro benzoyl protecting group. In certain embodiments, $R^{T7}$ is a pivaloyl protecting group. In certain embodiments, $R^{T7}$ is a t-butyl carbonate (BOC) protecting group. In certain embodiments, $R^{T7}$ is an acetal protecting group. In certain embodiments, $R^{T7}$ is a tetrahydropyranyl protecting group. In certain embodiments, $R^{T7}$ is an alkoxyalkyl protecting group. In certain embodiments, $R^{T7}$ is an ethoxyethyl protecting group.

Groups $X^T$, $R^{Z1}$, $R^{Z4}$, $R^{Z5}$, $R^{Z1a}$, $R^{Z4a}$, and $R^{Z5a}$

As generally described herein, $X^T$ is halogen (e.g., —F, —Cl, —Br, or —I). In certain embodiments, $X^T$ is bromine. In certain embodiments, $X^T$ is iodine.

As generally described herein, $R^{Z1}$ is —$CO_2R^{Z1a}$, wherein $R^{Z1a}$ is hydrogen, substituted or unsubstituted alkyl, or an oxygen protecting group. In certain embodiments, $R^{Z1a}$ is hydrogen. In certain embodiments, $R^{Z1a}$ is substituted or unsubstituted alkyl. In certain embodiments, $R^{Z1a}$ is substituted or unsubstituted $C_{1-6}$ alkyl. In certain embodiments, $R^{Z1a}$ is substituted or unsubstituted, branched $C_{1-6}$ alkyl. In certain embodiments, $R^{Z1a}$ is unsubstituted $C_{1-6}$ alkyl. In certain embodiments, $R^{Z1a}$ is methyl. In certain embodiments, $R^{Z1a}$ is ethyl. In certain embodiments, $R^{Z1a}$ is propyl. In certain embodiments, $R^{Z1a}$ is iso-propyl. In certain embodiments, $R^{Z1a}$ is t-butyl. In certain embodiments, $R^{Z1a}$ is an oxygen protecting group. In certain embodiments, $R^{Z1a}$ is a silyl protecting group. In certain embodiments, $R^{Z1a}$ is a trialkyl silyl protecting group. In certain embodiments, $R^{Z1a}$ is a t-butyldimethylsilyl protecting group. In certain embodiments, $R^{Z1a}$ is a trimethylsilyl protecting group. In certain embodiments, $R^{Z1a}$ is a triethylsilyl protecting group. In certain embodiments, $R^{Z1a}$ is a t-butyldiphenylsilyl protecting group. In certain embodiments, $R^{Z1a}$ is a triisopropylsilyl protecting group. In certain embodiments, $R^{Z1a}$ is a benzylic protecting group. In certain embodiments, $R^{Z1a}$ is a p-methoxybenzyl protecting group. In certain embodiments, $R^{Z1a}$ is an acyl protecting group. In certain embodiments, $R^{Z1a}$ is an acetyl protecting group. In certain embodiments, $R^{Z1a}$ is a benzoyl protecting group. In certain embodiments, $R^{Z1a}$ is a p-nitro benzoyl protecting group. In certain embodiments, $R^{Z1a}$ is a pivaloyl protecting group. In certain embodiments, $R^{Z1a}$ is a t-butyl carbonate (BOC) protecting group. In certain embodiments, $R^{Z1a}$ is an acetal protecting group. In certain embodiments, $R^{Z1a}$ is a tetrahydropyranyl protecting group. In certain embodiments, $R^{Z1a}$ is an alkoxyalkyl protecting group. In certain embodiments, $R^{Z1a}$ is an ethoxyethyl protecting group.

As generally described herein, $R^{Z4}$ is —$CH_2OR^{Z4a}$ or —CHO, wherein $R^{Z4a}$ is hydrogen, substituted or unsubstituted alkyl, optionally substituted acyl, or an oxygen protecting group. In certain embodiments, $R^{Z4a}$ is hydrogen. In certain embodiments, $R^{Z4a}$ is substituted or unsubstituted alkyl. In certain embodiments, $R^{Z4a}$ is substituted or unsubstituted $C_{1-6}$ alkyl. In certain embodiments, $R^{Z4a}$ is substituted or unsubstituted, branched $C_{1-6}$ alkyl. In certain embodiments, $R^{Z4a}$ is unsubstituted $C_{1-6}$ alkyl. In certain embodiments, $R^{Z4a}$ is methyl. In certain embodiments, $R^{Z4a}$ is ethyl. In certain embodiments, $R^{Z4a}$ is propyl. In certain embodiments, $R^{Z4a}$ is iso-propyl. In certain embodiments, $R^{Z4a}$ is t-butyl. In certain embodiments, $R^{Z4a}$ is an oxygen protecting group. In certain embodiments, $R^{Z4a}$ is a silyl protecting group. In certain embodiments, $R^{Z4a}$ is a trialkyl silyl protecting group. In certain embodiments, $R^{Z4a}$ is a t-butyldimethylsilyl protecting group. In certain embodiments, $R^{Z4a}$ is a trimethylsilyl protecting group. In certain embodiments, $R^{Z4a}$ is a triethylsilyl protecting group. In certain embodiments, $R^{Z4a}$ is a t-butyldiphenylsilyl protecting group. In certain embodiments, $R^{Z4a}$ is a triisopropylsilyl protecting group. In certain embodiments, $R^{Z4a}$ is a benzylic protecting group. In certain embodiments, $R^{Z4a}$ is a p-methoxybenzyl protecting group. In certain embodiments, $R^{Z4a}$ is an acyl protecting group. In certain embodiments, $R^{Z4a}$ is an acetyl protecting group. In certain embodiments, $R^{Z4a}$ is a benzoyl protecting group. In certain embodiments, $R^{Z4a}$ is a p-nitro benzoyl protecting group. In certain embodiments, $R^{Z4a}$ is a pivaloyl protecting group. In certain embodiments, $R^{Z4a}$ is a t-butyl carbonate (BOC) protecting group. In certain embodiments, $R^{Z4a}$ is an acetal protecting group. In certain embodiments, $R^{Z4a}$ is a tetrahydropyranyl protecting group. In certain embodiments, $R^{Z4a}$ is an alkoxyalkyl protecting group. In certain embodiments, $R^{Z4a}$ is an ethoxyethyl protecting group.

As generally described herein, $R^{Z5}$ is —$CO_2R^{Z5a}$, —$CH_2OR^{Z5a}$, or —CHO, wherein $R^{Z5a}$ is hydrogen, substituted or unsubstituted alkyl, optionally substituted acyl, or an oxygen protecting group. In certain embodiments, $R^{Z5}$ is —CH$_2$OR$^{Z5a}$. In certain embodiments, $R^{Z5}$ is —CHO. In certain embodiments, $R^{Z5}$ is —CO$_2$R$^{Z5a}$. In certain embodiments, $R^{Z5a}$ is hydrogen. In certain embodiments, $R^{Z5a}$ is substituted or unsubstituted alkyl. In certain embodiments, $R^{Z5a}$ is substituted or unsubstituted $C_{1-6}$ alkyl. In certain embodiments, $R^{Z5a}$ is substituted or unsubstituted, branched $C_{1-6}$ alkyl. In certain embodiments, $R^{Z5a}$ is unsubstituted $C_{1-6}$ alkyl. In certain embodiments, $R^{Z5a}$ is methyl. In certain embodiments, $R^{Z5}$ is —CH$_2$OR$^{Z5a}$; and $R^{Z5a}$ is methyl. In certain embodiments, $R^{Z5a}$ is ethyl. In certain embodiments, $R^{Z5a}$ is propyl. In certain embodiments, $R^{Z5a}$ is iso-propyl. In certain embodiments, $R^{Z5a}$ is t-butyl. In certain embodiments, $R^{Z5a}$ is an oxygen protecting group. In certain embodiments, $R^{Z5a}$ is a silyl protecting group. In certain embodiments, $R^{Z5a}$ is a trialkyl silyl protecting group. In certain embodiments, $R^{Z5a}$ is a t-butyldimethylsilyl protecting group. In certain embodiments, $R^{Z5a}$ is a trimethylsilyl protecting group. In certain embodiments, $R^{Z5a}$ is a triethylsilyl protecting group. In certain embodiments, $R^{Z5a}$ is a t-butyldiphenylsilyl protecting group. In certain embodiments, $R^{Z5a}$ is a triisopropylsilyl protecting group. In certain embodiments, $R^{Z5a}$ is a benzylic protecting group. In certain embodiments, $R^{Z5a}$ is a p-methoxybenzyl protecting group. In certain embodiments, $R^{Z5a}$ is an acyl protecting group. In certain embodiments, $R^{Z5a}$ is an acetyl protecting group. In certain embodiments, $R^{Z5a}$ is a benzoyl protecting group. In certain embodiments, $R^{Z5a}$ is a p-nitro benzoyl protecting group. In certain embodiments, $R^{Z5a}$ is a pivaloyl protecting group. In certain embodiments, $R^ZSa$ is a t-butyl carbonate (BOC) protecting group. In certain embodiments, $R^{Z5a}$ is an acetal protecting group. In certain embodiments, $R^{Z5a}$ is a tetrahydropyranyl protecting group. In certain embodiments, $R^{Z5a}$ is an alkoxyalkyl protecting group. In certain embodiments, $R^{Z5a}$ is an ethoxyethyl protecting group.

Groups $R^{Z2}$ and $R^{Z3}$

As generally described herein, $R^{Z2}$ is halogen (e.g., —F, —Cl, —Br, or —I) or a leaving group. In certain embodiments, $R^{Z2}$ is chlorine. In certain embodiments, $R^{Z2}$ is bromine. In certain embodiments, $R^{Z2}$ is iodine.

As generally described herein, $R^{Z3}$ is halogen (e.g., —F, —Cl, —Br, or —I). In certain embodiments, $R^{Z3}$ is bromine. In certain embodiments, $R^{Z3}$ is iodine.

Group $R^A$

As generally defined herein, each instance of $R^A$ is independently hydrogen, optionally substituted alkyl, or an oxygen protecting group; or optionally two $R^A$ are joined together with the intervening atoms to form optionally substituted heterocyclyl. In certain embodiments, at least one of $R^A$ is optionally substituted alkyl. In certain embodiments, at least one of $R^A$ is an oxygen protecting group. In certain embodiments, two $R^A$ are joined together to form optionally substituted heterocyclyl. In certain embodiments, two $R^A$ are joined together to form optionally substituted 5-to-6 membered heterocyclyl. In certain embodiments, two $R^A$ are joined together to form optionally substituted 6-membered heterocyclyl. In certain embodiments, two $R^A$ are joined together to form substituted 6-membered heterocyclyl. In certain embodiments, two $R^A$ are joined together to form the following structure:

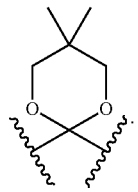 [SMILES: *C1(*)OCC(C)(C)CO1]

Group $R^B$

As generally defined herein, each instance of $R^B$ is independently hydrogen or optionally substituted alkyl. In certain embodiments, at least one instance of $R^B$ is optionally substituted alkyl. In certain embodiments, at least one instance of $R^B$ is optionally substituted alkyl. In certain embodiments, at least one instance of $R^B$ is optionally substituted $C_{1-6}$ alkyl. In certain embodiments, at least one instance of $R^B$ is optionally substituted $C_{1-3}$ alkyl. In certain embodiments, at least one instance of $R^B$ is unsubstituted $C_{1-3}$ alkyl (e.g., methyl, ethyl, n-propyl, iso-propyl). In certain embodiments, at least one instance of $R^B$ is methyl. In certain embodiments, both $R^B$ are methyl.

Group $R^B$

As generally defined herein, each instance of $R^B$ is independently hydrogen, optionally substituted alkyl, optionally substituted acyl, or an oxygen protecting group. In certain embodiments, at least one instance of $R^B$ is optionally substituted alkyl. In certain embodiments, at least one instance of $R^B$ is optionally substituted alkyl. In certain embodiments, at least one instance of $R^B$ is optionally substituted $C_{1-6}$ alkyl. In certain embodiments, at least one instance of $R^B$ is optionally substituted $C_{1-3}$ alkyl. In certain embodiments, at least one instance of $R^B$ is unsubstituted $C_{1-3}$ alkyl (e.g., methyl, ethyl, n-propyl, iso-propyl). In certain embodiments, at least one instance of $R^B$ is methyl. In certain embodiments, both $R^B$ are methyl.

Group $R^{PC}$

As generally defined herein, each instance of $R^{PC}$ is independently hydrogen, optionally substituted alkyl, optionally substituted acyl, or an oxygen protecting group. In certain embodiments, $R^{PC}$ is optionally substituted alkyl. In certain embodiments, $R^{PC}$ is optionally substituted alkyl. In certain embodiments, $R^{PC}$ is optionally substituted $C_{1-6}$ alkyl. In certain embodiments, $R^{PC}$ is optionally substituted $C_{1-3}$ alkyl. In certain embodiments, $R^{PC}$ is unsubstituted $C_{1-3}$ alkyl (e.g., methyl, ethyl, n-propyl, iso-propyl). In certain embodiments, $R^{PC}$ is methyl.

Group $R^{PC}$

As generally defined herein, each instance of $R^{PC}$ is independently hydrogen, optionally substituted alkyl, optionally substituted acyl, or an oxygen protecting group. In certain embodiments, $R^{PC}$ is optionally substituted alkyl. In certain embodiments, $R^{PC}$ is optionally substituted alkyl. In certain embodiments, $R^{PC}$ is optionally substituted $C_{1-6}$ alkyl. In certain embodiments, $R^{PC}$ is optionally substituted $C_{1-3}$ alkyl. In certain embodiments, $R^{PC}$ is unsubstituted $C_{1-3}$ alkyl (e.g., methyl, ethyl, n-propyl, iso-propyl). In certain embodiments, $R^P$C is methyl.

Group $R^{PC}$

As generally defined herein, each instance of $R^{PC}$ is independently hydrogen, optionally substituted alkyl, optionally substituted acyl, or an oxygen protecting group. In certain embodiments, $R^{PC}$ is optionally substituted alkyl. In certain embodiments, $R^{PC}$ is optionally substituted alkyl. In certain embodiments, $R^{PC}$ is optionally substituted $C_{1-6}$ alkyl. In certain embodiments, $R^{PC}$ is optionally substituted $C_{1-3}$ alkyl. In certain embodiments, $R^{PC}$ is unsubstituted $C_{1-3}$ alkyl (e.g., methyl, ethyl, n-propyl, iso-propyl). In certain embodiments, $R^{PC}$ is methyl.

Group $X^3$

As generally defined herein, $X^3$ is a halogen (e.g., —F, —Cl, —Br, or —I) or a leaving group. In certain embodiments, $X^3$ is a fluorine. In certain embodiments, $X^3$ is a chlorine. In certain embodiments, $X^3$ is a bromine. In certain embodiments, $X^3$ is an iodine. In certain embodiments, $X^3$ is a leaving group.

Compounds

In another aspect, provided herein are intermediates in the synthesis of halichondrins A, B, and C, and analogs thereof. In another aspect, provided herein are compounds of Formula (I-b-6):

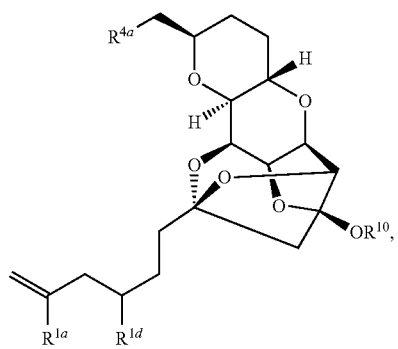

(I-b-6)

and salts, solvates, hydrates, polymorphs, co-crystals, tautomers, stereoisomers, and isotopically labeled derivatives thereof, wherein $R^{1a}$, $R^{1d}$, $R^{4a}$, and $R^{10}$ are as defined herein.

In another aspect, provided herein are compounds of Formula (I-b-7):

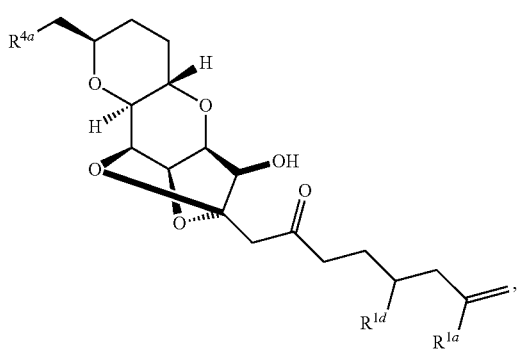

(I-b-7)

and salts, solvates, hydrates, polymorphs, co-crystals, tautomers, stereoisomers, and isotopically labeled derivatives thereof, wherein $R^{1a}$, $R^{1d}$, and $R^{4a}$ are as defined herein.

In another aspect, provided herein are compounds of Formula (I-b-12):

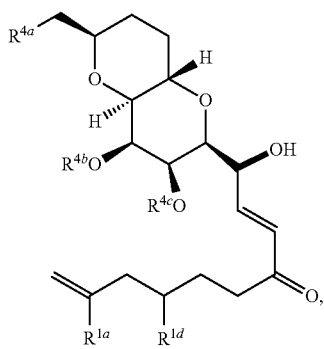

(I-b-12)

and salts, solvates, hydrates, polymorphs, co-crystals, tautomers, stereoisomers, and isotopically labeled derivatives thereof, wherein $R^{1a}$, $R^{1d}$, $R^{4a}$, $R^{4b}$, and $R^{4c}$ are as defined herein.

In another aspect, provided herein are compounds of Formula (III-2):

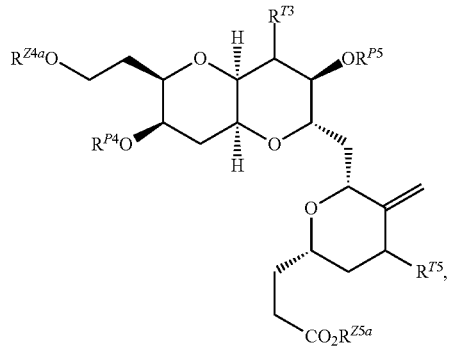

(III-2)

and salts, solvates, hydrates, polymorphs, co-crystals, tautomers, stereoisomers, and isotopically labeled derivatives thereof, wherein $R^{T3}$, $R^{P5}$, $R^{T5}$, $R^{Z5a}$, $R^{P4}$, and $R^{Z4a}$ are as defined herein.

In another aspect, provided herein are compounds of Formula (III-3):

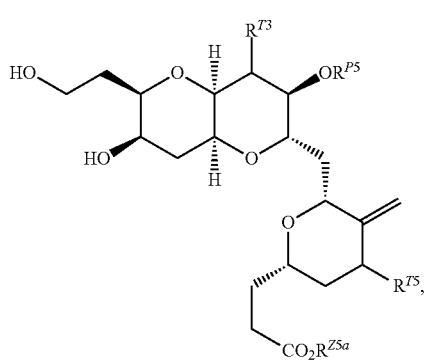

(III-3)

and salts, solvates, hydrates, polymorphs, co-crystals, tautomers, stereoisomers, and isotopically labeled derivatives thereof, wherein $R^{T3}$, $R^{P5}$, $R^{T5}$, and $R^{Z4a}$ are as defined herein.

In another aspect, provided herein are compounds of Formula (III-4):

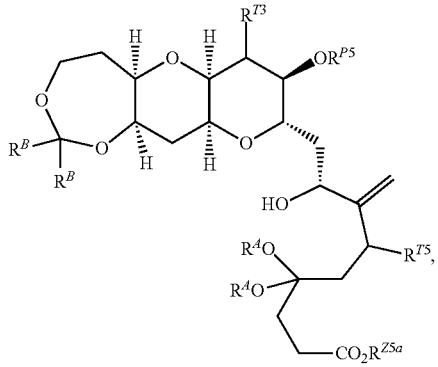

(III-4)

and salts, solvates, hydrates, polymorphs, co-crystals, tautomers, stereoisomers, and isotopically labeled derivatives thereof, wherein $R^{T3}$, $R^{P5}$, $R^{T5}$, $R^{Z5a}$, $R^A$, and $R^B$ are as defined herein.

In another aspect, provided herein are compounds of Formula (III-5):

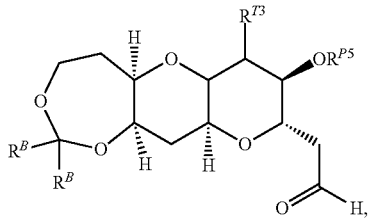

(III-5)

and salts, solvates, hydrates, polymorphs, co-crystals, tautomers, stereoisomers, and isotopically labeled derivatives thereof, wherein $R^{T3}$, $R^{P5}$, and $R^B$ are as defined herein.

In another aspect, provided herein are compounds of Formula (III-8):

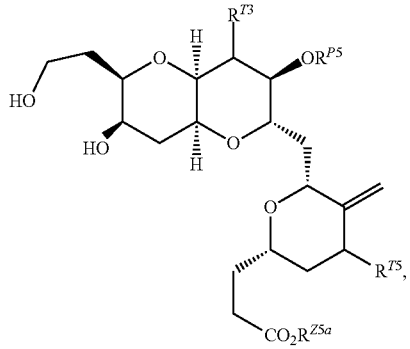

(III-8)

and salts, solvates, hydrates, polymorphs, co-crystals, tautomers, stereoisomers, and isotopically labeled derivatives thereof, wherein $R^{T3}$, $R^{T5}$, and $R^{Z5a}$ are as defined herein.

In another aspect, provided herein are compounds of Formula (III-9):

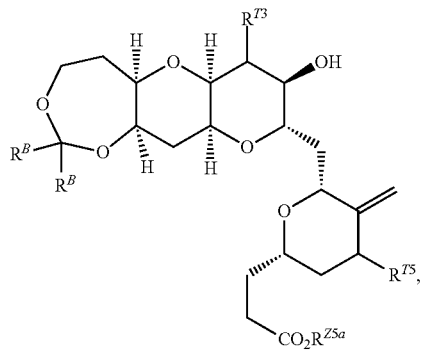

(III-9)

and salts, solvates, hydrates, polymorphs, co-crystals, tautomers, stereoisomers, and isotopically labeled derivatives thereof, wherein $R^{T3}$, $R^{T5}$, $R^B$, and $R^{Z5a}$ are as defined herein.

In another aspect, provided herein are compounds of Formula (III-10):

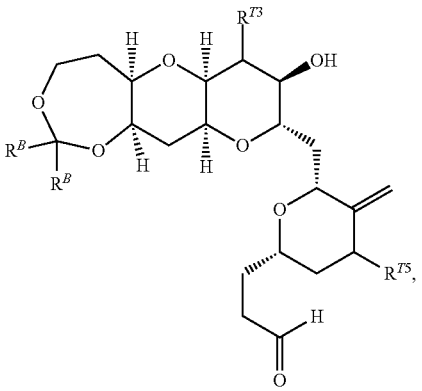

(III-10)

and salts, solvates, hydrates, polymorphs, co-crystals, tautomers, stereoisomers, and isotopically labeled derivatives thereof, wherein $R^{T3}$, $R^{T5}$, and $R^B$ are as defined herein.

In another aspect, provided herein are compounds of Formula (III-11):

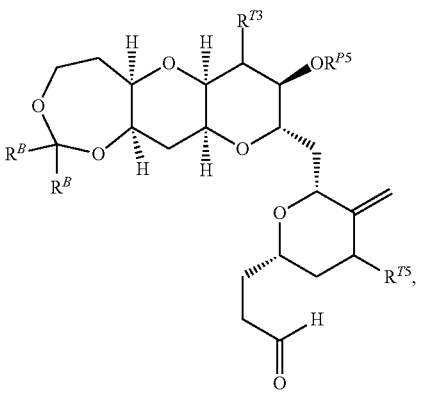

(III-11)

and salts, solvates, hydrates, polymorphs, co-crystals, tautomers, stereoisomers, and isotopically labeled derivatives thereof, wherein $R^{T3}$, $R^{T5}$, $R^{P5}$, and $R^B$ are as defined herein.

In another aspect, provided herein are compounds of Formula (TD-1):

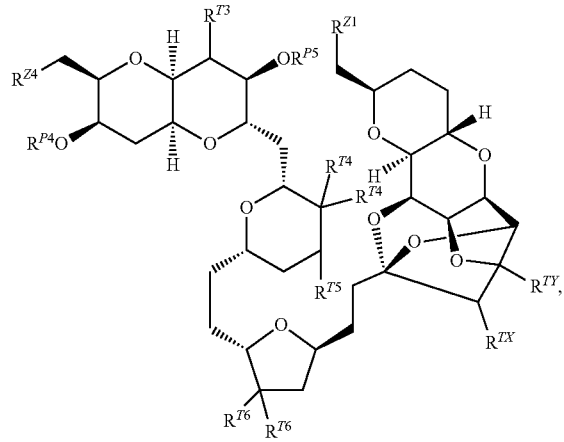

(TD-1)

and salts, solvates, hydrates, polymorphs, co-crystals, tautomers, stereoisomers, and isotopically labeled derivatives thereof, wherein $R^{Z4}$, $R^{P4}$, $R^{T3}$, $R^{P5}$, $R^{Z1}$, $R^{T4}$, $R^{T5}$, $R^{T6}$, $R^{TX}$, and $R^{TY}$ are as defined herein. In certain embodiments of Formula (TD-1), $R^{TX}$ is hydrogen, and $R^{TY}$ is —$OR^{TY1}$, wherein $R^{TY1}$ is as defined herein. In certain embodiments of Formula (TD-1), $R^{TY}$ is hydrogen, and $R^{TX}$ is —$OR^{TX1}$, wherein $R^{TX1}$ is as defined herein. In certain embodiments of Formula (TD-1), $R^{TY}$ is —$OR^{TX1}$, and $R^{TX}$ is —$OR^{TX1}$, wherein $R^{TX1}$ and $R^{TY1}$ are as defined herein.

In another aspect, provided herein are compounds of Formula (TE-1):

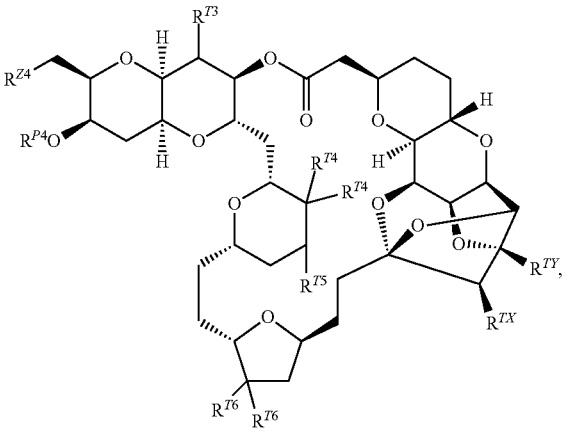

(TE-1)

and salts, solvates, hydrates, polymorphs, co-crystals, tautomers, stereoisomers, and isotopically labeled derivatives thereof, wherein $R^{Z4}$, $R^{P4}$, $R^{T3}$, $R^{T4}$, $R^{T5}$, $R^{T6}$, $R^{TX}$, and $R^{TY}$ are as defined herein. In certain embodiments of Formula (TE-1), $R^{TX}$ is hydrogen, and $R^{TY}$ is —$OR^{TY1}$, wherein $R^{TY1}$ is as defined herein. In certain embodiments of Formula (TE-1), $R^{TY}$ is hydrogen, and $R^{TX}$ is —$OR^{TX1}$, wherein $R^{TX1}$ is as defined herein. In certain embodiments of Formula (TE-1), $R^{TY}$ is —$OR^{TX1}$, and $R^{TX}$ is —$OR^{TX1}$, wherein $R^{TX1}$ and $R^{TY1}$ are as defined herein.

In another aspect, provided herein are compounds of Formula (TF-1):

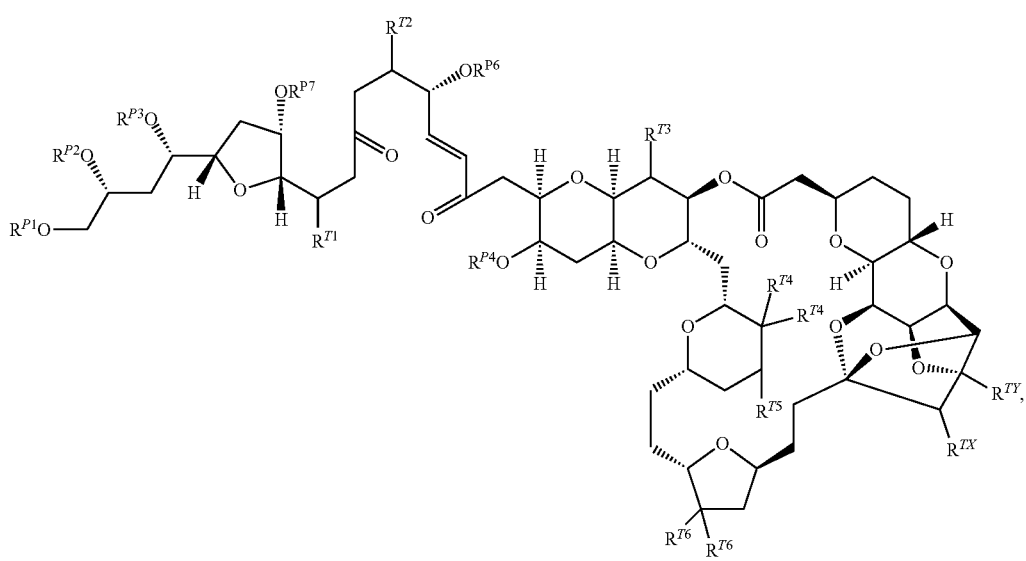

(TF-1)

and salts, solvates, hydrates, polymorphs, co-crystals, tautomers, stereoisomers, and isotopically labeled derivatives thereof, wherein $R^{P1}$, $R^{P2}$, $R^{P3}$, $R^{P7}$, $R^{T1}$, $R^{T2}$, $R^{P6}$, $R^{P4}$, $R^{T3}$, $R^{T4}$, $R^{T5}$, $R^{T6}$, $R^{TX}$, and $R^{TY}$ are as defined herein. In certain embodiments of Formula (TF-1), $R^{TX}$ is hydrogen, and $R^{TY}$ is —$OR^{TY1}$, wherein $R^{TY1}$ is as defined herein. In certain embodiments of Formula (TF-1), $R^{TY}$ is hydrogen, and $R^{TX}$ is —$OR^{TX1}$, wherein $R^{TX1}$ is as defined herein. In certain embodiments of Formula (TF-1), $R^{TY}$ is —$OR^{TX1}$, and $R^{TX}$ is —$OR^{TX1}$, wherein $R^{TX1}$ and $R^{TY1}$ are as defined herein.

In another aspect, provided herein are compounds of Formula (TG-1):

$$(TG-1)$$

and salts, solvates, hydrates, polymorphs, co-crystals, tautomers, stereoisomers, and isotopically labeled derivatives thereof, wherein $R^{T7}$, $R^{P8}$, $R^{P9}$, $R^{T1}$, $R^{T2}$, $R^{P10}$, $R^{P11}$, $R^{T3}$, $R^{T4}$, $R^{T5}$, $R^{T6}$, $R^{TX}$, and $R^{TY}$ are as defined herein. In certain embodiments of Formula (TG-1), $R^{TX}$ is hydrogen, and $R^{TY}$ is —$OR^{TY1}$, wherein $R^{TY1}$ is as defined herein. In certain embodiments of Formula (TG-1), $R^{TY}$ is hydrogen, and $R^{TX}$ is —$OR^{TX1}$, wherein $R^{TX1}$ is as defined herein. In certain embodiments of Formula (TG-1), $R^{TY}$ is —$OR^{TX1}$, and $R^{TX}$ is —$OR^{TX1}$, wherein $R^{TX1}$ and $R^{TY1}$ are as defined herein.

In another aspect, provided herein are compounds of Formula (TH-1):

$$(TH-1)$$

and salts, solvates, hydrates, polymorphs, co-crystals, tautomers, stereoisomers, and isotopically labeled derivatives thereof, wherein $R^{P13}$, $R^{P12}$, $R^{P14}$, $R^{T1}$, $R^{T2}$, $R^{P16}$, $R^{P15}$, $R^{T3}$, $R^{T4}$, $R^{T5}$, $R^{T6}$, $R^{TX}$, and $R^{TY}$ are as defined herein. In certain embodiments of Formula (TH-1), $R^{TX}$ is hydrogen, and $R^{TY}$ is —$OR^{TY1}$, wherein $R^{TY1}$ is as defined herein. In certain embodiments of Formula (TH-1), $R^{TY}$ is hydrogen, and $R^{TX}$ is —$OR^{TX1}$, wherein $R^{TX1}$ is as defined herein. In certain embodiments of Formula (TH-1), $R^{TY}$ is —$OR^{TX1}$, and $R^{TX}$ is —$OR^{TX1}$, wherein $R^{TX1}$ and $R^{TY1}$ are as defined herein.

EXAMPLES

In order that the invention described herein may be more fully understood, the following Examples are set forth. The synthetic and biological examples described in this Application are offered to illustrate the compounds, pharmaceutical compositions, and methods provided herein and are not to be construed in any way as limiting their scope.

General Procedures and Methods

NMR spectra were recorded on a Varian Inova 600 MHz, 500 MHz spectrometer. Chemical shifts are reported in parts per million (ppm). For $^1$H NMR spectra (CDCl$_3$ and C$_6$D$_6$), the residual solvent peak was used as the internal reference (7.26 ppm in CDCl$_3$; 7.16 ppm in C$_6$D$_6$), while the central solvent peak as the reference (77.0 ppm in CDCl$_3$, 128.0 ppm in C$_6$D$_6$) for $^{13}$C NMR spectra. Optical rotations were measured at 20° C. using a Perkin-Elmer 241 polarimeter. Analytical and semi-preparative thin layer chromatography (TLC) was performed with E. Merck pre-coated TLC plates, silica gel 60 F$_{254}$, layer thickness 0.50 and 1.00 mm, respectively. TLC plates were visualized by staining with p-anisaldehyde stain. Flash chromatography separations were performed on E. Merck Kieselgel 60 (230-400) mesh silica gel. High performance liquid chromatography (HPLC) was carried out with Waters 1525 on a UV spectrophotometric detector (254 nm, Waters 2489) to which a 21.2×250 mm size column (Zobrax SIL) packed with silica gel (7.0 µm) was attached. All moisture sensitive reactions were conducted under an inert atmosphere. Reaction vessels were oven-dried and allowed to cool under vacuum (1 mmHg). Reagents and solvents were commercial grade and were used as supplied, unless otherwise noted.

Example 1. Selective Activation/Coupling of Poly-Halogenated Nucleophiles in Ni/Cr-Mediated Reactions: Synthesis of C1-C19 Building Block of Halichondrin Bs The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Synthesis Outlined in FIG. 7

Synthesis of Model Trans-Haloenone (Taniguchi, M.; Kobayashi, S.; Nakagawa, M.; Hino, T.; Kishi, Y. Tetrahedron Lett. 1986, 27, 4763)

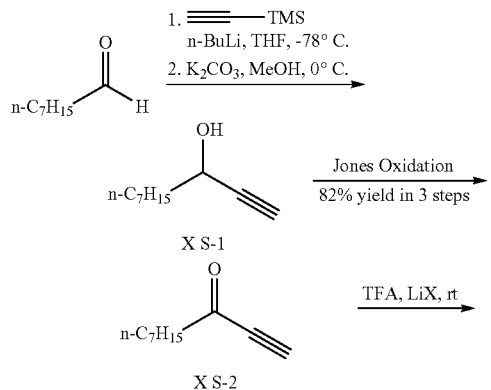

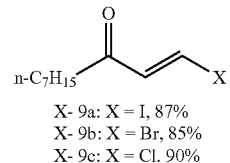

X- 9a: X = I, 87%
X- 9b: X = Br, 85%
X- 9c: X = Cl. 90%

To a solution of trimethylsilyl acetylene (5.4 g, 55 mmol) in THF (140 mL) was added slowly n-butyllithium (2.5 M in hexanes, 21 mL, 52.5 mmol) at −78° C. for about 30 min. After 1 h, a solution of octanal (6.4 g, 50 mmol) in THF (60 mL) was added over another 30 min. The resulting mixture was stirred at −78° C. for 2 h and then quenched by saturated NH$_4$Cl solution (100 mL) and extracted with EtOAc (150 mL×3). The extracts were washed with brine (300 mL), dried over MgSO$_4$, and then passed through a pad of silica gel (40 g; hexanes/EtOAc=10:1→4:1) and the eluent was concentrated under reduced pressure, to give the product as light yellow liquid. This material was immediately used for the next step without further purification.

To a solution of crude propargyl alcohol product from previous step in methanol (200 mL) was added K$_2$CO$_3$ (13.8 g, 100 mmol) at 0° C. After 6 h, to the reaction mixture was added 100 mL water to quench the reaction. The reaction mixture was extracted with EtOAc (100 mL×3) and the combined organic layer was washed with 200 mL brine, dried over anhydrous MgSO$_4$, and concentrated under reduced pressure. The residue was purified by flash column chromatography on silica gel with eluent of hexanes/EtOAc (10:1 to 3:1) to give pure alcohol product XS-1 as light yellow oil in 6.6 g.

Jones Oxidation:

To a solution of terminal propargyl alcohol XS-1 (6.6 g, 21.8 mmol) in acetone (106 mL) was added dropwise 30 mL of freshly prepared Jones' reagent ((a) Bowden, K.; Heilbron, I. M.; Jones, E. R. H.; Weedon, B. C. L. J. Chem. Soc. 1946, 39, (b) Eisenbraun, E. J. Org. Synth. 1965, 45, 28). The isopropyl alcohol was added dropwise until the excess Jones' reagent was destroyed (the color of reaction mixture became deep green). Saturated NaHCO$_3$ solution was added in small portions, and the suspension was stirred vigorously until the pH of the reaction mixture became neutral (pH=7). The suspension was filtered and the filter cake was washed with 50 mL of acetone. The filtrate was extracted with hexane (100 mL×3) and combined organic layer was washed with 200 mL brine. The organic layer was dried over anhydrous MgSO$_4$ and concentrated under reduced pressure. The residue was purified by flash column chromatography on silica gel with eluent of hexanes/EtOAc (10:1 to 2:1), to give 1-decyn-3-one XS-2 product as light yellow oil (6.2 g, 82% yield in 3 steps).

HX Addition of Ynone:

To a solution of 1-decyn-3-one XS-2 (0.76 g, 5 mmol) in trifluoroacetic acid (TFA, 10 mL) was added LiI, LiBr, or LiCl salt (5 mmol). The reaction mixture was stirred for 1 h, and then poured in 20 mL saturated NaHCO$_3$ solution. NaHCO$_3$ (solid) was added in small portions, and the solution was stirred vigorously until the pH of reaction became neutral. The reaction mixture was extracted with Et$_2$O (50 mL×3) and combined organic extracts were washed with 50 mL of saturated NaHCO$_3$ solution and 50 mL of brine. The organic layer was dried over anhydrous MgSO$_4$ an concentrated under reduced pressure. The residue was purified by flash column chromatography on silica gel with eluent of hexanes/Et$_2$O (100:1), to give trans-haloenone product X-9a-c as light yellow oil.

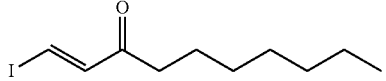

X-9a (E)-1-iododec-1-en-3-one (X-9a)

lithium salt was LiI, 87% yield; $^1$H NMR (500 MHz, CDCl$_3$) δ: 7.80 (d, J=15.0 Hz, 1H), 7.15 (d, J=15.0 Hz, 1H), 2.50 (t, J=7.5 Hz, 2H), 1.64-1.56 (m, 2H), 1.36-1.22 (m, 8H), 0.87 (t, J=7.5 Hz, 3H); $^{13}$C NMR (125 MHz, CDCl$_3$) δ: 197.6, 144.6, 98.6, 40.4, 31.6, 29.1, 29.0, 23.7, 22.6, 14.0; HRMS (ESI) m/z: [M+H]$^+$ calcd for C$_{10}$H$_{18}$IO, 281.0402; found, 281.0408.

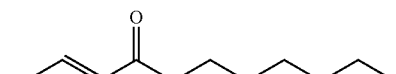

X-9b (E)-1-bromodec-1-en-3-one (X-9b)

lithium salt was LiBr, 85% yield; $^1$H NMR (500 MHz, CDCl$_3$) δ: 7.51 (d, J=14.0 Hz, 1H), 6.79 (d, J=14.0 Hz, 1H), 2.50 (t, J=7.5 Hz, 2H), 1.65-1.56 (m, 2H), 1.33-1.22 (m, 8H), 0.87 (t, J=7.5 Hz, 3H); $^{13}$C NMR (125 MHz, CDCl$_3$) δ: 197.5, 136.5, 125.7, 41.0, 31.6, 29.1, 29.0, 23.8, 22.6, 14.0; HRMS (ESI) m/z: [M+H]$^+$ calcd for C$_{10}$H$_{18}$BrO, 233.0541; found, 233.0540.

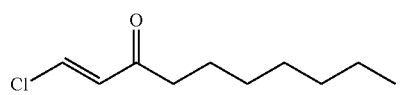

X-9c (E)-1-chlorodec-1-en-3-one (X-9c)

lithium salt was LiCl, 90% yield; $^1$H NMR (500 MHz, CDCl$_3$) δ: 7.28 (d, J=13.5 Hz, 1H), 6.52 (d, J=15.0 Hz, 1H), 2.51 (t, J=7.5 Hz, 2H), 1.66-1.56 (m, 2H), 1.36-1.22 (m, 8H), 0.88 (t, J=7.5 Hz, 3H); $^{13}$C NMR (125 MHz, CDCl$_3$) δ: 197.5, 136.3, 132.3, 41.4, 31.6, 29.1, 29.0, 23.8, 22.6, 14.0; HRMS (ESI) m/z: [M+H]$^+$ calcd for C$_{10}$H$_{18}$ClO, 189.1046; found, 189.1044.

General Procedure (A) of Asymmetric Catalytic Ni/Cr-Mediated Coupling with Trans-Haloenone X-9a-c

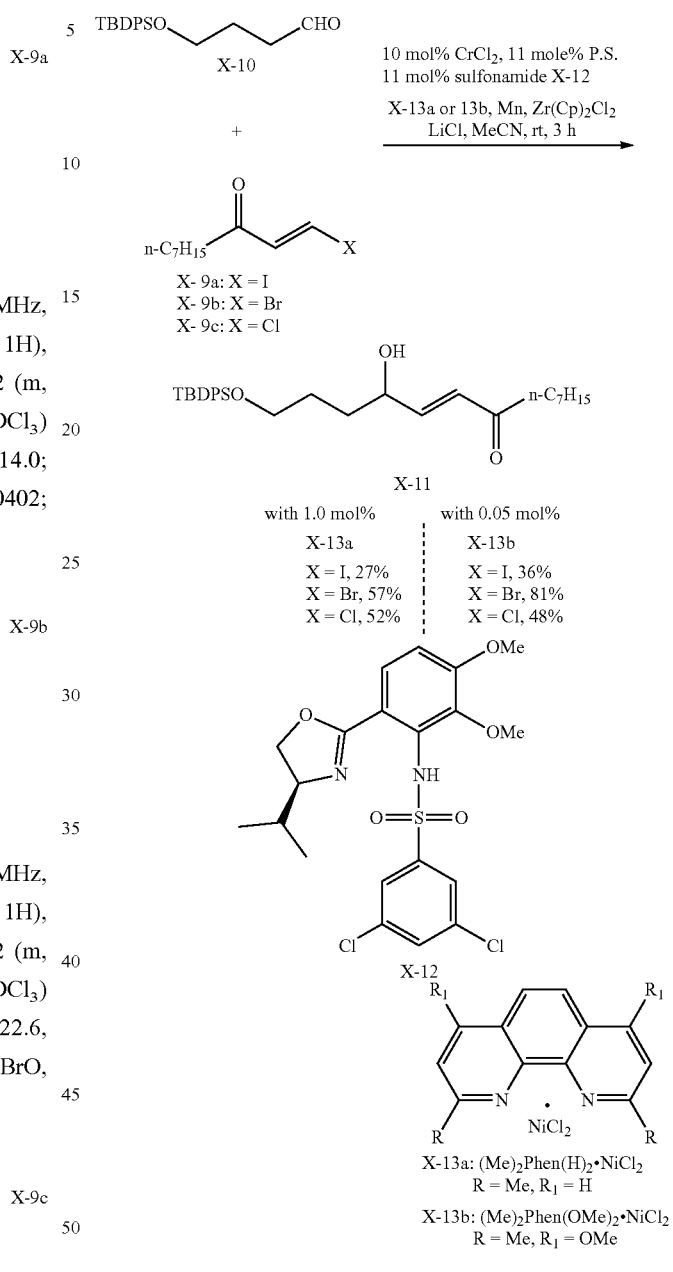

To a mixture of natural sulfonamide (Guo, H.; Dong, C. G.; Kim, D. S.; Urabe, D.; Wang, J.; Kim, J. T.; Liu, X.; Sasaki, T.; Kishi, Y. J. Am. Chem. Soc. 2009, 131, 15387) X-12 (5.20 mg, 11.0 μmol), proton sponge (Aldrich, purified by sublimation; 2.36 mg, 11.0 μmol) and CrCl$_2$ (Aldrich, 99.99% mg, 1.23 mg, 10.0 μmol) was added MeCN (Baker, ultra low water; 50 μL) in a glovebox. The mixture was stirred for 60 min at rt under nitrogen. To the second new vial were added Zr(cp)$_2$Cl$_2$ (Aldrich, 98%; 43.8 mg, 0.15 mmol), Mn powder (Aldrich, 99.99%, powder; 11.0 mg, 0.20 mmol), LiCl (Aldrich, anhydrous, grinded; 8.5 mg, 0.20 mmol), NiCl$_2$. complex (Liu, X.; Li, X.; Chen, Y.; Hu, Y.; Kishi, Y. J. Am. Chem. Soc. 2012, 134, 6136) (X-13a, 1.0 μmol for 1.0 mol % or X-13b, 0.05 μmol for 0.05 mol %), aldehyde X-10 (32.7 mg, 0.10 mmol) and trans-haloenone X-9a-c (0.15 mmol). The deep green mixture in the first vial was transferred to the second reaction vial with syringe under nitrogen. The reaction mixture was stirred under nitrogen until the reaction was completed (by TLC) about 3 h, and diluted with EtOAc (2.0 mL). Florisil (ca. 50 mg) was added, and the mixture was stirred for 30 min, filtered through a short silica gel pad using hexanes/EtOAc (1:1). The eluent was concentrated in vacuo to furnish the crude coupling product, which was purified by preparative TLC (hexanes/EtOAc=4:1) to give X-11 as yellow liquid.

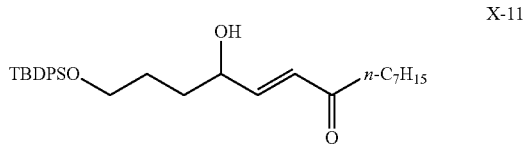

(E)-1-((tert-butyldiphenylsilyl)oxy)-4-hydroxytetradec-5-en-7-one (X-11)

$^1$H NMR (500 MHz, CDCl$_3$) δ: 7.71-7.63 (m, 4H), 7.47-7.36 (m, 6H), 6.80 (dd, J=15.5, 5.0 Hz, 1H), 6.34 (dd, J=16.0, 2.0 Hz, 1H), 4.44-4.32 (m, 1H), 3.70 (t, J=5.0 Hz, 2H), 2.90 (d, J=4.5 Hz, 1H), 2.54 (t, J=7.5 Hz, 2H), 1.87-1.78 (m, 1H), 1.74-1.58 (m, 5H), 1.38-1.19 (m, 8H), 1.06 (s, 9H), 0.88 (t, J=7.0 Hz, 3H); $^{13}$C NMR (125 MHz, CDCl$_3$) δ: 200.8, 147.6, 135.6, 133.2, 129.8, 128.1, 127.7, 70.9, 64.1, 40.9, 34.1, 31.7, 29.2, 29.1, 28.3, 26.8, 24.1, 22.6, 19.1, 14.1; HRMS (ESI) m/z: [M+H]$^+$ calcd for C$_{30}$H$_{45}$O$_3$Si, 481.3138; found, 481.3137.

Synthesis of Chiral Sulfonamide X-12

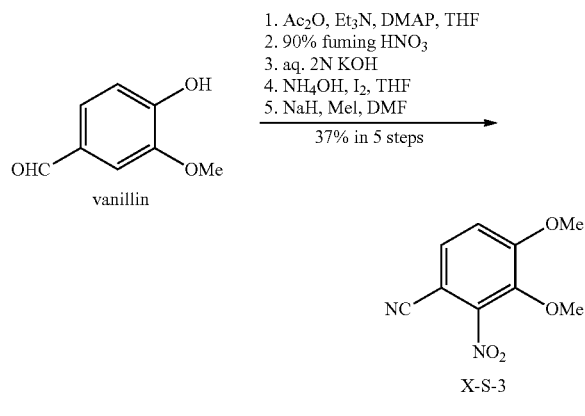

To a solution of vanillin (20.0 g, 0.13 mol) in THF (400 mL) was added acetic anhydride Ac$_2$O (15 mL, 0.16 mol), Et$_3$N (28 mL, 0.20 mol), and DMAP (50 mg). The solution was stirred at rt for 2 h, then concentrated under reduced pressure. 200 mL of CH$_2$Cl$_2$ and 200 mL of aq. 1N HCl were added. The organic layer was separated, and the aqueous layer was extracted with CH$_2$Cl$_2$ (100 mL×2). The combined organic solution was washed with brine, dried over anhydrous MgSO$_4$, filtered, and concentrated under reduced pressure, to give acetate product as a white solid (25.4 g), which was used directly for the next step without further purification (Rege, P. D.; Tian, Y.; Corey, E. *J. Org. Lett.* 2006, 8, 3117).

Fuming nitric acid (100 mL) was cooled to −15° C., and the acetate from the last step was carefully added in small portions. After addition, the resulting deep red solution was stirred for 3 h at −10-0° C., then poured into 400 mL of cold ice water and stirred for 20 min. The yellow solid formed was filtered, thoroughly washed with cold water, and dried under house vacuum overnight. The crude product (21.3 g) was directly used for the next step without further purification.

The yellow solid from the previous step was added to 200 mL of aq. 2N KOH solution. The reaction mixture was heated to reflux for 10 min, and then cooled to rt. A 50 mL of cold concentrated HCl was carefully added to quench the reaction. The light yellow solid formed was filtered, thoroughly washed with cold water, and dried at rt. The crude product phenol (15.7 g) was obtained.

The light yellow solid from the last step was dissolved in 200 mL of THF. To this solution was added aq. NH$_4$OH (28-30%) (200 mL) and iodine (38 g). The dark mixture was stirred at rt for 24 h, then acidified with aq. 2N HCl until pH=7, and extracted with Et$_2$O (200 mL×3). The combined organic layer was washed with 10% Na$_2$S$_2$O$_3$ solution and brine, dried over anhydrous MgSO$_4$, filtered, and concentrated under vacuum. The crude product obtained was further recrystallized in CH$_2$Cl$_2$ to give 4-hydroxy-3-methoxy-2-nitrobenzonitrile as light yellow crystal (11.8 g) (Talukdar, S.; Hsu, J. L.; Chou, T. C.; Fang, J. M. *Tetrahedron Lett.* 2001, 42, 1103).

To a mixture of NaH (3.0 g, 73.0 mmol) in 15 mL of DMF at 0° C., was added the solution of 4-hydroxy-3-methoxy-2-nitrobenzonitrile (11.8 g, 60.8 mmol) in 15 mL of DMF. After 30 min, MeI (17.3 g, 121.6 mmol) was added dropwise. The mixture was stirred at rt for 2 h, and heated up to 60° C. for 30 min. After cooled to rt, it was quenched with aq. 1N HCl. The reaction mixture was extracted with EtOAc (100 mL×3). The combined organic solution was washed with brine, dried over anhydrous MgSO$_4$, filtered, and concentrated under vacuum. The residue was purified by flash chromatography on silica gel (eluted with hexanes/EtOAc/CH$_2$Cl$_2$; 5:1:2, then 2:1:1), to give compound XS-3 as white solid (10.2 g, 37% yield over 5 steps).

3,4-dimethoxy-2-nitrobenzonitrile (XS-3)

m.p. 102-103° C.; $^1$H NMR (500 MHz, CDCl$_3$) δ: 7.49 (d, J=8.5 Hz, 1H), 7.08 (d, J=8.5 Hz, 1H), 4.00 (s, 3H), 3.98 (s, 3H); $^{13}$C NMR (125 MHz, CDCl$_3$) δ: 158.1, 142.5, 129.9, 114.5, 114.2, 98.0, 62.7, 57.0; HRMS (ESI) m/z: [M+Na]$^+$ calcd for C$_9$H$_8$N$_2$NaO$_4$, 231.0382; found, 231.0379.

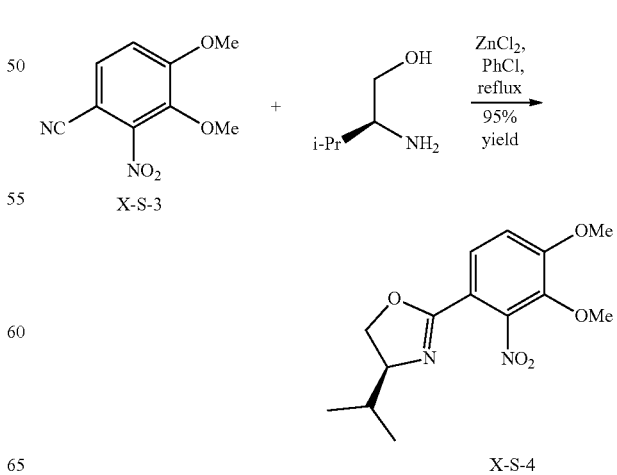

To a solution of XS-3 (2.47 g, 11.8 mmol) in anhydrous chlorobenzene (25 mL) was added anhydrous $ZnCl_2$ (3.38 g, 24.8 mmol) and (R)-valinol (1.82 g, 17.7 mmol) at rt. The solution was heated to reflux for 20 h before quenched with water. The slurry was treated with ammonium hydroxide (20 mL) with stirring for 30 min and extracted with EtOAc (20 mL×3). The combined organic layers were washed with brine, dried over anhydrous $Mg_2SO_4$ and filtered. The solvent was removed under vacuum and the residual was purified on silica gel by flash chromatography (eluted with hexanes/EtOAc (5:1 to 1:1)) to give product XS-4 (3.30 g, 95% yield) as a white solid.

(S)-2-(3,4-dimethoxy-2-nitrophenyl)-4-isopropyl-4,5-dihydrooxazole (XS-4)

$[\alpha]_{D}^{2}$=+64.0 (c 1.0, $CHCl_3$); m.p. 56-58° C.; $^1$H NMR (500 MHz, $CDCl_3$) δ: 7.66 (d, J=8.5 Hz, 1H), 6.98 (d, J=8.5 Hz, 1H), 4.36-4.29 (m, 1H), 4.12-4.02 (m, 2H), 3.94 (s, 3H), 3.91 (s, 3H), 1.85-1.74 (m, 1H), 0.97 (d, J=6.5 Hz, 3H), 0.88 (d, J=6.5 Hz, 3H); $^{13}$C NMR (125 MHz, $CDCl_3$) δ: 158.6, 155.6, 140.9, 125.6, 112.7, 112.6, 72.7, 70.4, 62.2, 56.4, 32.7, 18.6, 18.1; HRMS (ESI) m/z: [M+H]$^+$ calcd for $C_{14}H_{19}N_2O_5$, 295.1294; found, 295.1291.

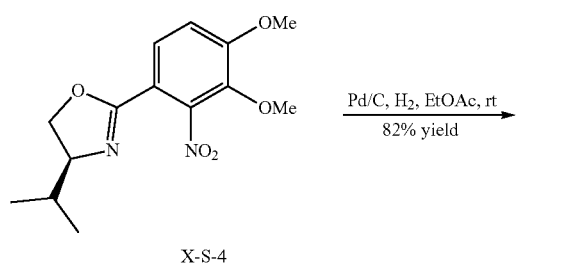

To a solution of XS-4 (3.30 g, 11.2 mmol) in EtOAc (22 mL) was added Pd/C (1.19 g, 10 mmol %). A hydrogen balloon was attached and the reaction was stirred for 3 h at rt. The slurry was filtered through Celite pad and concentrated under vacuum. The residue was purified on silica gel by flash chromatography (eluted with hexanes/EtOAc (10:1)) to give product XS-5 (2.43 g, 82%) as white solid.

(S)-6-(4-isopropyl-4,5-dihydrooxazol-2-yl)-2,3-dimethoxyaniline (XS-5)

$[\alpha]_D^{20}$=−26.4 (c 1.0, $CHCl_3$); m.p. 66-67° C.; $^1$H NMR (500 MHz, $CDCl_3$) δ: 7.42 (d, J=8.5 Hz, 1H), 6.32 (br, 2H), 6.27 (d, J=8.5 Hz, 1H), 4.29 (t, J=8.5 Hz, 1H), 4.07 (q, J=8.0 Hz, 1H), 3.97 (t, J=8.5 Hz, 1H), 3.87 (s, 3H), 3.82 (s, 3H), 1.82-1.72 (m, 1H), 1.03 (d, J=7.0 Hz, 3H), 0.93 (d, J=6.5 Hz, 3H); $^{13}$C NMR (125 MHz, $CDCl_3$) δ: 163.3, 154.4, 143.4, 134.5, 125.4, 104.1, 99.9, 72.9, 68.7, 59.6, 55.6, 33.2, 19.0, 18.6; HRMS (ESI) m/z: [M+H]$^+$ calcd for $C_{14}H_{21}N_2O_3$, 265.1552; found, 265.1549.

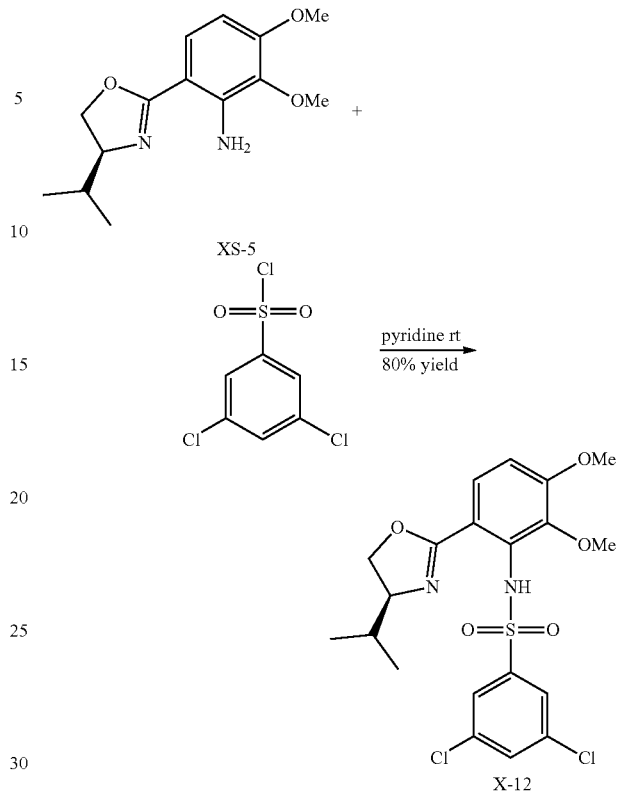

To a solution of XS-5 (0.90 g, 3.4 mmol) in anhydrous pyridine (8 mL) was added 3,5-dichlorobenzenesulfonyl chloride (1.68 g, 6.8 mmol). The solution was stirred overnight at rt, then quenched with water (10 mL). The mixture was extracted with EtOAc (20 mL×3) and the combined organic layers were washed with brine, dried over Na2SO4, and concentrated under vacuum. The residual was purified on silica gel by flash chromatography (eluted with hexanes/EtOAc (5:1)) to give pure product X-12 as a white solid (1.29 g, 80% yield). Recrystallization from hexanes gave white crystals.

(S)-3,5-dichloro-N-(6-(4-isopropyl-4,5-dihydrooxazol-2-yl)-2,3-dimethoxyphenyl)be-nzenesulfonamide (X-12)

$[\alpha]_D^{20}$=−16.2 (c 1.1, $CHCl_3$); m.p. 112-113° C.; $^1$H NMR (500 MHz, $CDCl_3$) δ: 12.60 (br, 1H), 7.93 (s, 2H), 7.56 (d, J=9.0 Hz, 1H), 7.52 (s, 1H), 6.70 (d, J=9.0 Hz, 1H), 4.41 (t, J=8.5 Hz, 1H), 4.17-4.07 (m, 2H), 3.88 (s, 3H), 3.19 (s, 3H), 1.88-1.80 (m, 1H), 1.10 (d, J=7.0 Hz, 3H), 1.00 (d, J=6.0 Hz, 3H); $^{13}$C NMR (125 MHz, $CDCl_3$) δ: 163.2, 155.9, 145.4, 140.9, 135.1, 133.4, 131.5, 125.2, 125.1, 110.4, 107.3, 72.4, 69.9, 59.3, 55.9, 33.2, 18.7; HRMS (ESI) m/z: [M+Na]$^+$ calcd for $C_{20}H_{22}Cl_2N_2NaO_5S$, 495.0524; found, 495.0533.

Synthesis of Trans-Bromoenone X-15-X-18 (FIG. 8)

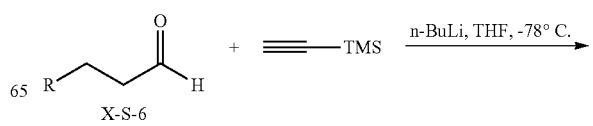

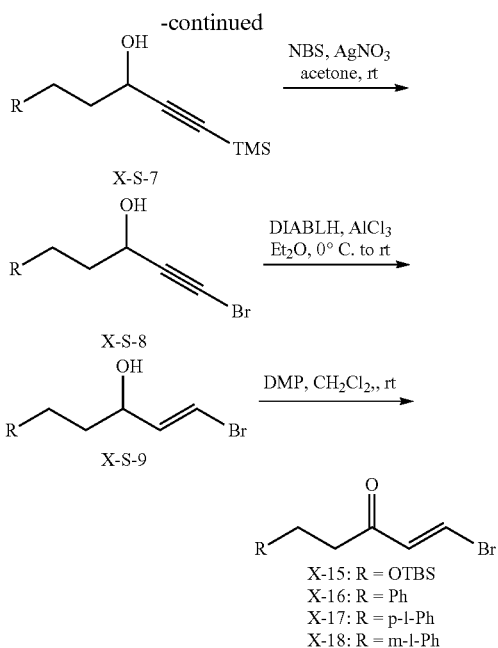

Acetylenide Addition:

To a solution of trimethylsilyl acetylene (196.5 mg, 2.0 mmol) in THF (8.0 mL) was added dropwise n-butyllithium (2.5 M in hexanes, 0.72 mL, 1.8 mmol) at −78° C. After 1 h, a solution of aldehyde XS-6 (1.0 mmol) in THF (2.0 mL) was added over 10 min. The resulting mixture was stirred at −78° C. for 2 h and then quenched with saturated NH$_4$Cl solution (10 mL). The aqueous layer was extracted with EtOAc (10 mL×3) and hexanes (20 mL). The combined organic extracts were washed with brine (500 mL), dried over Na$_2$SO$_4$, and then passed through a pad of silica gel (10 g). Elution with hexanes/EtOAc (1:4, 50 mL) and concentration gave the crude product XS-7, which was used for the next step without further purification.

Direct Bromination:

To a solution of propargyl alcohol XS-7 (1.0 mmol) in acetone (10 mL) was added NBS (267 mg, 1.5 mmol) and silver nitrate AgNO$_3$ (17.2 mg, 0.1 mmol) at rt. After 1 h, the reaction mixture was diluted with 10 mL Et$_2$O and quenched by 10 mL 10% Na$_2$S$_2$O$_3$ solution. The aqueous layer was extracted with Et$_2$O (10 mL×3) and the combined organic layer was washed with 10% Na$_2$S$_2$O$_3$ solution (10 mL×2) and 20 mL brine. The organic layer was dried over anhydrous MgSO$_4$ and concentrated under reduced pressure. The residue was passed through a silica gel pad (4:1 hexanes/EtOAc, 50 mL) and the eluents was concentrated. The crude product XS-8 (a yellow liquid) was used for the next step without further purification.

DIBAL Reduction:

To a solution of aluminum trichloride AlCl$_3$ (166 mg, 2.0 mmol) in Et$_2$O (5 mL) was added slowly DIBAL solution (1.0M in THF, 4.0 mL, 4.0 mmol) at 0° C. The white solid was precipitated out from the reaction solution with addition of DIBAL solution. On the continuous addition of DIBAL solution, the white solid dissolved, and the solution became clear yellow or white precipitated yellow color. After the completion of DIBAL addition, the reaction mixture was stirred for 10-15 min. The solution of propargyl alcohol XS-8 (~1.0 mmol) in ethyl ether Et$_2$O (4.0+1.0 mL) was slowly added to the reaction mixture for ~10 mins at 0° C. The reaction mixture was warmed to room temperature and stirred for 1 h. With the completion of reaction (check TLC to make sure no SM left), the reaction mixture was cooled down to 0° C. and quenched slowly by MeOH (1.0 mL) (hydrogen gas release rapidly). To the reaction mixture was added the 20 mL saturated sodium potassium tartrate solution, and the mixture was stirred vigorously overnight. The white aqueous layer was extracted with EtOAc (3×10 mL) and the combined organic layer was washed with 20 mL brine. The organic layer was dried over anhydrous MgSO$_4$ and concentrated under reduced pressure. The residue was purified by column chromatography on silica gel gave trans-allylic alcohol XS-9 as yellow oil.

Dess-Martin Oxidation:

trans-Allylic alcohol XS-9 was dissolved in wet CH$_2$Cl$_2$ (10 mL) at rt and then DMP (636 mg, 1.5 mmol) and NaHCO$_3$ (840 mg, 10 mmol) were added to the reaction solution. The reaction mixture was stirred for 1 h (monitored by TLC) and quenched by a mixture of 10% Na$_2$S$_2$O$_3$ solution (caution: cannot be saturated) (15 mL) and saturated NaHCO$_3$ solution (10 mL). The solution was diluted with CH$_2$Cl$_2$ (10 mL) and stirred vigorously for 15-30 min. The aqueous layer was extracted with CH$_2$Cl$_2$ (10 mL×4) and combined organic layer was washed with 10% Na$_2$S$_2$O$_3$ solution twice (10 mL), saturated aq. NaHCO$_3$ solution (10 mL) and brine (10 mL). The organic layer was dried over anhydrous MgSO$_4$ and concentrated under reduced pressure. The residue was purified by column chromatography on silica gel to give the desired trans-bromoenone X-15-X-18.

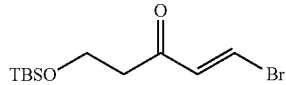

(E)-1-bromo-5-((tert-butyldimethylsilyl)oxy)pent-1-en-3-one (X-15)

42% yield as a yellow oil; $^1$H NMR (500 MHz, CDCl$_3$) δ: 7.56 (d, J=14.0 Hz, 1H), 6.84 (d, J=14.5 Hz, 1H), 3.91 (t, J=6.0 Hz, 2H), 2.73 (t, J=6.5 Hz, 2H), 0.87 (s, 9H), 0.04 (s, 6H); $^{13}$C NMR (125 MHz, CDCl$_3$) δ: 196.5, 137.2, 126.6, 58.8, 43.8, 25.8, 18.2, −5.5; HRMS (ESI) m/z: [M+Na]$^+$ calcd for C$_{11}$H$_{21}$BrNaO$_2$Si, 315.0392; found, 315.0390.

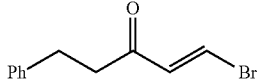

(E)-1-bromo-5-phenylpent-1-en-3-one (X-16)

56% yield as a yellow oil; $^1$H NMR (500 MHz, CDCl$_3$) δ: 7.53 (d, J=13.5 Hz, 1H), 7.29 (t, J=7.5 Hz, 2H), 7.21 (d, J=7.5 Hz, 1H), 7.19 (d, J=7.5 Hz, 2H), 6.80 (d, J=13.5 Hz, 1H), 2.98-2.92 (m, 2H), 2.88-2.83 (m, 2H); $^{13}$C NMR (125 MHz, CDCl$_3$) δ: 196.2, 140.6, 136.4, 128.5, 128.3, 126.3, 126.1, 42.5, 29.6; HRMS (ESI) m/z: [M+Na]$^+$ calcd for C$_{11}$H$_{11}$BrNaO, 260.9891; found, 260.9888.

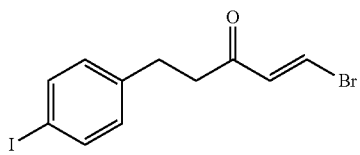

(E)-1-bromo-5-(4-iodophenyl)pent-1-en-3-one (X-17)

62% yield as a yellow oil; $^1$H NMR (500 MHz, CDCl$_3$) δ: 7.60 (d, J=8.0 Hz, 2H), 7.53 (d, J=13.0 Hz, 1H), 6.93 (d, J=7.5 Hz, 2H), 7.79 (d, J=14.0 Hz, 2H), 6.80 (d, J=13.5 Hz, 1H), 2.92-2.86 (m, 2H), 2.85-2.79 (m, 2H); $^{13}$C NMR (125 MHz, CDCl$_3$) δ: 195.8, 140.2, 137.6, 136.2, 130.4, 126.4, 91.4, 42.2, 28.9; HRMS (ESI) m/z: [M+H]$^+$ calcd for C$_{11}$H$_{11}$BrIO, 364.9038; found, 364.9041.

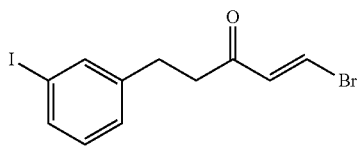

(E)-1-bromo-5-(3-iodophenyl)pent-1-en-3-one (X-18)

63% yield as a yellow oil; $^1$H NMR (500 MHz, CDCl$_3$) δ: 7.56 (d, J=14.0 Hz, 1H), 7.57 (s, 2H), 7.17 (d, J=7.5 Hz, 1H), 7.04 (t, J=7.5 Hz, 1H), 6.82 (d, J=14.0 Hz, 1H), 2.94-2.88 (m, 2H), 2.88-2.83 (m, 2H); $^{13}$C NMR (125 MHz, CDCl$_3$) δ: 195.6, 143.0, 137.3, 136.3, 135.4, 130.3, 127.7, 126.4, 94.5, 42.2, 28.9; HRMS (ESI) m/z: [M+H]$^+$ calcd for C$_{11}$H$_{11}$BrIO, 364.9038; found, 364.9032.

General Procedure (B) of Asymmetric Catalytic Ni/Cr-Mediated Coupling with Trans Bromoenone X-14-X-18

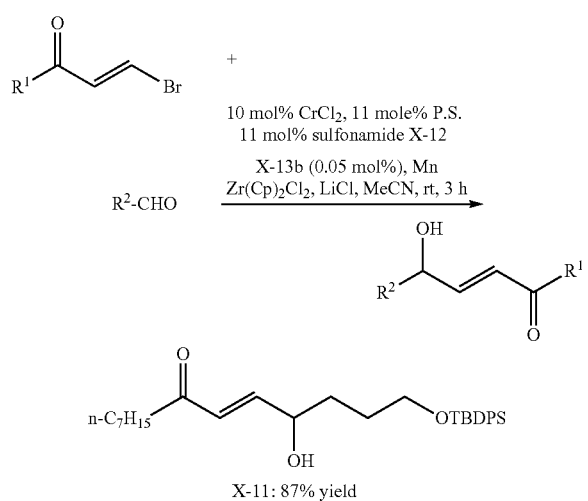

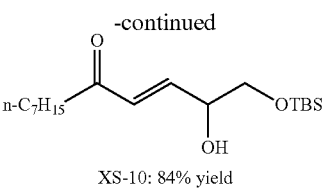

XS-10: 84% yield

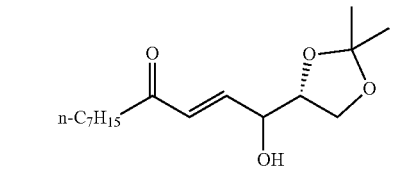

XS-11: 86% yield

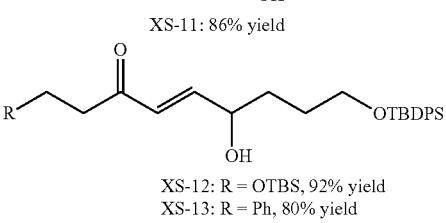

XS-12: R = OTBS, 92% yield
XS-13: R = Ph, 80% yield

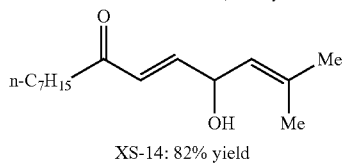

XS-14: 82% yield

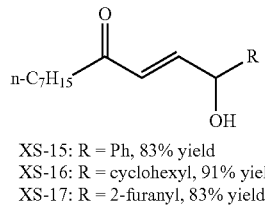

XS-15: R = Ph, 83% yield
XS-16: R = cyclohexyl, 91% yield
XS-17: R = 2-furanyl, 83% yield

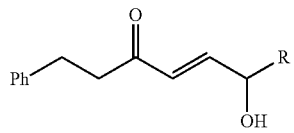

XS-18: R = Ph, 83% yield
XS-19: R = 2-furanyl, 90% yield

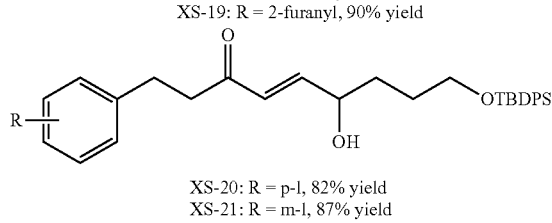

XS-20: R = p-I, 82% yield
XS-21: R = m-I, 87% yield

To a mixture of natural sulfonamide X-12 (5.20 mg, 11.0 μmol), proton sponge (Aldrich, purified by sublimation; 2.36 mg, 11.0 μmol) and CrCl$_2$ (Aldrich, 99.99% mg, 1.23 mg, 10.0 mol) was added MeCN (Baker, ultra low water; 100 μL) in a glovebox. The mixture was stirred for 60 min at rt under nitrogen. To the second new vial were added Zr(cp)$_2$Cl$_2$ (Aldrich, 98%; 43.8 mg, 0.15 mmol), Mn powder (Aldrich, 99.99%, powder; 11.0 mg, 0.20 mmol), LiCl (Aldrich, anhydrous, grinded; 8.5 mg, 0.20 mmol), NiCl$_2$ catalyst X-13b (0.033 mg, 0.05 μmol), aldehyde (32.7 mg, 0.10 mmol), trans-bromoenone X-14-X-18 (0.15 mmol) and MeCN (Baker, ultra low water; 150 μL). The mixture in the first vial was transferred to the second vial with syringe under nitrogen. The reaction mixture was stirred under nitrogen until the reaction was completed in about 3 h (by TLC), and diluted with EtOAc (2.0 mL). Florisil (ca. 50 mg) was added, and the mixture was stirred for 30 min, filtered through a short silica gel pad using EtOAc/hexanes (1:1). The eluent was concentrated in vacuo to furnish the crude coupling product. The crude product was purified by preparative TLC (EtOAc/hexanes=1:4) to give X-11 to XS-21 as a yellow liquid.

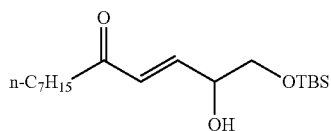

(E)-1-((tert-butyldimethylsilyl)oxy)-2-hydroxydodec-3-en-5-one (XS-10)

84% yield; $^1$H NMR (500 MHz, CDCl$_3$) δ: 6.73 (dd, J=15.5, 4.5 Hz, 1H), 6.40 (dd, J=16.0, 2.0 Hz, 1H), 4.39-4.33 (m, 1H), 3.74 (dd, J=10.0, 4.0 Hz, 1H), 3.49 (dd, J=10.0, 7.5 Hz, 1H), 2.70 (d, J=4.5 Hz, 1H), 2.53 (t, J=7.5 Hz, 2H), 1.64-1.56 (m, 2H), 1.33-1.21 (m, 8H), 0.90 (s, 9H), 0.87 (t, J=7.0 Hz, 3H), 0.08 (s, 3H), 0.07 (s, 3H); $^{13}$C NMR (125 MHz, CDCl$_3$) δ: 200.4, 143.2, 129.5, 71.5, 66.2, 40.9, 31.6, 29.2, 29.0, 25.8, 24.1, 22.6, 18.2, 14.0, −5.4, −5.5; HRMS (ESI) m/z: [M+Na]$^+$ calcd for C$_{18}$H$_{36}$NaO$_3$Si, 351.2331; found, 351.2321.

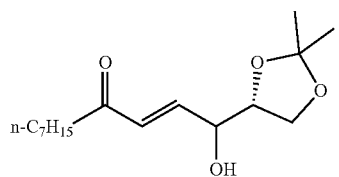

(E)-1-((R)-2,2-dimethyl-1,3-dioxolan-4-yl)-1-hydroxyundec-2-en-4-one (XS-11)

86% yield; $^1$H NMR (500 MHz, CDCl$_3$) δ: 6.75 (dd, J=16.0, 4.5 Hz, 1H), 6.43 (dd, J=16.0, 1.5 Hz, 1H), 4.50-4.44 (m, 1H), 4.15 (q, J=6.0 Hz, 1H), 3.94 (dd, J=8.5, 6.5 Hz, 1H), 3.87 (dd, J=8.5, 6.5 Hz, 1H), 2.53 (t, J=7.5 Hz, 2H), 1.64-1.55 (m, 2H), 1.44 (s, 3H), 1.35 (s, 3H), 1.32-1.19 (m, 8H), 0.86 (t, J=7.0 Hz, 3H); $^{13}$C NMR (125 MHz, CDCl$_3$) δ: 200.3, 142.1, 129.6, 109.8, 70.6, 64.7, 41.1, 31.6, 29.1, 29.0, 26.4, 24.9, 24.0, 22.6, 14.0; HRMS (ESI) m/z: [M+Na]$^+$ calcd for C$_{16}$H$_{28}$NaO$_4$, 307.1885; found, 307.1879.

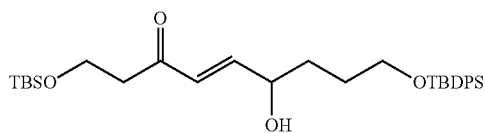

(E)-10-hydroxy-2,2,3,3,16,16-hexamethyl-15,15-diphenyl-4,14-dioxa-3,15-disilahept-adec-8-en-7-one (XS-12)

92% yield; $^1$H NMR (500 MHz, CDCl$_3$) δ: 7.70-7.64 (m, 4H), 7.47-7.36 (m, 6H), 6.82 (dd, J=16.0, 5.0 Hz, 1H), 6.36 (dd, J=16.0, 1.5 Hz, 1H), 4.41-4.34 (m, 1H), 3.94 (t, J=6.5 Hz, 2H), 3.70 (d, J=5.5 Hz, 2H), 2.98 (br, 1H), 2.79 (t, J=6.5 Hz, 2H), 1.86-1.77 (m, 1H), 1.74-1.61 (m, 3H), 1.06 (s, 9H), 0.88 (s, 9H), 0.06 (s, 6H); $^{13}$C NMR (125 MHz, CDCl$_3$) δ: 199.2, 148.4, 135.5, 133.2, 129.7, 128.6, 127.7, 70.8, 64.0, 59.0, 43.6, 33.9, 28.3, 26.8, 26.7, 25.8, 19.1, 18.2; HRMS (ESI) m/z: [M+Na]$^+$ calcd for C$_{31}$H$_{48}$NaO$_4$Si$_2$, 563.2989; found, 563.2980.

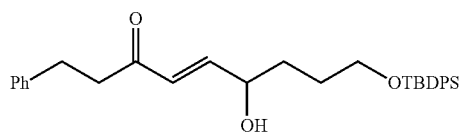

(E)-9-((tert-butyldiphenylsilyl)oxy)-6-hydroxy-1-phenylnon-4-en-3-one (XS-13)

80% yield; $^1$H NMR (500 MHz, CDCl$_3$) δ: 7.69-7.64 (m, 4H), 7.46-7.36 (m, 6H), 7.31-7.26 (m, 2H), 7.22-7.17 (m, 3H), 6.80 (dd, J=16.0, 4.5 Hz, 1H), 6.35 (dd, J=16.0, 2.0 Hz, 1H), 4.40-4.33 (m, 1H), 3.70 (t, J=5.5 Hz, 2H), 2.96 (t, J=7.5 Hz, 2H), 2.89 (t, J=7.5 Hz, 2H), 1.84-1.76 (m, 1H), 1.72-1.59 (m, 3H), 1.06 (s, 9H); $^{13}$C NMR (125 MHz, CDCl$_3$) δ: 199.4, 148.2, 141.1, 135.5, 133.2, 129.8, 128.5, 128.4, 128.0, 127.7, 126.1, 70.8, 64.1, 42.4, 34.0, 30.0, 28.3, 26.8, 19.1; HRMS (ESI) m/z: [M+Na]$^+$ calcd for C$_{31}$H$_{38}$NaO$_3$Si, 509.2488; found, 509.2479.

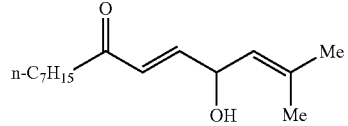

(E)-4-hydroxy-2-methyltetradeca-2,5-dien-7-one (XS-14)

82% yield; $^1$H NMR (500 MHz, CDCl$_3$) δ: 6.73 (dd, J=16.0, 5.0 Hz, 1H), 6.28 (dd, J=16.0, 2.0 Hz, 1H), 5.15 (dt, J=9.0, 1.5 Hz, 1H), 5.08-5.01 (m, 1H), 2.55 (t, J=7.5 Hz, 2H), 1.76 (d, J=1.0 Hz, 3H), 1.74 (d, J=1.0 Hz, 3H), 1.63-1.58 (m, 2H), 1.35-1.20 (m, 8H), 0.88 (t, J=7.0 Hz, 3H); $^{13}$C NMR (125 MHz, CDCl$_3$) δ: 201.0, 146.2, 137.4, 127.7, 124.3, 68.4, 40.6, 31.7, 29.2, 29.1, 25.8, 24.1, 22.6, 18.4, 14.0; HRMS (ESI) m/z: [M+Na]$^+$ calcd for C$_{15}$H$_{26}$NaO$_2$, 261.1830; found, 261.1835.

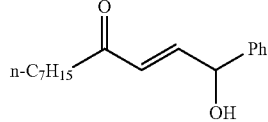

(E)-1-hydroxy-1-phenylundec-2-en-4-one (XS-15)

83% yield; $^1$H NMR (500 MHz, CDCl$_3$) δ: 7.42-7.30 (m, 5H), 6.88 (dd, J=15.5, 4.5 Hz, 1H), 6.42 (dd, J=16.0, 1.5 Hz, 1H), 5.38 (d, J=4.0 Hz, 1H), 2.56 (t, J=7.5 Hz, 2H), 2.15 (br, 1H), 1.66-1.54 (m, 4H), 1.36-1.18 (m, 6H), 0.87 (t, J=7.0 Hz, 3H); $^{13}$C NMR (125 MHz, CDCl$_3$) δ: 200.8, 146.0, 141.0, 128.9, 128.4, 128.1, 126.5, 73.8, 40.8, 31.7, 29.2, 29.1, 24.1, 22.6, 14.0; HRMS (ESI) m/z: [M+H]$^+$ calcd for C$_{17}$H$_{25}$O$_2$, 261.1855; found, 261.1873.

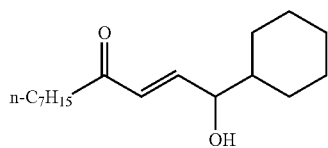

(E)-1-cyclohexyl-1-hydroxyundec-2-en-4-one (XS-16)

91% yield; $^1$H NMR (500 MHz, CDCl$_3$) δ: 6.80 (dd, J=16.0, 5.0 Hz, 1H), 6.29 (dd, J=16.0, 1.5 Hz, 1H), 4.09 (q, J=5.0 Hz, 1H), 2.55 (t, J=7.5 Hz, 2H), 1.82-1.72 (m, 3H), 1.71-1.65 (m, 2H), 1.64-1.59 (m, 2H), 1.55-1.47 (m, 1H), 1.33-1.24 (m, 8H), 1.24-1.00 (m, 6H), 0.88 (t, J=7.0 Hz, 3H); $^{13}$C NMR (125 MHz, CDCl$_3$) δ: 200.4, 143.2, 129.5, 71.5, 66.2, 40.9, 31.6, 29.2, 29.0, 25.8, 24.1, 22.6, 18.2, 14.0, −5.4, −5.5; HRMS (ESI) m/z: [M+H]$^+$ calcd for C$_{17}$H$_{31}$O$_2$, 267.2324; found, 267.2333.

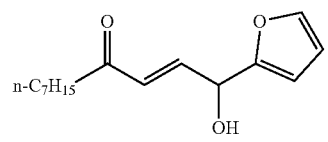

(E)-1-(furan-2-yl)-1-hydroxyundec-2-en-4-one (XS-17)

83% yield; $^1$H NMR (500 MHz, CDCl$_3$) δ: 7.41 (d, J=1.5 Hz, 1H), 6.94 (dd, J=16.0, 5.0 Hz, 1H), 6.46 (dd, J=16.0, 2.0 Hz, 1H), 6.35 (dd, J=3.0, 1.5 Hz, 1H), 6.28 (d, J=3.0 Hz, 1H), 5.41 (s, 1H), 2.58 (t, J=7.5 Hz, 2H), 2.40 (br, 1H), 1.65-1.56 (m, 2H), 1.36-1.16 (m, 8H), 0.87 (t, J=7.0 Hz, 3H); $^{13}$C NMR (125 MHz, CDCl$_3$) δ: 200.5, 153.2, 142.9, 142.5, 129.4, 110.5, 107.6, 67.0, 41.0, 31.6, 29.2, 29.0, 24.0, 22.6, 14.0; HRMS (ESI) m/z: [M+Na]$^+$ calcd for C$_{15}$H$_{22}$NaO$_3$, 273.1467; found, 273.1473.

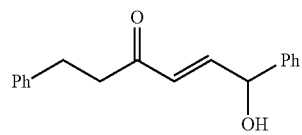

(E)-6-hydroxy-1,6-diphenylhex-4-en-3-one (XS-18)

83% yield; $^1$H NMR (500 MHz, CDCl$_3$) δ: 7.39-7.35 (m, 2H), 7.34-7.30 (m, 3H), 7.29-7.24 (m, 2H), 7.21-7.16 (m, 3H), 6.87 (dd, J=13.5, 3.5 Hz, 1H), 6.41 (dd, J=13.5, 1.5 Hz, 1H), 5.35 (s, 1H), 2.95-2.87 (m, 4H), 2.38 (d, J=3.0 Hz, 1H); $^{13}$C NMR (125 MHz, CDCl$_3$) δ: 199.5, 146.5, 141.0, 140.9, 128.9, 128.5, 128.4, 128.3, 127.9, 126.5, 126.1, 73.7, 42.2, 29.8; HRMS (ESI) m/z: [M+Na]$^+$ calcd for C$_{18}$H$_{18}$NaO$_2$, 289.1204; found, 289.1208.

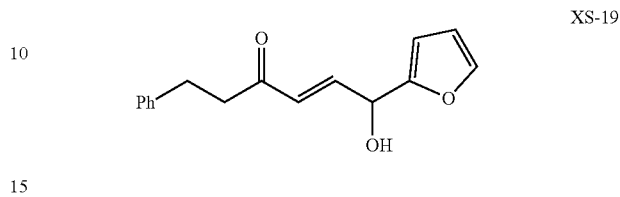

(E)-6-(furan-2-yl)-6-hydroxy-1-phenylhex-4-en-3-one (XS-19)

90% yield; $^1$H NMR (500 MHz, CDCl$_3$) δ: 7.42 (d, J=7.5 Hz, 1H), 7.30 (d, J=7.5 Hz, 2H), 7.24-7.18 (m, 3H), 6.95 (dd, J=16.0, 4.5 Hz, 1H), 6.48 (dd, J=16.0, 2.0 Hz, 1H), 6.37 (dd, J=3.5, 2.0 Hz, 1H), 6.28 (d, J=3.5 Hz, 1H), 6.41 (t, J=3.5 Hz, 1H), 3.01-2.88 (m, 4H), 2.46 (d, J=5.0 Hz, 1H); $^{13}$C NMR (125 MHz, CDCl$_3$) δ: 199.2, 153.1, 143.1, 142.9, 141.0, 129.3, 128.5, 128.3, 126.1, 110.5, 107.6, 66.9, 42.4, 29.8; HRMS (ESI) m/z: [M+Na]$^+$ calcd for C$_{16}$H$_{16}$NaO$_3$, 279.0997; found, 279.1005.

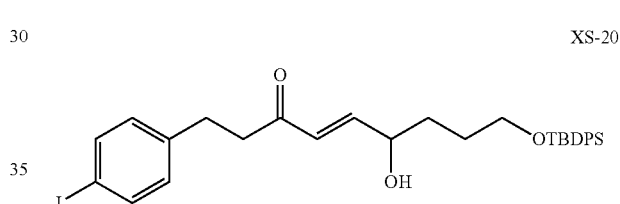

(E)-9-((tert-butyldiphenylsilyl)oxy)-6-hydroxy-1-(4-iodophenyl)non-4-en-3-one (XS-20)

82% yield; $^1$H NMR (500 MHz, CDCl$_3$) δ: 7.68-7.64 (m, 4H), 7.59 (d, J=8.5 Hz, 2H), 7.44-7.36 (m, 6H), 6.95 (d, J=8.0 Hz, 2H), 6.79 (dd, J=16.0, 4.5 Hz, 1H), 6.35 (dd, J=16.0, 2.0 Hz, 1H), 4.38-4.33 (m, 1H), 3.70 (t, J=5.0 Hz, 2H), 3.00 (d, J=4.5 Hz, 1H), 2.91-2.83 (m, 4H), 1.82-1.77 (m, 1H), 1.71-1.62 (m, 2H), 1.06 (s, 9H); $^{13}$C NMR (125 MHz, CDCl$_3$) δ: 198.9, 148.3, 140.8, 137.5, 135.5, 133.2, 130.5, 129.8, 127.9, 127.7, 91.1, 70.8, 64.1, 42.0, 34.1, 29.3, 28.3, 26.8, 19.1; HRMS (ESI) m/z: [M+Na]$^+$ calcd for C$_{31}$H$_{37}$INaO$_3$Si, 635.1454; found, 635.1450.

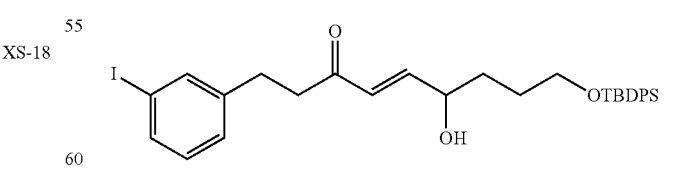

(E)-9-((tert-butyldiphenylsilyl)oxy)-6-hydroxy-1-(3-iodophenyl)non-4-en-3-one (XS-21)

87% yield; $^1$H NMR (500 MHz, CDCl$_3$) δ: 7.67-7.64 (m, 4H), 7.56 (s, 1H), 7.53 (d, J=7.5 Hz, 1H), 7.46-7.41 (m, 2H), 7.40-7.37 (m, 4H), 7.16 (d, J=8.0 Hz, 1H), 7.01 (t, J=8.0 Hz, 1H), 6.80 (dd, J=16.0, 4.5 Hz, 1H), 6.35 (dd, J=16.0, 1.5 Hz, 1H), 4.40-4.34 (m, 1H), 3.70 (t, J=5.5 Hz, 2H), 3.00 (d, J=4.0 Hz, 1H), 2.92-2.83 (m, 4H), 1.84-1.77 (m, 1H), 1.71-1.62 (m, 2H), 1.06 (s, 9H); $^{13}$C NMR (125 MHz, CDCl$_3$) δ: 198.8, 148.4, 143.6, 137.4, 135.5, 135.5, 135.2, 133.2, 130.2, 129.8, 127.9, 127.7, 94.5, 70.8, 64.1, 42.0, 34.1, 29.3, 28.3, 26.8, 19.1; HRMS (ESI) m/z: [M+Na]$^+$ calcd for C$_{31}$H$_{37}$INaO$_3$Si, 635.1454; found, 635.1446.

Synthesis Outlined in FIG. 9

Synthesis of Cis-Bromoenone X-19

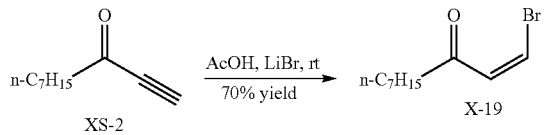

To a solution of 1-decyn-3-one XS-2 (0.26 g, 1.7 mmol) in acetic acid (AcOH, 3.4 mL) was added LiBr (174.0 mg, 2.0 mmol). The reaction mixture was stirred overnight, and then diluted with 20 mL H$_2$O. The aqueous solution was extracted with Et$_2$O (20 mL×3) and combined organic extracts were washed with saturated aq. NaHCO$_3$ solution (20 mL×2) and 20 mL of brine. The organic layer was dried over anhydrous MgSO$_4$ and concentrated under reduced pressure. The residue was purified by flash column chromatography on silica gel with eluent of hexanes/Et$_2$O (100:1). The (Z)-1-bromodec-1-en-3-one X-19 was obtained as light yellow oil (70% yield). $^1$H NMR (500 MHz, C$_6$D$_6$) δ: 6.16 (d, J=8.5 Hz, 1H), 6.05 (d, J=8.5 Hz, 1H), 2.18 (t, J=7.5 Hz, 2H), 1.49 (quint, J=7.5 Hz, 2H), 1.30-1.20 (m, 2H), 1.20-1.09 (m, 6H), 0.88 (t, J=7.5 Hz, 3H); $^{13}$C NMR (125 MHz, C$_6$D$_6$) δ: 197.6, 131.6, 115.5, 43.9, 32.0, 29.4, 29.3, 24.0, 22.9, 14.3; HRMS (ESI) m/z: [M+H]$^+$ calcd for C$_{10}$H$_{18}$BrO, 233.0541; found, 233.0544.

Asymmetric Catalytic Ni/Cr-Mediated Coupling with Cis-Bromoenone X-19

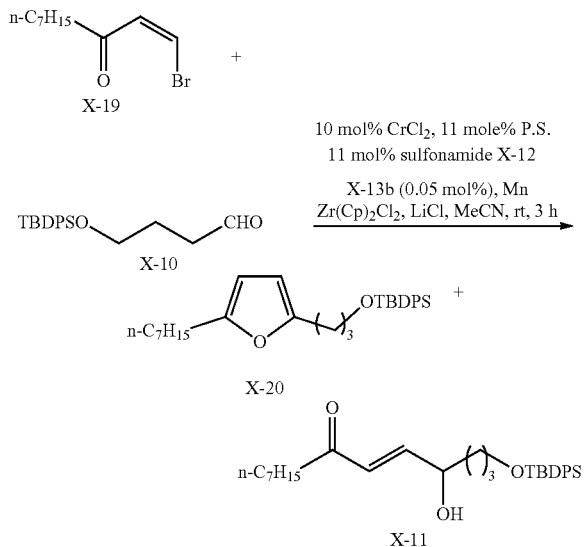

The procedure was the same as procedure B. The products were obtained as a mixture of furan X-20 and X-11 (80% yield, 1:9) (Sammond, D. M.; Sammakia, T. *Tetrahedron Lett.* 1996, 37, 6065).

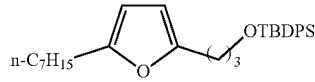

tert-butyl(3-(5-heptylfuran-2-yl)propoxy)diphenylsilane (X-20)

8% yield; $^1$H NMR (500 MHz, CDCl$_3$) δ: 7.70-7.64 (m, 4H), 7.45-7.35 (m, 6H), 5.83 (d, J=3.0 Hz, 1H), 5.82 (d, J=3.0 Hz, 1H), 3.71 (t, J=6.0 Hz, 2H), 2.71 (t, J=7.5 Hz, 2H), 2.55 (t, J=7.5 Hz, 2H), 1.89 (quint, J=6.5 Hz, 2H), 1.64-1.54 (m, 4H), 1.38-1.19 (m, 8H), 1.06 (s, 9H), 0.88 (t, J=7.0 Hz, 3H); $^{13}$C NMR (125 MHz, CDCl$_3$) δ: 154.8, 154.0 135.6, 134.0, 129.5, 127.6, 105.1, 104.8, 63.1, 31.8, 31.0, 29.2, 29.0, 28.1, 28.0, 26.8, 24.4, 22.6, 19.2, 14.1; HRMS (ESI) m/z: [M+H]$^+$ calcd for C$_{30}$H$_{43}$O$_2$Si, 463.3032; found, 463.3030.

Acid Catalyzed Formation of Furan from Corresponding Trans-Coupling Product

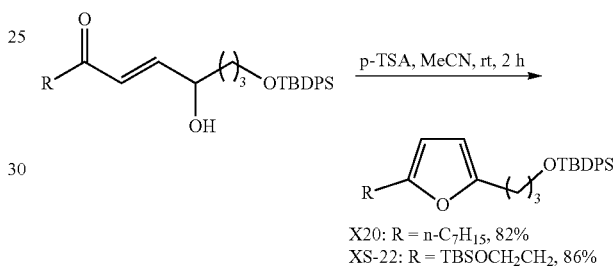

X20: R = n-C$_7$H$_{15}$, 82%
XS-22: R = TBSOCH$_2$CH$_2$, 86%

The trans-coupling product (20 μmol) was dissolved in MeCN (0.5 mL) containing p-toluenesulfonic acid (p-TSA, 0.69 mg, 4 μmol) and the reaction mixture was stirred at rt for 2 h. The reaction was quenched with solid NaHCO$_3$ (3.36 mg, 40 μmol) and passed through a short silica gel pad with Hex/EtOAc (10:1). On removal of solvent, the furan product was obtained as yellow oil.

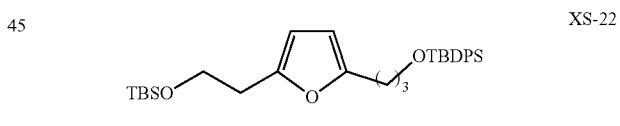

tert-butyl(3-(5-(2-((tert-butyldimethylsilyl)oxy) ethyl)furan-2-yl)propoxy)diphenylsil-ane (XS-22)

86% yield; $^1$H NMR (500 MHz, CDCl$_3$) δ: 7.70-7.66 (m, 4H), 7.45-7.40 (m, 2H), 7.39-7.36 (m, 4H), 5.92 (d, J=3.0 Hz, 1H), 5.84 (d, J=3.5 Hz, 1H), 3.83 (t, J=6.5 Hz, 2H), 3.72 (t, J=6.5 Hz, 2H), 2.80 (t, J=7.0 Hz, 2H), 2.71 (t, J=7.5 Hz, 2H), 1.89 (quint, J=6.5 Hz, 2H), 1.07 (s, 9H), 0.89 (s, 9H), 0.02 (s, 6H); $^{13}$C NMR (125 MHz, CDCl$_3$) δ: 154.3, 151.3, 135.6, 134.0, 129.5, 127.6, 106.5, 105.3, 63.1, 61.9, 32.0, 30.9, 26.8, 26.0, 24.4, 19.2, 18.3, -5.4; HRMS (ESI) m/z: [M+Na]$^+$ calcd for C$_{31}$H$_{46}$NaO$_3$Si$_2$, 545.2883; found, 545.2879.

Synthesis of Tri-Substituted Bromoenone X-21-X-22.

For the preparation of undec-2-yn-4-one, refer to the proceeding paper (Wender, P. A.; Bi, F. C.; Brodney, M. A.; Gosselin, F. *Org. Lett.* 2001, 3, 2105).

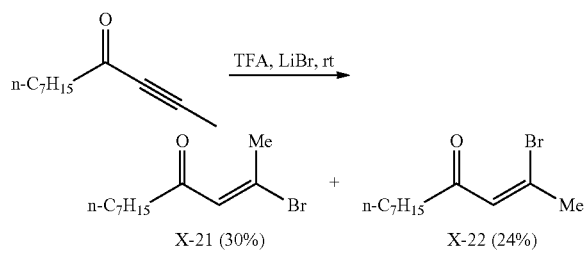

To a solution of undec-2-yn-4-one (0.33 g, 2 mmol) in trifluoroacetic acid (TFA, 4.0 mL) was added LiBr (208 mg, 2.4 mmol). The reaction mixture was stirred for 1 h, and then poured in 20 mL saturated aq. NaHCO$_3$ solution. NaHCO$_3$ (solid) was added in small portions, and the solution was vigorously stirred until the pH of the reaction mixture became neutral. The reaction mixture was extracted with Et$_2$O (30 mL×3) and combined organic extracts were washed with 50 mL of saturated NaHCO$_3$ solution and 30 mL of brine. The organic layer was dried over anhydrous MgSO$_4$ and concentrated under reduced pressure to give a residue, which was separated by preparative TLC (hexanes/EtOAc=4:1), to give E-isomer X-21 and Z-isomer X-22 as light yellow oils in 30% and 24% yields, respectively.

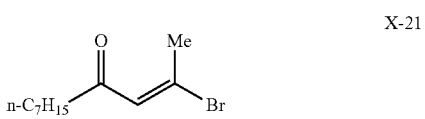

X-21

(E)-2-bromoundec-2-en-4-one (X-21)

30% yield; $^1$H NMR (500 MHz, CDCl$_3$) δ: 6.69 (s, 1H), 2.75 (s, 3H), 2.41 (t, J=7.5 Hz, 2H), 1.64-1.53 (m, 2H), 1.35-1.21 (m, 10H), 0.91-0.82 (m, 3H); $^{13}$C NMR (125 MHz, CDCl$_3$) δ: 198.5, 143.2, 129.9, 44.5, 31.6, 29.1, 29.0, 26.8, 24.0, 22.6, 14.0; HRMS (ESI) m/z: [M+H]$^+$ calcd for C$_{11}$H$_{20}$BrO, 247.0698; found, 247.0702.

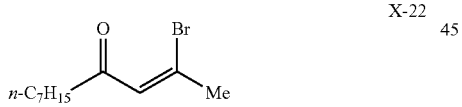

X-22

(Z)-2-bromoundec-2-en-4-one (X-22)

24% yield; $^1$H NMR (500 MHz, CDCl$_3$) δ: 6.56 (s, 1H), 2.53 (t, J=7.5 Hz, 2H), 2.44 (s, 3H), 1.64-1.55 (m, 2H), 1.35-1.21 (m, 10H), 0.91-0.82 (m, 3H); $^{13}$C NMR (125 MHz, CDCl$_3$) δ: 198.8, 132.3, 127.1, 44.0, 31.7, 31.1, 29.1, 29.0, 23.8, 22.6, 14.0; HRMS (ESI) m/z: [M+H]$^+$ calcd for C$_{11}$H$_{20}$BrO, 247.0698; found, 247.0690.

Asymmetric Catalytic Ni/Cr-Mediated Coupling with Tri-Substituted Bromoenone

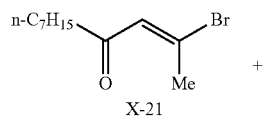

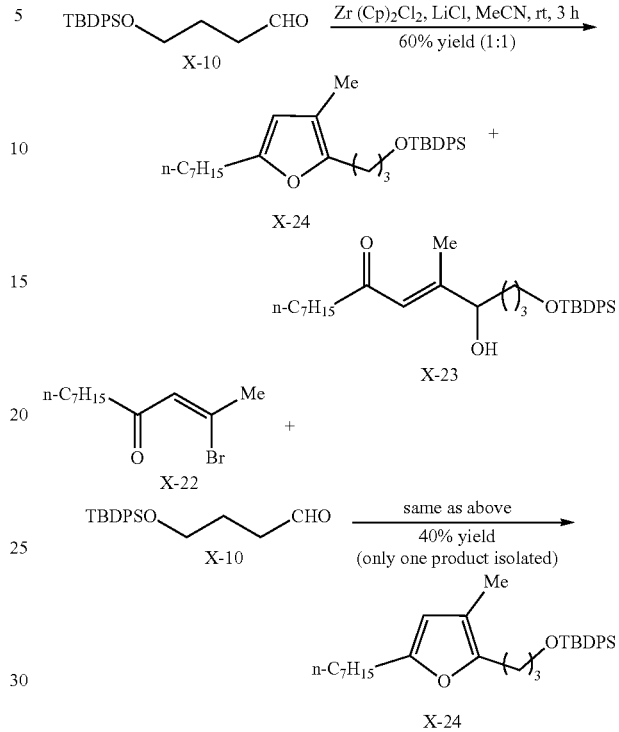

The procedure was similar to procedure A. The NiCl$_2$ catalyst was X-13b with 1.0 mol % loading. By preparative TLC (20% EtOAc in hexanes), alcohol X-23 and furan X-24 were isolated.

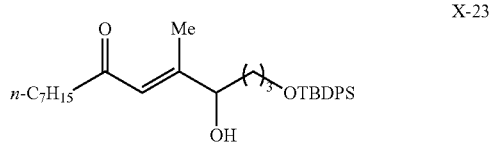

(E)-1-((tert-butyldiphenylsilyl)oxy)-4-hydroxy-5-methyltetradec-5-en-7-one (X-23)

$^1$H NMR (500 MHz, CDCl$_3$) δ: 7.69-7.64 (m, 4H), 7.46-7.35 (m, 6H), 6.36 (s, 1H), 4.10 (t, J=7.0 Hz, 1H), 3.69 (t, J=5.5 Hz, 2H), 2.44 (t, J=7.0 Hz, 2H), 2.08 (s, 3H), 1.83 (quin, J=7.5 Hz, 2H), 1.60-1.52 (m, 4H), 1.38-1.20 (m, 8H), 1.06 (s, 9H), 0.87 (t, J=7.0 Hz, 3H); $^{13}$C NMR (125 MHz, CDCl$_3$) δ: 202.0, 158.0, 135.5, 133.3, 129.8, 127.7, 121.7, 76.0, 64.1, 44.7, 32.4, 31.7, 29.3, 29.1, 28.3, 26.8, 24.2, 22.6, 19.1, 15.8, 14.1; HRMS (ESI) m/z: [M+Na]$^+$ calcd for C$_{31}$H$_{46}$NaO$_3$Si, 517.3114; found, 517.3120.

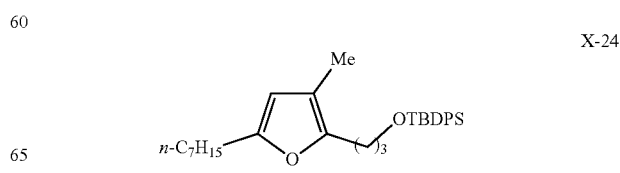

tert-butyl(3-(5-heptyl-3-methylfuran-2-yl)propoxy)diphenylsilane (X-24)

$^1$H NMR (500 MHz, CDCl$_3$) δ: 7.69-7.64 (m, 4H), 7.44-7.34 (m, 6H), 5.73 (s, 1H), 3.67 (t, J=6.0 Hz, 2H), 2.63 (t, J=7.5 Hz, 2H), 2.50 (t, J=7.5 Hz, 2H), 1.89 (s, 3H), 1.83 (quin, J=7.5 Hz, 2H), 1.60-1.52 (m, 4H), 1.38-1.20 (m, 8H), 1.06 (s, 9H), 0.87 (t, J=7.0 Hz, 3H); $^{13}$C NMR (125 MHz, CDCl$_3$) δ: 153.7, 148.7, 135.6, 134.0, 129.5, 127.6, 114.1, 107.6, 63.1, 31.8, 31.6, 29.2, 29.0, 28.1, 28.0, 26.9, 22.6, 22.1, 19.2, 14.1, 9.9. HRMS (ESI) m/z: [M+H]$^+$ calcd for C$_{31}$H$_{45}$O$_2$Si, 477.3189; found, 477.3194.
Synthesis Outlined in FIG. 11
Competition Studies of Ni/Cr-Mediated Coupling Reactions with Trans-Bromoenone and Alkenyl Iodides X-31a-c LiCl (Aldrich, anhydrous, grinded; 4.3 mg, 0.1 mmol), Mn powder (Aldrich, 99.99%, powder; 5.5 mg, 0.1 mmol), Zr(Cp)$_2$Cl$_2$ (Aldrich, 98%; 21.9 mg, 0.075 mmol), NiCl$_2$ catalyst X-13a or X-13b (x=0.05 mol %, 0.1 mol %, 0.5 mol % or 1.0 mol %) and MeCN (Baker, ultra low water; 75 μL). The green solution of chromium catalyst (50 μL) from the first vial was transferred to the second vial with microliter syringe. The reaction mixture was stirred under nitrogen for 3 h, and diluted with EtOAc (1.0 mL). Florisil (ca. 30 mg) was added, and the mixture was stirred for 30 min, filtered through a short silica gel pad twice using hexanes/EtOAc (1:1) The eluent was concentrated in vacuo to furnish the crude coupling product. The ratio analysis of crude coupling products X-32a-c was done with $^1$H NMR.

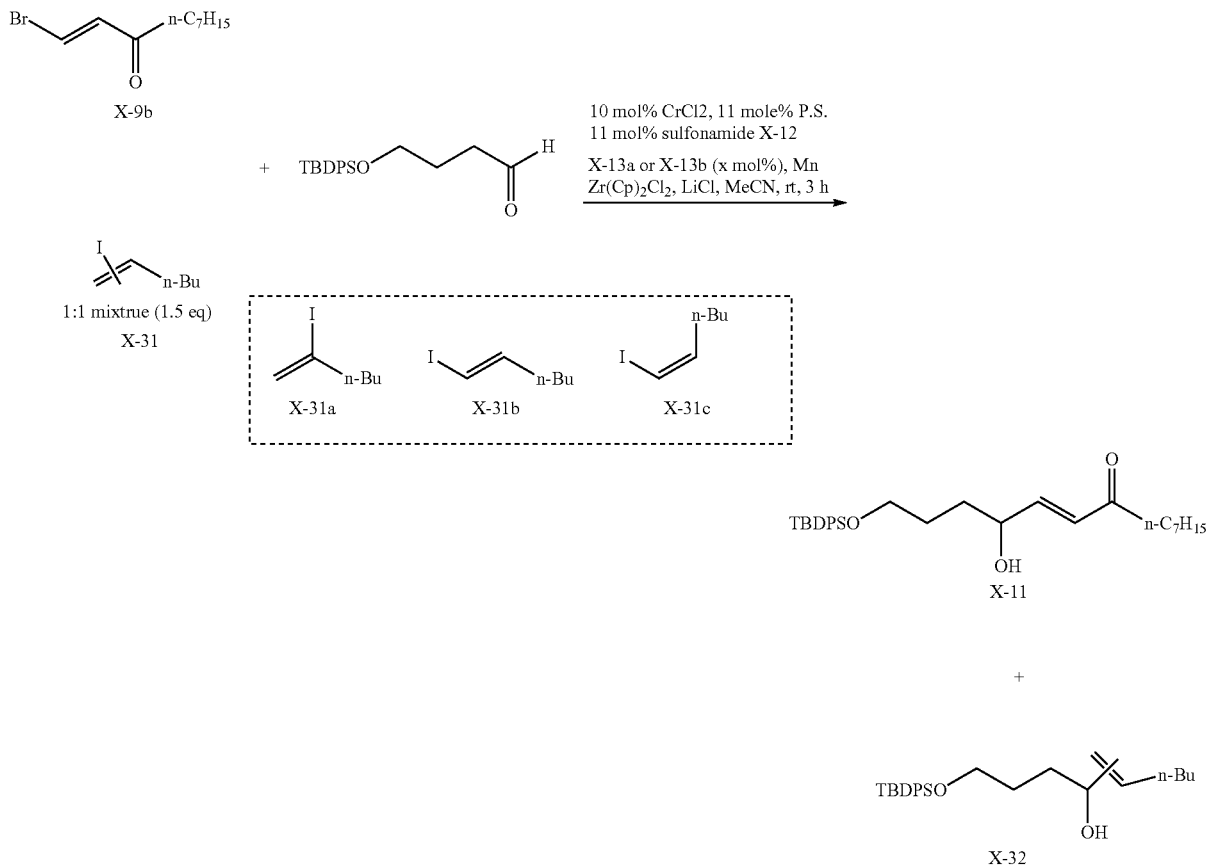

Preparation of Chromium Sulfonamide Solution:

In a glove box, to a 5.0 mL black cap vial, was added chiral sulfonamide X-12 (52.0 mg, 0.11 mmol), proton sponge (Aldrich, purified by sublimation; 23.6 mg, 0.11 mmol) and CrCl$_2$ (Aldrich, 99.99% mg, 12.3 mg, 0.1 mmol), and MeCN (Baker, ultra low water; 1.0 mL). The mixture was stirred for 60 min at rt under nitrogen and changed to deep green homogeneous solution which is ready to use for coupling reaction.

To a second 1.0 mL black cap vial were added aldehyde X-10 (16.4 mg, 0.05 mmol), bromoenone X-9b (17.5 mg, 0.075 mmol), vinyl iodide X-31a-c (15.8 mg, 0.075 mmol),

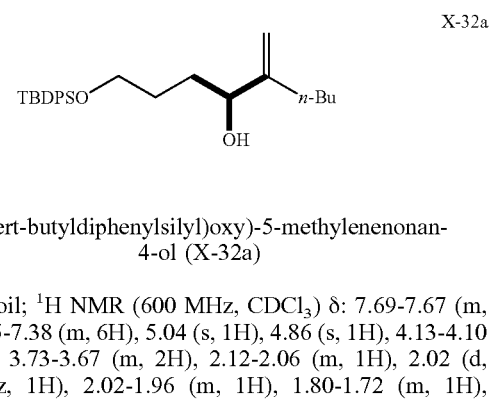

1-((tert-butyldiphenylsilyl)oxy)-5-methylenenonan-4-ol (X-32a)

Clear oil; $^1$H NMR (600 MHz, CDCl$_3$) δ: 7.69-7.67 (m, 4H), 7.45-7.38 (m, 6H), 5.04 (s, 1H), 4.86 (s, 1H), 4.13-4.10 (m, 1H), 3.73-3.67 (m, 2H), 2.12-2.06 (m, 1H), 2.02 (d, J=3.6 Hz, 1H), 2.02-1.96 (m, 1H), 1.80-1.72 (m, 1H), 1.70-1.60 (m, 3H), 1.50-1.45 (m, 2H), 1.41-1.32 (m, 2H), 1.07 (s, 9H), 0.93 (t, J=7.2 Hz, 3H); $^{13}$C NMR (150 MHz, CDCl$_3$) δ: 152.1, 135.6, 134.8, 133.7, 129.6, 127.6, 109.1, 75.0, 63.9, 32.3, 31.3, 30.2, 28.6, 26.8, 22.7, 19.2, 14.0; HRMS (ESI) m/z: [M+Na]$^+$ calcd for C$_{26}$H$_{38}$NaO$_2$Si, 433.2539; found, 433.2541.

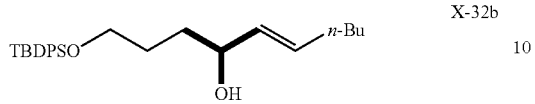

X-32b (E)-1-((tert-butyldiphenylsilyl)oxy)dec-5-en-4-ol (X-32b)

Clear oil; $^1$H NMR (600 MHz, CDCl$_3$) δ: 7.69-7.67 (m, 4H), 7.45-7.38 (m, 6H), 5.64 (dt, J=15.0, 7.2 Hz, 1H), 5.46 (dd, J=15.0, 7.2 Hz, 1H), 4.08 (m, 1H), 3.69 (t, J=6.0 Hz, 2H), 2.04 (q, J=7.2 Hz, 2H), 1.92 (d, J=3.6 Hz, 1H), 1.66-1.62 (m, 4H), 1.40-1.30 (m, 4H), 1.05 (s, 9H), 0.91 (t, J=6.6 Hz, 3H); $^{13}$C NMR (150 MHz, CDCl$_3$) δ: 135.5, 133.8, 132.9, 132.0, 129.6, 127.6, 72.8, 64.0, 34.1, 31.8, 31.3, 28.6, 26.8, 22.2, 19.2, 13.9; HRMS (ESI) m/z: [M+Na]$^+$ calcd for C$_{26}$H$_{38}$NaO$_2$Si, 433.2539; found, 433.2532.

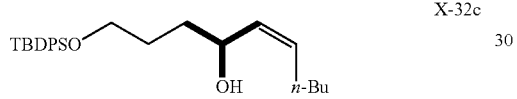

X-32c (Z)-1-((tert-butyldiphenylsilyl)oxy)dec-5-en-4-ol (X-32c)

Clear oil; $^1$H NMR (600 MHz, CDCl$_3$) δ: 7.69-7.67 (m, 4H), 7.45-7.38 (m, 6H), 5.51-5.47 (m, 1H), 5.41-5.38 (m, 1H), 4.47 (m, 1H), 3.73-3.67 (m, 2H), 2.13-2.03 (m, 2H), 1.88 (d, J=3.6 Hz, 1H), 1.72-1.57 (m, 4H), 1.39-1.30 (m, 4H), 1.06 (s, 9H), 0.91 (t, J=7.2 Hz, 3H); $^{13}$C NMR (150 MHz, CDCl$_3$) δ: 135.5, 133.7, 132.5, 132.1, 129.6, 127.6, 67.5, 63.9, 34.3, 31.8, 28.5, 27.4, 26.8, 22.3, 19.2, 13.9; HRMS (ESI) m/z: [M+Na]$^+$ calcd for C$_{26}$H$_{38}$NaO$_2$Si, 433.2539; found, 433.2529.

TABLE 1

| | Results | | | | | |
|---|---|---|---|---|---|---|
| loading | X-11:X-32a | | X-11:X-32b | | X-11:X-32c | |
| (mol %) | X-13a | X-13b | X-13a | X-13b | X-13a | X-13b |
| 0.05 | >100:1 | >100:1 | 38:1 | 71:1 | >100:1 | >100:1 |
| 0.1 | >100:1 | >100:1 | 30:1 | 36:1 | 42:1 | >100:1 |
| 0.5 | 38:1 | 66:1 | 1:1.1 | 12:1 | 16:1 | 46:1 |
| 1 | 22:1 | 26:1 | 1:2.3 | 1.5:1 | 4.6:1 | 5.2:1 |
| 2 | 6:1 | 11:1 | 1:13 | 0.7:1 | 1:1.8 | 1.2:1 |

Synthesis Outlined in FIG. 12
Synthesis of C$_{14}$-C$_{19}$ Building Block XS-27

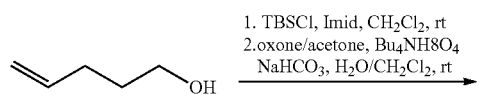

1. TBSCl, Imid, CH$_2$Cl$_2$, rt
2. oxone/acetone, Bu$_4$NH$_8$O$_4$ NaHCO$_3$, H$_2$O/CH$_2$Cl$_2$, rt

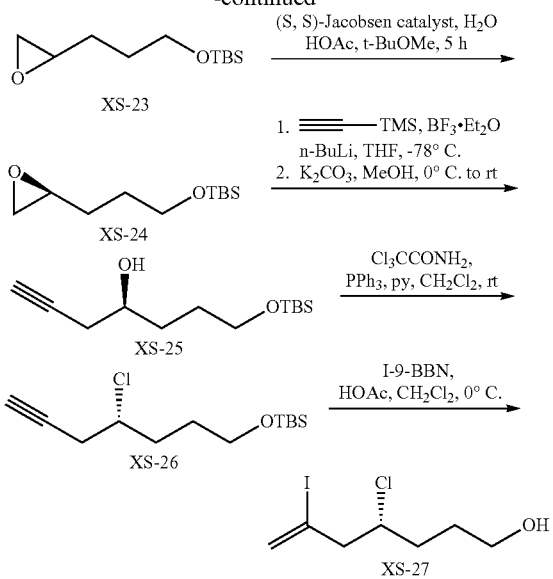

A 1000 mL round-bottom flask was charged with penten-1-ol (TCI, 51.8 g, 0.6 mol, 1.0 equiv) and dissolved in CH$_2$Cl$_2$ (500 mL, 1.2 M). The reaction was then added sequentially with tert-butyldimethylsilyl chloride (99.5 g, 0.66 mol, 1.1 equiv) and imidazole (49.0 g, 0.72 mol, 1.2 equiv), and allowed to stir at rt for 2 h. The reaction slurry was then washed with saturated NaCl solution (200 mL twice). The aqueous phase was extracted with CH$_2$Cl$_2$ (100 mL twice) and the combined organic layer was dried over anhydrous MgSO$_4$. The solvent was removed under reduced pressure to afford a crude product, which was purified by house vacuum distillation at 105° C. to afford the product tert-butyldimethyl(pent-4-en-1-yloxy)silane as a clear oil (119.3 g, 99% yield).

A solution of oxone (246.0 g, 0.40 mol) in water (1000 mL) was added dropwise at 0° C. to a vigorously stirred biphasic mixture of tert-butyldimethyl(pent-4-en-1-yloxy)silane (40.0 g, 0.4 mol), tetrabutylammonium hydrogen sulfate (22.6 g, 66.6 mmol), acetone (84 mL), CH$_2$Cl$_2$ (840 mL) and a saturated NaHCO$_3$ solution (1400 mL) (Lafont, D.; D'Attoma, J.; Gomez, R.; Goekjian, P. G. *Tetrahedron: Asymmetry* 2011, 22, 1197). With stirring, the mixture was maintained for 30 min at 0° C., and 40 h at room temperature. The aqueous phase was extracted with CH$_2$Cl$_2$ (400 mL twice) and the combined organic phases were washed with saturated Na$_2$S$_2$O$_3$ solution (400 mL twice), saturated NaHCO$_3$ solution (600 mL) and brine (400 mL twice) and dried over anhydrous MgSO$_4$. After filtration, the solution was concentrated under reduced pressure and the residue was purified by column chromatography to remove unreacted starting materials (about 10%), and the racemic epoxide XS-23 was obtained as a light yellow oil (38.0 g, 88% yield).

Catalyst Activation for Jacobsen Kinetic Resolution (Tokunaga, M.; Larrow, J. F.; Kakiuchi, F.; Jacobsen, E. N. *Science* 1997, 277, 936): a mixture of (S,S)-Jacobsen catalyst (604 mg, 1 mmol), toluene (11 mL), and acetic acid (120 mg, 2 mmol, 2 equivalents to catalyst) was stirred while open to the air for 2 h at room temperature. The solvent was removed by rotary evaporation, and the deep brown residue was dried under vacuum overnight.

The solution of racimic epoxide XS-23 (48 g, 0.22 mol) in tert-BuOMe (50 mL) and water (2.0 g, 0.11 mol) were added to the activated catalyst flask, and then the reaction mixture was stirred at room temperature for 6 h ($^1$H NMR indicated about 67% conversion). The reaction solvent was removed by reduced pressure and the residue was purified by column chromatography to yield (S)-epoxide product XS-24 (yellow oil, 20.8 g, 43% yield) and crude (R)-diol (23.4 g, 48% yield).

To a solution of trimethylsilyl acetylene (12.0 g, 122.2 mmol) in THF (150 mL) was added slowly n-butyllithium (1.6 M in hexanes, 76.4 mL, 122.2 mmol) at −78° C. After 1.5 h, a solution of boron trifluoride etherate $BF_3.Et_2O$ (16.8 mL, 135.8 mmol) in THF (30 mL) was added over 30 min and the mixture was stirred for another 1 h. A solution of chiral epoxide XS-24 (14.7 g, 67.9 mmol) in THF (30 mL) was added over 30 min. The resulting mixture was stirred at −78° C. for 2 h and then directly poured into a saturated aq. $NaHCO_3$ solution (500 mL) and extracted with EtOAc (500 mL×3) and hexanes (500 mL). The extracts were washed with brine (500 mL), dried over $Na_2SO_4$, passed through a pad of silica gel (60 g), and eluted with hexanes/EtOAc (1:4, 500 mL). The eluent was concentration under reduced pressure, to give the crude product (19.6 g), which was used for the next step without further purification.

The crude product (19.6 g, 62.3 mmol) was dissolved in anhydrous methanol (200 mL). To the solution, anhydrous $K_2CO_3$ (17.2 g, 124.6 mmol) was added in one portion and the reaction mixture was stirred at rt for 4 h. The mixture was filtrated to remove excess amount of $K_2CO_3$ solids and quenched by saturated $NaHCO_3$ solution (300 mL) and extracted with EtOAc (300 mL×3) and hexanes (300 mL). The combined extracts were washed with brine (400 mL) and dried over $Na_2SO_4$. Concentration of the extracts under reduced pressure gave a residue, which was purified by column chromatography (100 g of silica gel). The homopropargylic alcohol XS-25 was obtained as a yellow liquid (14.2 g, 86.5% in two steps). The optical purity of alcohol XS-25 was determined as >99% ee by $^1$H NMR (500 MHz) analysis of its (S)-(+)-Mosher ester.

(S)-7-((tert-butyldimethylsilyl)oxy)hept-1-yn-4-ol (XS-25)

$[\alpha]_D^{20}$=−11.0 (c 0.1, $CH_2Cl_2$); $^1$H NMR (500 MHz, $CDCl_3$) δ: 3.81-3.75 (m, 1H), 3.72-3.63 (m, 2H), 2.40-2.38 (m, 2H), 2.03 (t, J=2.5 Hz, 1H), 1.82-1.74 (m, 1H), 1.73-1.63 (m, 2H), 1.62-1.54 (m, 1H), 0.89 (s, 9H), 0.07 (s, 6H); $^{13}$C NMR (125 MHz, $CDCl_3$) □□ 81.2, 70.4, 69.8, 63.4, 33.6, 29.1, 27.2, 25.9, 18.3, −5.4; HRMS (ESI) m/z: [M+H]$^+$ calcd for $C_{13}H_{27}O_2Si$, 243.1780; found, 243.1787.

To a solution of homopropargylic alcohol XS-25 (7.3 g, 30.0 mmol) in $CH_2Cl_2$ (150 mL) was added pyridine (7.1 g, 90 mmol), triphenylphosphine (PPh$_3$, 11.8 g, 45 mmol) and trichloroacetamide (7.3 g, 45 mmol) at rt. The reaction was stirred at rt for 20 h under $N_2$, and then washed with brine (60 mL×3). The organic layer was dried over $Na_2SO_4$ and concentrated under reduced pressure. The residue was passed through a silica gel pad (50 g) with hexanes/EtOAc (30:1, 600 mL), to give homopropargylic chloride XS-26 (7.2 g, 92.0%) as a light yellow oil.

(R)-tert-butyl((4-chlorohept-6-yn-1-yl)oxy)dimethyl-silane (XS-26)

$[\alpha]_D^{20}$=+30.0 (c 0.1, $CH_2Cl_2$); $^1$H NMR (500 MHz, $CDCl_3$) δ: 4.06-4.00 (m, 1H), 3.68-3.62 (m, 2H), 2.73-2.62 (m, 2H), 2.09 (t, J=2.5 Hz, 1H), 2.08-2.01 (m, 1H), 1.83-1.72 (m, 2H), 1.69-1.59 (m, 1H), 0.89 (s, 9H), 0.05 (s, 6H); $^{13}$C NMR (125 MHz, $CDCl_3$) δ: 79.9, 70.9, 62.3, 59.8, 33.7, 29.5, 28.6, 25.9, 18.3, −5.3; HRMS (ESI) m/z: [M+H]$^+$ calcd for $C_{13}H_{26}ClOSi$, 261.1441; found, 261.1438.

To a solution of alkyne XS-26 (20.8 g, 80 mmol) in $CH_2Cl_2$ (400 mL) was dropped B-iodo-9-BBN (Liu, S.; Kim, J. T.; Dong, C. G.; Kishi, Y. Org. Lett. 2009, 11, 4520) solution (1 M in $CH_2Cl_2$, 96 mL, 96 mmol) at 0° C. and stirred for 4 h at the same temperature prior to the addition of AcOH (18.2 mL, 320 mmol). After stirring at 0° C. for 60 min, the reaction mixture was titrated with 30% aqueous $H_2O_2$ solution (red color) and then with slow addition of aqueous $Na_2S_2O_3$ (colorless) (caution: this process released tremendous heat). The aqueous phase was extracted with $CH_2Cl_2$ three times and the combined organic extracts were washed with 10 wt. % $Na_2S_2O_3$ and saturated $NaHCO_3$ solution, dried over anhydrous $MgSO_4$, and concentrated under vacuum. The residue was purified by flash column chromatography on silica gel eluted with hexanes/EtOAc (10:1 to 2:1) to give alcohol XS-27 (18.8 g, 86%) as a light yellow liquid.

(R)-4-chloro-6-iodohept-6-en-1-ol (XS-27)

$[\alpha]_D^{20}$=+1.2 (c 1.00, $CHCl_3$); $^1$H NMR (500 MHz, $C_6D_6$) δ: 5.73 (d, J=1.0 Hz, 1H), 5.58 (d, J=1.0 Hz, 1H), 4.08-4.00 (m, 1H), 3.20 (t, J=5.5 Hz, 2H), 2.42 (dd, J=14.5, 8.0 Hz, 1H), 2.35 (dd, J=14.5, 5.5 Hz, 1H), 1.57-1.48 (m, 2H), 1.47-1.40 (m, 1H), 1.38-1.28 (1H, m); $^{13}$C NMR (125 MHz, $C_6D_6$) δ: 128.7, 106.7, 61.8, 61.2, 53.5, 33.9, 29.6; HRMS (ESI) m/z: [M+Na]$^+$ calcd for $C_7H_{12}OIClNa$, 296.9519; found, 296.9513.

The optical purity of alcohol XS-27 was determined as >99% ee by HPLC analysis (OJ-H chiral column) of its 4-acetylphenylurethane derivative XS-28 prepared from XS-27.

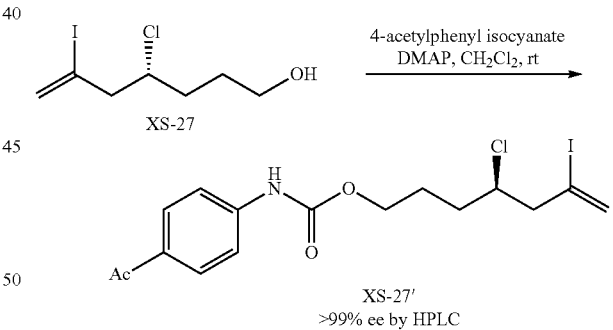

Figure 1:
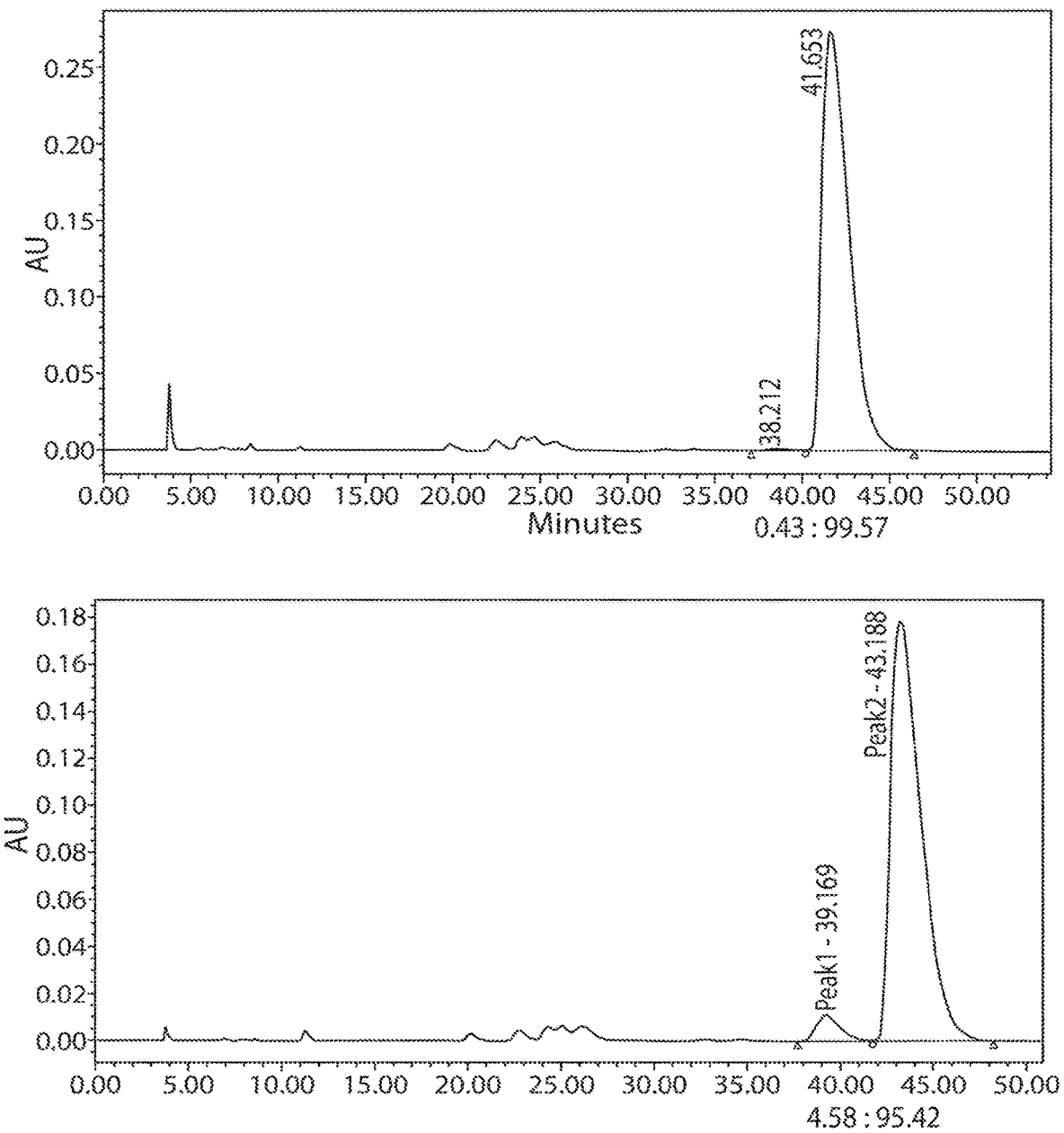
FIG. 1 shows HPLC analysis of (R)-XS-27' (top) and rac-XS-27' (bottom) (see Example 1).

To a solution of alcohol XS-27 (51 mg, 0.2 mmol) in $CH_2Cl_2$ (1.0 mL) were added 4-acetylphenyl isocyanate (52 mg, 0.24 mmol) and DMAP (4 mg, 40 µmol) at room temperature. The reaction mixture was stirred for 1 h at the same temperature prior to quenching with saturated $NaHCO_3$ solution. The aqueous phase was extracted with EtOAc twice and the combined organic phases were dried over anhydrous $MgSO_4$ and concentrated in vacuo. The residue was purified by preparative TLC (hexanes/EtOAc=2:1) to give urethane XS-27' (74 mg, 85%) as a white solid. The optical purity of urethane XS-27' was determined as >99% ee by HPLC analysis (FIG. 1).

HPLC Condition. Column: chiralpak OJ-H; solvent system: hexanes/i-propanol/diethylamine=85%/15%/0.1%;

flow rate=1.0 mL/min; detector=UV at 277 nm; retention time: 41.6 and 38.2 min for (R)- and (S)-enantiomers, respectively.

Synthesis of $C_{12}$-$C_{19}$ Building Block X-34

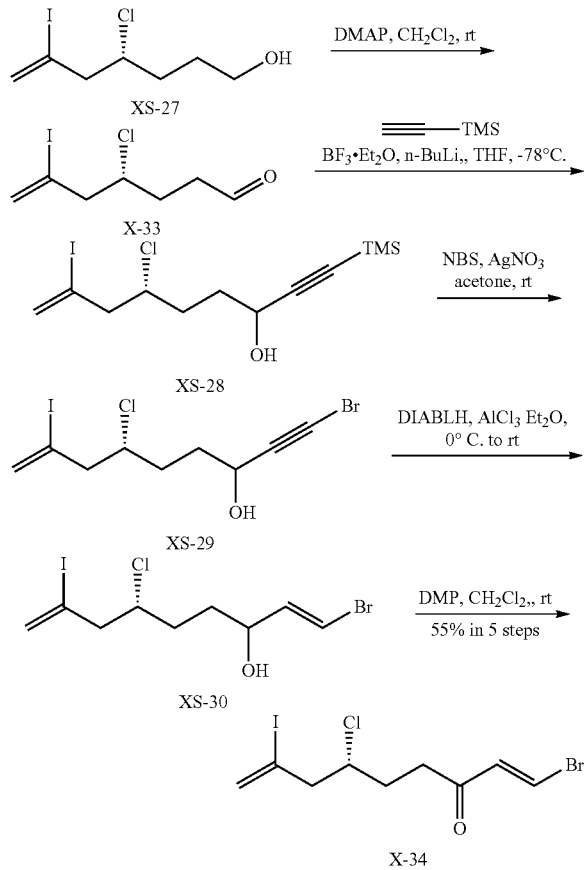

Aldehyde X-33 was obtained from Dess-Martin oxidation of alcohol XS-27 with the procedure same as shown in section 3.1.

To a solution of trimethylsilyl acetylene (3.63 g, 37 mmol) in THF (30 mL) was added slowly n-butyllithium (2.5 M in hexanes, 14.8 mL, 37 mmol) at −78° C. about 30 min. After 1 h, a solution of boron trifluoride etherate (5.6 g, 39.6 mmol) in THF (20 mL) was added over 30 min and the mixture was stirred for another 1 h (Yamauchi, M.; Hirao, I. Tetrahedron Lett. 1983, 24, 391). A solution of aldehyde X-33 (3.6 g, 13.2 mmol) in THF (20 mL) was added over another 30 min. The resulting mixture was stirred at −78° C. for 3 h, then directly poured into a saturated NaHCO$_3$ solution (300 mL), and extracted with EtOAc (200 mL×3) and hexanes (200 mL×2). The extracts were washed with brine (300 mL), dried over anhydrous MgSO$_4$, and then passed through a pad of silica gel (40 g). Elution with hexanes/EtOAc (1:4, 500 mL) and concentration gave the crude product, which was purified by silica gel column chromatography (hexanes/CH$_2$Cl$_2$=50:1→25:1→10:1→5:1→2:1), to give XS-28 (4.4 g) as a yellow oil.

(6R)-6-chloro-8-iodo-1-(trimethylsilyl)non-8-en-1-yn-3-ol (XS-28)

$^1$H NMR (500 MHz, CDCl$_3$) δ: 6.18 (s, 1H), 5.85 (s, 1H), 4.42 (d, J=6.0 Hz, 1H), 4.24-4.12 (m, 1H), 2.77 (d, J=7.0 Hz, 2H), 2.12-1.94 (m, 2H), 1.90-1.74 (m, 2H), 0.17 (s, 9H); $^{13}$C NMR (125 MHz, CDCl$_3$) δ: 128.9, 106.0, 105.9, 90.1, 62.1, 60.5, 53.4, 34.3, 32.6, −0.16; HRMS (ESI) m/z: [M+H]$^+$ calcd for C$_{12}$H$_{21}$ClIOSi, 371.0095; found, 371.0103.

To a solution of propargyl alcohol XS-28 (4.4 g, 11.8 mmol) in acetone (60 mL) was added NBS (3.15 g, 17.7 mmol) and silver nitrate AgNO$_3$ (0.4 g, 2.36 mmol) at rt. After 1.0 h, the reaction mixture was diluted with 200 mL EtOAc and quenched by 100 mL saturated aq. Na$_2$S$_2$O$_3$ solution. The aqueous layer was extracted with EtOAc (2×100 mL) and the combined organic layer was washed with saturated Na$_2$S$_2$O$_3$ solution (2×100 mL) and 200 mL brine. The organic solution was dried over anhydrous MgSO$_4$ and concentrated under reduced pressure. The residue was passed through a silica gel pad with eluent (2:1 hexanes/EtOAc, 300 mL), to give crude XS-29 (4.1 g, silica gel TLC R$_f$~0.5 in 6:1 hexanes/EtOAc) as a yellow oil. The crude XS-29 was used for the next step without further purification.

(6R)-1-bromo-6-chloro-8-iodonon-8-en-1-yn-3-ol (XS-29)

$^1$H NMR (500 MHz, CDCl$_3$) δ: 6.18 (s, 1H), 5.86 (s, 1H), 4.47 (q, J=7.5 Hz, 1H), 4.22-4.12 (m, 1H), 2.77 (d, J=7.5 Hz, 2H), 2.08-1.96 (m, 2H), 1.94-1.79 (m, 2H); $^{13}$C NMR (125 MHz, CDCl$_3$) δ: 129.0, 105.8, 80.4, 62.7, 60.5, 53.4, 45.9, 34.3, 32.6; HRMS (ESI) m/z: [M+H]$^+$ calcd for C$_9$H$_{12}$BrClIO, 376.8805; found, 376.8811.

To a solution of AlCl$_3$ (2.9 g, 21.8 mmol) in Et$_2$O (40 mL) was added slowly DIBAL solution (1.0 M in THF, 43.6 mL, 43.6 mmol) at 0° C. (The white solid was precipitated out from the reaction mixture on adding DIBAL. The white solid dissolved with a continuous addition of DIBAL solution, and eventually the solution became clear yellow or white precipitated yellow color). The reaction mixture was stirred for 100 (40 mL) was added slowly DIBAL solution (1.0 M in THF, 43.6 mL, 43.6 mmol) at XS-29 from the previous step in ethyl ether Et$_2$O (40+20+10 mL) was added slowly in the reaction mixture about 10 mins. After 1 h (TLC monitor for no SM left), the reaction mixture was cooled down to 0° C. and quenched slowly by MeOH (20 mL). To the reaction mixture was added the 200 mL saturated sodium potassium tartrate solution and then stirred vigorously for overnight. The white aqueous layer was extracted with EtOAc (3×100 mL) and combined organic layer was washed with 200 mL brine. The organic layer was dried over anhydrous MgSO$_4$ and concentrated to dryness under reduced pressure. The residue was purified by silica gel column chromatography (hexanes/Et$_2$O=50:1→25:1→10:1→5:1→2:1→1:1), to give XS-30 (3.5 g) as a yellow oil.

(6R,E)-1-bromo-6-chloro-8-iodonona-1,8-dien-3-ol (XS-30)

$^1$H NMR (500 MHz, CDCl$_3$) δ: 6.38 (d, J=13.0 Hz, 1H), 6.25 (ddd, J=13.0, 6.5, 3.5 Hz, 1H), 6.17 (s, 1H), 5.85 (s, 1H), 4.26-4.08 (m, 2H), 2.76 (d, J=6.0 Hz, 2H), 2.04-1.67 (m, 4H); $^{13}$C NMR (125 MHz, CDCl$_3$) δ: 140.0, 129.0, 107.8, 107.7, 105.9, 72.2, 71.2, 60.8, 60.6, 53.5, 53.4, 33.5, 33.2, 33.0, 32.5; HRMS (ESI) m/z: [M+Na]$^+$ calcd for C$_9$H$_{13}$BrClINaO, 400.8781; found, 400.8780.

Alcohol XS-30 was subjected to Dess-Martin oxidation reaction. The crude product was purified by silica gel column chromatography (hexanes/CH$_2$Cl$_2$=100:1→50:

1→25:1→10:1→5:1→2:1), to yield trans-bromoenone X-34 (3.0 g) as a light yellow oil.

(R,E)-1-bromo-6-chloro-8-iodonona-1,8-dien-3-one (X-34)

$[\alpha]_D^{20}$=+10.5 (c 1.0, CHCl$_3$); $^1$H NMR (500 MHz, C$_6$D$_6$) δ: 6.93 (d, J=13.5 Hz, 1H), 6.26 (d, J=14.0 Hz, 1H), 5.68 (s, 1H), 5.55 (s, 1H), 3.98-3.88 (m, 1H), 2.32 (dd, J=15.0, 9.0 Hz, 1H), 2.26 (dd, J=15.0, 6.0 Hz, 1H), 2.08 (ddd, J=18.0, 9.0, 5.0 Hz, 1H), 1.88 (ddd, J=18.0, 9.0, 6.0 Hz, 1H), 1.78-1.67 (m, 1H), 1.58-1.46 (m, 1H); $^{13}$C NMR (125 MHz, C$_6$D$_6$) δ: 194.5, 136.5, 129.0, 125.5, 106.1, 60.6, 53.6, 37.4, 31.0; HRMS (ESI) m/z: [M+H]$^+$ calcd for C$_9$H$_{12}$BrClIO, 376.8805; found, 376.8800.

Synthesis Outlined in FIG. 13
Synthesis of Polyether Phenanthroline Ligands

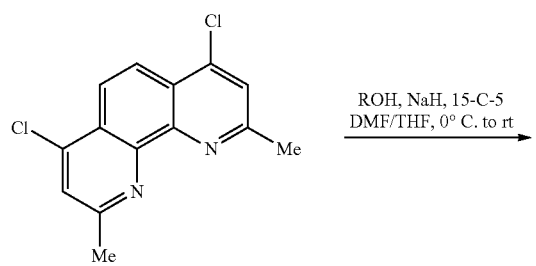

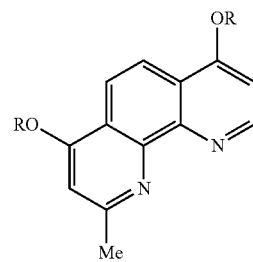

To a mixture of NaH (60% dispersion in mineral oil, 0.40 g, 1.0 mmol, 5.5 equiv.) in 18 mL of DMF at 0° C., was added 15-C-5 (1.25 mL, 3.5 equiv.) and alcohol (1.0 mL, 3.5 equiv.). After 30 min, a solution of 4,7-dichloro-2,9-dimethyl-1,10-phenanthroline ((a) Larsen, A. F.; Ulven, T. Org. Lett. 2011, 13, 3546, (b) Schmittel, M.; Ammon, H. Eur. *J. Org. Chem.* 1998, 5, 785) (0.50 g, 1.8 mmol) in a 1:1 mixture of DMF and THF (total: 16 mL) was slowly added. After addition, the purple solution was warmed to room temperature and stirred for 3 h. The reaction was quenched with addition of 10 mL of water at 0° C., and concentrated under vacuum. The residue was purified on Wakogel (50NH$_2$; eluted with first 1:1 hexanes/EtOAc, then pure EtOAc, finally 10:1 EtOAc/MeOH), to give the desired product as a yellow solid.

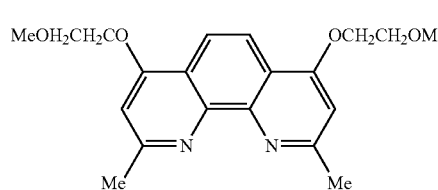

4,7-bis(2-methoxyethoxy)-2,9-dimethyl-1,10-phenanthroline (XS-31)

The desired product (0.22 g, 34% yield) was obtained from 2-methoxyethanol. m.p. 115-117° C.; $^1$H NMR (500 MHz, CDCl$_3$) δ: 8.11 (s, 2H), 6.86 (s, 2H), 4.37 (t, J=5.0 Hz, 4H), 3.93 (t, J=5.0 Hz, 4H), 3.52 (s, 6H), 2.88 (s, 6H); $^{13}$C NMR (125 MHz, CDCl$_3$) δ: 161.5, 160.1, 145.7, 119.4, 118.1, 103.4, 70.6, 67.9, 59.4, 26.4; HRMS (ESI) m/z: [M+H]$^+$ calcd for C$_{20}$H$_{25}$N$_2$O$_4$, 357.1814; found, 357.1831.

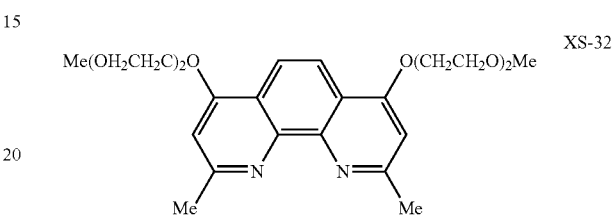

4,7-bis(2-(2-methoxyethoxy)ethoxy)-2,9-dimethyl-1,10-phenanthroline (XS-32)

The desired product (0.47 g, 58% yield) was obtained from 2-(2-methoxyethoxy)ethanol. m.p. 91-93° C.; $^1$H NMR (500 MHz, CDCl$_3$) δ: 8.10 (s, 2H), 6.85 (s, 2H), 4.39 (t, J=5.0 Hz, 4H), 4.04 (t, J=5.0 Hz, 4H), 3.80 (m, 4H), 3.60 (m, 4H), 3.40 (s, 6H), 2.87 (s, 6H); $^{13}$C NMR (125 MHz, CDCl$_3$) δ: 161.2, 159.8, 145.7, 119.1, 117.8, 103.2, 71.7, 70.6, 69.2, 67.6, 58.8, 26.3; HRMS (ESI) m/z: [M+H]$^+$ calcd for C$_{24}$H$_{33}$N$_2$O$_6$ 445.2339; found, 445.2361.

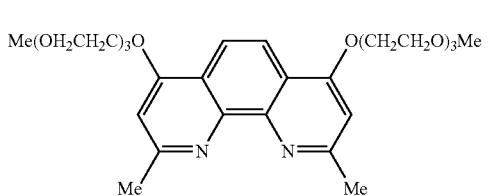

4,7-bis(2-(2-(2-methoxyethoxy)ethoxy)ethoxy)-2,9-dimethyl-1,10-phenanthroline (X-37c)

The desired product (0.94 g, 98% yield) was obtained from triethylene glycol monomethyl ether. m.p. 63-64° C.; $^1$H NMR (500 MHz, CDCl$_3$) δ: 8.06 (s, 2H), 6.81 (s, 2H), 4.33 (t, J=5.5 Hz, 4H), 3.99 (t, J=5.0 Hz, 4H), 3.77 (m, 4H), 3.67 (m, 4H), 3.62 (m, 4H), 3.50 (m, 4H), 3.32 (s, 6H), 2.83 (s, 6H); $^{13}$C NMR (125 MHz, CDCl$_3$) δ: 160.8, 159.4, 145.3, 118.8, 117.4, 102.8, 71.2, 70.3, 70.0, 69.9, 68.7, 67.3, 58.3, 25.9; HRMS (ESI) m/z: [M+H]$^+$ calcd for C$_{28}$H$_{41}$N$_2$O$_8$, 533.2863; found, 533.2879.

Preparation of NiCl₂ Complexes X-37a-c

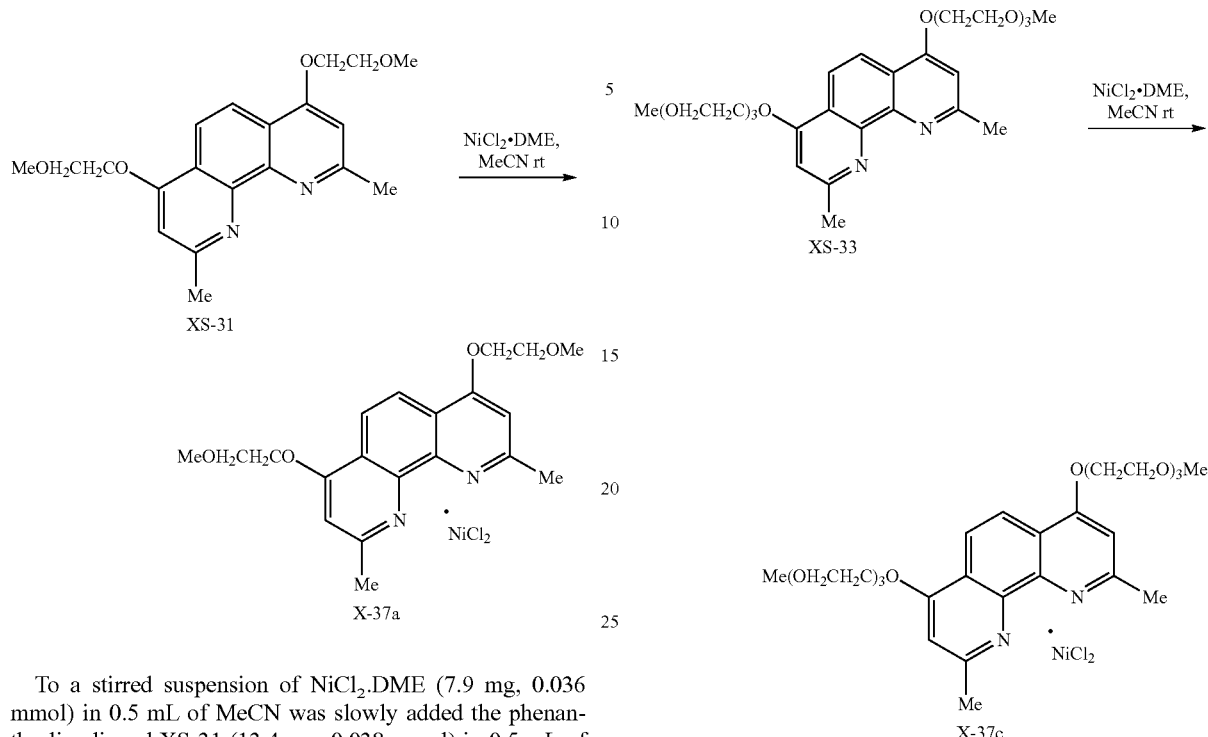

To a stirred suspension of NiCl₂.DME (7.9 mg, 0.036 mmol) in 0.5 mL of MeCN was slowly added the phenanthroline ligand XS-31 (13.4 mg, 0.038 mmol) in 0.5 mL of MeCN. During the reaction, the Ni-complex precipitate out, which was filtered and dried under vacuum. The complex X-37a was obtained as a purple powder in 12.2 mg, which can be used directly for the Ni/Cr-mediated coupling reaction.

To a stirred suspension of NiCl₂.DME (7.9 mg, 0.036 mmol) in 0.5 mL of MeCN was slowly added the phenanthroline ligand XS-32 (16.7 mg, 0.038 mmol) in 0.5 mL of MeCN. The resulting clear purple solution was stirred for 24 h at rt, then filtered, concentrated, and dried under high vacuum. The complex X-37b was obtained as a purple paste in 21.6 mg, which can be used directly for the Ni/Cr-mediated coupling reaction.

To a stirred suspension of NiCl₂-DME (7.9 mg, 0.036 mmol) in 0.5 mL of MeCN was slowly added the phenanthroline ligand XS-33 (20.0 mg, 0.038 mmol) in 0.5 mL of MeCN. The resulting clear purple solution was stirred for 24 h at rt, then filtered, concentrated, and dried under high vacuum. The complex X-37c was obtained as a purple paste in 25.3 mg, which can be used directly for the Ni/Cr-mediated coupling reaction.

Synthesis of X-36 from Ni/Cr-Mediated Coupling Reaction Between X-34 and X-35

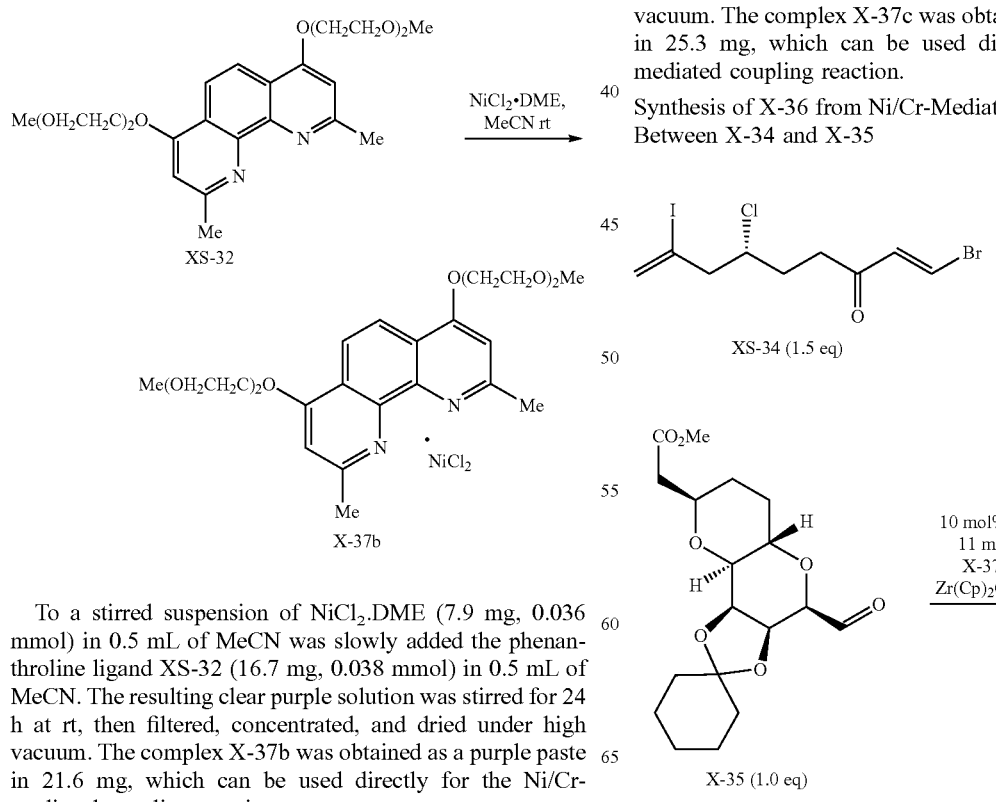

-continued

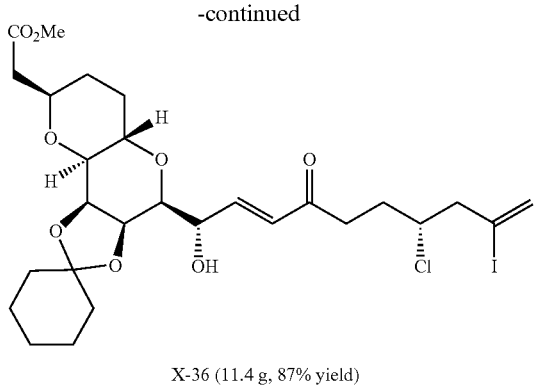

X-36 (11.4 g, 87% yield)

Preparation of Chromium Sulfonamide Solution:

In a glove box, to a 50 mL round-bottom flask, was added chiral sulfonamide X-12 (1.20 g, 2.2 mmol), proton sponge (Aldrich, purified by sublimation; 542.2 mg, 2.2 mmol) and $CrCl_2$ (Aldrich, 99.99% mg, 246 mg, 2.0 mmol), and MeCN (Baker, ultra low water; 30.0 mL). The mixture was stirred for 60 min at rt under nitrogen and changed to a deep green homogeneous solution which is ready to use for coupling reaction.

To a 250 mL round-bottom flask with $C_1$-$C_{11}$ aldehyde X-35 (7.09 g, 20 mmol), was added LiCl (Aldrich, anhydrous, grinded; 1.70 mg, 40 mmol), Mn powder (Aldrich, 99.99%, powder; 2.20 g, 40 mmol), $Zr(cp)_2Cl_2$ (Aldrich, 98%; 8.77 g, 30 mmol) and a solution of bromoenone X-34 (11.3 g, 30 mmol) in MeCN (Baker, ultra low water; 25.0 mL). Then, a red MeCN-solution of $NiCl_2$-catalyst X-37c (6.70 mg, 0.01 mmol, 0.05 mol %; 2.0 mL MeCN (Baker, ultra low water) was added and, lastly, the deep green solution of Cr-catalyst was transferred from the first flask to the reaction flask with syringe. The reaction mixture was stirred under nitrogen for 3 h, and diluted with EtOAc (60 mL). Florisil (ca. 1.0 g) was added, and the mixture was stirred for 30 min, filtered through a silica gel pad (ca. 60 g) using EtOAc/hexanes (1:1). The eluent was concentrated in vacuo to furnish the crude coupling product, which can be used for the next step without further purification.

Coupling Product X-36:

yellow oil; $[\alpha]_D^{20}$=−11.8 (c 0.65, $CHCl_3$); $^1H$ NMR (500 MHz, $C_6D_6$) δ: 7.16 (dd, J=16.0, 4.0 Hz, 1H), 6.54 (dd, J=16.0, 1.5 Hz, 1H), 5.73 (d, J=1.5 Hz, 1H), 5.57 (d, J=1.5 Hz, 1H), 4.50 (dd, J=5.0, 1.0 Hz, 1H), 4.21 (dd, J=8.0, 3.5 Hz, 1H), 4.16 (d, J=8.5 Hz, 1H), 4.12-4.04 (m, 1H), 4.02 (dt, J=11.0, 5.0 Hz, 1H), 3.81-3.72 (m, 1H), 3.30 (s, 3H), 3.26 (d, J=7.5 Hz, 1H), 3.03 (dd, J=10.0, 2.5 Hz, 1H), 2.54 (ddd, J=18.0, 8.5, 5.0 Hz, 1H), 2.47 (dd, J=16.0, 8.0 Hz, 1H), 2.44 (ddd, J=18.0, 9.0, 7.0 Hz, 1H), 2.36 (d, J=7.0 Hz, 2H), 2.47 (dd, J=16.0, 4.5 Hz, 1H), 2.30-2.24 (m, 1H), 1.98-1.87 (m, 2H), 1.85-1.68 (m, 4H), 1.62-1.50 (m, 2H), 1.49-1.38 (m, 4H), 1.34-1.18 (m, 2H), 1.17-1.00 (m, 2H); $^{13}C$ NMR (125 MHz, $C_6D_6$) δ: 197.7, 171.1, 146.2, 129.1, 128.8, 110.7, 106.3, 76.1, 75.0, 74.4, 72.6, 71.7, 71.2, 66.7, 61.0, 53.6, 51.1, 40.3, 36.2, 33.9, 30.8, 30.1, 25.4, 24.3, 23.9; HRMS (ESI) m/z: $[M+H]^+$ calcd for $C_{27}H_{39}ClIO_8$, 653.1378; found, 653.1369.

Synthesis Outlined in FIG. 14

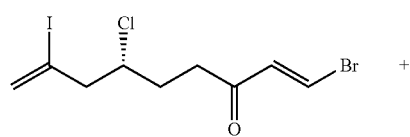 +

-continued

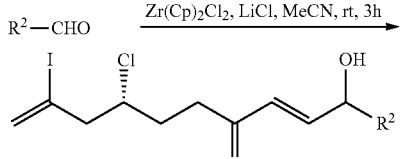

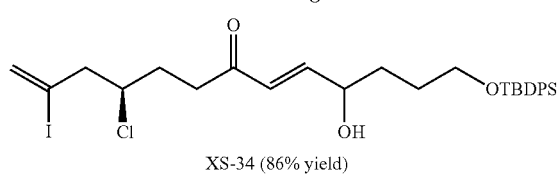

XS-34 (86% yield)

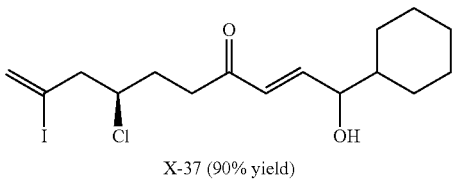

X-37 (90% yield)

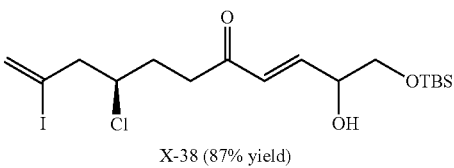

X-38 (87% yield)

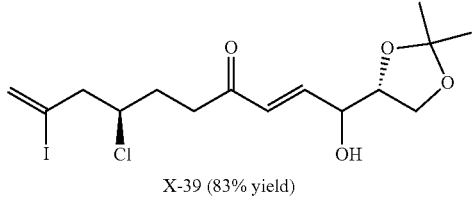

X-39 (83% yield)

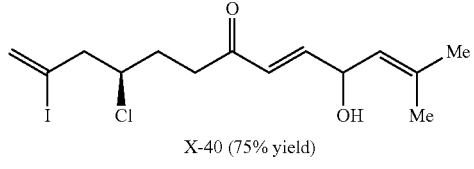

X-40 (75% yield)

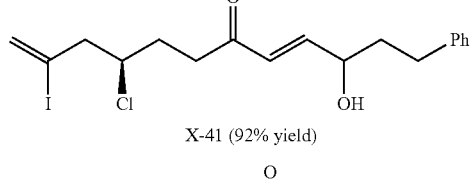

X-41 (92% yield)

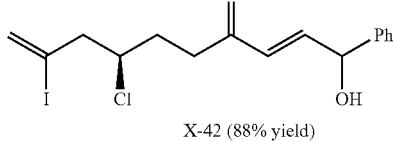

X-42 (88% yield)

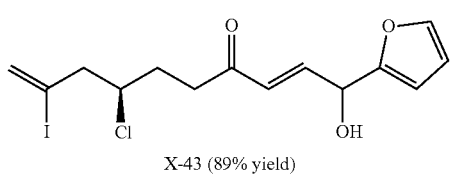

X-43 (89% yield)

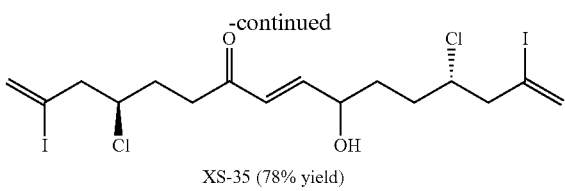

XS-35 (78% yield)

To a mixture of sulfonamide X-12 (2.60 mg, 5.5 µmol), proton sponge (Aldrich, purified by sublimation; 1.18 mg, 5.5 µmol) and CrCl$_2$ (Aldrich, 99.99% mg, 0.62 mg, 5.0 µmol) was added MeCN (Baker, ultra low water; 50 µL) in a glovebox. The mixture was stirred for 60 min at rt under nitrogen. To the second new vial were added Zr(cp)$_2$Cl$_2$ (Aldrich, 98%; 21.9 mg, 75 µmol), Mn powder (Aldrich, 99.99%, powder; 5.5 mg, 100 µmol), LiCl (Aldrich, anhydrous, grinded; 4.3 mg, 100 µmol), aldehyde (16.4 mg, 50 µmol), trans-bromoenone X-34 (75 µmol) and MeCN (Baker, ultra low water; 75 µL). Ni-catalyst X-37c (0.033 mg, 0.05 µmol) was added as a solution of MeCN (2.0 mg/mL, 16 µL). The mixture in the first vial was transferred to the second vial with syringe under nitrogen. The reaction mixture was stirred under nitrogen until the reaction was completed (TLC minitor) about 3 h, and diluted with EtOAc (1.0 mL). Florisil (ca. 30 mg) was added, and the mixture was stirred for 30 min, filtered through a short silica gel pad with 1:1 EtOAc/hexanes. The eluent was concentrated in vacuo to furnish the crude coupling product, which was purified by preparative TLC (EtOAc/hexanes=1:4) to give the desired product as a yellow liquid.

X-S-34

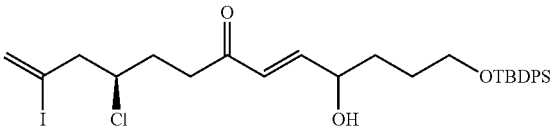

(E)-13-((tert-butyldiphenylsilyl)oxy)-4-chloro-10-hydroxy-2-iodotrideca-1,8-dien-7-one (XS-34)

$^1$H NMR (500 MHz, C$_6$D$_6$) δ: 7.79-7.68 (m, 4H), 7.26-7.17 (m, 6H), 6.60 (dd, J=16.0, 4.0 Hz, 1H), 6.22 (dd, J=16.0, 1.5 Hz, 1H), 5.69 (d, J=1.5 Hz, 1H), 5.54 (d, J=1.5 Hz, 1H), 4.10-4.01 (m, 1H), 3.91-3.83 (m, 1H), 3.54 (t, J=6.0 Hz, 2H), 2.43 (ddd, J=17.5, 9.0, 5.0 Hz, 1H), 2.34 (t, J=4.0 Hz, 2H), 2.30 (ddd, J=17.5, 8.5, 6.5 Hz, 1H), 1.97-1.85 (m, 1H), 1.78 (br, 1H), 1.52-1.28 (m, 5H), 1.13 (s, 9H); $^{13}$C NMR (125 MHz, C$_6$D$_6$) δ: 197.6, 148.0, 135.9, 133.9, 130.1, 128.9, 128.5, 128.3, 106.3, 70.7, 64.3, 61.0, 53.6, 37.6, 33.8, 31.6, 28.7, 27.0, 19.4; HRMS (ESI) m/z: [M+Na]$^+$ calcd for C$_{29}$H$_{38}$ClINaO$_3$Si, 647.1221; found, 647.1233.

X-37

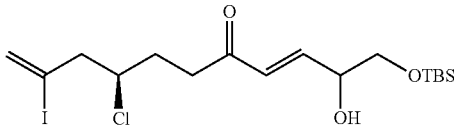

(E)-1-((tert-butyldimethylsilyl)oxy)-8-chloro-2-hydroxy-10-iodoundeca-3,10-dien-5-one (X-37)

$^1$H NMR (500 MHz, CDCl$_3$) δ: 6.78 (dd, J=16.0, 4.5 Hz, 1H), 6.43 (dd, J=16.0, 2.0 Hz, 1H), 6.18 (d, J=1.5 Hz, 1H), 5.85 (d, J=1.5 Hz, 1H), 4.45-4.34 (m, 1H), 4.22-4.12 (m, 1H), 3.75 (dd, J=10.0, 3.5 Hz, 1H), 3.50 (dd, J=10.0, 7.0 Hz, 1H), 2.94-2.66 (m, 4H), 2.26-2.15 (m, 1H), 1.97-1.85 (m, 1H), 0.90 (s, 9H), 0.08 (s, 6H); $^{13}$C NMR (125 MHz, CDCl$_3$) δ: 194.5, 136.5, 129.0, 125.5, 106.1, 60.6, 53.6, 37.4, 31.0; HRMS (ESI) m/z: [M+Na]$^+$ calcd for C$_{17}$H$_{30}$ClINaO$_3$Si, 495.0595; found, 495.0613.

X-38

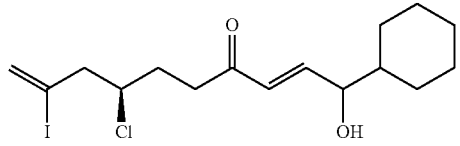

(E)-7-chloro-1-cyclohexyl-1-hydroxy-9-iododeca-2,9-dien-4-one (X-38)

$^1$H NMR (500 MHz, C$_6$D$_6$) δ: 6.65 (dd, J=16.0, 5.0 Hz, 1H), 6.15 (dd, J=16.0, 1.5 Hz, 1H), 5.69 (d, J=1.0 Hz, 1H), 5.54 (d, J=1.5 Hz, 1H), 4.13-4.05 (m, 1H), 3.95-3.87 (m, 1H), 3.58 (t, J=6.0 Hz, 2H), 2.46 (ddd, J=18.0, 9.0, 5.0 Hz, 1H), 2.34 (t, J=4.0 Hz, 2H), 2.30 (ddd, J=18.0, 9.0, 7.0 Hz, 1H), 1.98-1.89 (m, 1H), 1.76-1.65 (m, 1H), 1.64-1.54 (m, 3H), 1.53-1.47 (m, 1H), 1.46-1.39 (m, 1H), 1.19-1.10 (m, 1H), 1.09-0.94 (m, 2H), 0.93-0.80 (m, 2H); $^{13}$C NMR (125 MHz, C$_6$D$_6$) δ: 197.5, 147.1, 128.9, 128.8, 128.5, 106.3, 75.4, 61.0, 53.6, 43.8, 37.6, 31.6, 29.2, 28.0, 26.6, 26.4, 26.3; HRMS (ESI) m/z: [M+H]$^+$ calcd for C$_{16}$H$_{25}$ClIO$_2$, 411.0588; found, 411.0580.

X-39

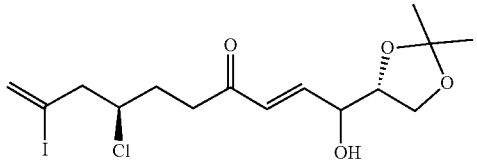

(E)-7-chloro-1-((R)-2,2-dimethyl-1,3-dioxolan-4-yl)-1-hydroxy-9-iododeca-2,9-dien-4-one (X-39)

$^1$H NMR (500 MHz, CDCl$_3$) δ: 6.81 (dd, J=16.0, 4.0 Hz, 1H), 6.46 (dd, J=16.0, 2.0 Hz, 1H), 6.18 (d, J=2.0 Hz, 1H), 5.85 (d, J=2.0 Hz, 1H), 4.53-4.46 (m, 1H), 4.20-4.12 (m, 2H), 3.95 (t, J=7.5 Hz, 1H), 3.88 (dd, J=9.0, 6.5 Hz, 1H), 2.94-2.79 (m, 2H), 2.77 (d, J=7.5 Hz, 2H), 2.43 (d, J=3.5 Hz, 1H), 2.25-2.15 (m, 1H), 1.96-1.85 (m, 1H), 1.45 (s, 3H), 1.36 (s, 3H); $^{13}$C NMR (125 MHz, CDCl$_3$) δ: 198.4, 142.8, 129.4, 129.0, 109.8, 105.6, 77.3, 70.6, 64.7, 60.5, 53.6, 37.6, 31.0, 26.4, 24.9; HRMS (ESI) m/z: [M+Na]$^+$ calcd for C$_{15}$H$_{22}$ClINaO$_4$, 451.0149; found, 451.0141.

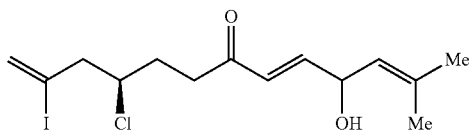

(E)-4-chloro-10-hydroxy-2-iodo-12-methyltrideca-1,8,11-trien-7-one (X-40)

$^1$H NMR (500 MHz, CDCl$_3$) δ: 6.78 (dd, J=16.0, 4.5 Hz, 1H), 6.31 (dd, J=16.0, 1.5 Hz, 1H), 6.19 (d, J=1.5 Hz, 1H), 5.85 (d, J=1.5 Hz, 1H), 5.17-5.12 (m, 1H), 5.09-5.04 (m, 1H), 4.20-4.12 (m, 1H), 2.93-2.75 (m, 4H), 2.25-2.16 (m, 1H), 1.95-1.86 (m, 1H), 1.76 (d, J=1.0 Hz, 3H), 1.74 (d, J=1.0 Hz, 3H), 1.64 (d, J=3.5 Hz, 1H); $^{13}$C NMR (125 MHz, CDCl$_3$) δ: 199.1, 146.9, 137.7, 129.0, 127.5, 124.1, 105.7, 68.4, 60.6, 53.6, 37.2, 31.1, 25.8, 18.4; HRMS (ESI) m/z: [M+Na]$^+$ calcd for C$_{14}$H$_{20}$ClINaO$_2$, 405.0094; found, 405.0085.

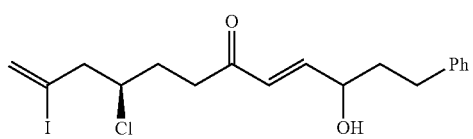

(E)-9-chloro-3-hydroxy-11-iodo-1-phenyldodeca-4,11-dien-6-one (X-41)

$^1$H NMR (500 MHz, CDCl$_3$) δ: 7.32-7.27 (m, 2H), 7.23-7.17 (m, 3H), 6.84 (dd, J=16.0, 5.0 Hz, 1H), 6.32 (dd, J=16.0, 1.0 Hz, 1H), 6.19 (d, J=1.0 Hz, 1H), 5.86 (d, J=1.5 Hz, 1H), 4.39-4.32 (m, 1H), 4.19-4.12 (m, 1H), 2.91-2.68 (m, 6H), 2.26-2.14 (m, 1H), 1.99-1.84 (m, 3H), 1.75 (d, J=4.0 Hz, 1H); $^{13}$C NMR (125 MHz, CDCl$_3$) δ: 198.8, 148.0, 141.1, 129.0, 128.5, 128.4, 128.0, 126.1, 105.6, 70.4, 60.5, 53.6, 38.0, 37.4, 31.4, 31.1; HRMS (ESI) m/z: [M+Na]$^+$ calcd for C$_{18}$H$_{22}$ClINaO$_2$, 455.0251; found, 455.0245.

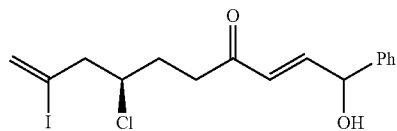

(E)-7-chloro-1-hydroxy-9-iodo-1-phenyldeca-2,9-dien-4-one (X-42)

$^1$H NMR (500 MHz, CDCl$_3$) δ: 7.45-7.31 (m, 5H), 6.94 (dd, J=16.0, 5.0 Hz, 1H), 6.45 (dd, J=16.0, 1.5 Hz, 1H), 6.17 (s, 1H), 5.85 (s, 1H), 5.40 (s, 1H), 4.22-4.12 (m, 1H), 2.95-2.72 (m, 4H), 2.26-2.12 (m, 2H), 1.96-1.84 (m, 1H); $^{13}$C NMR (125 MHz, CDCl$_3$) δ: 198.9, 146.6, 140.8, 129.0, 128.9, 128.5, 127.8, 126.5, 105.6, 73.7, 60.5, 53.6, 37.4, 31.1; HRMS (ESI) m/z: [M+Na]$^+$ calcd for C$_{16}$H$_{18}$ClINaO$_2$, 426.9938; found, 426.9951.

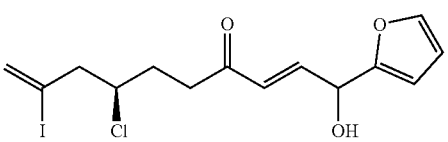

(E)-7-chloro-1-(furan-2-yl)-1-hydroxy-9-iododeca-2,9-dien-4-one (X-43)

$^1$H NMR (500 MHz, C$_6$D$_6$) δ: 7.01 (d, J=1.0 Hz, 1H), 6.76 (dt, J=16.0, 4.0 Hz, 1H), 6.29 (dt, J=16.0, 2.0 Hz, 1H), 6.00 (t, J=2.5 Hz, 1H), 5.97 (t, J=3.6 Hz, 1H), 5.72 (s, 1H), 5.57 (s, 1H), 4.92 (s, 1H), 4.07-3.98 (m, 1H), 2.44-2.29 (m, 4H), 2.28-2.18 (m, 1H), 1.93-1.82 (m, 1H), 1.73-1.62 (m, 1H); $^{13}$C NMR (125 MHz, C$_6$D$_6$) δ: 197.4, 154.2, 143.0, 142.6, 129.3, 128.9, 110.6, 107.4, 106.3, 67.1, 60.8, 53.6, 37.5, 31.4; HRMS (ESI) m/z: [M+Na]$^+$ calcd for C$_{14}$H$_{16}$ClINaO$_3$, 416.9730; found, 416.9733.

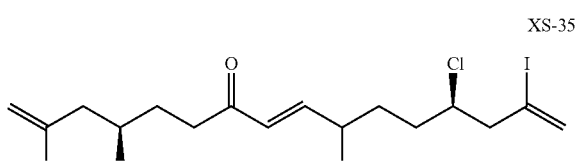

(13S,E)-4,13-dichloro-10-hydroxy-2,15-diiodohexadeca-1,8,15-trien-7-one (XS-35)

$^1$H NMR (500 MHz, CDCl$_3$) δ: 6.85 (dd, J=15.5, 5.0 Hz, 1H), 6.46 (dd, J=15.5, 1.0 Hz, 1H), 6.19 (d, J=1.5 Hz, 1H), 6.17 (d, J=1.5 Hz, 1H), 5.85 (t, J=2.0 Hz, 2H), 4.46-4.38 (m, 1H), 4.20-4.12 (m, 2H), 2.94-2.79 (m, 2H), 2.78 (d, J=7.0 Hz, 2H), 2.76 (d, J=7.0 Hz, 2H), 2.26-2.16 (m, 1H), 1.99-1.76 (m, 6H); $^{13}$C NMR (125 MHz, CDCl$_3$) δ: 198.8, 147.6, 129.1, 128.3, 105.9, 105.6, 70.3, 60.6, 60.5, 53.6, 53.4, 37.5, 33.0, 32.5, 31.1; HRMS (ESI) m/z: [M+Na]$^+$ calcd for C$_{16}$H$_{22}$Cl$_2$I$_2$NaO$_2$, 592.8984; found, 592.8980.

Synthesis Outlined in FIG. 15
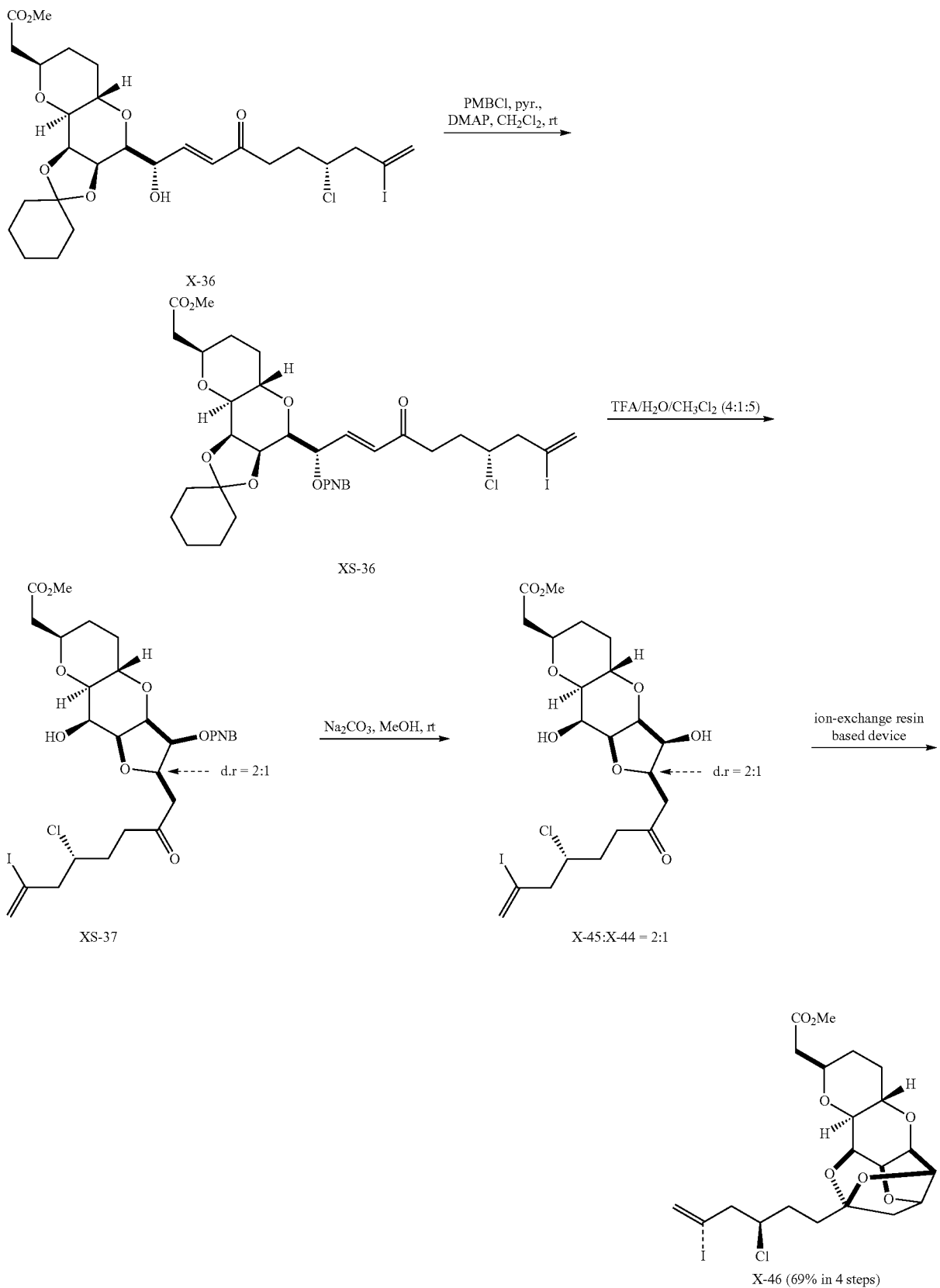

To a solution of X-36 (11.4 g, 17.5 mmol) in $CH_2Cl_2$ (175 mL) were added pyridine (4.5 mL, 52.5 mmol), PNBCl (6.5 g, 35.0 mmol), and DMAP (214 mg, 1.75 mmol) at 0° C., and the reaction mixture was warmed to room temperature. After stirring for 12 h, the solvent of reaction mixture was removed under reduced pressure and then passed through the silica gel pad with eluent of hexanes/EtOAc (1:1, 1500 mL). The eluent was removed to give the crude product XS-36, which can be used for the next step without further purification.

PNB XS-36: yellow oil; $[\alpha]_D^{20}$=−26.5 (c 0.40, $CHCl_3$); $^1H$ NMR (500 MHz, $C_6D_6$) δ: 7.84 (d, J=8.0 Hz, 2H), 7.72 (d, J=8.0 Hz, 2H), 7.23 (dd, J=16.0, 5.0 Hz, 1H), 6.41 (dd, J=16.0, 1.0 Hz, 1H), 6.08 (dt, J=5.0, 1.0 Hz, 1H), 5.71 (s, 1H), 5.56 (s, 1H), 4.30 (dd, J=8.0, 3.0 Hz, 1H), 4.08 (d, J=10.5 Hz, 1H), 4.08-3.98 (m, 1H), 3.84-3.76 (m, 1H), 3.64 (dd, J=6.5, 1.5 Hz, 1H), 3.31 (s, 3H), 3.09 (dd, J=10.5, 3.0 Hz, 1H), 2.49 (ddd, J=18.0, 9.0, 6.5 Hz, 1H), 2.47 (dd, J=16.0, 8.0 Hz, 1H), 2.38 (ddd, J=18.0, 9.0, 7.0 Hz, 1H), 2.33 (d, J=6.5 Hz, 2H), 2.00 (dd, J=16.0, 4.0 Hz, 1H), 1.92-1.72 (m, 4H), 1.68-1.58 (m, 2H), 1.42-1.13 (m, 9H), 1.10-0.96 (m, 2H); $^{13}C$ NMR (125 MHz, $C_6D_6$) δ: 197.2, 171.1, 163.3, 150.9, 140.9, 134.8, 130.9, 130.6, 128.9, 123.7, 111.1, 106.2, 75.9, 75.1, 74.3, 73.6, 71.8, 71.7, 66.9, 60.8, 53.6, 51.1, 40.2, 36.2, 33.8, 30.7, 30.0, 25.3, 24.3, 23.8; HRMS (ESI) m/z: $[M+H]^+$ calcd for $C_{34}H_{42}ClNO_{11}$, 802.1491; found, 802.1499.

To the crude product XS-36 from the previous step was added a solvent mixture of 4:1:5 $TFA/H_2O/CH_2Cl_2$ (950 mL). The reaction mixture was stirred for 2 h (TLC monitor), and then poured in small portions into saturated aq. $NaHCO_3$ solution (1000 mL). The aqueous mixture solution was neutralized with excess amount of solid $NaHCO_3$, and extracted with EtOAc (500 mL×5). The combined organic layer was washed with saturated $NaHCO_3$ solution, saturated $NH_4Cl$ solution, brine, and dried over $MgSO_4$. The solvent was removed to give crude product XS-37, which can be used for the next step without further purification.

XS-37-major: yellow oil; $[\alpha]_D^{20}$=+1.0 (c 0.37, $CHCl_3$); $^1H$ NMR (500 MHz, $C_6D_6$) δ: 8.19 (d, J=9.0 Hz, 2H), 7.68 (d, J=9.0 Hz, 2H), 5.69 (d, J=1.5 Hz, 1H), 5.55 (d, J=1.5 Hz, 1H), 5.52-5.56 (m, 1H), 4.20-4.12 (m, 2H), 4.08 (dd, J=10.0, 5.0 Hz, 1H), 4.02 (dt, J=10.0, 5.0 Hz, 1H), 3.99-3.93 (m, 1H), 3.81-3.73 (m, 1H), 3.66 (dd, J=10.0, 5.0 Hz, 1H), 3.29 (s, 3H), 2.83 (s, 1H), 2.73 (dd, J=10.0, 2.5 Hz, 1H), 2.53 (dd, J=15.5, 3.0 Hz, 1H), 2.39 (dd, J=17.0, 7.5 Hz, 1H), 2.30 (dt, J=15.0, 8.0 Hz, 1H), 2.28 (dt, J=14.0, 6.0 Hz, 1H), 2.19 (dd, J=17.0, 6.0 Hz, 1H), 2.17-1.97 (m, 2H), 1.88-1.76 (m, 2H), 1.56-1.44 (m, 1H), 1.32-1.18 (m, 2H), 1.15-1.02 (m, 1H), 0.96-0.82 (m, 1H); $^{13}C$ NMR (125 MHz, $C_6D_6$) δ: 204.4, 170.9, 164.0, 151.0, 134.6, 131.1, 128.9, 123.9, 105.9, 77.3, 75.1, 74.8, 74.7, 73.7, 73.2, 65.9, 65.4, 60.6, 53.4, 51.0, 42.0, 40.3, 39.6, 30.8, 30.2, 30.0; HRMS (ESI) m/z: $[M+H]^+$ calcd for $C_{28}H_{34}ClNO_{11}$, 722.0865; found, 722.0860.

To a solution of crude product XS-37 from the previous step in 50 mL $CH_2Cl_2$ was added a mixture of 18:1 $MeOH/H_2O$ (950 mL) and $Na_2CO_3$ solid (10.6 g, 100 mmol). The reaction mixture was stirred until the reaction was completed (TLC monitor) about 6 h. The reaction mixture was diluted with 500 mL $Et_2O$ and passed through a pad of Celite to remove white solid. The eluent was concentrated under reduced pressure, to give the crude product, which was purified by flash silica gel column chromatography (hexanes/EtOAc=20:1→1:2), to give a mixture of diastereomers (X-45: X-44=2:1; 8.2 g) as a yellow liquid.

Preparation of Ion-Exchange Resin Device ((a) Namba, K.; Jun, H. S.; Kishi, Y. *J. Am. Chem. Soc.* 2004, 126, 7770, (b) Kaburagi, Y.; Kishi, Y. *Org. Lett.* 2007, 9, 723): A cartridge column (Biotage, 25 g) was cleaned, filled with polymer-bound pyridinium p-toluenesulfonate resin (20.0 g, Aldrich #82817, ~3.5 mmol/g toluene 4-sulfonate loading), dehydrating reagent, 3 A molecular sieves (Fisher Sci, 3.0 g) and another cartridge column (Biotage, 25 g) was cleaned, filled with polymer-bound 1,3,4,6,7,8-hexahydro-2H-pyrimido[1,2-a]pyrimi-dine resin (20.0 g, Aldrich #358754, 2.6 mmol/g loading, 2% cross-linked with divinylbenzene) and washed with 100 mL 200 proof pure EtOH (Koptec, V1016).

The mixture of X-44 and X-45 (8.2 g) was dissolved in 500 mL EtOH in a 2000 mL round flask. A pump, reaction flask and ion-exchange column were connected as shown in FIG. 2. The mixture (10 mg/mL solution in EtOH) was circulated for 10 h (flow rate: 2 mL/min). The column was washed with ethanol (300 mL). The combined EtOH solutions were concentrated under reduced pressure. The residue was passed through a short silica gel plug (elution with hexanes/EtOAc=10:1 to 1:1) to give product X-46 as a yellow oil.

C1-C19 BB of halichondrin Bs X-46: yellow oil, $[\alpha]_D^{20}$=−25.8 (c 1.0, $CHCl_3$); $^1H$ NMR (500 MHz, $C_6D_6$) δ: 5.83 (s, 1H), 5.67 (s, 1H), 4.41 (dt, J=10.0, 4.0 Hz, 1H), 4.02 (dt, J=10.0, 5.0 Hz, 1H), 4.36 (s, 1H), 4.14 (sep, J=5.0 Hz, 2H), 4.08 (t, J=5.0 Hz, 1H), 3.89 (dd, J=6.5, 5.0 Hz, 1H), 3.76-3.69 (m, 1H), 3.66 (dd, J=6.5, 4.0 Hz, 1H), 3.30 (s, 3H), 2.58 (dt, J=15.0, 5.0 Hz, 2H), 2.51 (dd, J=15.5, 3.0 Hz, 1H), 2.17 (dd, J=16.0, 5.0 Hz, 1H), 2.22-2.12 (m, 1H), 2.10-1.75 (m, 5H), 1.44-1.37 (m, 1H), 1.35 (dd, J=13.0, 5.0 Hz, 1H), 1.33-1.16 (m, 2H); $^{13}C$ NMR (125 MHz, $C_6D_6$) δ: 170.9, 128.8, 109.7, 106.8, 82.4, 80.8, 78.5, 76.9, 74.9, 74.7, 74.2, 68.5, 61.8, 53.4, 51.1, 47.4, 40.7, 36.3, 32.4, 30.8, 30.7; HRMS (ESI) m/z: $[M+H]^+$ calcd for $C_{21}H_{29}ClIO_7$, 555.0646; found, 555.0655.

Synthesis of C1-C19 Thioester for X-Ray Structure Determination

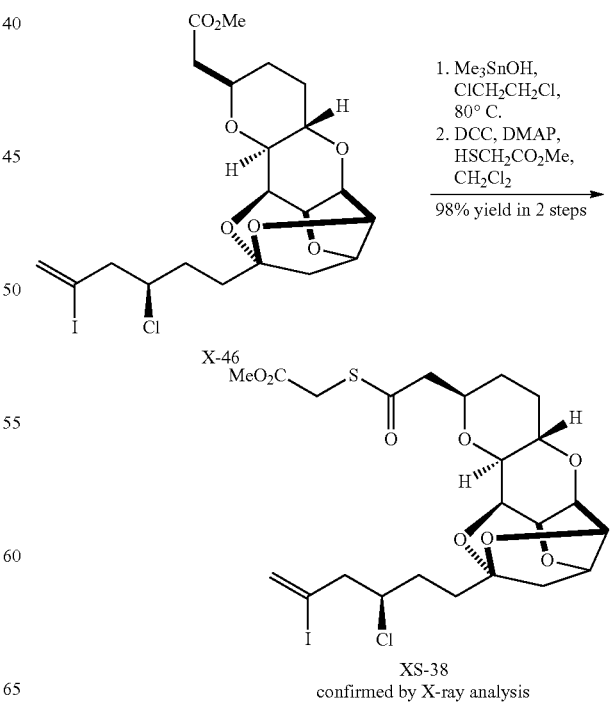

XS-38
confirmed by X-ray analysis

The C1-C19 carboxylic ester X-46 (200 mg, 0.37 mmol) was dissolved in 3.7 mL of freshly distilled 1,2-dichloroethane and after addition of Me$_3$SnOH (532 mg, 2.94 mmol), the mixture was heated to 80° C. until TLC analysis indicated a complete reaction (about 48 h). After completion of the reaction, the mixture was concentrated in vacuo, and the residue was taken up in 100 mL EtOAc. The organic layer was washed with aqueous 1N HCl solution (20 mL×3) and then washed with brine (15 mL) and dried over anhydrous MgSO$_4$. Removal of the solvent in vacuo afforded the crude product C1-C19 carboxylic acid, which was used directly for the next step without further purification (Nicolaou, K. C.; Estrada, A. A.; Zak, M.; Lee, S. H.; Safina, B. S. *Angew. Chem. Int. Ed.* 2005, 44, 1378).

Figure 3:
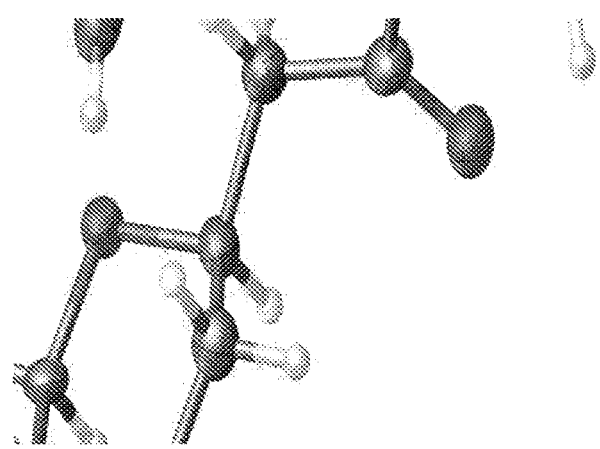
FIG. 3 shows the crystal structure of XS-38.

To the solution of crude C1-C19 carboxylic acid product from the previous step in anhydrous CH$_2$Cl$_2$ (37 mL) was added DCC (169.3 mg, 0.74 mmol), methyl 2-mercaptoacetate (58.9 mg, 0.56 mmol) and DMAP (5.0 mg, 0.0387 mmol). The reaction mixture was stirred at rt for 4 h (TLC monitor), filtered through a short Celite pad and the eluent was concentrated under reduced pressure. The residue was purified by flash chromatography (EtOAc/hexane=1:1) to give the product XS-38 as a white solid (90% yield) (Xiao, J. P.; Tolbert, T. *J. Org. Lett.* 2009, 11, 4144). Compound XS-38 was obtained from the mixture solvent (hexanes and EtOAc) and subjected to X-ray analysis (FIG. 3).

Coupling Efficiency of β-Haloenones with Aldehydes

The synthesis of C1-C19 building block X-D relies on a C—C bond formation between aldehyde X-A with a vinylogous acyl anion generated from β-haloenone X-B. There are several methods reported for C—C bond formation between "masked" vinylgous acyl anions and aldehydes (Cohen, T.; Bennett, A. B.; Mura, Jr., A. J. *J. Org. Chem.* 1976, 41, 2506. (b) Debal, A.; Cuvigny, T.; Larcheveque, *Tetrahedron Lett.* 1977, 36, 3187; Piers, E.; Morton, H. E. *J. Org. Chem.* 1979, 44, 3437. (d) Ren, H.; Krasovskiy, A.; Knochel, P. *Org. Lett.* 2004, 6, 4215). In 1992, a coupling reaction between methyl β-iodoacrylate X-2 and aldehyde X-1 was reported, which allowed the effective formation of the C$_{29}$-C$_{30}$ bond of halichondrins. Since then, the original stoichiometric, non-asymmetric reaction to the catalytic, asymmetric version has been improved (Aicher, T. D.; Buszek, K. R.; Fang, F. G.; Forsyth, C. J.; Jung, S. H.; Kishi, Y.; Scola, P. M. *Tetrahedron Lett.* 1992, 33, 1549. (b) Chen, C.; Tagami, K.; Kishi, Y *J. Org. Chem.* 1995, 60, 5386. (c) Namba, K.; Kishi, Y. *Org. Lett.* 2004, 6, 5031. (d) Guo, H.; Dong, C.-G.; Kim, D.-S.; Urabe, D.; Wang, J.; Kim, J. T.; Liu, X.; Sasaki, T.; Kishi, Y. *J. Am. Chem. Soc.* 2009, 131, 15387). Knochel and Rao disclosed a coupling of β-iodocyclohexenone X-4 with aldehydes in the presence of CrCl$_2$ in DMF (Knochel, P.; Rao, C. J. *Tetrahedron,* 1993, 49, 29). In connection with the synthetic efforts on the taxane class of natural products, the Ni/Cr-mediated coupling reaction was used to construct the taxane ring system, cf., X-7 →X-8 (Kress, M. H.; Ruel, R.; Miller, W. H.; Kishi, Y. *Tetrahedron Lett.* 1993, 34, 6003; Michael H. Kress, "Applications of the Ni(II)/Cr(II)-Mediated Coupling Reaction to the Synthesis of the Taxane Diterpenes" (January, 1995, Harvard University). (2) Xiaoning Christopher Sheng, "Total Synthesis of (+)-Cinnamoyltaxicin-I Triacetate" (September, 1998, Harvard University). (3) Jongwon Lim, "Total Synthesis of Taxol" (July, 2000, Harvard University)). These examples relied on Cr-organometallics. Based on this observation, Ni/Cr-mediated coupling was focused on, to realize the coupling X-A+X-B→X-C.

The first phase of the study was to assess the coupling efficiency of β-iodoenones with aldehydes, with use of model substrates (FIG. 7). The coupling efficiency between β-iodoenone X-9a and aldehyde X-10 with 10 mol % Cr-catalyst, prepared from (S)-sulfonamide X-12, and 1 mol % (Me)$_2$Phen(H)$_2$.NiCl$_2$ X-13a in MeCN (FIG. 7) was tested.

β-Iodoenone X-9a was compared with β-bromo- and β-chloroenones X-9b,c. X-9b,c might be less reactive than X-9a because of electronic effects and, therefore, might have a better reactivity-balance between the Ni- and Cr-catalytic cycles. This experiment showed that: (1) X-9b,c gave a better coupling efficiency than X-9a and (2) X-9b gave a slightly better coupling efficiency than X-9c.

β-bromoenone X-9b was used to conduct a second experiment. The overall coupling efficiency with less reactive Ni-catalyst and, then, with a lesser amount of the Ni-catalyst was tested. (Me)$_2$Phen(OMe)$_2$.NiCl$_2$ X-13b is a slower activator, based on previous studies, of vinyl iodides than (Me)$_2$Phen(H)$_2$.NiCl$_2$ X-13a (Liu, X.; Li, X.; Yu Chen, Hu, Y.; Kishi, Y. *J. Am. Chem. Soc.* 2012, 134, 6136). On replacing X-13a with X-13b, the coupling efficiency was noticeably improved. The ratio of Ni- over Cr-catalysts was optimized; with 10 mol % Cr-catalyst fixed, 1, 0.5. 0.1, 0.05, and 0.01 mol % Ni-catalyst loadings were tested, thereby revealing that: (1) the coupling efficiency improved with lowering the Ni-catalyst loading and (2) the coupling efficiency reached the plateau at the 0.05-0.01 mol % Ni-catalyst loading. It is worthwhile noting that the coupling reaction did not proceed without Ni-catalysts.

The coupling condition of "10 mol % Cr-catalyst, prepared from sulfonamide X-12, 0.05 mol % Ni-complex X-13b, Zr(cp)$_2$Cl$_2$ (1.5 eq), LiCl (2 eq), and Mn (2 eq) in MeCN ([C]0.4 M) at room temperature" is used for a study of coupling efficiency. FIG. 8 summarizes the coupling efficiency for di-substituted trans-β-bromoenones with aldehydes. The products thus obtained were stable enough to isolate and characterize. However, on standing in benzene, methylene chloride, and other solvents, at room temperature, they gradually decomposed, to yield the corresponding furans. With acid treatment (p-TSA or CSA/MeCN/RT), they gave the furans almost instantaneously. On acylation, however, the coupling products became stable even in the presence of acids (aq. TFA, CH$_2$Cl$_2$, RT).

FIG. 9 summarizes applying this coupling reaction to other types of β-bromoenones. The first case studied was cis-β-bromoenone X-19; a ~9:1 mixture of coupling product X-11 was obtained, similar to the coupling product obtained from trans-β-bromoenone X-9b, and furan X-20. Trans tri-substituted P-bromoenone X-21 gave a 1:1 mixture of coupling product X-23 and furan X-24, whereas cis tri-substituted P-bromoenone 22 gave only furan X-24.

Figure 4:
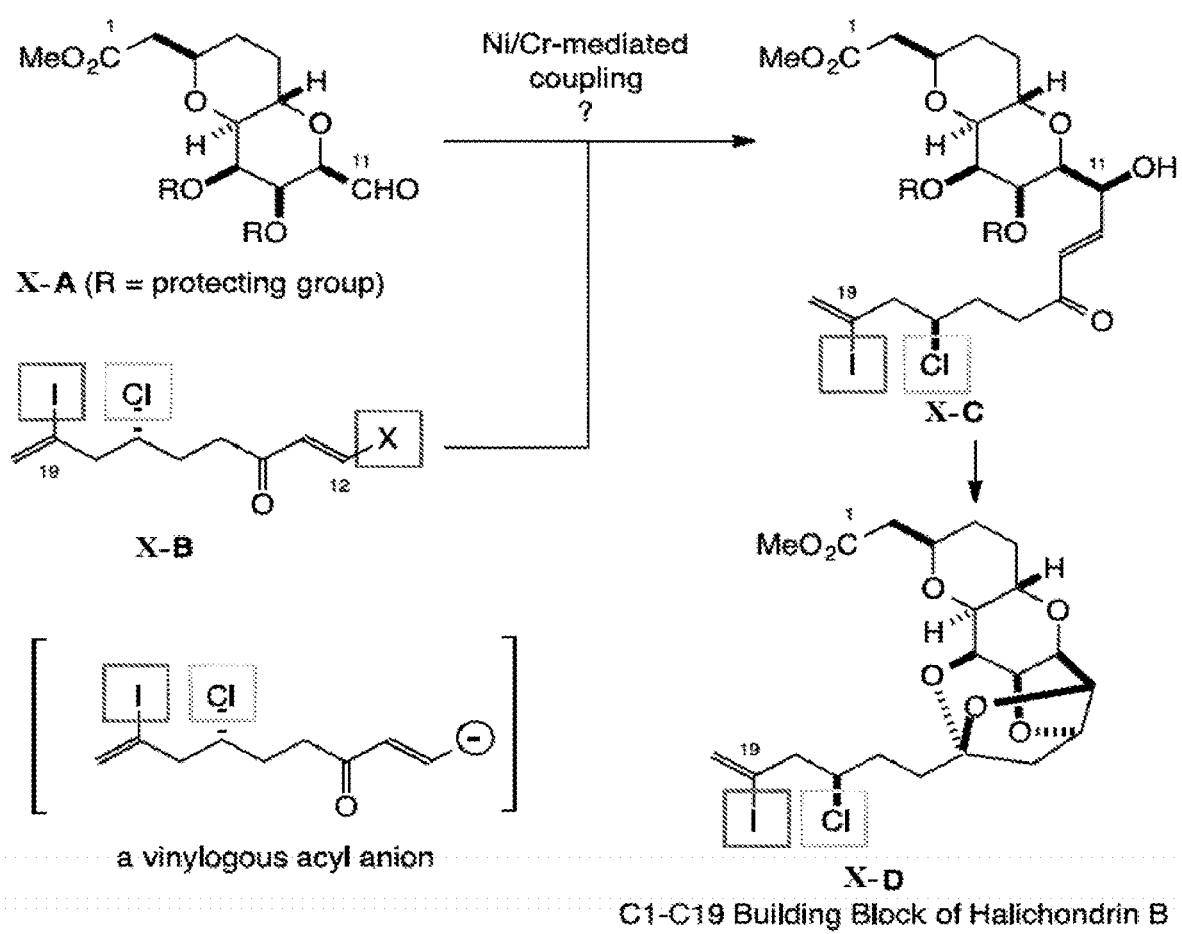
FIG. 4 shows a novel approach to the synthesis of the C1-C19 building block in the halichondrins.
Figure 5:
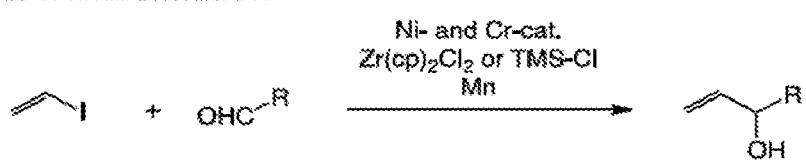
FIG. 5 shows catalytic Ni/Cr-mediated coupling reaction.
Figure 5:
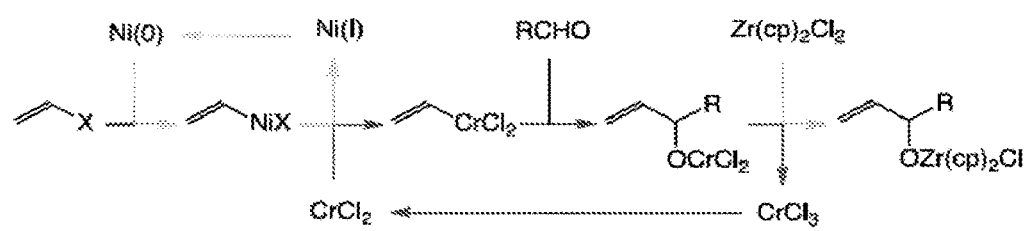
Figure 6:
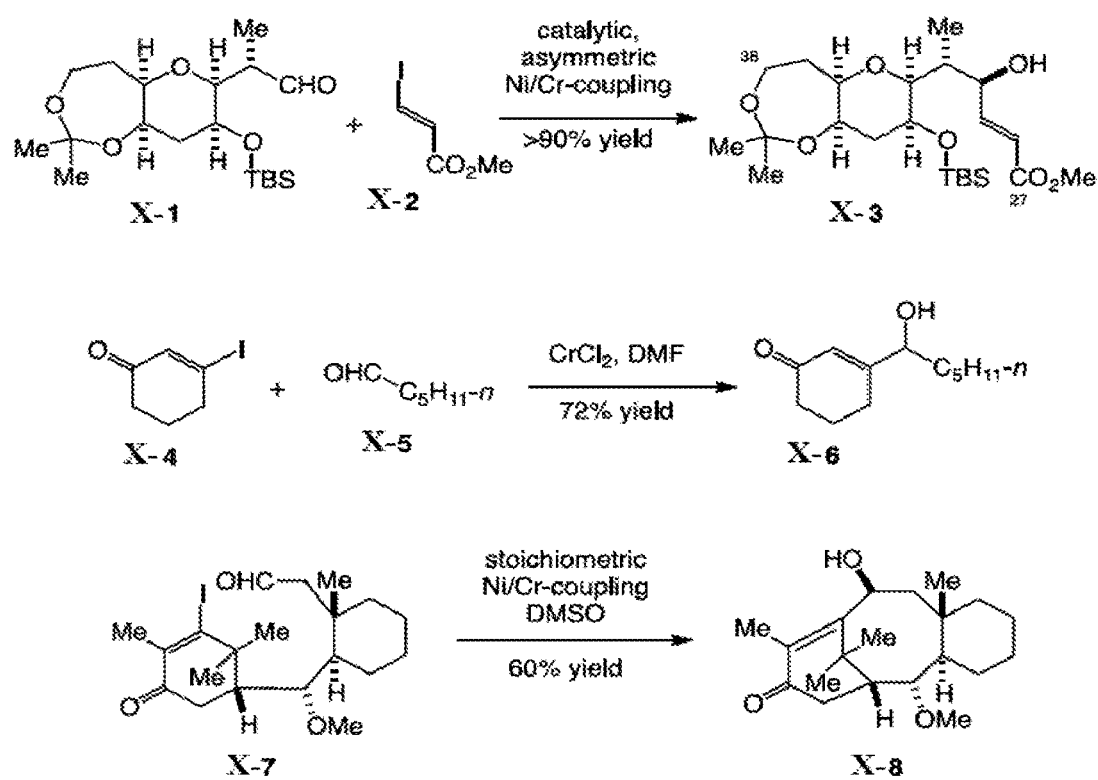
FIG. 6 shows three coupling examples reported in the literature (Aicher, T. D.; Buszek, K. R.; Fang, F. G.; Forsyth, C. J.; Jung, S. H.; Kishi, Y.; Scola, P. M. *Tetrahedron Lett.* 1992, 33, 1549; Chen, C.; Tagami, K.; Kishi, Y. *J. Org.*

Overall, the disclosed coupling reaction between an aldehyde and a "naked" vinylogous acyl anion is synthetically useful at least for di-substituted trans-β-bromoenones. Interestingly, the method meets the need to achieve the proposed coupling reaction X-A+X-B→X-C (FIG. 4).

Selective Activation of β-Bromoenone Over Vinyl Iodide and Saturated Chloride

FIG. 10 shows exemplary reported selective activation/coupling of a poly-halogenated nucleophile in the Ni/Cr-mediated coupling reactions is shown in FIG. 10. The first example shows that a selective activation/coupling is possible with the use of selective activator in the Cr-mediated couplings; namely, cobalt- and iron-salts are known to activate saturated halides, but not vinyl halides (Takai, K.; Nitta, K.; Fujimura, O.; Utimoto, K. *J. Org. Chem.* 1989, 4732). The second example shows that a selective activation of iodoacetylene in the Ni/Cr-mediated reaction is possible without disturbing the vinyl iodide present in the electrophile.

Competition experiments were conducted to study the selective activation/coupling. Aldehyde X-10 was coupled with a 1:1 mixture of 1-bromoenone X-9b and vinyl iodide X-31a, b, or c in the presence of a different amount of Ni-catalysts X-13a,b, followed by ratio-analysis of the two expected products X-11 and X-32 ($^1$H NMR) (FIG. 11). The competition experiments demonstrated that: (1) 0.05 and 0.1 mol % Ni-catalyst loadings, against 10 mol % Cr-catalyst loading, allow selectively to activate/couple β-bromoenone X-9b over all the three types of vinyl iodides X-31a-c and (2) Ni-catalyst X-13b gives a better discrimination of β-bromoenone X-9b over vinyl iodides X-31a-c than Ni-catalyst X-13a. Interestingly, 0.05 and 0.1 mol % Ni-catalyst loadings coincided with the Ni-catalyst amount ideal for β-bromoenone couplings (see the previous section).

The coupling study of X-34 and X-35 can be found in FIG. 13. Requisite nucleophile 34 was readily prepared from the previously reported, optically pure aldehyde 33 (FIG. 12) (Liu, S.; Kim, J. T.; Dong, C.-G.; Kishi, Y. Org. Lett. 2009, 11, 4520). With respect to the electrophile, several possible protecting groups at C8 and C9 were tested, thereby showing that the cyclohexylidene is the best option.

Aldehyde X-35 was subjected to the Ni/Cr-coupling reaction (10 mol % Cr-catalyst, prepared from sulfonamide X-12, and 0.05 mol % Ni-catalyst X-13b), to furnish a single coupling product in 46% yield. The spectroscopic analysis (HR-MS, $^1$H NMR, and $^{13}$C NMR) demonstrated that the isolated product was the desired coupling product X-36. In particular, the C10-C11 vicinal proton spin-coupling constant (1.0 Hz) allowed for the assignment of the desired β-configuration to the newly introduced alcohol. Based on the previous examples similar to the present case, the desired diastereomer was anticipated to be formed in a high stereoselectivity with the Cr-catalyst prepared from (S)-sulfonamide X-12 (Aicher, T. D.; Kishi, Y. Tetrahedron Lett. 1987, 28, 3463).

Three polyether-type phenanthrene.NiCl$_2$ complexes X-37a-c were prepared. The solubility of these complexes, particularly X-37b and X-37c, was improved. With the use of X-37c, the coupling yield was improved (The coupling yields with X-37a and X-37b were 59% and 75%, respectively. A Ni-catalyst with n-dodecyloxy substituents is also prepared, i.e., X=n-C12H25O in X-13, but found that its solubility was roughly same as that of X-13b and the coupling yield with this Ni-catalyst was 60%).

FIG. 14 summarizes the coupling of β-bromoenone X-34 with various aldehydes. Among them, the result with aldehyde X-33 shows a selective activation of a β-bromoenone over a vinyl iodide. Activation of vinyl iodide in X-33 can induce cyclization with the aldehyde.

Synthesis of C1-C19 Building Block of Halichondrin Bs and Analogs Thereof

The coupling product X-36 was prone to furan-formation, but this instability could be overcome by acylation of the resultant allylic alcohol. Among several acyl groups tested, p-nitrobenzoate was chosen, because it was found to be stable under the aq. TFA condition required for hydrolysis of the C8,C9-cyclohexylidene group, cf., step 2 in FIG. 15.

On treatment with aqueous Na$_2$CO$_3$, the p-nitrobenzoate group of aq. TFA-hydrolysis product was smoothly hydrolyzed, followed by an oxy-Michael reaction of the C9 hydroxyl group to the α,β-unsaturated ketone, to furnish a ~1:2 mixture of X-44 and X-45 (FIG. 15). In the previous studies, the chemical behaviors of these oxy-Michael products, including: (1) PPTS treatment allows to convert the C12-β oxy-Michael product X-45 to the desired polycycle, cf., X-46; (2) undesired C12-α oxy-Michael product X-44 can be recycled via retro oxy-Michael/oxy-Michael equilibration under basic condition; (3) an ion-exchange resin based device allows to convert the mixture of oxy-Michael products to the desired polycycle without isolation and recycling of the undesired oxy-Michael product (Namba, K.; Jun, H.-S.; Kishi, Y. J. Am. Chem. Soc. 2004, 126, 7770. (b) Kaburagi, Y.; Kishi, Y. Org. Lett. 2007, 9, 723).

An experiment was set up to convert oxy-Michael products X-44 and X-45 into polycycle X-46, thereby revealing that: (1) transformation of X-45 into X-46 under the PPTS condition was cleaned facile, but (2) isomerization of X-44 to X-45 under the previously established basic conditions or ion-exchange-resin protocol was problematic; one problem identified was the elimination of HCl to form iodo-diene (see the lower half of FIG. 15). With this information, a reaction condition to establish the equilibrium between two oxy-Michael products without elimination of HCl was searched for, and eventually found that the equilibration can be established with DBU or tetramethylguanidine in isopropanol or ethanol at room temperature, without the undesired elimination. DBU, Triton B(OMe), and tetramethylguanidine were tested. DBU and tetramethylguanidine established an equilibrium in isopropanol or ethanol at RT without an elimination of HCl, whereas caused an elimination of HCl in DMF and MeCN. Triton B(OMe) caused unknown decomposition of the oxy-Michael products.

Some of these conditions were translated to an ion-exchange resin based device and found that polymer-bound guanidine base, coupled with polymer-bound PPTS, was effective directly to convert a mixture of oxy-Michael products X-44 and X-45 to polycycle X-46 in a high yield without isolation/separation/equilibration (FIG. 16). Basic ion-exchange resins tested included: Amberlite IRA-400, Amberlite IRA-402, Amberlite IRA-900, Amberlite A-21, Amberlite A-26, ans Amberlite A-27. Acidic ion-exchange resins tested included: Rexyn 101, Amberlite IR-120, Amberlite 15, and Amberlite IRC-86. Both purchased from Aldrich: polymer-bound guanidine: #358754; polymer-bound PPTS: #82817. As ethanol was used as the solvent, an ester exchange was noticed if the reaction was run over 1 day. However, it did not present an issue for preparative purpose, as the conversion was usually complete within 12 hours. The structure of C1-C19 building block X-46 thus synthesized was fully supported by spectroscopic data (HR-MS, $^1$H and $^{13}$C NMR), which was further confirmed by X-ray analysis of its derivative.

The synthesis reported is easy to scale; the overall yield of X-46 from X-36 was 69% in a 11.4 g scale.

The C1-C19 building block X-46 of halichondrin Bs was synthesized via a selective activation/coupling of β-bromoenone X-34 with aldehyde X-35 in a Ni/Cr-mediated reaction. The first phase of study was a method development to effect a coupling of a "naked" vinylogous anion with an aldehyde. The study with the coupling of X-9+X-10→X-11 revealed: (1) β-bromoenone X-9b is a better nucleophile than the corresponding β-iodo- and β-chloroenones X-9a,c; (2) (Me)$_2$Phen(OMe)$_2$.NiCl$_2$ X-13b is a better Ni-catalyst than (Me)$_2$Phen(H)$_2$.NiCl$_2$ X-13a; (3) a low Ni-catalyst loading, for example 0.05-0.01 mol % Ni-catalyst against 10 mol % Cr-catalyst, is crucial for an effective coupling. The second phase of study was a method development to realize a selective activation/coupling of poly-halogenated nucleophiles such as X-34. The competition experiment of X-10+X-9b over X-10+X-31a~c revealed: (1) (Me)$_2$Phen (OMe)$_2$.NiCl$_2$ X-13b is more effective than (Me)$_2$Phen (H)$_2$.NiCl$_2$ X-13a for the required selective activation/coupling; (2) a low Ni-catalyst loading, for example 0.05-0.01 mol % Ni-catalyst against 10 mol % Cr-catalyst, can be important for discriminating β-bromoenone X-9b from the three types of vinyl iodides X-31a~c. The third phase of study was an application of the developed method to execute the proposed coupling of X-34+X-35→X-36. For this application, a polyether-type Ni-catalyst X-37c, readily soluble in the reaction medium, was introduced to achieve the selective activation/coupling with higher efficiency. With use of ion-exchange-resin based device, the coupling product X-36 was transformed to the C1-C19 building block X-46 of halichondrin Bs without purification/separation of the intermediates.

Nucleophile X-34 are designed selectively to achieve specific bond-formation in a controlled manner, as illustrated in the synthesis of right-half of halichondrin A (FIG. 17).[3c] Namely, C19 vinyl iodide was used for the Ni/Cr-mediated coupling stereoselectively to form the C$_{19}$-C$_{20}$ bond, whereas C17 chloride allowed stereospecifically to form the tetrahydrofuran ring in an S$_{N2}$ fashion.

Example 2. Unified Synthesis of C1-C19 Building Blocks of Halichondrins Via Selective Activation/Coupling of Poly-Halogenated Nucleophiles in (Ni)/Cr-Mediated Reactions Synthesis Outlined in FIG. 21

Synthesis of Model Halo-Acetylenic Ketones Y-18a-c

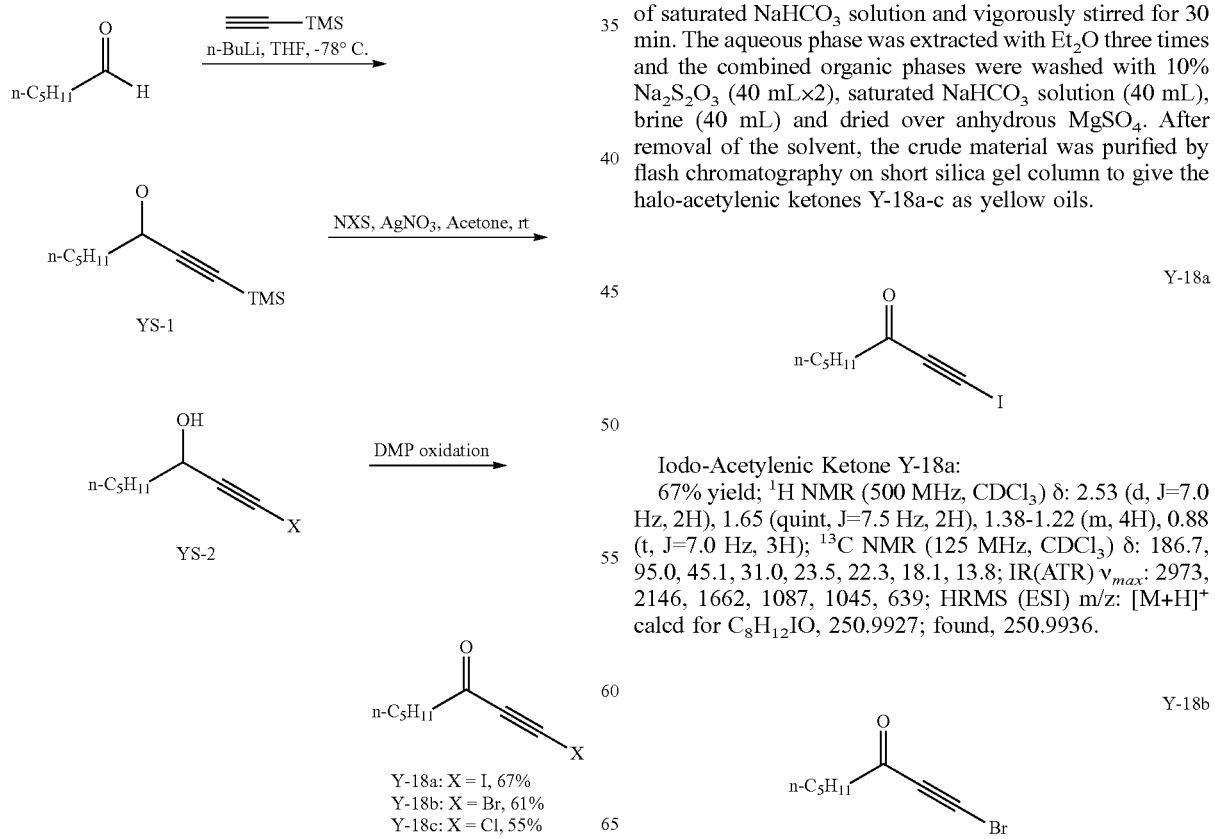

Y-18a: X = I, 67%
Y-18b: X = Br, 61%
Y-18c: X = Cl, 55%

To a solution of trimethylsilyl acetylene (432 mg, 4.4 mmol) in THF (14 mL) was added slowly n-BuLi (2.5 M in hexanes, 1.7 mL, 4.2 mmol) at −78° C. about 30 minutes. After 1 h, a solution of hexanal (400 mg, 4.0 mmol) in THF (6 mL) was added over another 30 min. The resulting mixture was stirred at −78° C. for 2 h and then quenched by saturated NH$_4$Cl solution (10 mL) and extracted with EtOAc (15 mL×3). The extracts were washed with brine (30 mL), dried over anhydrous MgSO$_4$, and then passed through a pad of silica gel (10 g). Elution with hexanes/EtOAc (10:1 to 4:1) and concentration gave the crude product YS-1 as light yellow liquid. This material was immediately used for the next step without further purification.

To a solution of propargyl alcohol YS-1 (800 mg, 4.0 mmol) in dry acetone (20 mL) was added silver nitrate AgNO$_3$ (135.9 mg, 0.80 mmol) and N-hlaosuccinimide (NIS: 1.50 g; NBS: 1.07 g; NCS: 801 mg; 6.0 mmol) at room temperature. After being stirred at room temperature for 0.5 h (overnight for NCS case), the reaction mixture was diluted with Et$_2$O (40 mL) and then quenched by 30 mL of 10% aqueous Na$_2$S$_2$O$_3$. The aqueous layer was extracted with Et$_2$O (20 mL×3) and combined organic layer was washed with brine, dried over anhydrous MgSO$_4$, and concentrated under vacuum. Purification of the residue by flash column chromatography on silica gel afforded halogenated propargyl alcohol YS-2 as colorless oil. The material was immediately used for the next step without further purification.

A solution of halogenated propargyl alcohol YS-2 (4.0 mmol) in CH$_2$Cl$_2$ (40 mL) were added NaHCO$_3$ (3.36 g, 40 mmol) and Dess-Martin periodinane (2.54 g, 6.0 mmol) at room temperature and stirred for 1 h at room temperature. The reaction mixture was diluted with Et$_2$O (60 mL) and then quenched with 10% Na$_2$S$_2$O$_3$ solution (60 mL), 40 mL of saturated NaHCO$_3$ solution and vigorously stirred for 30 min. The aqueous phase was extracted with Et$_2$O three times and the combined organic phases were washed with 10% Na$_2$S$_2$O$_3$ (40 mL×2), saturated NaHCO$_3$ solution (40 mL), brine (40 mL) and dried over anhydrous MgSO$_4$. After removal of the solvent, the crude material was purified by flash chromatography on short silica gel column to give the halo-acetylenic ketones Y-18a-c as yellow oils.

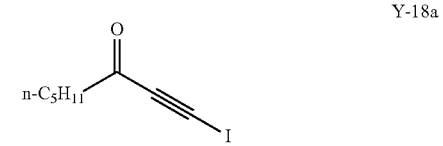

Y-18a

Iodo-Acetylenic Ketone Y-18a:

67% yield; $^1$H NMR (500 MHz, CDCl$_3$) δ: 2.53 (d, J=7.0 Hz, 2H), 1.65 (quint, J=7.5 Hz, 2H), 1.38-1.22 (m, 4H), 0.88 (t, J=7.0 Hz, 3H); $^{13}$C NMR (125 MHz, CDCl$_3$) δ: 186.7, 95.0, 45.1, 31.0, 23.5, 22.3, 18.1, 13.8; IR(ATR) ν$_{max}$: 2973, 2146, 1662, 1087, 1045, 639; HRMS (ESI) m/z: [M+H]$^+$ calcd for C$_8$H$_{12}$IO, 250.9927; found, 250.9936.

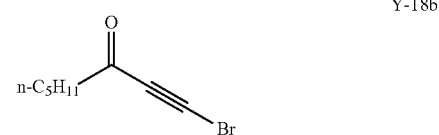

Y-18b

Bromo-Acetylenic Ketone Y-18b:

61% yield; $^1$H NMR (500 MHz, CDCl$_3$) δ: 2.54 (d, J=7.0 Hz, 2H), 1.65 (quint, J=7.5 Hz, 2H), 1.38-1.22 (m, 4H), 0.88 (t, J=7.0 Hz, 3H); $^{13}$C NMR (125 MHz, CDCl$_3$) δ: 186.6, 79.9, 56.8, 45.3, 31.0, 23.5, 22.3, 13.8; IR(ATR) ν$_{max}$: 2955, 2179, 1672, 1246, 1220, 687; HRMS (ESI) m/z: [M+H]$^+$ calcd for C$_8$H$_{12}$BrO, 203.0072; found, 203.0076.

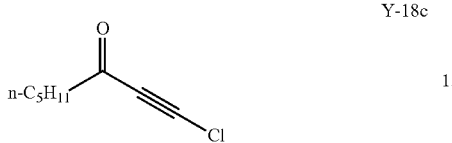

Y-18c

Chloro-Acetylenic Ketone Y-18c:

55% yield; $^1$H NMR (500 MHz, CDCl$_3$) δ: 2.58 (d, J=7.0 Hz, 2H), 1.68 (quint, J=7.5 Hz, 2H), 1.38-1.24 (m, 4H), 0.89 (t, J=7.5 Hz, 3H); $^{13}$C NMR (125 MHz, CDCl$_3$) δ: 187.6, 81.4, 78.2, 45.4, 31.0, 23.4, 22.3, 13.8; IR(ATR) ν$_{max}$: 2954, 1815, 1731, 1462, 1230, 749; HRMS (ESI) m/z: [M+H]$^+$ calcd for C$_8$H$_{12}$ClO, 159.0577; found, 159.0570.

Synthesis of Model Halo-Acetylenic Ketals Y-19a-c

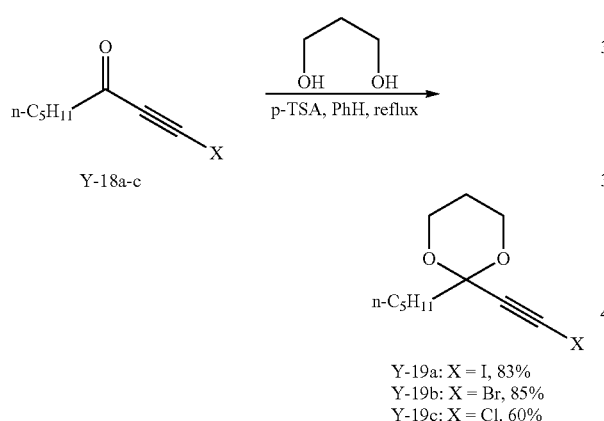

Y-19a: X = I, 83%
Y-19b: X = Br, 85%
Y-19c: X = Cl. 60%

To a solution of the above halo-acetylenic ketones Y-18a-c (1.5 mmol) in benzene (30 mL) were added 1,3-propanediol (1.14 g, 15 mmol) and p-TsOH.H$_2$O (14.3 mg, 0.075 mmol) at room temperature and then refluxed for 12 h with azeotropic removal of water using a Dean-Stark trap. The reaction mixture was poured into saturated NaHCO$_3$ aq. solution, extracted with Et$_2$O and the extract was washed with brine, dried over by anhydrous MgSO$_4$. After removal of the solvent, the crude material was purified by flash chromatography on short silica gel column to give ketals Y-19a-c as yellow oils.

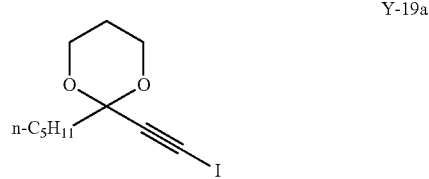

Y-19a

Iodo-Acetylenic Ketal Y-19a:

83% yield; $^1$H NMR (500 MHz, CDCl$_3$) δ: 4.20 (dt, J=13.0, 2.5 Hz, 2H), 3.88 (dd, J=11.5, 5.0 Hz, 2H), 2.09-1.96 (m, 1H), 1.79-1.74 (m, 2H), 1.53-1.44 (m, 2H), 1.39-1.22 (m, 5H), 0.88 (t, J=7.0 Hz, 3H); $^{13}$C NMR (125 MHz, CDCl$_3$) δ: 97.4, 91.6, 62.5, 41.8, 31.6, 25.1, 22.9, 22.5, 14.0, 4.3; HRMS (ESI) m/z: [M+Na]$^+$ calcd for C$_{11}$H$_{17}$INaO$_2$, 331.0165; found, 331.0162.

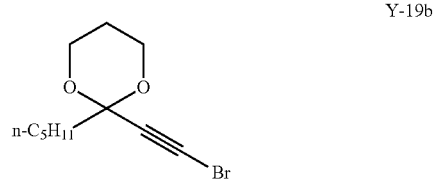

Y-19b

Bromo-Acetylenic Ketal Y-19b:

85% yield; $^1$H NMR (500 MHz, CDCl$_3$) δ: 4.18 (dt, J=12.0, 3.0 Hz, 2H), 3.87 (dd, J=12.0, 5.5 Hz, 2H), 2.08-1.95 (m, 1H), 1.79-1.72 (m, 2H), 1.52-1.44 (m, 2H), 1.37-1.23 (m, 5H), 0.87 (t, J=7.5 Hz, 3H); $^{13}$C NMR (125 MHz, CDCl$_3$) δ: 97.1, 76.9, 62.4, 47.1, 41.8, 31.6, 25.1, 22.8, 22.5, 14.0; HRMS (ESI) m/z: [M+H]$^+$ calcd for C$_{11}$H$_{18}$BrO$_2$, 261.0490; found, 261.0483.

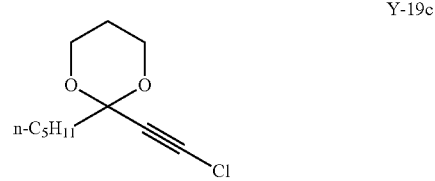

Y-19c

Chloro-Acetylenic Ketal Y-19c:

60% yield; $^1$H NMR (500 MHz, CDCl$_3$) δ: 4.24 (dt, J=12.5, 2.5 Hz, 2H), 3.88 (dd, J=12.5, 5.5 Hz, 2H), 2.09-1.98 (m, 1H), 1.80-1.75 (m, 2H), 1.56-1.48 (m, 2H), 1.37-1.23 (m, 5H), 0.88 (t, J=7.0 Hz, 3H); $^{13}$C NMR (125 MHz, CDCl$_3$) δ: 96.2, 79.6, 75.0, 62.3, 41.8, 31.8, 25.2, 22.8, 22.5, 14.0; HRMS (ESI) m/z: [M+H]$^+$ calcd for C$_{11}$H$_{18}$ClO$_2$, 217.0995; found, 217.0998.

General Procedure of Catalytic, Asymmetric (Ni)/Cr-Mediated Coupling with Halo-Acetylenic Ketones Y-18a-c and Halo-Acetylenic Ketals Y-19a-c
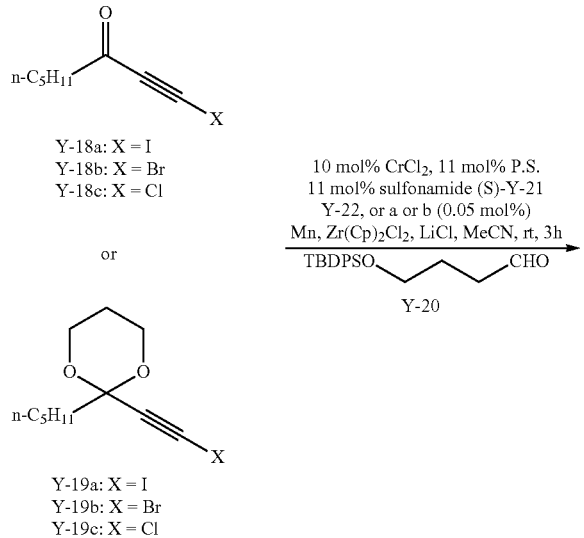
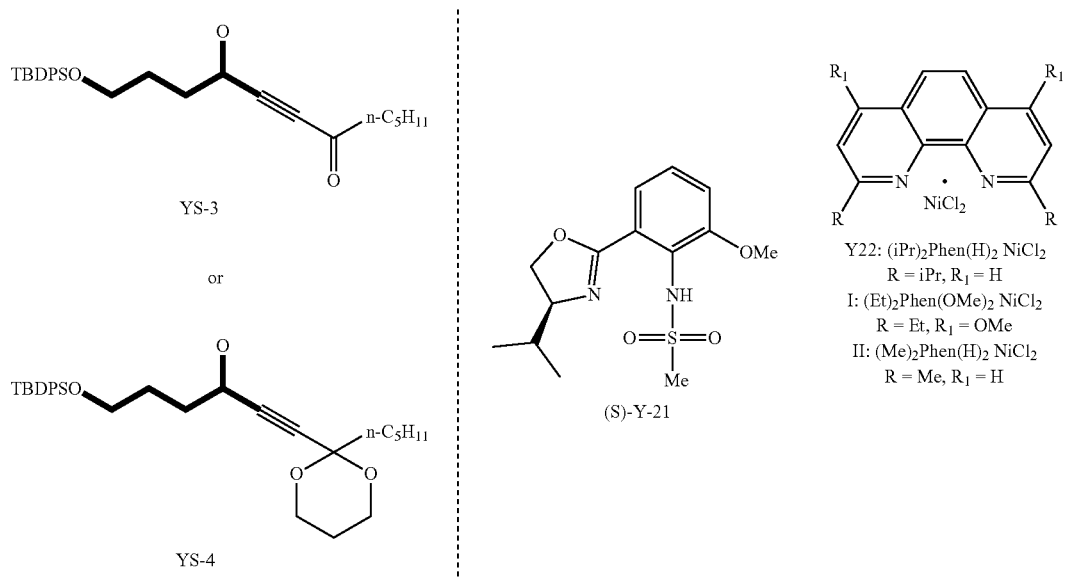

Synthesis of (S)-Y-21, a, and b is available from Liu, X.; Li, X.; Chen, Y.; Hu, Y.; Kishi, Y. *J. Am. Chem. Soc.* 2012, 134, 6136. Ni-catalyst Y-22 was synthesized with the following procedure.

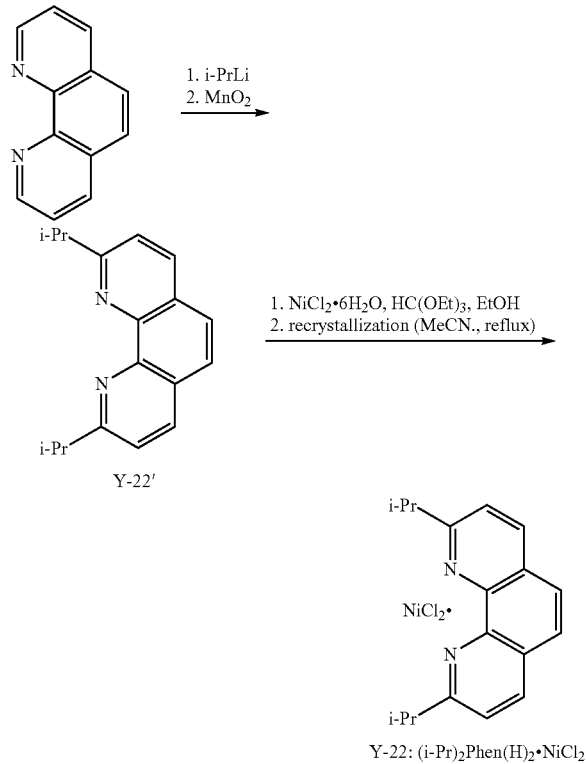

To a stirred solution of 1,10-phenanthroline anhydrous (5.0 g, 27.7 mmol) in toluene (200 mL) and THF (25 mL) was added 0.7M i-PrLi in pentane solution (24 mL, 84 mmol) dropwise at room temperature. After stirring for 16 h at room temperature, the mixture was added $H_2O$ (100 mL). The separated aqueous layer was extracted with $CH_2Cl_2$ (50 mL×3) and the combined organic layer was treated with $MnO_2$ (20 g, 230 mmol) at room temperature. After stirring for 2 h, the mixture was added $MgSO_4$ (20 g) and stirred for 15 min. The mixture was filtered through Celite and the filtrate was concentrated. The crude mixture was purified by $SiO_2$ flash column chromatography (hexanes/EtOAc=9:1) to provide (i-Pr)$_2$Phen(H)$_2$ Y-22'(6.3 g, 23.8 mmol, 86%) (Metallinos, C.; Barrett, F. B.; Wang, Y.; Xu, S. F.; Taylor, N. *J. Tetrahedron* 2006, 62, 11145).

Y-22':
$^1$H NMR (500 MHz, CDCl$_3$) δ 1.48 (d, J=7.0 Hz, 12H), 1.94 (hept, J=7.0 Hz, 2H), 7.55 (d, J=8.0 Hz, 2H), 7.68 (s, 2H), 8.14 (d, J=8.0 Hz, 2H); $^{13}$C NMR (125 MHz, CDCl$_3$) δ 22.9, 37.3, 120.1, 125.4, 127.2, 136.4, 145.2, 167.8; HRMS (ESI) m/z: [M+Na]$^+$ calcd for C$_{18}$H$_{20}$ON$_2$Na, 287.1524; found, 287.1527.

To a stirred solution of (i-Pr)$_2$Phen(H)$_2$ Y-22' (6.3 g, 23.8 mmol) in EtOH (100 mL) and triethyl room temperature hoformate (3 mL) was added a solution of NiCl$_2$.6H$_2$O (17 g, 71.5 mmol) in EtOH (100 mL) dropwise at room temperature. After stirring for overnight at room temperature, the precipitate was filtered and the resulting solid was washed Et$_2$O. This purple solid was dissolved into CH$_3$CN and the mixture was refluxed under N$_2$ atmosphere. Then this solution was cooled to room temperature, to give purple crystals. The crystals were filtered and washed with Et$_2$O and dried under reduced pressure for overnight to provide Y-22 (4.5 g, 11.4 mmol, 48%) as purple shiny crystal.

General Procedure of Asymmetric Catalytic Ni/Cr-Mediated Coupling.

Cr-Catalyst Preparation:

To a mixture of natural sulfonamide (Guo, H.; Dong, C. G.; Kim, D. S.; Urabe, D.; Wang, J.; Kim, J. T.; Liu, X.; Sasaki, T.; Kishi, Y. *J. Am. Chem. Soc.* 2009, 131, 15387) (S)-Y-21 (3.44 mg, 11.0 μmol), proton sponge (Aldrich, purified by sublimation; 2.36 mg, 11.0 μmol) and CrCl$_2$ (Aldrich, 99.99% mg, 1.23 mg, 10.0 μmol) was added MeCN (Baker, ultra low water; 50 μL) in a glovebox. The mixture was stirred for 60 min at room temperature under nitrogen.

Coupling:

To a separate vial were added ZrCp$_2$Cl$_2$ (Aldrich, 98%; 43.8 mg, 0.15 mmol), Mn powder (Aldrich, 99.99%, powder; 11.0 mg, 0.20 mmol), LiCl (Aldrich, anhydrous, grinded; 8.5 mg, 0.20 mmol), NiCl$_2$. complex Y-22 or i or ii (0.05 mol %) or no NiCl$_2$. catalyst, aldehyde Y-20 (32.7 mg, 0.10 mmol) and halo-acetylenic ketones Y-18a-c or halo-acetylenic ketals Y-19a-c (0.17 mmol). The deep green Cr-catalyst in the first vial was transferred to the second reaction vial with syringe under nitrogen. The reaction mixture was stirred under nitrogen until the reaction was completed (~3 hr, TLC monitor), and diluted with EtOAc (2.0 mL). Florisil (ca. 50 mg) was added, and the mixture was stirred for 30 min, filtered through a short silica gel pad with 1:1 hexanes/EtOAc. The eluent was concentrated in vacuo to furnish the crude coupling product, which was purified by preparative TLC (hexanes/EtOAc=4:1) to give YS-3 as yellow liquid or YS-4 as colorless oil.

The isolated yield for coupling reactions with Ni-catalysts Y-22 or i or ii and no added Ni-catalyst are summarized below (Table 2).

TABLE 2

Results

| Isolated yield | I<br>Y-18a | Br<br>Y-18b | Cl<br>Y-18c |
|---|---|---|---|
| Y-22 | 11% | 49% | 20% |
| i | 15% | 48% | 18% |
| ii | 8% | 26% | 10% |
| no Ni | 18% | 50% | 22% |

TABLE 2-continued

Results

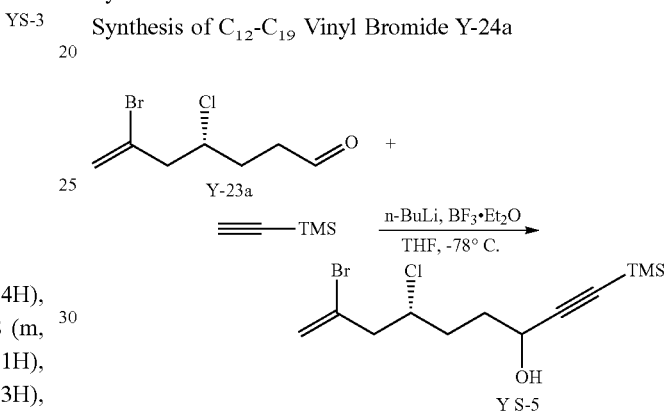

| Isolated yield | Y-19a | Y-19b | Y-18c |
|---|---|---|---|
| Y-22 | 82% | 93% | 8% |
| i | 81% | 94% | <5% |
| ii | 79% | 90% | 6% |
| no Ni | 85% | 97% | 9% |

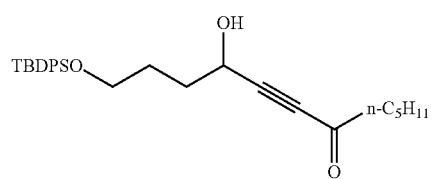

YS-3

Coupling Product YS-3:

$^1$H NMR (500 MHz, CDCl$_3$) δ: 7.70-7.61 (m, 4H), 7.47-7.32 (m, 6H), 4.62 (q, J=6.0 Hz, 1H), 3.78-3.58 (m, 2H), 3.28 (d, J=6.0 Hz, 1H), 2.55 (t, J=7.5 Hz, 1H), 2.00-1.90 (m, 1H), 1.89-1.79 (m, 1H), 1.77-1.62 (m, 3H), 1.37-1.24 (m, 4H), 1.06 (s, 9H), 1.05-1.02 (m, 2H), 0.89 (s, 3H); $^{13}$C NMR (125 MHz, CDCl$_3$) δ: 187.9, 135.6, 133.1, 129.8, 127.8, 92.0, 83.6, 63.9, 62.0, 45.4, 34.6, 31.1, 28.1, 26.8, 23.6, 22.4, 19.1, 13.9; IR(ATR) ν$_{max}$: 2930, 1676, 1427, 1111, 823, 701, 505; HRMS (ESI) m/z: [M+K]$^+$ calcd for C$_{28}$H$_{38}$KO$_3$Si, 489.2222; found, 489.2224.

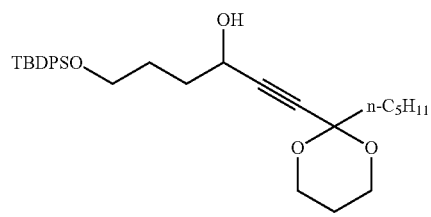

YS-4

Coupling Product YS-4:

$^1$H NMR (500 MHz, CDCl$_3$) δ: 7.71-7.68 (m, 4H), 7.46-7.42 (m, 2H), 7.41-7.37 (m, 4H), 4.58 (q, J=6.0 Hz, 1H), 4.27-4.20 (m, 2H), 3.90-3.85 (m, 2H), 3.77-3.67 (m, 2H), 2.82 (d, J=6.0 Hz, 1H), 2.09-1.98 (m, 1H), 1.97-1.83 (m, 3H), 1.82-1.71 (m, 3H), 1.57-1.49 (m, 2H), 1.34-1.26 (m, 5H), 1.06 (s, 9H), 0.88 (s, 3H); $^{13}$C NMR (125 MHz, CDCl$_3$) δ: 135.5, 133.4, 129.7, 127.7, 96.5, 88.1, 80.6, 63.8, 62.3, 62.1, 41.9, 35.1, 31.7, 28.2, 26.8, 25.3, 23.0, 22.5, 19.1, 14.0; HRMS (ESI) m/z: [M+K]$^+$ calcd for C$_{31}$H$_{44}$KO$_4$Si, 547.2640; found, 547.2637.

Synthesis Outlined in FIG. 22

Synthesis of C$_{12}$-C$_{19}$ Vinyl Bromide Y-24a

For the preparation of Y-23a ((a) Liu, S.; Kim, J. T.; Dong, C. G.; Kishi, Y. Org. Lett. 2009, 11, 4520, (b) Ueda, A.; Yamamoto, A.; Kato, D.; Kishi, Y. *J. Am. Chem. Soc.* 2014, 136, 5171).

To a solution of trimethylsilyl acetylene (4.93 g, 50 mmol) in THF (50 mL) was added slowly n-BuLi (2.5 M in hexanes, 14.56 mL, 53 mmol) at −78° C. After 1 h, a solution of BF$_3$.Et$_2$O (4.66 mL, 54 mmol) in THF (10 mL) was added over 30 min using syringe pump and the mixture was stirred at −78° C. for 1 h. Then a solution of aldehyde Y-23a (18 mmol) in THF (15 mL) was added over 10 min. After stirring at −78° C. for 3 h, the resulting mixture was poured into a saturated NaHCO$_3$ solution at 0° C. The aqueous layer was extracted with EtOAc three times and the combined organic layer was washed with brine, dried over anhydrous Na$_2$SO$_4$, and concentrated under vacuum. Purification of the residue by flash column chromatography on silica gel afforded propargylic alcohol YS-5 (3.21 g, 90%) as a colorless oil.

Propargylic Alcohol YS-5:

$^1$H NMR (500 MHz, C$_6$D$_6$) δ: 5.27 (s, 1H), 5.23 (s, 1H), 4.10-4.05 (m, 2H), 2.42 (dd, J=15.0, 3.5 Hz, 1H), 2.42 (dd, J=15.0, 5.0 Hz, 1H), 1.84-1.55 (m, 4H), 0.17 (s, 9H); $^{13}$C NMR (125 MHz, C$_6$D$_6$) δ: 129.7, 119.9, 107.4, 89.3, 62.1, 59.6, 49.9, 34.5, 33.2, −0.07; HRMS (ESI) m/z: [M+H]$^+$ calcd for C$_{12}$H$_{20}$BrClNaOSi, 345.0053; found, 345.0059.

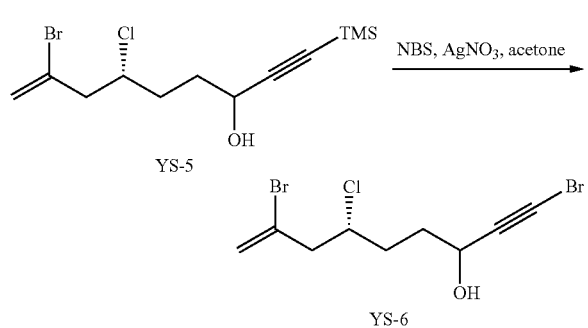

YS-5

YS-6

To a solution of propargyl alcohol YS-5 (998 mg, 3.1 mmol) in dry acetone (12 mL) was added silver nitrate (105 mg, 0.62 mmol) and N-bromosuccinimide (822 mg, 4.6 mmol) at room temperature. The reaction vessel was wrapped by aluminum foil to avoid light. After being stirred at room temperature for 0.5 h, the reaction mixture was cooled to 0° C. and then quenched by water. Then the solution was extracted with ether and the combined organic layer was washed with 10% aqueous $Na_2S_2O_3$ and brine, dried over anhydrous $Na_2SO_4$, and concentrated under vacuum. Purification of the residue by flash column chromatography on silica gel afforded bromo-propargyl alcohol YS-6 as a colorless oil. This material was immediately used for the next step without further purification.

Bromo-Propargylic Alcohol YS-6:

$^1$H NMR (500 MHz, $C_6D_6$) δ: 5.27 (s, 1H), 5.23 (s, 1H), 4.02-3.96 (m, 1H), 3.94-3.84 (m, 1H), 2.36 (dd, J=15.0, 3.5 Hz, 1H), 2.26 (dd, J=15.0, 3.5 Hz, 1H), 1.72-1.42 (m, 4H); $^{13}$C NMR (125 MHz, $C_6D_6$) δ: 129.7, 120.0, 81.5, 62.5, 59.5, 49.9, 45.3, 34.3, 33.0; HRMS (ESI) m/z: [M+H]$^+$ calcd for $C_9H_{12}Br_2ClO$, 328.8943; found, 328.8938.

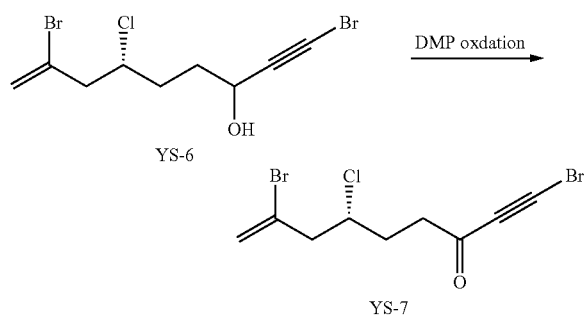

YS-6

YS-7

To a solution of the above proparglic alcohol YS-6 in $CH_2Cl_2$ (15 mL) were added $NaHCO_3$ (2.6 g, 31 mmol) and Dess-Martin periodinane (2.0 g, 4.6 mmol) at room temperature and stirred for 0.5 h at room temperature. The reaction mixture was quenched with 10% $Na_2S_2O_3$ and saturated $NaHCO_3$ solution and vigorously stirred for 30 min. The aqueous phase was extracted with $CH_2Cl_2$ three times and the combined organic phases were washed with 10% $Na_2S_2O_3$ and saturated $NaHCO_3$ solution and then dried over anhydrous $Na_2SO_4$. After removal of solvent, the crude material was purified by flash chromatography on short silica gel column to give ynone YS-7 as colorless oil. This material was immediately used for the next step without further purification.

Acetylenic Ketone YS-7:

$[α]_D^{20}$=+13.5 (c 1.0, CHCl$_3$); $^1$H NMR (500 MHz, C$_6$D$_6$) δ: 5.24 (s, 1H), 5.19 (s, 1H), 3.91-3.85 (m, 1H), 2.32 (ddd, J=18.0, 9.0, 5.0 Hz, 1H), 2.29 (dd, J=14.5, 8.5 Hz, 1H), 2.18 (dd, J=15.0, 5.5 Hz, 1H), 2.13 (ddd, J=18.5, 9.5, 6.5 Hz, 1H), 1.70-1.62 (m, 1H), 1.52-1.44 (m, 1H); $^{13}$C NMR (125 MHz, C$_6$D$_6$) δ: 183.5, 129.3, 120.1, 80.3, 58.8, 56.7, 49.8, 42.2, 31.0; IR(ATR) $v_{max}$: 3019, 1677, 1214, 749, 668; HRMS (ESI) m/z: [M+Na]$^+$ calcd for $C_9H_9Br_2ClNaO$, 348.8606; found, 348.8600.

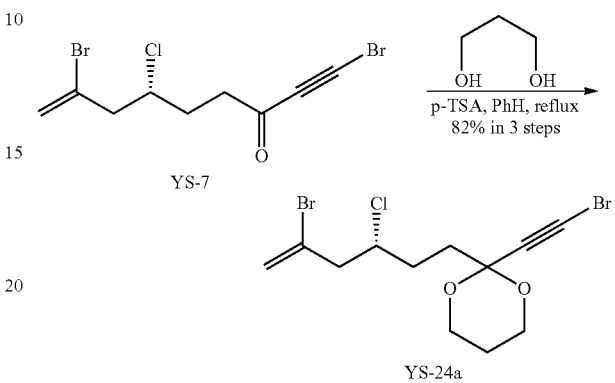

YS-7

YS-24a

To a solution of the above ynone YS-7 (3.1 mmol) in benzene (62 mL) were added 1,3-propanediol (2.4 g, 31.0 mmol) and p-TsOH·H$_2$O (29.3 mg, 0.16 mmol) at room temperature and then refluxed for 12 h with azetropic removal of water using a Dean-Stark trap. The reaction mixture was poured into saturated NaHCO$_3$aq. solution, extracted with EtOAc and the extract was washed with brine, dried over sodium sulfate. After removal of the solvent, the crude material was purified by flash chromatography on short silica gel column to give the ketal derivative Y-24a (976 mg, 82% in three steps) as colorless oil.

Ketal Y-24a:

$[α]_D^{20}$ +6.6 (c 0.92, CHCl$_3$); $^1$H NMR (600 MHz, C$_6$D$_6$) δ: 5.22-5.21 (m, 1H), 5.17-5.16 (m, 1H), 4.13 (tdd, J=8.7, 5.2, 3.5 Hz, 1H), 3.88-3.84 (m, 2H), 3.48 (ddd, J=12.0, 5.1, 1.2 Hz, 2H), 2.37 (dd, J=14.8, 8.5 Hz, 1H), 2.33-2.29 (m, 1H), 2.26-2.21 (m, 1H), 2.07-2.01 (m, 2H), 1.93-1.87 (m, 1H), 1.60 (dddt, J=18.1, 13.6, 7.8, 5.2 Hz, 1H), 0.55-0.52 (m, 1H); $^{13}$C NMR (125 MHz, C$_6$D$_6$) δ: 129.8, 119.8, 96.8, 77.8, 62.4, 59.6, 49.8, 47.5, 38.9, 31.6, 25.2; HRMS (ESI) m/z: [M+Na]$^+$ calcd for $C_{12}H15Br_2ClO2Na$, 406.9025; found, 406.9029.

Synthesis of $C_{12}$-$C_{19}$ Vinyl Iodide Y-24b

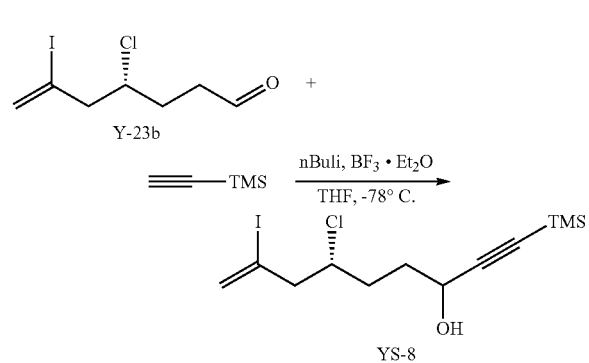

Y-23b

YS-8

To a solution of trimethylsilyl acetylene (1.0 g, 10.2 mmol) in THF (10 mL) was added slowly n-BuLi (2.5 M in hexanes, 4.1 mL, 10.2 mmol) at −78° C. After 1 h, a solution of BF$_3$.Et$_2$O (1.4 mL, 11.0 mmol) in THF (2.5 mL) was added over 30 min using syringe pump and the mixture was stirred at −78° C. for 1 h (Yamauchi, M.; Hirao, I. Tetrahedron Lett. 1983, 24, 391). Then a solution of aldehyde Y-23b (1.0 g, 3.6 mmol) in THF (2.5 mL) was added over 30 min. After stirring at −78° C. for 3 h, the resulting mixture was poured into a saturated NaHCO$_3$ solution at 0° C. The aqueous layer was extracted with EtOAc three times and the combined organic layers were washed with brine, dried over Na$_2$SO$_4$, and concentrated under vacuum. Purification of the residue by flash column chromatography on silica gel afforded proparglic alcohol YS-8 (1.15 g, 80%) as a colorless oil.

Propargylic Alcohol YS-8:

$^1$H NMR (500 MHz, CDCl$_3$) δ: 6.18 (s, 1H), 5.85 (s, 1H), 4.42 (d, J=6.0 Hz, 1H), 4.24-4.12 (m, 1H), 2.77 (d, J=7.0 Hz, 2H), 2.12-1.94 (m, 2H), 1.90-1.74 (m, 2H), 0.17 (s, 9H); $^{13}$C NMR (125 MHz, CDCl$_3$) δ: 128.9, 106.0, 105.9, 90.1, 62.1, 60.5, 53.4, 34.3, 32.6, −0.16; HRMS (ESI) m/z: [M+H]$^+$ calcd for C$_{12}$H$_{21}$ClIOSi, 371.0095; found, 371.0103.

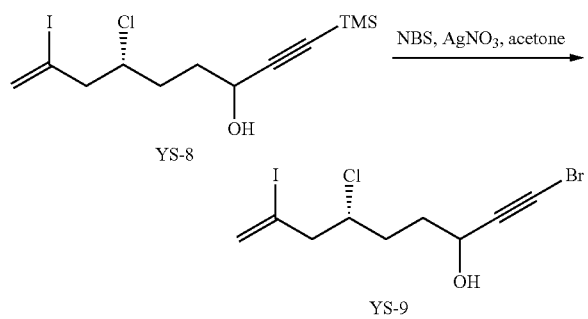

To a solution of the above trimethylsilyl acetylene YS-8 (1.10 g, 3.0 mmol) in dry acetone (15 mL) was added silver nitrate AgNO$_3$ (103 mg, 0.60 mmol) and NBS (806 mg, 4.5 mmol) at room temperature. The reaction vessel was wrapped by aluminum foil to avoid light. After being stirred at room temperature for 0.5 h, the reaction mixture was cooled to 0° C. and then quenched by water. Then the solution was extracted with ether and the combined organic layer was washed with 10% aqueous Na$_2$S$_2$O$_3$ and brine, dried over Na$_2$SO$_4$, and concentrated under vacuum. Purification of the residue by flash column chromatography on silica gel afforded bromoacetylene YS-9 as a colorless oil. This material was immediately used for the next step without further purification.

Bromoacetylene YS-9:

$^1$H NMR (500 MHz, CDCl$_3$) δ: 6.18 (s, 1H), 5.86 (s, 1H), 4.47 (q, J=7.5 Hz, 1H), 4.22-4.12 (m, 1H), 2.77 (d, J=7.5 Hz, 2H), 2.08-1.96 (m, 2H), 1.94-1.79 (m, 2H); $^{13}$C NMR (125 MHz, CDCl$_3$) δ: 129.0, 105.8, 80.4, 62.7, 60.5, 53.4, 45.9, 34.3, 32.6; HRMS (ESI) m/z: [M+H]$^+$ calcd for C$_9$H$_{12}$BrClIO, 376.8805; found, 376.8811.

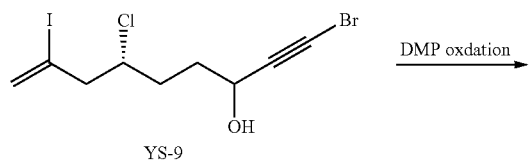

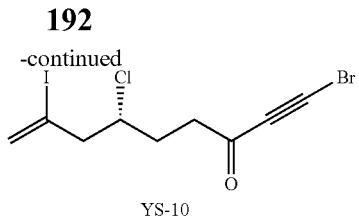

A solution of the above propargylic alcohol YS-9 (3.0 mmol) in CH$_2$Cl$_2$ (15 mL) were added NaHCO$_3$ (2.5 g, 30.0 mmol) and Dess-Martin periodinane (1.9 g, 4.5 mmol) at room temperature and stirred for 0.5 h at room temperature. The reaction mixture was quenched with 10% Na$_2$S$_2$O$_3$ solution and saturated NaHCO$_3$ solution and vigorously stirred for 30 min. The aqueous phase was extracted with CH$_2$Cl$_2$ three times and the combined organic phase was washed with 10% Na$_2$S$_2$O$_3$ solution and saturated NaHCO$_3$ solution and then dried over anhydrous Na$_2$SO4. After removal of solvent, the crude material was purified by flash chromatography on short silica gel column to give the ynone YS-10 as colorless oil. This material was immediately used for the next step without further purification.

Bromo-Acetylenic Ketone YS-10:

[α]$_D^{20}$=+10.4 (c 1.0, CHCl$_3$); $^1$H NMR (500 MHz, C$_6$D$_6$) δ: 5.65 (s, 1H), 5.53 (s, 1H), 3.87-3.81 (m, 1H), 2.32 (ddd, J=18.0, 9.0, 5.0 Hz, 1H), 2.24 (dd, J=14.5, 9.0 Hz, 1H), 2.18 (dd, J=15.5, 5.5 Hz, 1H), 2.13 (ddd, J=18.0, 8.5, 6.5 Hz, 1H), 1.69-1.61 (m, 1H), 1.53-1.45 (m, 1H); $^{13}$C NMR (125 MHz, C$_6$D$_6$) δ: 183.5, 129.0, 105.9, 80.3, 60.0, 56.7, 53.3, 42.2, 30.8; IR(ATR) ν$_{max}$: 2900, 2158, 1672, 1614, 1109, 899, 752; HRMS (ESI) m/z: [M+Na]$^+$ calcd for C$_9$H$_9$BrClINaO, 396.8468; found, 396.8459.

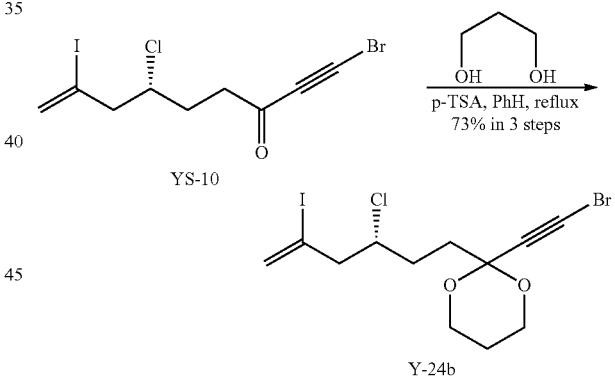

To a solution of the above acetylenic ketone YS-10 (3.0 mmol) in benzene (60 mL) were added 1,3-propanediol (2.3 g, 30.0 mmol) and p-TsOH.H$_2$O (28.5 mg, 0.15 mmol) at room temperature and then refluxed for 12 h with azetropic removal of water using a Dean-Stark trap. The reaction mixture was poured into saturated NaHCO$_3$aq. solution, extracted with EtOAc and the extract was washed with brine, dried over sodium sulfate. After removal of the solvent, the crude material was purified by flash chromatography on short silica gel column to give the ketal Y24b (956 mg, 73% in three steps) as colorless oil.

Ketal Y24b:

[α]$_D^{20}$=+5.6 (c 1.0, CHCl$_3$); $^1$H NMR (500 MHz, C$_6$D$_6$) δ: 5.66 (s, 1H), 5.51 (s, 1H), 4.12-4.06 (m, 1H), 3.87 (td, J=12.4, 2.3 Hz, 2H), 3.52-3.48 (m, 2H), 2.33 (d, J=6.4 Hz, 2H), 2.21-2.15 (m, 1H), 2.05-1.97 (m, 2H), 1.91-1.84 (m, 1H), 1.67-1.58 (m, 1H), 0.60 (ddq, J=12.1, 2.6, 1.3 Hz, 1H); $^{13}$C NMR (125 MHz, C$_6$D$_6$) δ: 128.6, 106.5, 96.7, 77.7, 62.4, 60.8, 53.2, 47.5, 38.8, 31.4, 25.1; HRMS (ESI) m/z: [M+Na]$^+$ calcd for C$_{12}$H$_{15}$BrClIO$_2$Na, 454.8886; found, 454.8892.

Synthesis Outlined in FIG. 24

Synthesis of Y-27a Via (Ni)/Cr-Mediated Coupling of Y-11 and Y-24a

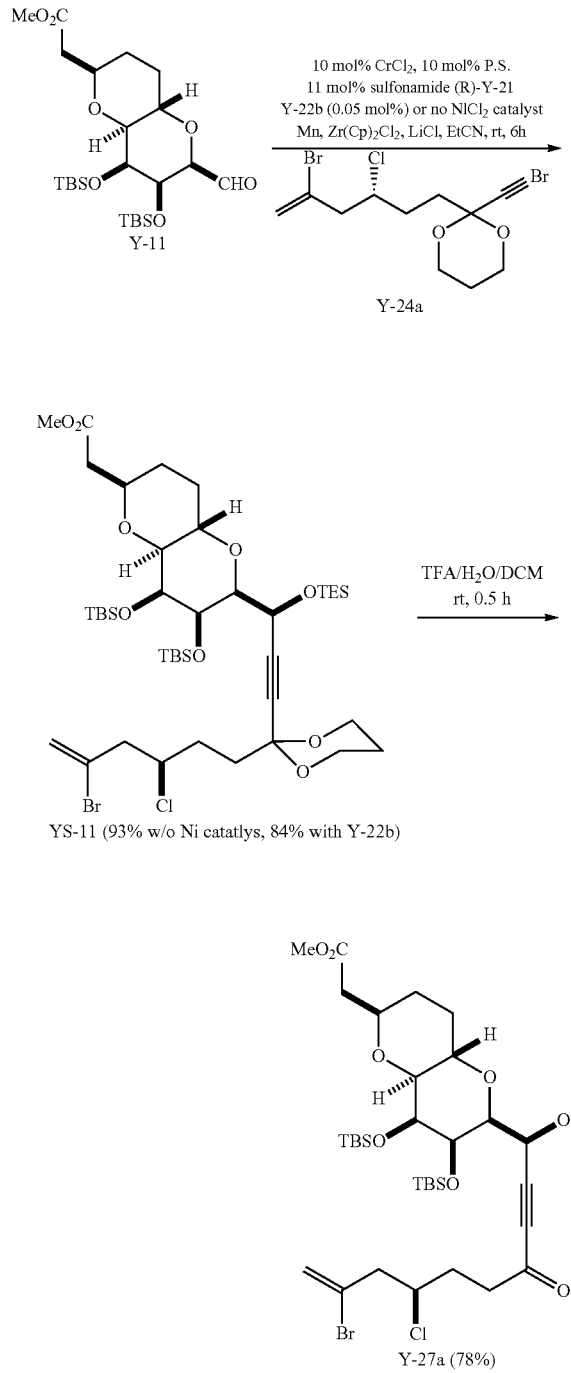

YS-11 (93% w/o Ni catatlys, 84% with Y-22b)

Y-27a (78%)

To a mixture of CrCl$_2$ (49.2 mg, 0.4 mmol), (R)-Y-21((a) Choi, H.; Demeke, D.; Kang, F.-A.; Kishi, Y.; Nakajima, K.; Nowak, P.; Wan, Z.-K.; Xie, C. *Pure Appl. Chem.* 2003, 75, 1, (b) Reference 3) (137 mg, 0.44 mmol), and proton sponge (94.3 mg, 0.44 mmol) in a glove box was added EtCN (5.0 mL, 0.4 M) and stirred for 1 h at room temperature. In a separate flask, bromo-acetylene Y-24a (1.35 g, 3.5 mmol), aldehyde Y-11 (1.0 g, 2.0 mmol), LiCl (339.1 mg, 8.0 mmol), Mn (439.5 mg, 8.0 mmol) were mixed together and the Cr-complex solution was transferred to the flask. Then TES-CL (0.84 mL, 5.0 mmol) was added into the reaction mixture. After stirring for 6 h at room temperature, the reaction was removed from the glove box and diluted with anhydrous Et$_2$O. Sat. aq. NaHCO$_3$, followed by potassium serinate solution, was added carefully to quench the reaction and the corresponding mixture was stirred vigorously for 30 min. The resultant mixture was filtered through short pad of silica gel and concentrated. The crude material was purified by flash chromatography on silica gel to give TES-protected alcohol YS-11 (1.70 g, 92% yield).

The fractions eluded with 1:10 EtOAc/hexanes were combined and purified with silica gel column chromatography (1:10 EtOAc/hexanes) to give reduced bromoacetylene YS-12 (~400 mg, ~38%) and a fraction containing homo-dimer YS-13. This faction was further purified with preparative TLC (1:10 EtOAc/hexanes), to give homo-dimer YS-13 (5.9 mg, 0.3%).

Coupling Product YS-11:

[α]$^{20}_D$ −22.3 (c 1.0, CHCl$_3$); $^1$H NMR (600 MHz, C$_6$D$_6$) δ: 5.70 (d, J=4.4 Hz, 1H), 5.27 (s, 1H), 5.28-5.26 (d, J=9.5 Hz, 1H), 4.37-4.24 (m, 4H), 4.14-4.12 (m, 1H), 4.09-4.07 (m, 1H), 4.03 (tt, J=10.1, 5.0 Hz, 1H), 3.85 (dt, J=6.4, 3.1 Hz, 1H), 3.79-3.74 (m, 1H), 3.67 (ddd, J=16.3, 11.3, 5.0 Hz, 2H), 3.34-3.33 (m, 3H), 2.86 (dd, J=9.5, 2.2 Hz, 1H), 2.53-2.51 (m, 2H), 2.45-2.38 (m, 3H), 2.28-2.21 (m, 2H), 2.18-2.13 (m, 1H), 2.10 (dd, J=15.1, 5.0 Hz, 1H), 1.85-1.74 (m, 1H), 1.49-1.43 (m, 1H), 1.42-1.32 (m, 1H), 1.25-1.17 (m, 1H), 1.12 (t, J=7.9 Hz, 9H), 1.09-1.08 (s, 9H), 0.87 (m, 6H), 0.27 (s, 3H), 0.25 (s, 3H), 0.07 (s, 3H), 0.06 (s, 3H); $^{13}$C NMR (125 MHz, C$_6$D$_6$) δ: 170.5, 129.6, 119.5, 96.1, 86.0, 83.2, 81.0, 78.9, 74.12, 72.7, 70.3, 64.5, 63.4, 62.2, 62.0, 59.8, 50.8, 49.8, 40.5, 39.0, 31.7, 30.6, 28.9, 26.3, 26.1, 25.3, 18.8, 18.5, 7.2, 5.6, −4.3, −4.5, −4.7, −5.1; HRMS (ESI) m/z: [M+H]$^+$ calcd for C$_{42}$H$_{77}$BrClO$_9$Si$_3$, 923.3742; found, 923.3705.

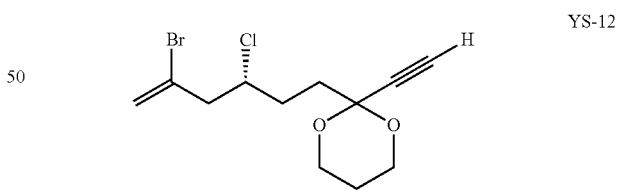

Reduced Bromoacetylene YS-12:

[α]$^{20}_D$ +6.9 (c 1.0, CHCl$_3$); $^1$H NMR (500 MHz, C$_6$D$_6$) δ: 5.24 (d, J=2.0 Hz, 1H), 5.21 (d, J=1.5 Hz, 1H), 4.24-4.18 (m, 1H), 4.12 (t, J=13.0 Hz, 2H), 3.58 (dd, J=12.0, 6.0 Hz, 2H), 2.44 (dd, J=14.0, 8.0 Hz, 1H), 2.39 (dd, J=13.5, 5.5 Hz, 1H), 2.36-2.29 (m, 1H), 2.18-2.10 (m, 2H), 2.09 (s, 1H), 2.05-1.97 (m, 1H), 1.74-1.65 (m, 1H), 0.64 (d, J=13.0 Hz, 1H); $^{13}$C NMR (125 MHz, C6D$_6$) δ: 129.6, 119.6, 95.7, 79.8, 74.8, 62.0, 59.5, 49.6, 38.7, 31.5, 25.1; HRMS (ESI) m/z: [M+Na]$^+$ calcd for C$_{12}$H$_{16}$BrClNaO$_2$, 218.9914; found, 328.9910.

YS-13

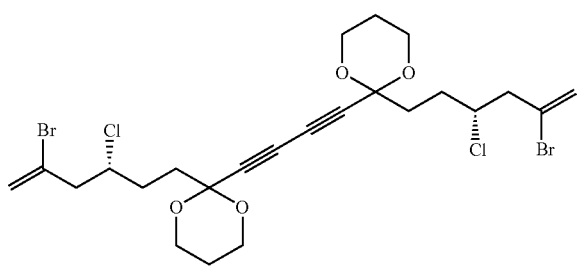

Homo-Dimer YS-13:

$[\alpha]^{20}{}_D$ +6.8 (c 1.0, CHCl$_3$); $^1$H NMR (500 MHz, C$_6$D$_6$) δ: 5.26 (d, J=2.0 Hz, 1H), 5.22 (d, J=1.0 Hz, 1H), 4.21-4.15 (m, 1H), 4.12 (dt, J=12.0, 3.0 Hz, 2H), 3.58-3.54 (m, 2H), 2.45-2.33 (m, 3H), 2.18-2.10 (m, 2H), 2.04-1.95 (m, 1H), 1.71-1.60 (m, 1H), 0.60 (d, J=12.5 Hz, 1H); $^{13}$C NMR (125 MHz, C$_6$D$_6$) δ: 129.8, 119.9, 96.6, 77.6, 70.6, 62.8, 59.7, 49.9, 39.1, 31.7, 25.1; HRMS (ESI) m/z: [M+H]$^+$ calcd for C$_{24}$H$_{31}$Br$_2$Cl$_2$O$_4$, 610.9906; found, 610.9904.

To a solution of TES-protected alcohol YS-11 (25.5 mg, 27.6 μmol) in CH$_2$Cl$_2$ (89 μL) was added co-solvent mixture TFA/H$_2$O/CH$_2$Cl$_2$ (4:1:10) (42.3 μL) at 0° C. The reaction mixture was stirred vigorously at room temperature until TLC showed a complete disappearance of the starting material (around 0.5 h). The reaction was diluted with EtOAc, quenched carefully with sat. NaHCO$_3$aq., and the organic phases were separated and the aqueous phase was extracted with EtOAc three times, washed with brine. The combined organic phases were dried over Na$_2$SO$_4$ and concentrated. The crude material was flushed through a short silica gel column to afford acetylenic ketone Y-27a (16.1 mg, 78%) as colorless oil.

Coupling Product Y-27a:

$[\alpha]^{20}{}_D$ −52.3 (c 1.0, CHCl$_3$); $^1$H NMR (600 MHz, C$_6$D$_6$) δ: 6.15 (d, J=9.4 Hz, 1H), 5.21 (s, 1H), 5.16 (s, 1H), 4.11 (s, 1H), 4.08-4.06 (m, 2H), 3.88-3.84 (m, 2H), 3.73-3.67 (m, 2H), 3.33 (s, 3H), 2.79 (dd, J=9.5, 2.2 Hz, 1H), 2.48 (ddt, J=17.8, 9.0, 4.3 Hz, 1H), 2.38-2.28 (m, 2H), 2.23 (dd, J=14.9, 8.8 Hz, 1H), 2.16 (dd, J=14.9, 5.0 Hz, 1H), 0.02 (m, 2H), 1.72 (m, 1H), 1.56 (dtd, J=14.4, 9.5, 5.0 Hz, 1H), 1.39-1.19 (m, 3H), 1.03 (s, 9H), 0.80 (s, 9H), 0.16 (m, 6H), −0.11 (s, 3H), −0.12 (s, 3H); $^{13}$C NMR (125 MHz, C$_6$D$_6$) δ: 182.4, 168.0, 126.8, 117.2, 88.8, 81.8, 76.8, 72.9, 71.9, 70.45, 70.3, 62.6, 61.4, 56.2, 48.4, 47.0, 39.6, 37.9, 28.6, 27.7, 27.4, 26.8, 23.5, 23.3, 16.0, 15.6, −6.5, −7.4. IR (ATR) ν$_{max}$: 3018, 1733, 1675, 1214, 1073, 751; HRMS (ESI) m/z: [M+Na]$^+$ calcd for C$_{33}$H$_{56}$BrClO$_8$Si$_2$Na, 773.2283; found, 773.2285.

On treatment with TBS protection (TBS-Cl, imidazole, CH$_2$Cl$_2$), coupling product Y-27a furnished the acetylenic ketone previously synthesized with use of two (Ni)/Cr-mediated coupling reactions (Ueda, A.; Yamamoto, A.; Kato, D.; Kishi, Y. J. Am. Chem. Soc. 2014, 136, 5171).

Synthesis of Y-27b Via (Ni)/Cr-Mediated Coupling of Y-11 and Y-24b

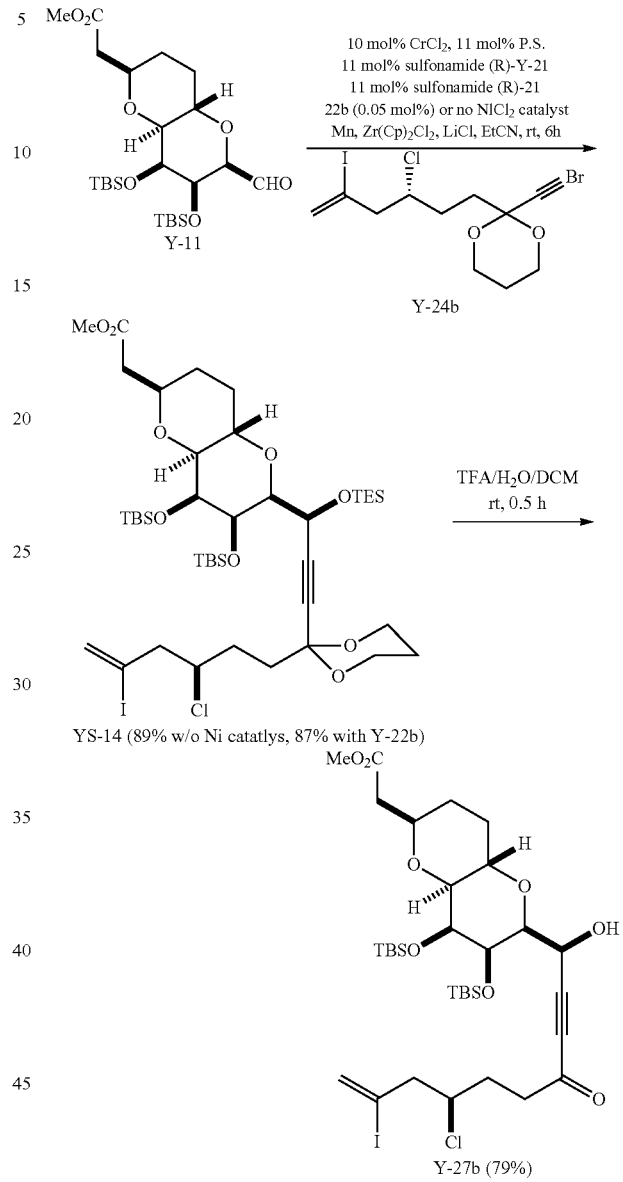

To a mixture of CrCl$_2$ (16.4 mg, 0.13 mmol), (R)-Y-21 (Choi, H.; Demeke, D.; Kang, F.-A.; Kishi, Y.; Nakajima, K.; Nowak, P.; Wan, Z.-K.; Xie, C. Pure Appl. Chem. 2003, 75, 1) (41.6 mg, 0.15 mmol), and proton sponge (32.1 mg, 0.15 mmol) in a glove box was added EtCN (1.5 mL) and stirred for 1 h at room temperature. In a separate flask, bromo-acetylene Y-27b (441 mg, 1.0 mmol), aldehyde Y-11 (305 mg, 0.61 mmol), LiCl (103 mg, 2.5 mmol), Mn (133 mg, 2.5 mmol) were mixed together and the Cr-complex solution was transferred to the flask. Then TES-Cl (254 μL, 1.5 mmol) was added into the reaction mixture. After stirring for 6 h at room temperature, the reaction was removed from the glove box and diluted with anhydrous Et$_2$O. Sat. aq. NaHCO$_3$, followed by potassium serinate solution, was added carefully to quench the reaction and the corresponding mixture was stirred vigorously for 30 min. The resultant mixture was filtered through short pad of silica gel and concentrated. The crude material was purified by flash chromatography on silica gel to give TES-protected alcohol YS-14 (529 mg, 89%).

The fractions eluded with 1:10 EtOAc/hexanes were combined and purified with silica gel column chromatography (1:10 EtOAc/hexanes) to give reduced bromoacetylene YS-15 (~100 mg, ~28%) and a fraction containing homo-dimer YS-16. This faction was further purified with preparative TLC (1:10 EtOAc/hexanes), to give homo-dimer YS-16 (2.6 mg, 0.4%).

Coupling Product YS-14:

$[\alpha]^{20}_D$ −29.4 (c 0.98, CHCl$_3$); $^1$H NMR (500 MHz, C$_6$D$_6$) δ: 5.78 (m, 1H), 5.74 (d, J=4.3 Hz, 1H), 5.59 (m, 1H), 4.40-4.25 (m, 3H), 4.16 (m, 1H), 4.12 (dd, J=6.4, 4.4 Hz, 1H), 4.07 (td, J=10.2, 4.2 Hz, 1H), 3.91-3.86 (m, 1H), 3.80 (ddd, J=10.9, 8.0, 5.3 Hz, 1H), 3.74-3.69 (m, 2H), 3.39 (s, 3H), 2.89 (dd, J=9.5, 2.0 Hz, 1H), 2.57 (dd, J=14.8, 4.9 Hz, 1H), 2.52-2.44 (m, 3H), 2.35-2.11 (m, 5H), 1.82 (dddt, J=17.3, 12.8, 8.4, 4.5 Hz, 1H), 1.50-1.46 (m, 1H), 1.14-1.35 (m, 1H), 1.30-1.19 (m, 2H), 1.19 (t, J=7.9 Hz, 9H), 1.12 (s, 9H), 0.91 (s, 9H), 0.91 (m, 6H), 0.27 (s, 3H), 0.25 (s, 3H), 0.07 (s, 3H), 0.06 (s, 3H); $^{13}$C NMR (125 MHz, C6D$_6$) δ: 170.9, 128.7, 106.8, 96.4, 86.3, 83.6, 81.3, 80.5, 79.3, 74.5, 73.1, 70.6, 64.9, 63.8, 62.6, 62.4, 61.3, 53.5, 51.1, 40.9, 39.4, 31.9, 30.9, 29.3, 26.6, 26.5, 25.6, 7.5, 5.9, −4.0, −4.1, −4.3, −4.7. HRMS (ESI) m/z: [M+Na]$^+$ calcd for C$_{42}$H$_{76}$ClIO$_9$Si$_3$Na, 993.3428; found, 993.3429.

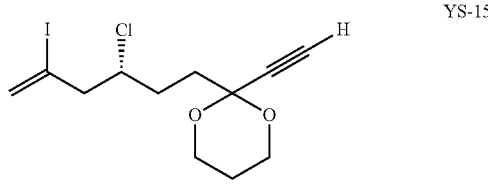 [SMILES: C#CC1(CC[C@@H](Cl)CC(=C)I)OCCCO1]

YS-15

Reduced Bromoacetylene YS-15:

$[\alpha]^{20}_D$ +6.0 (c 1.0, CHCl$_3$); $^1$H NMR (500 MHz, C$_6$D$_6$) δ: 5.67 (d, J=1.0 Hz, 1H), 5.53 (d, J=1.5 Hz, 1H), 4.21-4.15 (m, 1H), 4.02 (dt, J=13.0, 2.5 Hz, 2H), 3.58 (dd, J=12.0, 6.0 Hz, 2H), 2.38 (dd, J=6.5, 1.0 Hz, 2H), 2.34-2.27 (m, 1H), 2.17-2.11 (m, 2H), 2.10 (s, 1H), 2.05-1.97 (m, 1H), 1.76-1.64 (m, 1H), 0.64 (d, J=13.0 Hz, 1H); $^{13}$C NMR (125 MHz, C6D$_6$) δ: 128.4, 106.3, 95.6, 79.8, 74.8, 62.0, 60.7, 53.0, 38.6, 31.3, 25.0; HRMS (ESI) m/z: [M+Na]$^+$ calcd for C$_{12}$H$_{16}$ClINaO$_2$, 376.9781; found, 376.9780.

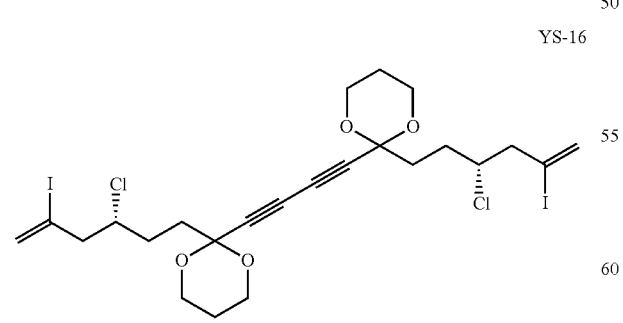

YS-16

Homo-Coupling Product YS-16:

$[\alpha]^{20}_D$ +5.9 (c 1.0, CHCl$_3$); $^1$H NMR (500 MHz, C$_6$D$_6$) S: 5.67 (d, J=1.5 Hz, 1H), 5.54 (d, J=1.5 Hz, 1H), 4.17-4.11 (m, 1H), 3.99 (dt, J=12.0, 3.0 Hz, 2H), 3.58-3.54 (m, 2H), 2.37-2.30 (m, 3H), 2.17-2.08 (m, 2H), 2.03-1.94 (m, 1H), 1.71-1.58 (m, 1H), 0.59 (d, J=13.0 Hz, 1H); $^{13}$C NMR (125 MHz, C$_6$D$_6$) δ: 128.8, 106.5, 96.6, 77.6, 70.6, 62.8, 60.8, 53.2, 39.1, 31.4, 25.1 HRMS (ESI) m/z: [M+H]$^+$ calcd for C$_{24}$H$_{31}$Cl$_2$I$_2$O$_4$, 706.9683; found, 706.9658.

To a solution of TES-protected alcohol YS-14 (16.2 g, 16.7 mmol) in CH$_2$Cl$_2$ (167 mL) was added co-solvent mixture TFA/H$_2$O/CH$_2$Cl$_2$ (4:1:10) (25.6 mL) at 0° C. The reaction mixture was stirred vigorously at room temperature until TLC showed a complete disappearance of the starting material (around 0.5 h). The reaction was diluted with EtOAc, quenched carefully with sat. NaHCO$_3$aq., and the organic phases were separated and the aqueous phase was extracted with EtOAc three times, washed with brine. The combined organic phases were dried over Na$_2$SO$_4$ and concentrated. The crude material was flushed through a short silica gel column to afford the ynone Y-27b (10.9 g, 79%) as colorless oil.

Coupling Product Y-27b:

$^1$H NMR (500 MHz, C$_6$D$_6$) δ: 6.14 (d, J=9.3 Hz, 1H), 5.63 (s, 1H), 5.50 (s, 1H), 4.11 (s, 1H), 4.07 (s, 1H), 4.07 (t, J=7.4 Hz, 2H), 3.87-3.81 (m, 2H), 3.70 (td, J=10.0, 4.0 Hz, 2H), 3.33 (s, 3H), 2.79 (dd, J=9.5, 2.1 Hz, 1H), 2.47 (ddd, J=17.9, 9.2, 5.2 Hz, 1H), 2.39-2.27 (m, 2H), 2.18 (m, 2H), 2.06-1.99 (m, 2H), 1.75-1.69 (m, 1H), 1.61-1.54 (m, 1H), 1.35-1.20 (m, 2H), 1.03 (s, 9H), 0.80 (s, 9H), 0.16 (m, 6H), −0.10 (s, 3H), −0.11 (s, 3H); $^{13}$C NMR (125 MHz, C$_6$D$_6$) δ: 170.5, 128.5, 128.0, 105.8, 91.2, 84.2, 79.2, 75.4, 74.3, 72.8, 72.7, 65.0, 63.8, 59.8, 52.8, 50.8, 42.0, 40.3, 30.8, 30.1, 29.3, 25.9, 25.7, 18.4, 18.0, −4.1, −5.0, −5.7. HRMS (ESI) m/z: [M+Na]$^+$ calcd for C$_{33}$H$_{56}$ClIO$_8$Si$_2$Na, 821.2145; found, 821.2147.

Synthesis Outlined in FIG. 25

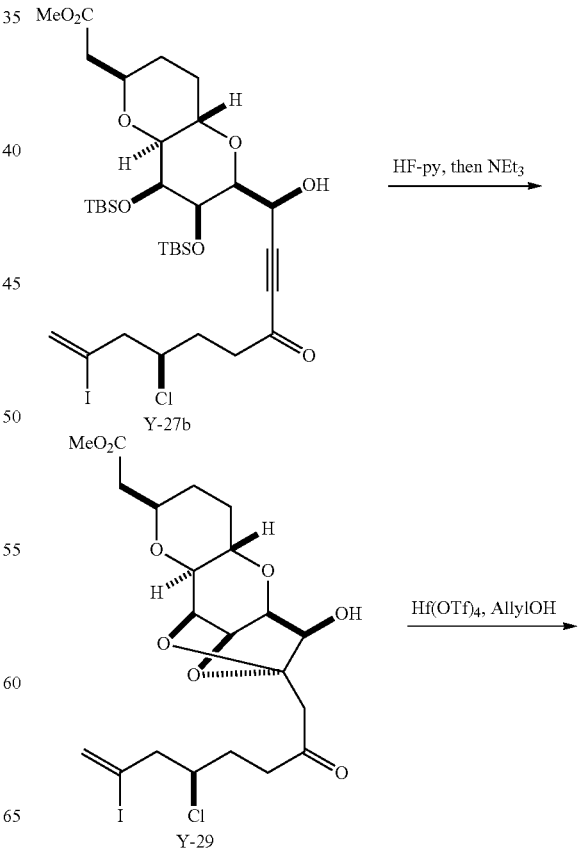

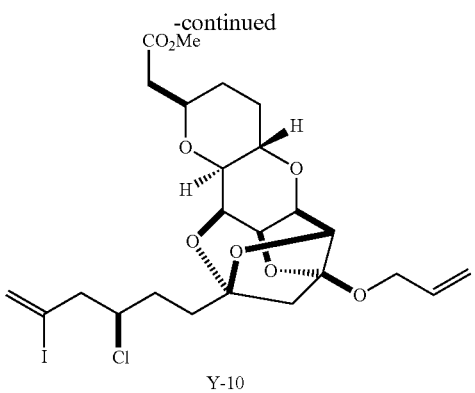

Y-10

To a 0° C. solution of acetylenic ketone Y-27b (74.5 mg, 93 μmol) in MeCN (1.9 mL, 0.05 M) and imidazole (443 mg, 6.5 mmol) in a plastic vial was added HF. pyridine complex (70% HF content, 0.17 mL, 6.5 mmol) and stirred at room temperature for 70 h. Then triethylamine (856 mg, 8.5 mmol) was added into the reaction mixture at 0° C. After stirring at room temperature for 1 h, the reaction was carefully neutralized with saturated NaHCO$_3$ solution and NaHCO$_3$ solid. The mixture was extracted with EtOAc four times, the combined organic phase was washed by 1 N HCl solution and brine before drying over anhydrous Na$_2$SO$_4$, and then concentrated under reduced pressure. The crude material was purified by flash column chromatography on silica gel to afford double oxy-Michael product Y-29 (46.3 g, 81%).

Double Oxy-Michael Product Y-29:

$[\alpha]^{20}{}_D$ −15.9 (c 1.20, CHCl$_3$); $^1$H NMR (500 MHz, C$_6$D$_6$) δ: 5.71 (d, J=1.5 Hz, 1H), 5.57 (d, J=1.5 Hz, 1H), 4.62-4.57 (dt, J=10.5, 4.5 Hz, 1H), 4.19 (s, 1H), 3.94 (m, 1H), 3.90 (m, 1H), 3.84 (m, 1H), 3.80-3.77 (m, 2H), 3.48 (s, 1H), 3.31 (s, 3H), 2.82 (d, J=15.0 Hz, 1H), 2.74 (d, J=9.6 Hz, 1H), 2.52 (d, J=15.0 Hz, 1H), 2.45 (m, 1H), 2.29 (m, 1H), 2.25 (m, 2H), 2.15-2.10 (m, 1H), 2.04-1.99 (m, 2H), 1.60-1.53 (m, 2H); 1.29-1.26 (m, 2H), 1.11-1.08 (m, 1H); $^{13}$C NMR (125 MHz, C$_6$D$_6$) δ: 206.7, 171.5, 129.3, 108.0, 106.7, 78.5, 78.3, 77.8, 76.1, 75.5, 68.7, 67.5, 61.0, 53.8, 51.5, 45.6, 41.6, 40.9, 31.4, 31.0, 29.9. HRMS (ESI) m/z: [M+Na]$^+$ calcd for C$_{21}$H$_{28}$ClIO$_8$Na, 593.0410; found, 593.0407.

To a solution of double oxy-Michael product Y-29 (473 mg, 0.83 mmol) in a mixture of anhydrous THF (69 mL, 0.012M) and allyl alcohol (6.9 mL) was added Hf(OTf)$_4$ (161 mg, 0.21 mmol). The reaction was stirred for 3 h at room temperature in a glovebox. Then the reaction was quenched by triethylamine, diluted with EtOAc, and quenched with saturated NaHCO$_3$ solution. The aqueous layer was extracted with EtOAc, and the combined organic phase was washed with brine, dried over Na$_2$SO$_4$ then concentrated under vacuum. Purification of the residual material by flash chromatograph on silica gel afforded halichondrin-C C1-C19 building block Y-10 (374 mg, 74%) as white foam.

Halichondrin-Y-C C1-C19 Building Block Y-10:

$[\alpha]^{20}{}_D$ −37.0 (c 1.0, CHCl$_3$); $^1$H NMR (500 MHz, C$_6$D$_6$) δ: 5.71 (d, J=1.5 Hz, 1H), 5.57 (d, J=1.5 Hz, 1H), 4.62-4.57 (dt, J=10.5, 4.5 Hz, 1H), 4.19 (s, 1H), 3.94 (m, 1H), 3.90 (m, 1H), 3.84 (m, 1H), 3.80-3.77 (m, 2H), 3.48 (s, 1H), 3.31 (s, 3H), 2.82 (d, J=15.0 Hz, 1H), 2.74 (d, J=9.6 Hz, 1H), 2.52 (d, J=15.0 Hz, 1H), 2.45 (m, 1H), 2.29 (m, 1H), 2.25 (m, 2H), 2.15-2.10 (m, 1H), 2.04-1.99 (m, 2H), 1.60-1.53 (m, 2H); 1.29-1.26 (m, 2H), 1.11-1.08 (m, 1H); $^{13}$C NMR (125 MHz, C$_6$D$_6$) δ: 206.7, 171.5, 129.3, 108.0, 106.7, 78.5, 78.3, 77.8, 76.1, 75.5, 68.7, 67.5, 61.0, 53.8, 51.5, 45.6, 41.6, 40.9, 31.4, 31.0, 29.9. HRMS (ESI) m/z: [M+H]$^+$ calcd for C$_{24}$H$_{33}$ClIO$_8$, 611.0942; found, 611.0959.

Synthesis Outlined in FIG. 26

Synthesis of Halichondrin-B C1-C19 Building Block Y-9 from E-Isomer (E)-Y-31

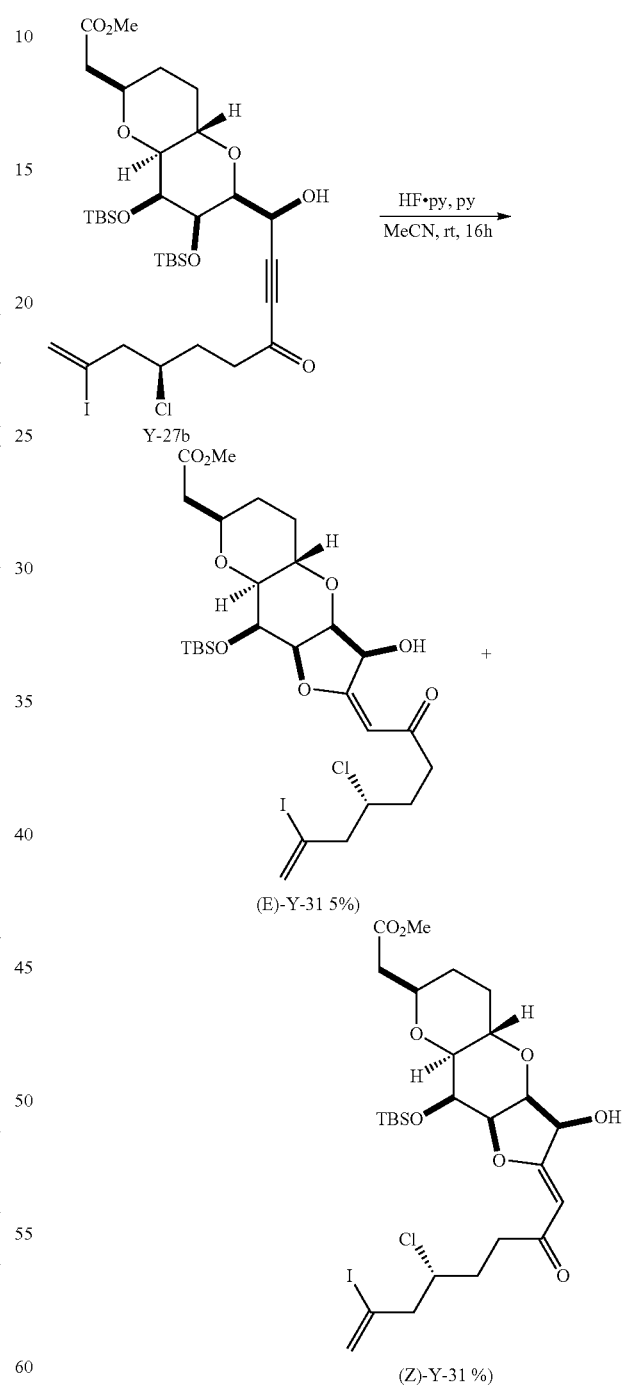

To a 0° C. solution of acetylenic ketone Y-27b (331 mg, 0.36 mmol) in pyridine (3.0 mL, 36.0 mmol) and MeCN (8.1 mL) in a plastic vial was added HF.pyridine complex (70% HF content, 0.95 mL, 36.2 mmol) and stirred at room temperature. Once the reaction was completed, the reaction was cooled to 0° C. and carefully neutralized with saturated NaHCO$_3$ solution and NaHCO$_3$ solid. The mixture was extracted with EtOAc four times, and the combined EtOAc extracts were dried over anhydrous Na$_2$SO4 and concentrated under reduced pressure. The crude material was purified by flash column chromatography on silica gel to afford (E)-Y-31 (161 mg, 65%) and (Z)-Y-31 (18.4 mg, 7%).

Enone (E)-Y-31:

$[\alpha]^{20}{}_D$ −125.3 (c 0.12, CHCl$_3$); $^1$H NMR (600 MHz, C$_6$D$_6$) δ: 5.75 (1H, d, J=0.8 Hz, H-13), 5.73 (ddd, J=1.5, 1.2, 0.9 Hz, 1H), 5.57 (d, J=1.5 Hz, 1H), 5.10 (ddd, J=7.9, 7.3, 0.8 Hz, 1H), 4.86 (d, J=7.3 Hz, 1H), 4.30 (ddd, J=10.5, 9.8, 4.8 Hz, 1H), 4.08 (dddd, J=9.8, 7.6, 5.9, 3.2 Hz, 1H), 3.91 (dd, J=4.7, 1.6 Hz, 1H), 3.85 (1H, dd, J=8.5, 7.9 Hz, 1H), 3.78 (dd, J=8.5, 4.7 Hz, 1H), 3.68 (dddd, J=10.9, 8.8, 4.3, 1.9 Hz, 1H), 3.39 (s, 3H), 2.54 (dd, J=9.8, 1.6 Hz, 1H), 2.53 (ddd, J=17.1, 8.5, 5.3 Hz, 1H), 2.42-2.34 (m, 3H), 2.33 (dd, J=15.5, 8.8 Hz, 1H), 2.04-1.96 (m, 3H), 1.73 (dddd, J=14.6, 9.8, 8.5, 5.3 Hz, 1H), 1.27-1.15 (m, 2H), 1.02 (s, 9H), 0.98-0.91 (m, 1H), 0.19 (s, 3H), 0.16 (s, 3H); $^{13}$C NMR (150 MHz, C$_6$D$_6$) δ: 198.0, 176.5, 170.9, 128.8, 106.3, 102.3, 77.4, 77.1, 74.7, 71.1, 69.7, 67.7, 66.0, 60.9, 53.6, 51.1, 40.5, 40.2, 31.9, 30.1, 29.9, 26.0 (3C), 18.7, −4.4, −4.6. HRMS (ESI) m/z: [M+H]$^+$ calcd for C$_{27}$H$_{43}$ClIO$_8$Si, 685.1455; found, 685.1455.

temperature for 30 min. The mixture was then added to a solution of (E)-Y-31 (23.1 mg, 33.7 μmol) in CH$_3$CN (20 μL). The resulting solution was stirred at −30° C. and slowly warmed up to 0° C. The reaction was quenched by addition of an aqueous solution of sodium, potassium tartrate followed by solid Na$_2$CO$_3$. The aqueous phase was extracted with CH$_2$Cl$_2$, and the combined organic phase was dried over Na$_2$SO$_4$ and concentrated under vacuum. Purification of residual material by flash column chromatograph on silica gel afforded a ketone Y-32 (colorless oil, 19.6 mg, 85% yield) as a ~5:1 mixture of Y-12α and Y-12β diastereomers.

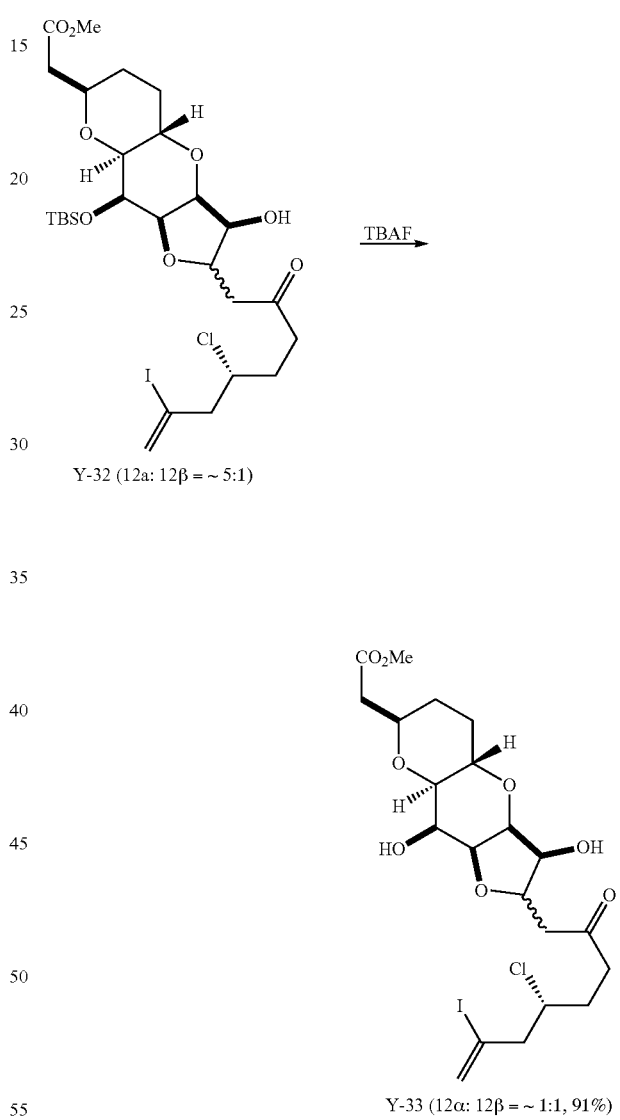

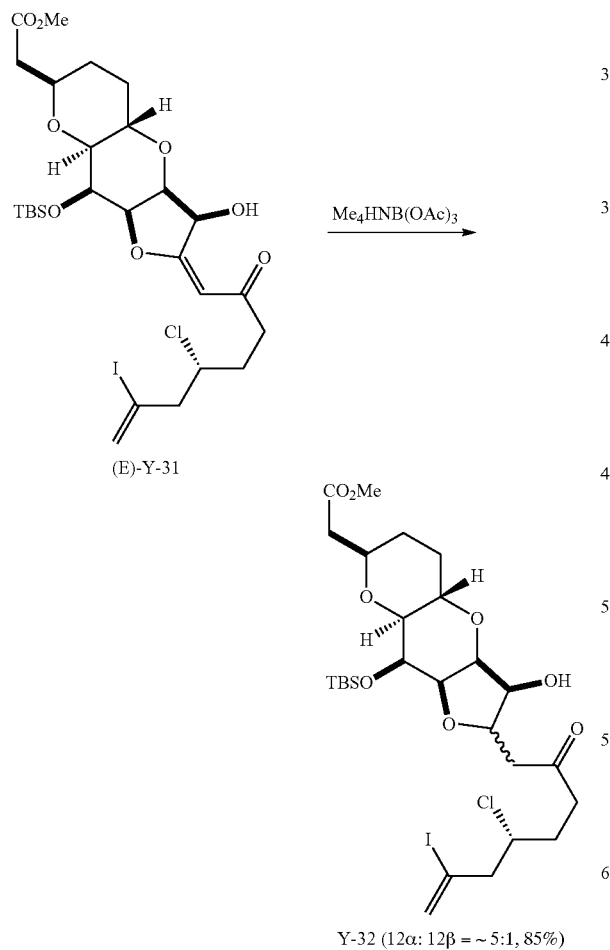

To a slurry of tetramethylammonium triacetoxyborohydride (71 mg, 0.27 mmol) in CH$_3$CN (90 μL) at −30° C. was added acetic acid (90 μL) and the mixture was stirred at this To ketone Y-32 (17.5 mg, 25.4 μmol) was added TBAF solution in THF (2 equiv, buffered with 0.25 equiv. of imidazole hydrochloride) at room temperature. After stirring for 0.5 h at the same temperature, the reaction solution was diluted with DCM followed by EtOAc. The mixture was filtered through silica gel pad (5% MeOH in EtOAc) to remove TBAF residue. After removal of the solvent, the crude diol Y-33 (13.2 mg, 91% yield, ~1:1 mixture of Y-12α and Y-12β (diastereomers) was directly used for the next step.

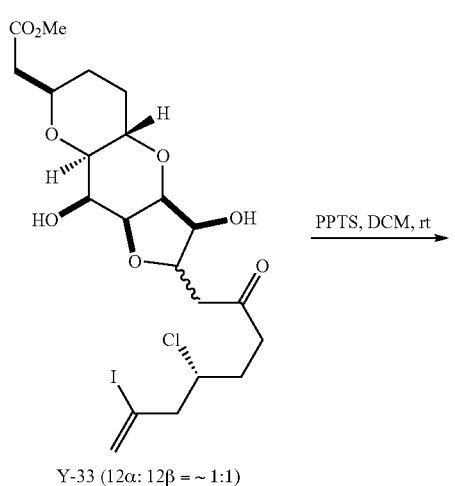

Y-33 (12α:12β = ~1:1)

PPTS, DCM, rt

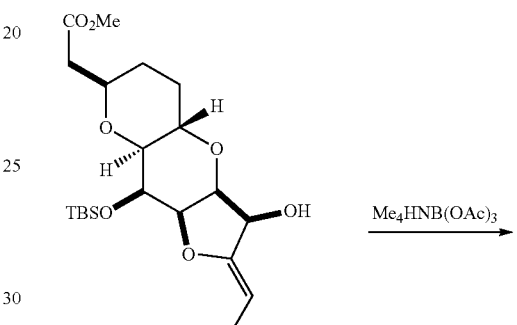

Y-9 (46%)

+

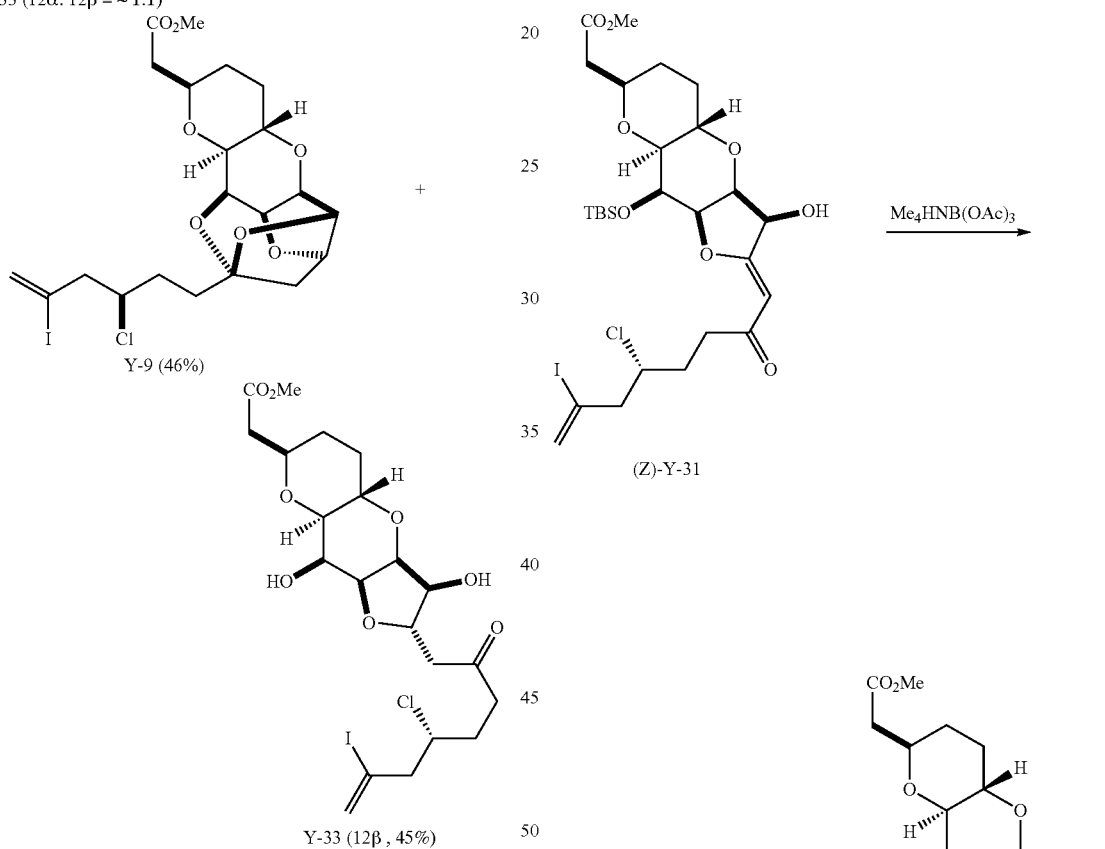

Y-33 (12β, 45%)

The crude Y-33 was dissolved in CH$_2$Cl$_2$ (0.5 mL) and treated with PPTS (2 equiv) at room temperature. After stirring for 2 h at room temperature, the solvent was removed, to give the residue that was purified by PTLC, to furnish halichondrin-B C1-C19 building block Y-9 (6.1 mg, 46%) and undesired Y-12α Y-33 (6.0 mg, 45%).

Halichondri-B C1-C19 Building Block 9:

yellow oil, $[\alpha]_D^{20}$=−25.8 (c 1.0, CHCl$_3$); $^1$H NMR (500 MHz, C$_6$D$_6$) δ: 5.83 (s, 1H), 5.67 (s, 1H), 4.41 (dt, J=10.0 Hz, 4.0 Hz, 1H), 4.02 (dt, J=10.0 Hz, 5.0 Hz, 1H), 4.36 (s, 1H), 4.14 (sep, J=5.0 Hz, 2H), 4.08 (t, J=5.0 Hz, 1H), 3.89 (dd, J=6.5 Hz, 5.0 Hz, 1H), 3.76-3.69 (m, 1H), 3.66 (dd, J=6.5 Hz, 4.0 Hz, 1H), 3.30 (s, 3H), 2.58 (dt, J=15.0 Hz, 5.0 Hz, 2H), 2.51 (dd, J=15.5 Hz, 3.0 Hz, 1H), 2.17 (dd, J=16.0 Hz, 5.0 Hz, 1H), 2.22-2.12 (m, 1H), 2.10-1.75 (m, 5H), 1.44-1.37 (m, 1H), 1.35 (dd, J=13.0 Hz, 5.0 Hz, 1H), 1.33-1.16 (m, 2H); $^{13}$C NMR (125 MHz, C$_6$D$_6$) S: 170.9, 128.8, 109.7, 106.8, 82.4, 80.8, 78.5, 76.9, 74.9, 74.7, 74.2, 68.5, 61.8, 53.4, 51.1, 47.4, 40.7, 36.3, 32.4, 30.8, 30.7; HRMS (ESI) m/z: [M+H]j calcd for C$_{21}$H$_{29}$ClIO$_7$, 555.0646; found, 555.0655.

On comparison of spectroscopic and chromatographic properties, halichondrin-B C1-C19 building block Y-9 and diol Y-33 thus obtained were found to be identical with the authentic samples synthesized via a different route (Yan, W.; Li, Z.; Kishi, Y. *J. Am. Chem. Soc.* 2015, 137, 0000). Also, that previous work has demonstrated that diol Y-33 with the undesired C12α-stereochemistry can be transformed to Y-9 via ion-exchange resin based device or base-induced equilibration, followed by PPTS treatment.

Reduction of (Z)-Y-31 to Y-32

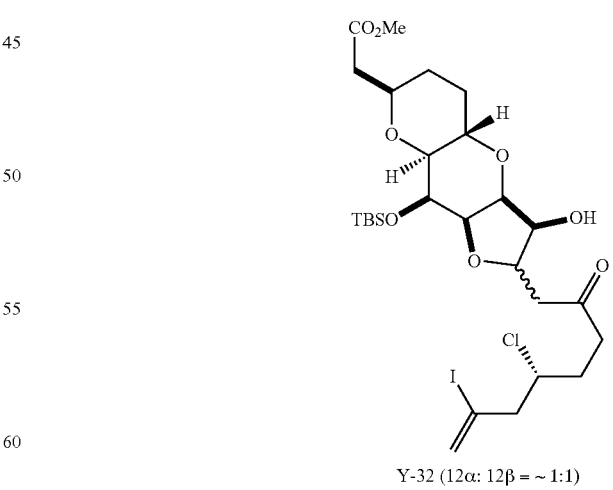

(Z)-Y-31

Me$_4$HNB(OAc)$_3$

Y-32 (12α: 12β = ~1:1)

Following the procedure given above for reduction of (E)-Y-31, (Z)-Y-31 (2.7 mg) was transformed into ketone product that was identical to Y-32, based on comparison of spectroscopic and chromatographic properties.

Synthesis of Halichondrin-B C1-C19 Building Block Y-9 from a (E)- and (Z)-Mixture of Y-31

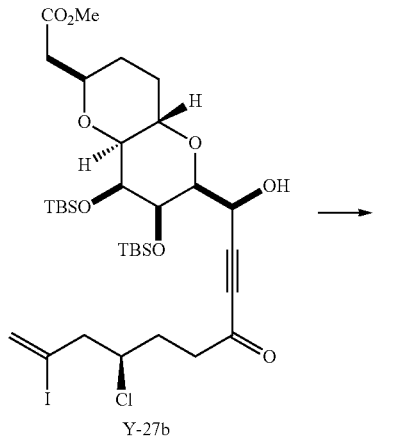

Y-27b

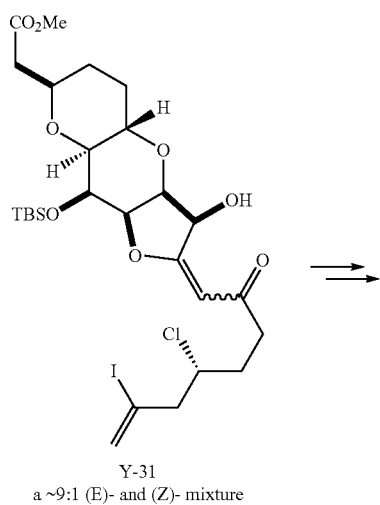

Y-31
a ~9:1 (E)- and (Z)- mixture

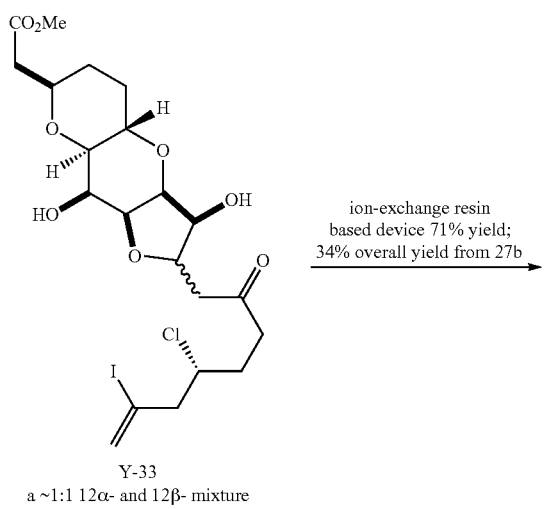

Y-33
a ~1:1 12α- and 12β- mixture ion-exchange resin based device 71% yield;
34% overall yield from 27b

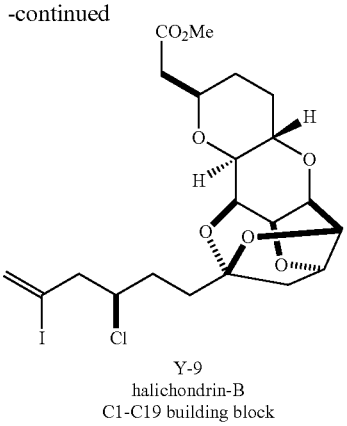

Y-9
halichondrin-B
C1-C19 building block

Following the procedures given above, Y-27b (51 mg) was transformed into halichondrin-B C1-C19 building block Y-9 (12.3 mg), without isolation/separation of intermediates.

In this experiment, the crude Y-33 (13.2 mg, a 1:1 Y-12α- and Y-12β-diastereomeric mixture) was dissolved in 2 mL EtOH in a black-cap vial and then connected to ion-exchange resin based device ((a) Namba, K.; Jun, H. S.; Kishi, Y. *J. Am. Chem. Soc.* 2004, 126, 7770. (b) Kaburagi, Y.; Kishi, Y. *Org. Lett.* 2007, 9, 723). The reaction completed in 10 h, and both basic and acidic resins were washed with ethanol (3 mL). The combined EtOH solutions were concentrated under reduced pressure. The residue was passed through a short silica gel plug (elution with hexanes/EtOAc=10:1 to 1:1) to give product Y-9 (12.3 mg, 34% overall yield from Y-27b).

Synthetic Plan

All of C1-C19 building blocks Y-8-Y-10 could be synthesized from acetylenic ketone Y-15a,b, by adjusting its oxidation state (FIG. 20). C1-C19 building block Y-8 of halichondrin A was synthesized with this strategy (Halichondrin As: Ueda, A.; Yamamoto, A.; Kato, D.; Kishi, Y. *J. Am. Chem. Soc.* 2014, 136, 5171). In the halichondrin A synthesis, acetylenic ketone Y-15a was synthesized via two (Ni)/Cr-mediated couplings. In light of the successful selective activation/coupling of poly-halogenated nucleophile Y-17 in a Ni/Cr-mediated coupling, it was recognized that Y-15a,b could be synthesized in one step, cf., Y-11+Y-16a,b→Y-15a, b. In the halichondrin B series, a selective activation/coupling of the trans-β-bromoenone was realized with use of a trace amount of a polyether-type Ni-catalyst (Uemura, D.; Takahashi, K.; Yamamoto, T.; Katayama, C.; Tanaka, J.; Okumura, Y.; Hirata, Y. *J. Am. Chem. Soc.* 1985, 107, 4796; Hirata, Y.; Uemura, D. *Pure Appl. Chem.* 1986, 58, 701). Activation of halo-acetylenes is achieved with a trace amount of Ni-catalyst or even no added Ni-catalyst. A selective activation of the halo-acetylene over the vinyl iodide or bromide and saturated chloride is established in Y-16a,b (Pettit, G. R.; Herald, C. L.; Boyd, M. R.; Leet, J. E.; Dufresne, C.; Doubek, D. L.; Schmidt, J. M.; Cerny, R. L.; Hooper, J. N. A.; Riitzler, K. C. *J. Med. Chem.* 1991, 34, 3339; Pettit, G. R.; Tan, R.; Gao, F.; Williams, M. D.; Doubek, D. L.; Boyd, M. R.; Schmidt, J. M.; Chapuis, J.-C.; Hamel, E.; Bai, R.; Hooper, J. N. A.; Tackett, L. P. *J. Org. Chem.* 1993, 58, 2538; Litaudon, M.; Hart, J. B.; Blunt, J. W.; Lake, R. J.; Munro, M. H. G. *Tetrahedron Lett.* 1994, 35, 9435; Litaudon, M.; Hickford, S. J. H.; Lill, R. E.; Lake, R. J.; Blunt, J. W.; Munro, M. H. G. *J. Org. Chem.* 1997, 62, 1868; Hickford, S. J. H.; Blunt, J. W.; Munro, M. H. G. *Bioorg. Med. Chem.* 2009, 17, 2199).

Model Study on Coupling Efficiency

Six halo-acetylenes Y-18a~c and Y-19a~c and aldehyde Y-20 were chosen (FIG. 21). The coupling efficiency of halo-acetylenic ketones Y-18a~c over halo-acetylenic ketals Y-19a-c, under the coupling conditions: 10 mol % Cr-catalyst, prepared from (S)-sulfonamide Y-21, Ni-catalyst Y-22 (0.05 mol %) or no added Ni-catalyst, Zr(cp)$_2$Cl$_2$ (1.5 eq), Mn (2 eq), and LiCl (2 eq) in MeCN ([C] 0.4M) at room temperature were compared (Hart, J. B.; Lill, R. E.; Hickford, S. J. H.; Blunt, J. W.; Munro, M. H. G. Drugs from the Sea, Ed. Fusetani, N., Ed.; Karger, Basel, 2000, 134; Jackson, K. L.; Henderson, J. A.; Phillips, A. J. Chem. Rev. 2009, 109, 3044). This experiment demonstrated: (1) halo-acetylenic ketones Y-18a~c gave the desired product in only modest yields, with the order of coupling efficiency being Y-18b (49%)>Y-18c (20%)>Y-18a (11%); (2) halo-acetylenic ketals Y-19a,b gave the desired product in good yields, with the order of coupling efficiency being Y-19b (93%)>Y-19a (82%)>>Y-19c (8%); (3) no significant difference was detected between 0.05 mol % and no added Ni-catalyst. In addition, a brief study on solvents and concentration revealed: (1) the solvent choice being EtCN >MeCN >DME >THF, but not DMF and (2) the optimum concentration being a range of 0.4~0.8 M.

Coupling in the Halichodrin Series

The nucleophiles Y-24a,b were readily prepared from the previously reported, optically pure aldehydes Y-23a,b (FIG. 22) (Hart, J. B.; Lill, R. E.; Hickford, S. J. H.; Blunt, J. W.; Munro, M. H. G. Drugs from the Sea, Ed. Fusetani, N., Ed.; Karger, Basel, 2000, 134; Jackson, K. L.; Henderson, J. A.; Phillips, A. J. Chem. Rev. 2009, 109, 3044). With respect to the electrophile, several possible C8,C9-protecting groups were screened, thereby showing bis-TBS aldehyde Y-27 as the best option ((Pettit, G. R.; Herald, C. L.; Boyd, M. R.; Leet, J. E.; Dufresne, C.; Doubek, D. L.; Schmidt, J. M.; Cerny, R. L.; Hooper, J. N. A.; Riitzler, K. C. J. Med. Chem. 1991, 34, 3339; Pettit, G. R.; Tan, R.; Gao, F.; Williams, M. D.; Doubek, D. L.; Boyd, M. R.; Schmidt, J. M.; Chapuis, J.-C.; Hamel, E.; Bai, R.; Hooper, J. N. A.; Tackett, L. P. J. Org. Chem. 1993, 58, 2538; Litaudon, M.; Hart, J. B.; Blunt, J. W.; Lake, R. J.; Munro, M. H. G. Tetrahedron Lett. 1994, 35, 9435; Litaudon, M.; Hickford, S. J. H.; Lill, R. E.; Lake, R. J.; Blunt, J. W.; Munro, M. H. G. J. Org. Chem. 1997, 62, 1868; Hickford, S. J. H.; Blunt, J. W.; Munro, M. H. G. Bioorg. Med. Chem. 2009, 17, 2199).

Compounds Y-11 and Y-24a were subjected to the coupling reaction under the condition used in the model study, to furnish the desired product Y-27a in 55% yield, with a 10:1 stereoselectivity. The structure of Y-27a was established via correlation with the authentic sample obtained in the previous route.[5c] As anticipated, a product derived through activation of the vinyl iodide or saturated chloride present in Y-24a was not detected.

In order to improve the observed stereoselectivity, the toolbox approach was used and a representative set of sulfonamides was screened (FIG. 23) (Guo, H.; Dong, C.-G.; Kim, D.-S.; Urabe, D.; Wang, J.; Kim, J. T.; Xiang Liu, Sasaki, T.; Kishi, Y. J. Am. Chem. Soc. 2009, 131, 15387). This screening showed that: (1) as previously observed, the stereochemistry outcome was dictated by the substrate structure rather than the chirality present in the Cr-catalyst and (2) for this coupling, sulfonamides in the (R)-series gave a better stereoselectivity than the corresponding sulfonamides in the (S)-series. Among the tested ligands, sulfonamide (R)-21 and Ni-catalyst 22 were chosen for the following study.

It was found that the coupling rate with TES-Cl was slower than that with Zr(cp)$_2$Cl$_2$, yet the coupling yield with TES-Cl was noticeably better than that with Zr(cp)$_2$Cl$_2$, i.e., 85% with TES-Cl vs. 70% with Zr(cp)$_2$Cl$_2$. Although its mechanistic reason was not clear, the TES-Cl condition made it possible to achieve the proposed coupling with the synthetically useful efficiency.

As noted before, Cr-mediated coupling of a halo-acetylene with an aldehyde is known to proceed with only a trace amount of Ni-catalyst or even no added Ni-catalyst (Aicher, T. D.; Kishi, Y. Tetrahedron Lett. 1987, 28, 3463. (b) Usanov, D.; Yamamoto, H. J. Am. Chem. Soc. 2011, 133, 1286). The coupling of Y-11+Y-24a→Y-27a was studied "with" and "without" added Ni-catalyst, thereby showing the coupling efficiency to be comparable. There is no definite experimental evidence to conclude whether this coupling involves activation of bromoacetylene with Ni-catalyst, followed by Cr-mediated coupling, or activation/coupling with only a Cr-catalyst. The homo-dimer of bromoacetylene was isolated in ca. 0.3% yield (based on Y-24a) in the coupling without added Ni-catalyst. Therefore, the coupling is referred to as (Ni)/Cr-mediated reaction.

The coupling studies were carried out with both Y-24a,b simultaneously and obtained the virtually identical results in the both series, although a small reduction in yield was noticed in the Y-24b-series.

Synthesis of C1-C19 Building Blocks of Halichondrins A-C from the Common Synthetic Intermediate Y-27

Synthesis of C1-C19 Building Block of Halichondrin A

In the halichondrin A synthesis, the transformation of Y-27a into C1-C19 building block Y-8 was established (FIG. 25). The key reactions in this transformation included: (1) a selective TBS-deprotection to form E-enone Y-28 and (2) a highly stereoselective DMDO-oxidation to introduce the C13 hydroxyl group. The C1-C19 building block Y-8 bears the C19 vinyl bromide, because the corresponding vinyl iodide was not compatible with the DMDO oxidation (Halichondrin As: Ueda, A.; Yamamoto, A.; Kato, D.; Kishi, Y. J. Am. Chem. Soc. 2014, 136, 5171).

Synthesis of C1-C19 Building Block of Halichondrin C

In the halichondrin Y-C synthesis, a synthetic route to construct the polyclic ring system from an acetylenic ketone was reported (Halichondrin Cs: Yamamoto, A.; Ueda, A.; Brémond, P.; Tiseni, P. S.; Kishi, Y. J. Am. Chem. Soc. 2012, 134, 893). There was no unexpected difficulty in the transformation of Y-27b to Y-10 in 60% overall yield (FIG. 25). The key reactions in this transformation included: (1) double oxy-Michael addition of C8,C9-hydroxyl groups to the acetylenic ketone to form ketal Y-29 and (2) Hf(OTf)$_4$-induced conversion of the double oxy-Michael product Y-29 to polycycle Y-10 in ally alcohol. The structure Y-10 was fully supported by the spectroscopic data (HR-MS, $^1$H and $^{13}$C NMR).

Synthesis of C1-C19 Building Block of Halichondrin B

In order to synthesize C1-C19 building block Y-9 in the halichondrin B series from the common synthetic intermediate, an acetylene-to-olefin reduction was needed and tested first the reactivity of Y-27b and its C11-OTBS derivative against CuH, HN=NH, and CrCl$_2$ (FIG. 26), thereby indicating that the C11-OTBS substrate exhibited a very poor reactivity. Based on this observation, Y-27b was used for a search of a satisfactory reducing reagent/condition. Among reagents tested, (BDP)CuH, a Stryker CuH modified by Lipshutz, gave a mixture of E- and Z-enones (FIG. 26). As discussed in the preceding paper, Z-enone was found to form readily the furan (Yan, W.; Li, Z.; Kishi, Y. J. Am. Chem. Soc. 2015, 137, 0000). Thus, although it was a minor product, Z-enone was wasted. This reduction gave the desired E-enone Y-31 as the major product, but the isolated yield varied from 55% up to 80%.

Under this circumstance, (Me)$_4$NBH(OAc)$_3$ reduced the vinylogous ester E-Y-31 to give Y-32 in 80% yield as a 5:1 mixture of Y-12α:Y-12β diastereomers. (Me)$_4$NBH(OAc)$_3$ is so-called hydroxyl-directing setting. It was also found that the substrate with the C11-OH masked with a TBS was inert to the reduction.

It was observed that (Me)$_4$NBH(OAc)$_3$ reduction of the corresponding Z-enone Z-Y-31 gave Y-32 as a mixture of 1 Y-2α: Y-12β stereoisomers. Thus, for the preparative purpose, it was not necessary to separate E- and Z-enones Y-31.

On TBAF treatment, Y-32 furnished Y-33 as a ~1:1 mixture of Y-12α:Y-12β diastereomers. With ion-exchange resin based device, this mixture was transformed cleanly to C1-C19 building block Y-9 of halichondrin B without isolation/separation/equilibration of intermediates. On comparison of spectroscopic data ($^1$H and $^{13}$C NMR, MS, TLC), Y-9 thus obtained was found to be superimposable on the authentic sample (Yan, W.; Li, Z.; Kishi, Y. *J. Am. Chem. Soc.* 2015, 137, 0000).

A unified synthesis of the C1-C19 building blocks Y-8-Y-10 of halichondrins A-C was developed from the common synthetic intermediates Y-27a,b. Acetylenic ketones Y-27a,b were in turn synthesized via selective activation/coupling of poly-halogenated nucleophiles Y-24a,b with aldehyde Y-11 in a (Ni)/Cr-mediated coupling reaction. Compared with Ni/Cr-mediated couplings of vinyl iodides and aldehydes, this (Ni)/Cr-mediated coupling exhibited two unique features. First, the coupling was found to proceed with a trace amount or no added Ni-catalyst. Second, TES-Cl, a dissociating agent to regenerate the Cr-catalyst, was found to give a better yield than Zr(cp)$_2$Cl$_2$.

An adjustment of the oxidation state was required to transform acetylenic ketones Y-27a,b into C1-C19 building blocks Y-8 and Y-9 of halichondrins A and B, respectively. In the halichondrin B series, a hydroxyl-directed (Me)$_4$NBH (OAc)$_3$ reduction of E- and Z-vinylogous esters Y-31 was found cleanly to achieve the required transformation, whereas a DMDO oxidation of E-vinylogous ester Y-28 allowed to introduce the C13 hydroxyl group with a high stereoselectivity in the halichondrin A series. In the halichondrin C series, Hf(OTf)$_4$ was used to convert double oxy-Michael product Y-29 into C1-C19 building block Y-10.

Synthesis of C20-C38 Building Blocks

One of the key intermediates in the halichondrin syntheses described herein is the C20-C38 aldehyde B, which can be synthesized from methyl ester A. As described herein, this transformation can be achieved in 6 or 7 synthetic steps as depicted in Scheme 4.

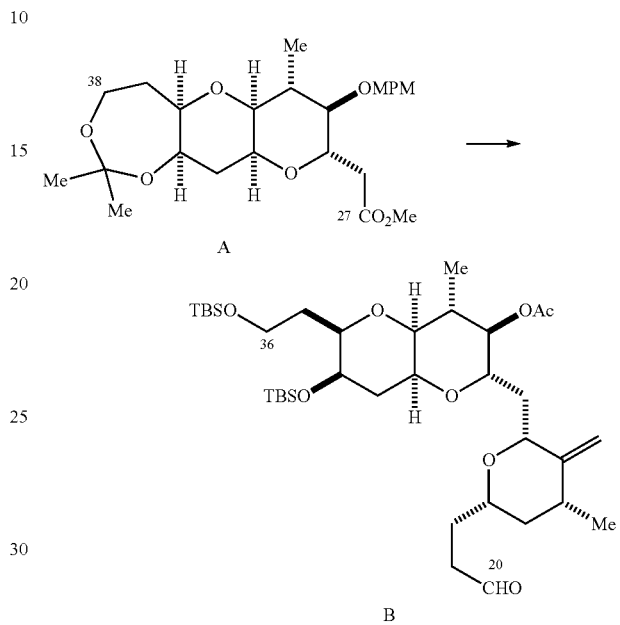

Following the previously reported method (*J. Am. Chem. Soc.* 136, 5171 (2014)), both 5 and 6 can be converted into the right half of halichondrins A-C in 4 steps (1. Ni/Cr-mediated coupling, 2. base-induced cyclization, 3. ester/acetate hydrolysis, 4. macrolactonization), with modification of the second step of sequence, i.e., CaCO$_3$ or SrCO$_3$ in aq. t-BuOH at 100° C., instead of AgOTf-Ag$_2$O in THF at 0° C.

Scheme 4

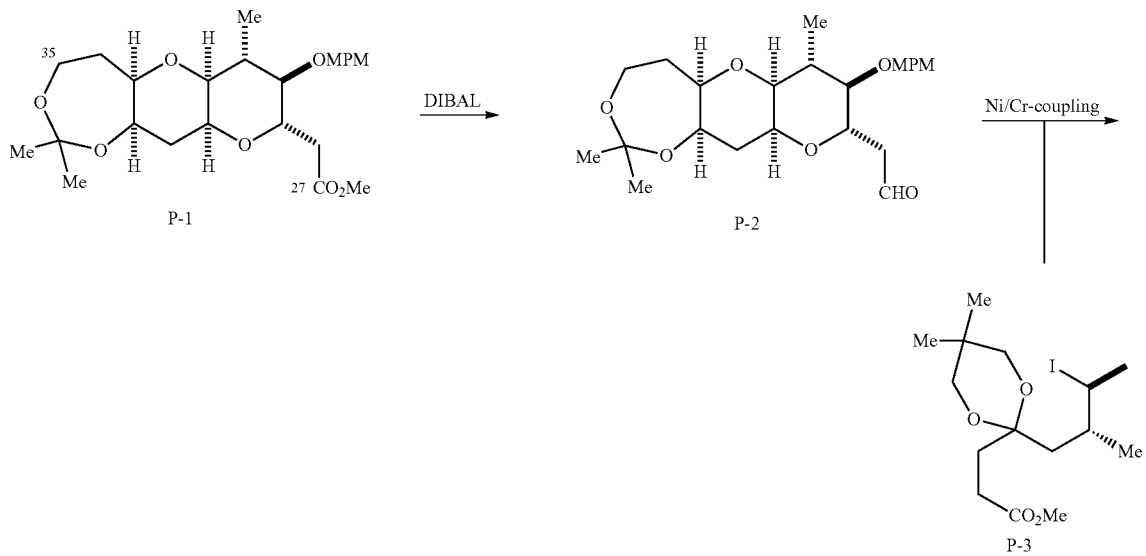

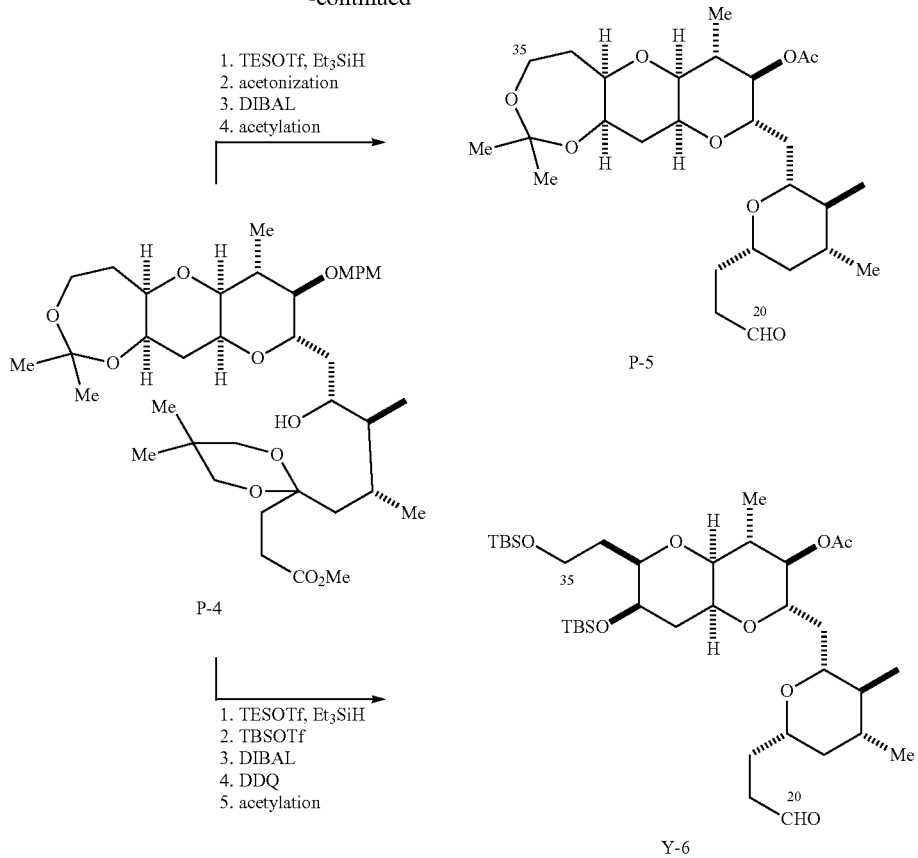

Experimental Procedures for the Synthesis of C20-C38 Building Blocks

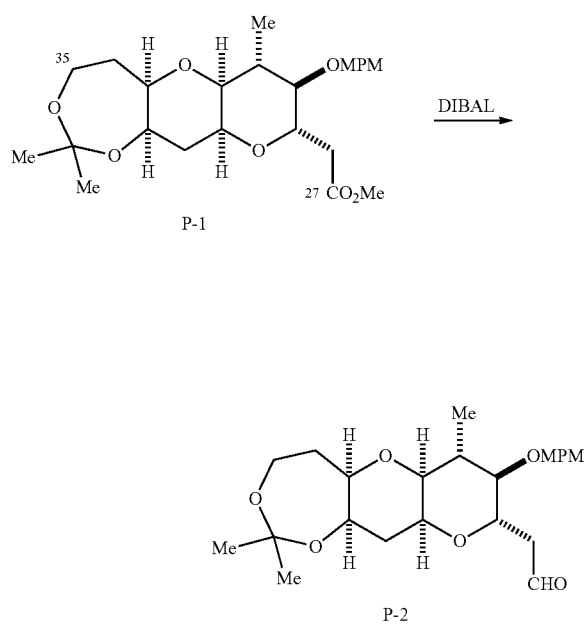

To a solution of P-1 (132 mg) in CH$_2$Cl$_2$ (2.8 mL) at −78° C. was added DIBAL (1.0 M in hexane, 0.43 mL). After stirred for 1 h at the same temperature, the reaction was quenched with EtOAc (5 mL) at −78° C. and 10% aqueous Rochelle's salt (5 mL), then stirred for 1 h. The mixture was extracted with EtOAc, and the organic layer was dried over Na$_2$SO$_4$, filtered, and concentrated. Flash silica gel column chromatography of the residue (EtOAc/hexanes 10% to 60%) gave P-2 (108 mg, 89% yield). $^1$H-NMR (600 MHz, C$_6$D$_6$) δ: 10.05 (1H, dd, J=2.9, 2.9 Hz), 7.19 (2H, m), 6.78 (2H, m), 5.13 (1H, ddd, J=9.1, 9.1, 4.7 Hz), 4.42 (1H, J=11.2 Hz), 4.24 (1H, J=11.2 Hz), 3.97 (1H, dd, J=11.4 Hz), 3.55 (1H, dd, J=3.5, 3.5 Hz), 3.51 (1H, ddd, J=5.0, 2.8, 2.8 Hz), 3.30 (1H, dd, J=3.3, 3.3 Hz), 3.28 (3H, s), 3.13 (1H, dd, 2.9, 2.9 Hz), 2.96 (1H, dd, J=9.4, 2.9 Hz), 2.92 (1H, m), 2.76 (1H, ddd, J=15.3, 4.7, 2.9 Hz), 2.46 (1H, ddd, J=15.3, 8.2, 2.9 Hz), 2.26 (1H, m), 1.95 (1H, ddd, 14.7, 2.6, 2.6 Hz), 1.69 (1H, m), 1.56 (1H, m), 1.21-1.30 (7H, m), 0.87 (3H, dd, J=7.6, 7.6 Hz).

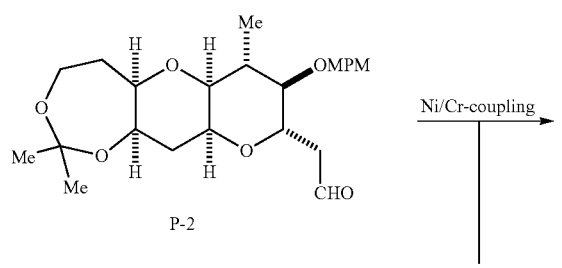

P-2

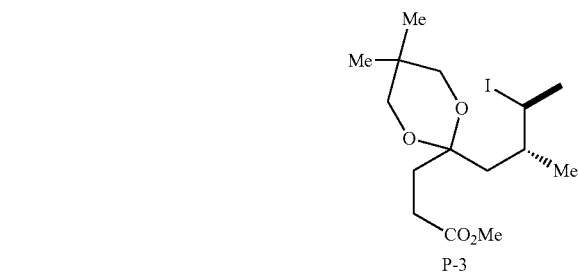

P-3

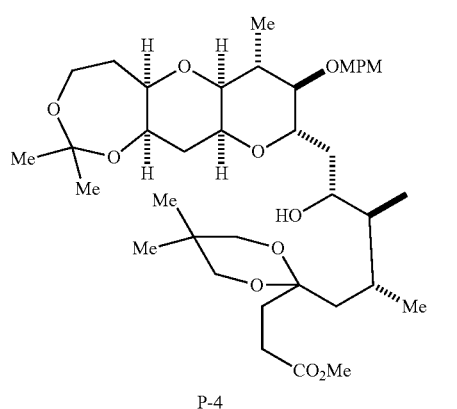

P-4

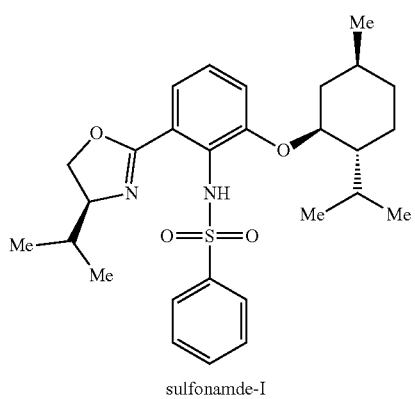

sulfonamde-I

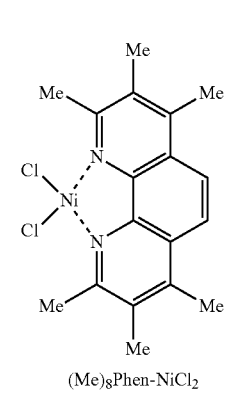

(Me)₈Phen-NiCl₂

To a mixture of CrCl₂ (3.6 mg), sulfonamide-I (15.9 mg), and proton sponge (6.8 mg) in a glove box was added MeCN (0.73 mL) and stirred for 2 h at room temperature. In a separate flask, P-2 (126 mg), P-3 (170 mg), LiCl (24.6 mg), Mn (63.7 mg), Cp₂ZrCl₂ (84.8 mg) were mixed together and the above Cr-complex solution was transferred to the flask. Then (Me)₆Phen-NiCl₂ (5.7 mg) was added. After 1 hr, additional (Me)₆Phen-NiCl₂ (5.7 mg) was added. The reaction mixture was stirred for 3 h (total) at room temperature, and diluted with EtOAc. Florisil was added and the suspension was vigorously stirred for 30 min. The resultant suspension was filtered through a short pad of silica gel (1 cm) with EtOAc, and concentrated. The crude material was purified with silica gel flash column chromatography (EtOAc/hexanes 0% to 50%) to give P-4 (170 mg, 83% yield). ¹H-NMR (600 MHz, C₆D₆) δ: 7.25 (2H, m), 6.85 (2H, m), 5.67 (1H, s), 5.09 (1H, s), 4.83 (1H, m), 4.74 (1H, d, J=10.6 Hz), 4.51 (1H, d, J=11.2 Hz), 4.44 (1H, s), 4.36 (1H, d, J=11.2 Hz), 4.07 (1H, dd, J=11.4, 11.4 Hz), 3.57 (1H, m), 3.48 (1H, m), 3.40-3.34 (5H, m), 3.33 (3H, s), 3.27 (2H, m), 3.05 (1H, m), 2.97-2.90 (2H, m), 2.74 (1H, m), 2.61 (2H, m), 2.49 (1H, brd, J=14.1 Hz), 2.38 (1H, m), 2.27-2.19 (2H, m), 2.13 (1H, dd, J=14.7, 4.7 Hz), 1.92 (1H, dd, J=14.7, 7.0 Hz), 1.85 (1H, ddd, J=14.8, 2.6, 2.6 Hz), 1.79 (1H, ddd, J=13.9, 10.3, 10.3 Hz), 1.69 (1H, m), 1.64-1.55 (4H, m), 1.42 (3H, d, J=7.0 Hz), 1.34 (3H, s), 1.18 (1H, ddd, J=14.8, 4.3, 4.3 Hz), 0.88 (3H, d, J=7.6 Hz), 0.75 (3H, s), 0.68 (3H, s).

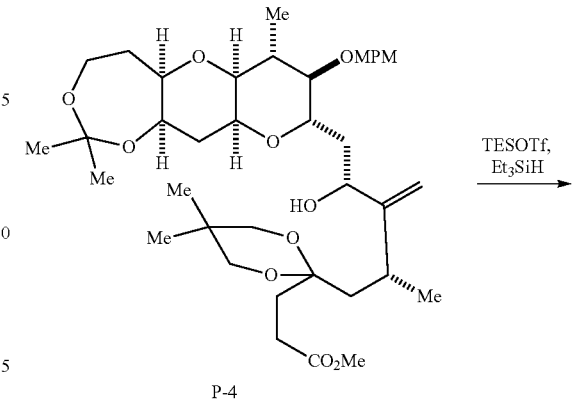

P-4

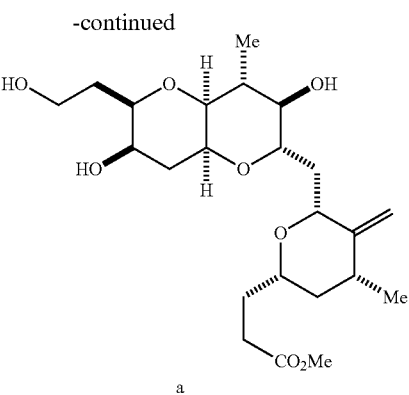

a

To a solution of P-4 (100 mg) in CH$_2$Cl$_2$ (2.8 mL) was added triethylsilane (0.68 mL). The mixture was cooled to −78° C. then TESOTf (0.39 mL) was added. After being stirred for 90 min at the same temperature the reaction was quenched with CH$_2$Cl$_2$ (3 mL) wetted with saturated aqueous NaHCO$_3$, then saturated aqueous NaHCO$_3$ (3 mL). The mixture was warmed to room temperature, and then extracted with EtOAc. The organic layer was washed with saturated aqueous NaCl, dried over Na$_2$SO$_4$, filtered, and concentrated. Silica gel flash column chromatography of the residue (EtOAc/hexanes 50% to 100% then MeOH/EtOAc 0.5%) gave a (55 mg, 88%). $^1$H-NMR (600 MHz, CD$_3$OD) δ: 4.93 (1H, brs), 4.83 (1H, brd, J=1.8 Hz), 3.96 (1H, dd, J=6.0 Hz), 3.92 (1H, m), 3.89 (1H, dd, J=6.5, 6.5 Hz), 3.73-3.66 (2H, m), 3.65 (3H, s), 3.61 (1H, m), 3.54 (1H, dd, J=8.8, 4.7 Hz), 3.51 (1H, m), 3.41-3.37 (2H, m), 2.53-2.39 (2H, m), 2.30 (1H, m), 2.20 (1H, ddd, J=14.2, 5.5, 5.5 Hz), 2.15 (1H, ddd, J=14.7, 2.9, 2.9 Hz), 1.96-1.85 (4H, m), 1.84-1.64 (5H, m), 1.16 (3H, d, J=7.0 Hz), 1.10 (3H, d, J=6.5 Hz), 1.03 (1H, dd, J=24.0, 12.6 Hz).

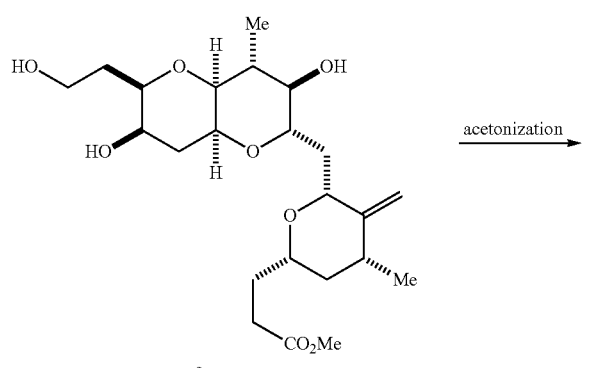

a

→ acetonization

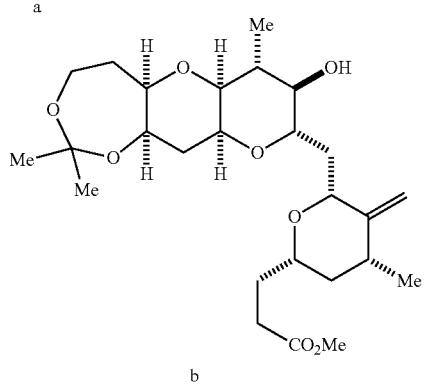

b

To a (5.0 mg) was added a solution of 2,2-dimethoxypropane (11 μL), 2-methoxypropene (20 μL), PPTS (0.22 mg) in acetone (0.44 mL) at room temperature and the reaction was stirred for 1 day at room temperature. The reaction was quenched with saturated aqueous NaHCO$_3$. The mixture was extracted with EtOAc, and the organic layer was washed with saturated aqueous NaCl, dried over Na$_2$SO$_4$, filtered, and concentrated. Silica gel preparative TLC purification (EtOAc) gave b (4.6 mg, 85% yield). $^1$H-NMR (600 MHz, C$_6$D$_6$) S: 4.95 (1H, brs), 4.74 (1H, brd, J=1.8 Hz), 4.51 (1H, m), 4.09 (1H, dd, J=8.2, 4.1 Hz), 3.99 (1H, m), 3.7 (1H, m), 3.65 (1H, m), 3.48 (1H, m), 3.43-3.34 (5H, m), 3.31 (1H, d, J=7.6 Hz), 3.15 (1H, dd, J=2.9, 2.9 Hz), 3.05 (1H, m), 2.46-2.40 (2H, m), 2.33 (1H, m), 2.26 (1H, m), 2.19 (1H, ddd, J=14.4, 4.2, 4.2 Hz), 2.10 (1H, ddd, J=14.2, 3.7, 3.7 Hz), 1.90 (1H, m), 1.76 (1H, m), 1.73-1.56 (3H, m), 1.39 (1H, ddd, J=14.1, 4.1, 4.1 Hz), 1.36 (3H, s), 1.29 (3H, s), 1.27 (1H, ddd, J=12.6, 4.4, 1.8 Hz), 1.16 (3H, d, J=7.6 Hz), 0.90 (1H, dd, J=24.1, 12.3 Hz), 0.87 (3H, d, J=6.5 Hz).

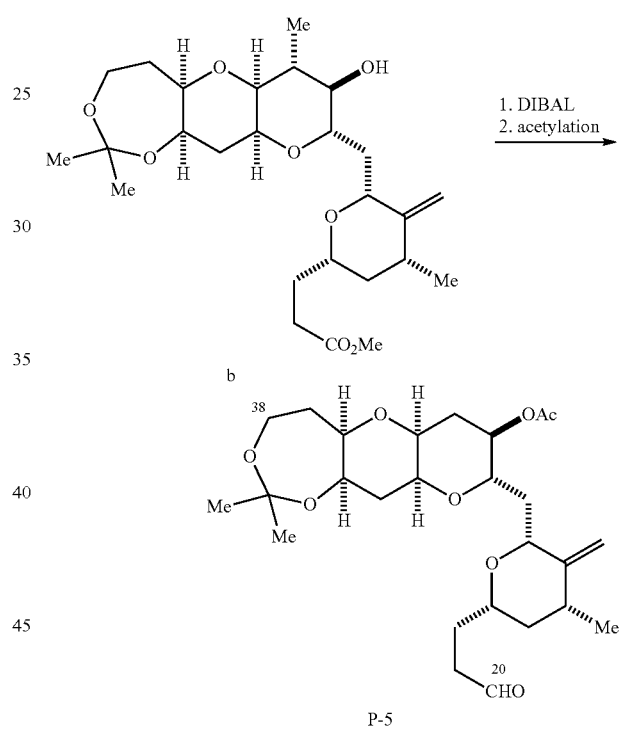

P-5

To a solution of b (4.6 mg) in CH$_2$Cl$_2$ (0.2 mL) at −78° C. was added DIBAL (1.0 M solution in hexane, 26 μL). After being stirred for 50 min, the reaction was quenched with EtOAc (5 mL) and 10% aqueous Rochelle's salt (5 mL). The mixture was warmed to room temperature then stirred for 1 h, then extracted with EtOAc. The organic layer was washed with saturated aqueous NaCl, dried over Na$_2$SO$_4$, filtered, and concentrated to give aldehyde-alcohol, which was used for the next step without further purification.

To a solution of crude aldehyde-alcohol in CH$_2$Cl$_2$ (0.18 mL) at room temperature was added pyridine (7.1 μL), acetic anhydride (4.2 μL), and DMAP (1.0 mg). After being stirred for 70 min at the same temperature, the reaction was quenched with saturated aqueous NaHCO$_3$. The mixture was extracted with EtOAc, and the organic layer was washed with saturated aqueous NaCl, dried over Na$_2$SO$_4$, filtered, and concentrated. Silica gel flash column chromatography (EtOAc/hexanes 50%) gave P-5 (3.0 mg, 64% yield for 2 steps). $^1$H-NMR (600 MHz, C$_6$D$_6$) δ: 9.54 (1H, t, J=1.5 Hz), 5.03 (1H, s), 4.95 (1H, dd, J=9.1, 5.6 Hz), 4.80 (1H, brd, J=2.0 Hz), 4.67 (1H, m), 4.12 (1H, dd, J=6.5, 6.5 Hz), 4.02 (1H, ddd, J=12.0, 10.0, 2.1 Hz), 3.63 (1H, ddd, J=4.4, 4.4, 1.8 Hz), 3.61 (1H, dd, J=8.8, 4.1 Hz), 3.40 (1H, ddd, J=11.9, 4.3, 4.3 Hz), 3.3 (1H, m), 3.09 (1H, dd, J=3.8, 3.8 Hz), 3.04 (1H, m), 2.35-2.17 (5H, m), 1.20 (1H, ddd, J=14.1, 4.1, 4.1), 1.96 (1H, m), 1.82 (1H, m), 1.68 (3H, s), 1.62-1.54 (3H, m), 1.43 (1H, ddd, J=14.1, 4.7, 4.7 Hz), 1.36 (3H, s), 1.30 (3H, s), 1.27 (1H, ddd, J=13.0, 4.5, 2.2 Hz), 1.24 (3H, d, J=7.0 Hz), 0.92 (3H, d, J=6.5 Hz), 0.91 (1H, dd, J=23.5, 12.3 Hz).

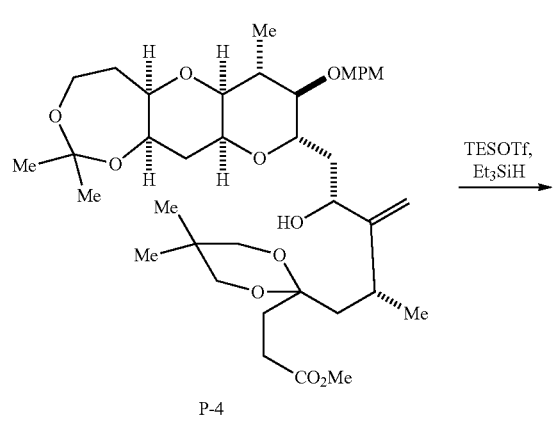

P-4

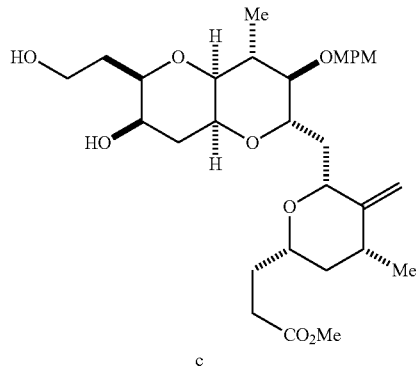

c

To a solution of methyl allylic alcohol P-4 (25 mg) in CH$_2$Cl$_2$ (0.7 mL) was added triethylsilane (0.22 mL). After the mixture was cooled to −78° C., TESOTf (47 μL) was added. After being stirred for 15 min, the reaction was quenched CH$_2$Cl$_2$ (2 mL) wetted with saturated aqueous NaHCO$_3$ (2 mL) then saturated aqueous NaHCO$_3$ (2 mL). The mixture was extracted with EtOAc. The organic layer was dried over sodium sulfate, filtered, and concentrated. Silica gel preparative TLC purification (EtOAc) gave methyl diol c (14.5 mg, 74% yield). $^1$H-NMR (600 MHz, CD$_3$OD) δ: 7.29 (2H, m), 6.89 (2H, m), 4.87 (1H, brs), 4.81 (1H, brd, J=1.8 Hz), 4.59 (1H, d, J=11.2 Hz), 4.48 (1H, d, J=11.2 Hz), 4.09 (1H, m), 3.89 (1H, m), 3.80-3.75 (4H, m), 3.74-3.68 (2H, m), 3.64 (3H, s), 3.58-3.51 (2H, m), 3.48 (1H, m), 3.35 (1H, m), 3.39-3.28 (3H, m), 2.50-2.37 (2H, m), 2.29-2.10 (4H, m), 1.98-1.83 (3H, m), 1.82-1.64 (4H, m), 1.16 (3H, d, J=7.6 Hz), 1.09 (3H, d, J=6.5 Hz), 1.02 (1H, dd, J=24.0, 12.6 Hz).

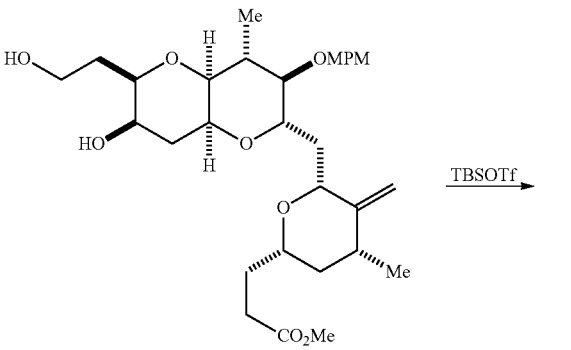

c

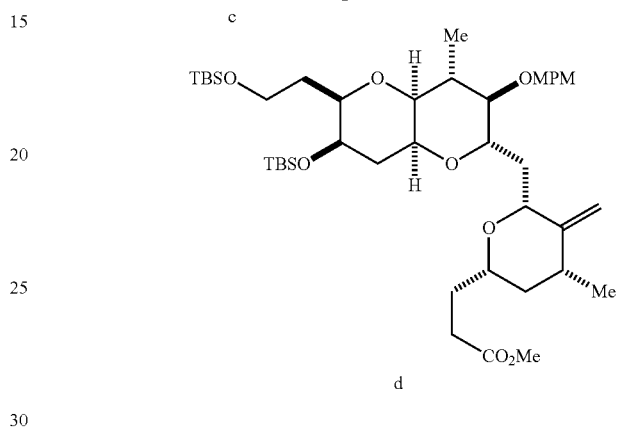

d

To a solution of diol c (12.3 mg) in CH$_2$Cl$_2$ (0.22 mL) at −78° C. was added TBSOTf (15 μL). The reaction mixture was stirred for 50 min, and then quenched with saturated aqueous NaHCO$_3$. The mixture was extracted with EtOAc, and the organic layer was washed with saturated aqueous NaCl, dried over Na$_2$SO4, filtered, and concentrated. Silica gel flash column chromatography of the residue (EtOAc/hexanes 0% to 20%) gave 4 (16.4 mg, 95% yield). $^1$H-NMR (600 MHz, C$_6$D$_6$) δ: 7.28 (2H, m), 6.81 (2H, m), 5.11 (1H, brs), 4.81 (1H, brd, J=1.2 Hz), 4.50 (2H, dd, J=18.0, 11.4 Hz), 4.27-4.19 (2H, m), 3.97 (1H, ddd, J=9.7, 9.7, 4.1 Hz), 3.78 (1H, m), 3.70 (1H, m), 3.60 (1H, ddd, J=9.7, 2.5, 2.5 Hz), 3.53 (1H, m), 3.45 (1H, m), 3.39 (3H, s), 3.32 (1, dd, J=6.2, 3.8 Hz), 3.30 (3H, s), 3.17 (1H, dd, J=8.8, 8.8 Hz), 2.49 (1H, m), 2.44-2.35 (2H, m), 2.32-2.20 (2H, m), 2.16-2.03 (3H, m), 1.84-1.72 (3H, m), 1.61 (1H, ddd, J=14.1, 4.7, 0.47 Hz), 1.35 (1H, ddd, J=12.3, 4.7, 1.8 Hz), 1.25 (3H, d, J=7.0 Hz), 1.04 (9H, s), 1.03-0.94 (10H, m), 0.92 (3H, d, J=6.5 Hz), 0.14 (3H, s), 0.13 (3H, s), 0.11 (3H, s), 0.05 (3H, s).

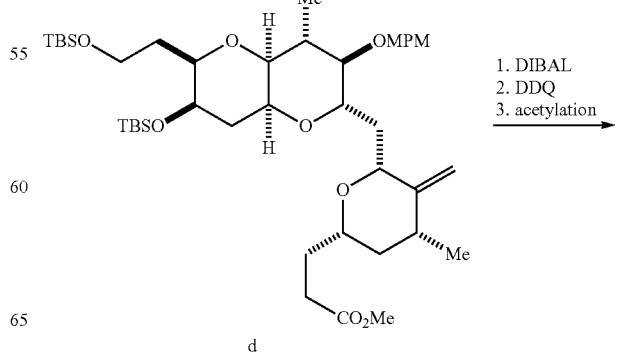

d

-continued

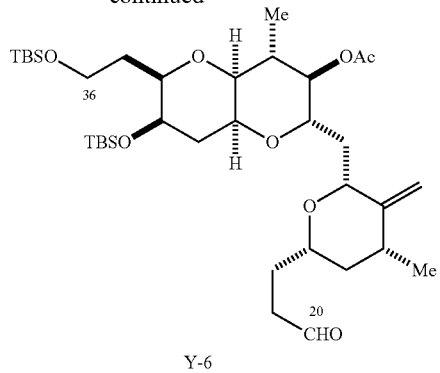

Y-6

To a solution of d (16.4 mg) in $CH_2Cl_2$ (0.2 mL) at −78° C. was added DIBAL (1.0 M in hexane, 41 μL). After being stirred for 50 min at the same temperature, the reaction was quenched with EtOAc (5 mL) followed by 10% aqueous Rochelle's salt (5 mL). The mixture was stirred for 1 h, and then extracted with EtOAc. The organic layer was washed with saturated aqueous NaCl, dried over $Na_2SO_4$, filtered, and concentrated, to give aldehyde, which was used for the next step without further purification. $^1$H-NMR (600 MHz, $C_6D_6$) δ: 7.26 (2H, m), 6.81 (2H, m), 5.12 (1H, brs), 4.81 (1H, brd, J=1.8 Hz), 4.48 (1H, d, J=11.4 Hz), 4.42 (1H, dd, J=11.4 Hz), 4.23-4.14 (2H, m), 3.95 (1H, ddd, J=9.7, 9.7, 4.7 Hz), 3.78 (1H, m), 3.67 (1H, m), 3.59 (1H, ddd, J=9.5, 2.9, 2.9 Hz), 3.52 (1H, m), 3.37-3.18 (5H, m), 3.07 (1H, dd, J=8.8, 8.8 Hz), 2.38 (1H, m), 2.31-2.01 (7H, m), 1.76 (1H, m), 1.65-1.46 (3H, m), 1.42-1.26 (2H, m), 1.23 (3H, d, J=7.0 Hz), 1.04 (9H, s), 1.00 (9H, s), 0.97-0.88 (4H, m), 0.14 (3H, s), 0.13 (3H, s), 0.11 (3H, s), 0.05 (3H, s).

To a solution of the above aldehyde in $CH_2Cl_2$ (0.6 mL) and phosphate buffer (1.0 M, pH=7.0, 0.2 mL) was added DDQ (7 mg). The reaction was stirred for 30 min then added another DDQ (7 mg). After being stirred for additional 30 min, the reaction was quenched with 10% aqueous $Na_2S_2O_3$ (3 mL). The mixture was extracted with EtOAc. The organic layer was washed with saturated aqueous NaCl, dried over $Na_2SO_4$, filtered, and concentrated, to give alcohol C30-alcohol, which was used for next step without further purifications.

To a solution of C30-alcohol in pyridine (0.2 mL) was added acetic anhydride (20 μL) and DMAP (1 mg). After being stirred for 30 min, the reaction was quenched with saturated aqueous $NH_4Cl$. The mixture was extracted with EtOAc and the organic layer was washed with saturated aqueous NaCl, dried over $Na_2SO_4$, filtered and concentrated. Silica gel flash column chromatography of the residue (EtOAc/hexanes 0% to 30%) gave Y-6 (5.3 mg, 38% yield for 3 steps). $^1$H NMR (600 MHz, $C_6D_6$) δ: 9.56 (1H, dd, J=1.5 Hz), 4.99 (1H, br s), 4.96 (1H, dd, J=8.3, 7.5 Hz), 4.82 (1H, d, J=1.2 Hz), 4.38 (1H, ddd, J=8.3, 5.6, 5.6 Hz), 4.08 (1H, dd, J=6.2, 6.2 Hz), 3.90 (1H, ddd, J=9.9, 9.6, 4.5 Hz), 3.75 (1H, ddd, J=9.9, 5.5, 4.2 Hz), 3.59 (1H, ddd, J=4.5, 4.1, 3.7 Hz), 3.49-3.42 (2H, m), 3.41-3.34 (1H, m), 3.18 (1H, dd, J=4.8, 3.7 Hz), 2.33-2.24 (3H, m), 2.21 (1H, ddd, J=7.2, 7.2, 5.0 Hz), 2.15 (1H, ddd, J=14.4, 6.4, 5.6 Hz), 2.09-2.00 (3H, m), 1.76-1.71 (1H, m), 1.69 (3H, s), 1.62-1.56 (2H, m), 1.48 (1H, ddd, J=14.4, 4.5, 4.5 Hz), 1.30 (1H, ddd, J=12.5, 4.2, 2.1 Hz), 1.21 (3H, d, J=7.3 Hz), 1.02 (9H, s), 1.01 (9H, s), 0.93 (3H, d, J=6.4 Hz), 0.94-0.89 (1H, m), 0.11 (3H, s), 0.11 (6H, s), 0.04 (3H, s).

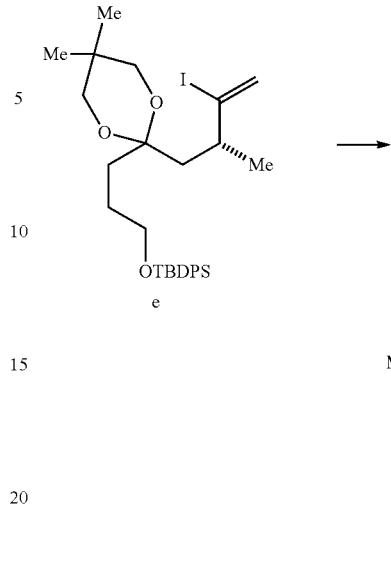

Using the following sequence, vinyl iodide P-3 was prepared from the previously reported e. To a solution of e (594 mg) in THF (4.9 mL) at room temperature was added a mixture of TBAF (1.0 M in THF, 1.96 mL) and imidazole hydrochloride (20.5 mg). The reaction was stirred for 4 h, and then quenched with aqueous saturated $NH_4Cl$. The mixture was extracted with EtOAc, and the organic layer was washed with saturated aqueous NaCl, dried over $Na_2SO_4$, filtered, and concentrated. Silica gel flash column chromatography of the residue (EtOAc/hexanes 10% to 50%) gave primary alcohol (303 mg, 84% yield). $^1$H-NMR (600 MHz, $C_6D_6$) δ: 5.91 (1H, brs), 5.57 (1H, brd, J=1.2 Hz), 3.39 (2H, m), 3.25-3.34 (4H, m), 2.31 (1H, m), 2.03 (1H, dd, J=14.7, 5.3 Hz), 1.86 (1H, m), 1.67-1.79 (2H, m), 1.62 (2H, m), 1.13 (3H, d, J=6.5 Hz), 0.75 (3H, s), 0.72 (3H, s).

To a solution of primary alcohol (157 mg) in $CH_2Cl_2$ (2.2 mL) at room temperature was added $NaHCO_3$ (361 mg, 4.3 mmol) and Dess-Martin periodinane (274 mg). After being stirred for 70 min, the reaction was quenched with 10% aqueous $Na_2S_2O_3$. The mixture was extracted with EtOAc, washed with saturated aqueous NaCl, dried over $Na_2SO_4$, filtered, and concentrated. Silica gel flash column chromatography of the residue (EtOAc/hexanes 20%) gave aldehyde (129 mg, 82% yield). $^1$H-NMR (600 MHz, $C_6D_6$) δ: 9.44 (1H, t, J=1.5 Hz), 5.85 (1H, brs), 5.54 (1H, brd, J=1.2 Hz), 3.20-3.32 (2H, m), 3.11-3.17 (2H, m), 2.25 (2H, m), 2.09 (1H, m), 1.97 (1H, m), 1.88 (2H, dd, J=14.7, 6.5 Hz), 1.57 (1H, dd, J=15.0, 5.6 Hz), 1.03 (3H, d, J=7.0 Hz), 0.76 (3H, s), 0.60 (3H, s).

To a solution of aldehyde (102 mg, 0.28 mmol) in t-BuOH (5.5 mL) and 2-methyl-2-butene (2.2 mL) at room temperature was added a solution of $NaClO_2$ (198 mg) and $NaH_2PO_4$—$H_2O$ (304 mg) in $H_2O$ (2.0 mL). After being stirred for 2.5 h, diluted with $H_2O$ (10 mL) and EtOAc (10 mL). The mixture was extracted with EtOAc, and the organic layer was washed with saturated aqueous NaCl, dried over Na2SO4, filtered, and concentrated to give carboxylic acid, which was used for the next step without further purification. $^1$H-NMR (600 MHz, $C_6D_6$) δ: 5.86 (1H, brs), 5.54 (1H, brd, J=1.3 Hz), 3.28 (2H, m), 3.18 (2H, m), 2.25 (2H, m), 2.14 (2H, m), 2.04 (1H, m), 1.94 (1H, dd, J=14.8, 5.6 Hz), 1.58 (1H, dd, J=14.7, 5.7 Hz), 1.02 (3H, d, J=6.6 Hz), 0.75 (3H, s), 0.61 (3H, s).

To a solution of carboxylic acid in toluene (2.8 mL) and MeOH (0.28 mL) at room temperature was added TMSCHN$_2$ (2.0 M solution in Et$_2$O, 0.42 mL). After being stirred for 2 h, the reaction was concentrated. Silica gel flash column chromatography of the residue (EtOAc/hexanes 0% to 10%) gave P-3 (99.7 mg, 90% yield for 2 steps). $^1$H-NMR (600 MHz, C$_6$D$_6$) δ: 5.87 (1H, brs), 5.54 (1H, brd, J=1.8 Hz), 3.37 (3H, s), 3.19-3.32 (4H, m), 2.54 (2H, m), 2.09-2.26 (3H, m), 1.97 (1H, dd, J=14.7, 5.3 Hz), 1.60 (1H, dd, J=14.7, 5.9 Hz), 1.04 (3H, d, J=6.5 Hz), 0.71 (3H, s), 0.66 (3H, s).

Exemplary Synthesis of Halichondrins from Right Half/Left Half Fragments

Using the previously developed methods (See, e.g., *J. Am. Chem. Soc.* 2012, 134, 893; 2014, 136, 5171) requisite enones can be prepared from right and left haves bearing proper protecting groups. An exemplary procedure for halichondrin C is shown below. Using the same experimental procedures, halichondrins A and B can also be prepared. Likewise, the enones of norhalichondrins A-C can be prepared from the C39-C53 iodoolefin of norhalihondrin.

To a stirred solution of the above diol (azeotropically dried with benzene prior to use) in DCM (5.5 mL) and triethylamine (0.55 mL) at 0° C. was added p-nitrobenzoyl chloride (150 mg). The reaction was quenched with MeOH (0.2 mL) at 0° C. and the resultant mixture was further stirred for 15 min at room temperature. The reaction was diluted with Et$_2$O (8 mL) to precipitate white solid and the reaction flask was sonicated for five seconds. After filtration through a Celite pad (1 cm) and evaporation of the solvent, the crude material was purified by silica gel flash column chromatography (DCM to EtOAc/hexanes 1/3 to 1/2) to give p-nitrobenzoate.

To a mixture of p-nitrobenzoate (azeotropically dried with benzene prior to use) and imidazole (110 mg) in DCM (3.0 mL) was added TES-Cl (0.14 mL) at room temperature and the reaction mixture was stirred for 5 h at the same temperature prior to the addition of H$_2$O. The aqueous phase was extracted with EtOAc twice and combined organic phases were dried over Na$_2$SO$_4$, concentrated under reduced pressure. The obtained residue was purified by silica gel flash column chromatography (EtOAc/hexanes 1/5 to 1/3) to give TES ether (253 mg, 87% for 3 steps).

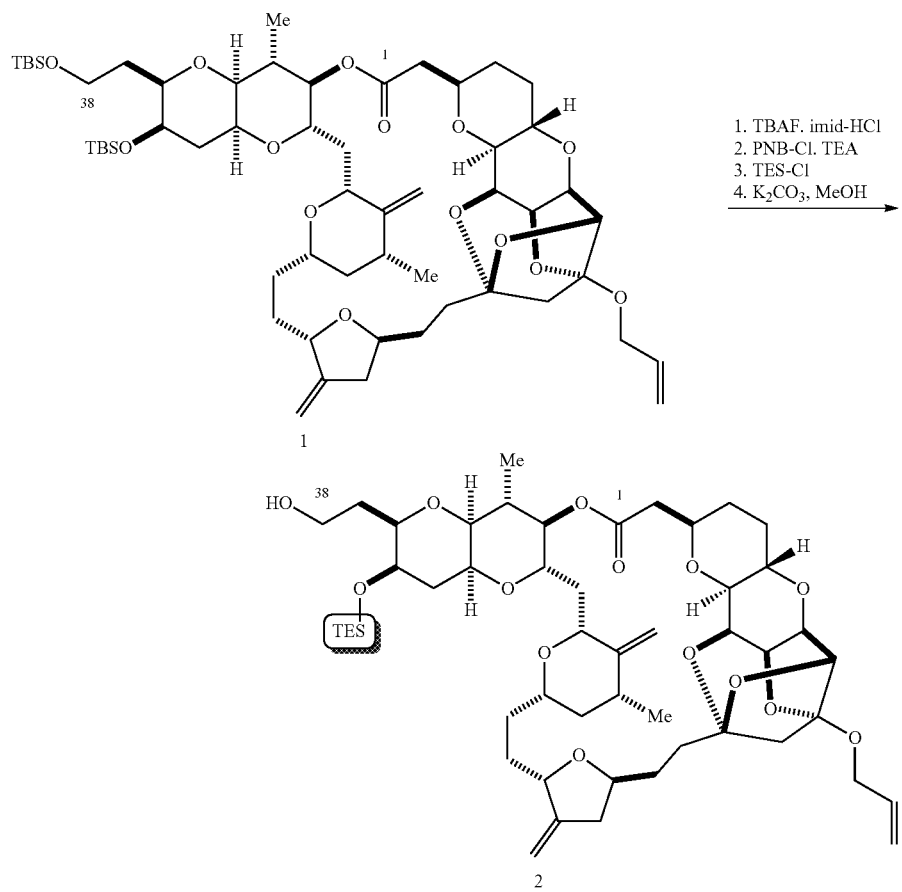

To a solution of bis-TBS ether 1 (280 mg) in THF (5.5 mL) was added TBAF solution (1 M in THF, buffered with 0.5 eq of imidazole hydrochloride, 1.1 mL) at room temperature. After stirring for 20 h at room temperature, solvent was removed under reduced pressure. The residue was purified by silica gel flash column chromatography (DCM/hexanes 1:1 to EtOAc/hexanes 1/1 to 2/1 to EtOAc) to give diol.

$^1$H NMR (600 MHz, C$_6$D$_6$) δ: 7.86 (2H, d, J=8.7 Hz), 7.72 (2H, d, J=8.7 Hz), 5.76 (1H, dddd, J=16.7, 10.5, 5.4, 5.4 Hz), 5.18-5.14 (2H, m), 5.07 (1H, d, J=1.2 Hz), 4.99-4.95 (2H, m), 4.88-4.83 (2H, m), 4.79 (1H, s), 4.66-4.62 (2H, m), 4.58 (1H, ddd, J=10.8, 7.2, 5.1 Hz), 4.52 (1H, ddd, J=10.5, 10.5, 4.2 Hz), 4.38 (1H, dd, J=3.9, 2.1 Hz), 4.33 (1H, d, J=4.8 Hz), 4.12 (1H, dd, J=6.6, 4.8 Hz), 4.05-3.98 (2H, m), 3.85-3.80 (3H, m), 3.74-3.69 (2H, m), 3.50 (1H, dd, J=8.1, 3.9 Hz), 3.46 (1H, dd, J=6.3, 4.2 Hz), 3.21 (1H, ddd, J=9.4, 2.7, 2.7 Hz), 3.09 (1H, dd, J=3.9, 3.9 Hz), 2.78 (1H, dd, J=16.5, 7.5 Hz), 2.68-2.64 (1H, m), 2.56 (1H, dd, J=9.6, 1.8 Hz), 2.39-2.08 (14H, m), 1.98-1.84 (3H, m), 1.77-1.72 (1H, m), 1.58-1.56 (1H, m), 1.53-1.42 (4H, m), 1.39-1.30 (2H, m), 1.17 (3H, d, J=7.2 Hz), 1.13-1.07 (1H, m), 1.05 (9H, t, J=7.9 Hz), 1.01 (3H, d, J=6.6 Hz), 0.685 (6H, q, J=7.9 Hz).
Enone intermediates can be prepared by coupling left half and right half fragments using Ni/Cr coupling reaction as demonstrated:
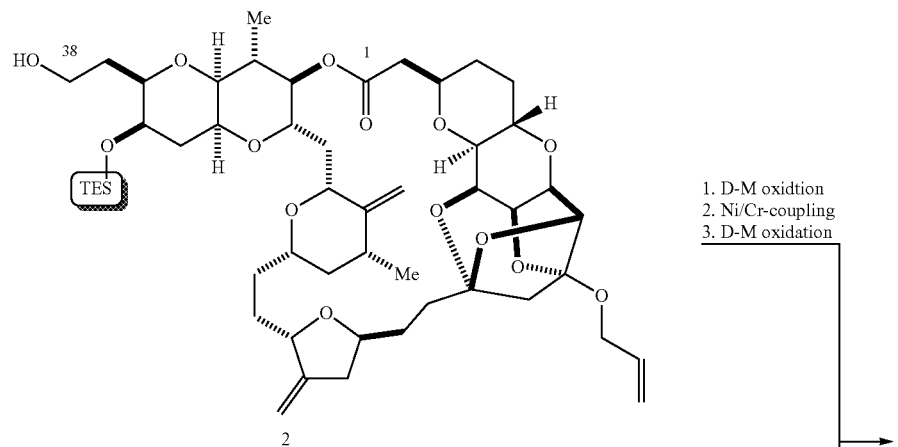
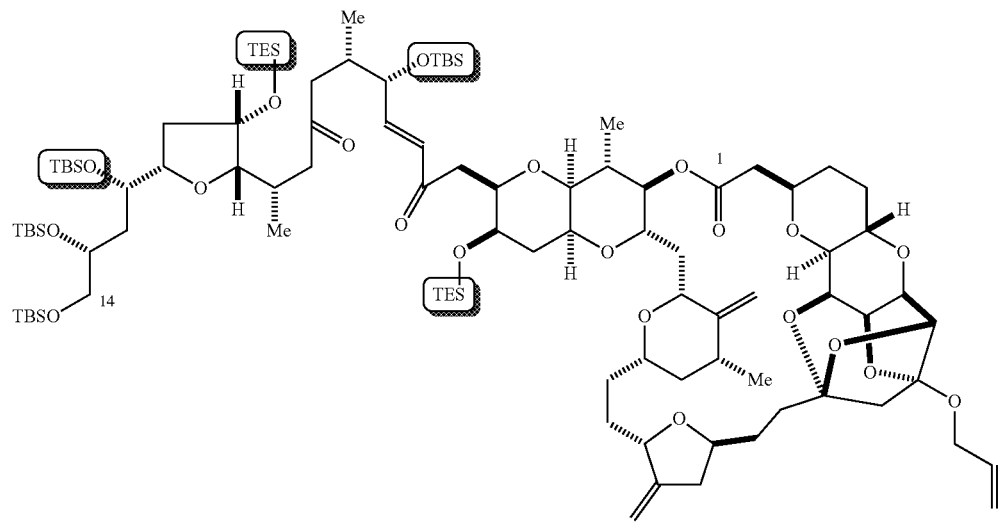

To a solution of 2 (57.3 mg) in DCM (1.0 mL) were added NaHCO$_3$ (55.0 mg) and Dess-Martin periodinane (55 mg) at room temperature and the reaction mixture was stirred for 1 h at the same temperature. The reaction was quenched by adding 10 wt % Na$_2$S$_2$O$_3$ aq. and sat. NaHCO$_3$aq. and then vigorously stirred for 30 min at room temperature. The aqueous phase was extracted with DCM three times and combined organic phases were dried over Na$_2$SO4. After evaporation of the solvent, the crude material was purified by silica gel flash chromatography (EtOAc/hexanes 1:5 to 1:3 to 1:2) to give aldehyde.

To a mixture of CrCl$_2$ (40.0 mg), (S)-i-Pr/Me/OMe sulfonamide (111 mg), and proton sponge (76.1 mg) in a glove box was added MeCN (3.2 mL) and stirred for 1 h at room temperature. In a separate flask, above aldehyde, iodoolefin 3 (88.8 mg), NiCl$_2$-DMP (0.10 mg, doped in LiCl), LiCl (5.0 mg), were mixed together and the Cr-complex solution was transferred to the flask. After stirring for 1 h at room temperature, the reaction was removed from the glove box and diluted with EtOAc (1.5 mL) and added florisil and the mixture was stirred vigorously for 30 min. The resultant mixture was filtered through silica gel plug, and concentrated. The crude material was purified by silica gel flash column chromatography (EtOAc/hexanes 1:10 to 1:5 to 1:3) to give allyl alcohol.

To a solution of the above allyl alcohol in DCM (2.0 mL) were added NaHCO$_3$ (60 mg) and Dess-Martin periodinane (60 mg) at room temperature and the reaction mixture was stirred for 1 h at room temperature. The reaction was quenched with 10 wt % Na$_2$S$_2$O$_3$ aq. and sat. NaHCO$_3$aq. and vigorously stirred for 30 min. The aqueous phase was extracted with DCM three times and the combined organic phases were dried over Na$_2$SO4 and concentrated under vacuum. The residue was purified by silica gel preparative TLC (EtOAc/hexanes 1:2) to provide 4 (51.2 mg, 45% in 3 steps).

$^1$H NMR (600 MHz, C$_6$D$_6$) δ: 6.89 (1H, dd, J=16.2, 4.8 Hz), 6.48 (1H, dd, J=16.2, 1.8 Hz), 5.76 (1H, dddd, J=16.8, 10.2, 5.3, 5.3 Hz), 5.20 (1H, brs), 5.17 (1H, dd, J=17.4, 1.2 Hz), 5.10 (1H, brs), 4.99-4.95 (2H, m), 4.86-4.82 (2H, m), 4.79 (1H, brs), 4.67 (1H, brs, J=10.2 Hz), 4.52 (1H, ddd, J=10.2, 10.2, 4.2 Hz), 4.38-4.37 (1H, m), 4.33 (1H, d, J=4.8 Hz), 4.28-4.25 (1H, m), 4.15 (1H, dd, J=3.9, 3.9 Hz), 4.12 (1H, dd, J=6.6, 4.8 Hz), 4.10-3.98 (5H, m), 3.93 (1H, brd, J=2.4 Hz), 3.85-3.71 (8H, m), 3.48 (1H, dd, J=8.7, 4.5 Hz), 3.20-3.15 (2H, m), 3.12 (1H, dd, J=8.1, 3.9 Hz), 3.09-3.03 (2H, m), 2.83-2.73 (3H, m), 2.57 (1H, dd, J=10.2, 1.8 Hz), 2.53-2.46 (2H, m), 2.38-2.19 (9H, m), 2.14-2.10 (3H, m), 2.07-2.06 (1H, m), 2.02-1.94 (3H, m), 1.86-1.83 (1H, m), 1.79-1.72 (2H, m), 1.66-1.60 (2H, m), 1.55-1.49 (3H, m), 1.36-1.29 (2H, m), 1.21 (3H, d, J=7.2 Hz), 1.17 (9H, t, J=7.8 Hz), 1.09 (9H, s), 1.08 (9H, t, J=8.1 Hz), 1.05 (9H, s), 1.02 (9H, s), 1.01 (9H, t, J=7.8 Hz), 1.09-0.995 (9H, m), 0.861-0.817 (6H, m), 0.696 (6H, q, J=8.0 Hz), 0.586 (6H, q, J=7.6 Hz), 0.293 (3H, s), 0.286 (3H, s), 0.169 (3H, s), 0.167 (3H, s), 0.094 (3H, s), 0.091 (3H, s).

An exemplary two-step deprotection/cyclization toward halichondrin C is shown below:

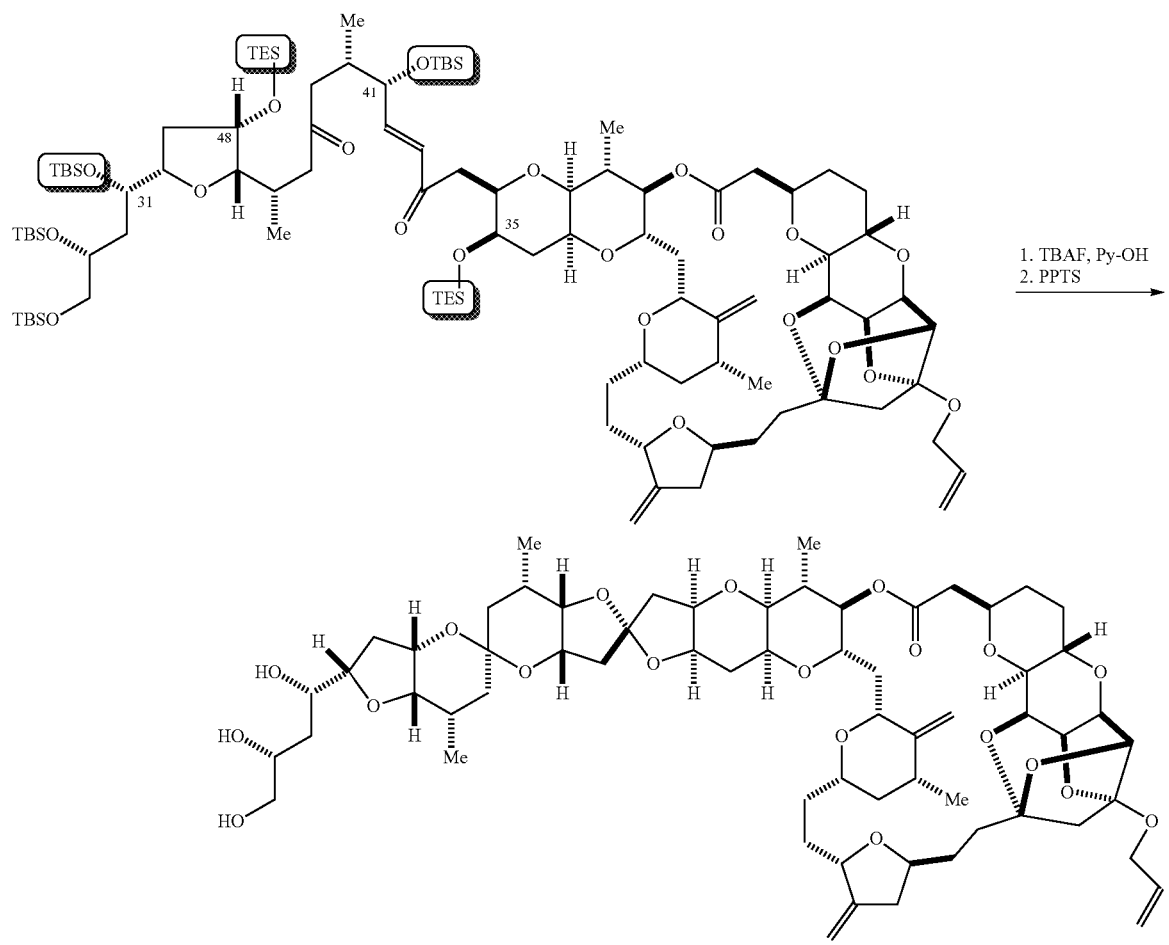

Buffered TBAF solution (0.5 M) was prepared by mixing TBAF (0.5 mL of 1 M solution in THF: TCI (#T1125)), pivalic acid (Pv-OH, 0.3 mL of 1M solution in DMF), and DMF (0.2 mL).

To a solution of enone (21.8 mg) in DMF (2.1 mL) was added the above TBAF solution (0.23 mL) via a syringe pomp at 0° C. over 1 h. After stirring for 1 h at the same temperature, the cooling bath was removed and the reaction mixture was stirred for 12 h (24 h for Nor-series) at room temperature. The reaction was quenched by adding $CaCO_3$ (500 mg) and DOWEX 50WX8 (1.3 g: 200-400 mesh $H^+$-form). After stirring for 1 h at room temperature, the resulting suspension was diluted with EtOAc (ca. 2 mL) and filtered through a pad of Celite, and the filter cake was washed with EtOAc. The obtained solution was concentrated under reduced pressure, and the residue was dissolved in $CH_2Cl_2$ (2.3 mL).

To the solution was added PPTS (29 mg) at room temperature. After stirring for 2.5 h at the same temperature, Wakogel 50NH$_2$ (ca. 200 mg) and DCM (2.0 mL) was added. The resulting slurry was loaded onto a column of Wakogel 50NH$_2$ (neutral silica gel from Kanto Chemicals was used for Nor-series), and purified (EtOAc/hexanes: 1/5 to 1/2 to 1/1 then MeOH/EtOAc: 1/20 (100% EtOAc for Nor-series)), to furnish a 4:1 mixture of allyl-protected halichondrin-C and its C38-epimer. The obtained mixture was purified with HPLC (YMS-Pack C-18 column; MeCN/ $H_2O$, gradient) to give allyl-protected halichondrin C (5.2 mg, 38% for 2 steps) and C38-epi halichondrin C (1.3 mg, 9% for 2 steps).

$^1$H NMR (600 MHz, C6D$_6$) S: 5.75 (1H, dddd, J=17.3, 10.5, 5.3, 5.3 Hz), 5.15 (1H, dddd, J=17.3, 1.7, 1.7, 1.7 Hz), 5.03 (1H, d, J=1.8 Hz), 4.97 (1H, dddd, J=10.5, 1.5, 1.5, 1.5 Hz), 4.97-4.95 (1H, m), 4.93-4.88 (2H, m), 4.82 (1H, s), 4.63-4.56 (2H, m), 4.54-4.49 (1H, m), 4.39 (1H, dd, J=3.8, 1.8 Hz), 4.32 (1H, d, J=4.7 Hz), 4.19 (1H, s), 4.12 (1H, dd, J=6.6, 4.8 Hz), 4.08 (1H, ddd, J=10.5, 6.0, 6.0 Hz), 4.05-3.97 (3H, m), 3.96-3.91 (1H, m), 3.87-3.76 (5H, m), 3.72-3.57 (6H, m), 3.55-3.50 (1H, m), 3.43-3.38 (1H, m), 3.35 (1H, t, J=2.6 Hz), 3.16 (1H, dd, J=2.6, 1.8 Hz), 3.04-2.98 (1H, m), 2.76-2.64 (3H, m), 2.61 (1H, dd, J=9.7, 1.8 Hz), 2.41-2.32 (3H, m), 2.32-2.09 (13H, m), 2.08-2.02 (3H, m), 2.01-1.94 (1H, m), 1.92-1.86 (2H, m), 1.85-1.78 (1H, m), 1.73-1.62 (4H, m), 1.57-1.41 (5H, m), 1.39-1.25 (5H, m), 1.18 (3H, d, J=6.7 Hz), 1.16-1.09 (1H, m), 1.06 (3H, d, J=7.0 Hz), 1.04 (3H, d, J=6.7 Hz), 0.95 (3H, d, J=7.0 Hz).

For the deprotection protocol of C11- and C12-hydroxyl groups, see: A. Yamamoto, A. Ueda, P. Brdmond, P. S. Tiseni, and Y. Kishi, *J. Am. Chem. Soc.* 134, 893 (2012); A. Ueda, A. Yamamoto, D. Kato, and Y. Kishi, *J. Am. Chem. Soc.* 136, 5171 (2014).

For the protocol for isomerization of C38-epi halichondrin C to halichondrin C, see: A. Ueda, A. Yamamoto, D. Kato, and Y. Kishi, *J. Am. Chem. Soc.* 136, 5171 (2014).

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I-b-12) or (I-a-5):

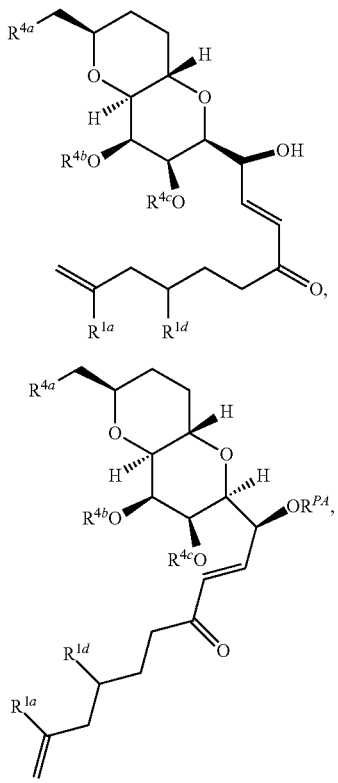

or a salt thereof,
wherein:
- $R^{4a}$ is —$CO_2R^{4d}$, wherein $R^{4d}$ is hydrogen, optionally substituted alkyl, or an oxygen protecting group;
- $R^{4b}$ is hydrogen, optionally substituted alkyl, or an oxygen protecting group;
- $R^{4c}$ is hydrogen, optionally substituted alkyl, or an oxygen protecting group; or $R^{4b}$ and $R^{4c}$ are taken together with the intervening atoms to form an optionally substituted heterocyclic ring;
- $R^{PA}$ is optionally substituted alkyl or an oxygen protecting group;
- $R^{1a}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and
- $R^{1d}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

2. The compound of claim 1, wherein the compound is of Formula (I-b-12), or a salt thereof.

3. The compound of claim 1, wherein the compound is of Formula (I-a-5), or a salt thereof.

4. The compound of claim 1, wherein $R^{4d}$ is optionally substituted $C_{1-6}$ alkyl.

5. The compound of claim 1, wherein $R^{4d}$ is unsubstituted $C_{1-6}$ alkyl.

6. The compound of claim 1, wherein $R^{4d}$ is methyl.

7. The compound of claim 1, wherein $R^{4b}$ and $R^{4c}$ are taken together with the intervening atoms to form an optionally substituted heterocyclic ring.

8. The compound of claim 1, wherein $R^{4b}$ and $R^{4c}$ are taken together with the intervening atoms to form:

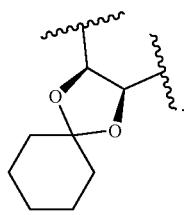 [SMILES: *[C@@H]1OC2(CCCCC2)O[C@@H]1*]

9. The compound of claim 3, wherein $R^{PA}$ is an oxygen protecting group.

10. The compound of claim 3, wherein $R^{PA}$ is para-methoxy benzyl (PNB).

11. The compound of claim 1, wherein $R^{1a}$ is halogen.

12. The compound of claim 1, wherein $R^{1a}$ is —I.

13. The compound of claim 1, wherein $R^{1d}$ is halogen.

14. The compound of claim 1, wherein $R^{1d}$ is —Cl.

15. The compound of claim 2, wherein the compound is the following:

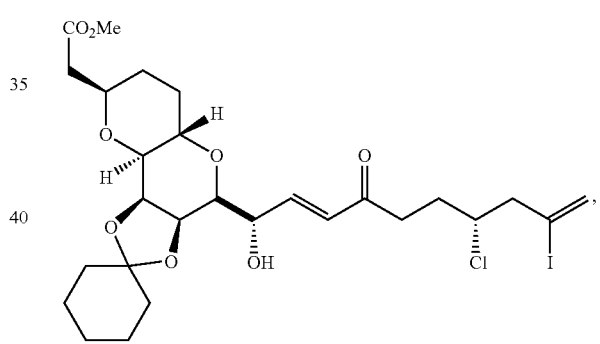

or a salt thereof.

16. The compound of claim 3, wherein the compound is the following:

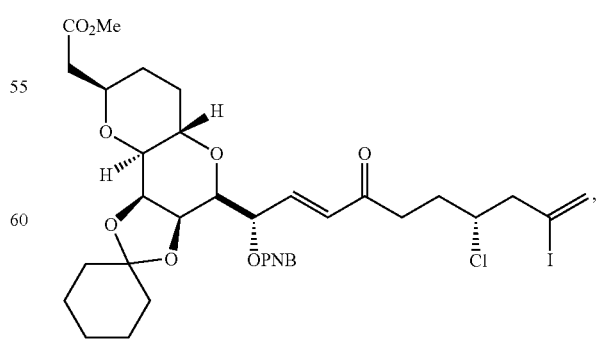

or a salt thereof.

17. A compound of Formula (i-a-3):

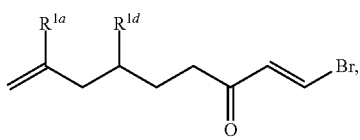

or a salt thereof, wherein:
  $R^{1a}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and
  $R^{1d}$ is independently hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

18. The compound of claim 17, wherein the compound is the following:

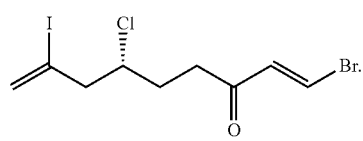

19. A method of preparing the compound of claim 18, the method comprising a step of oxidizing a compound of the formula:

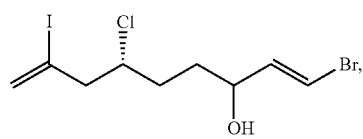

or a salt thereof, to yield the following compound:

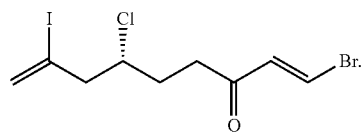

20. The compound of claim 17, wherein $R^{1a}$ is halogen.
21. The compound of claim 17, wherein $R^{1a}$ is —I.
22. The compound of claim 17, wherein $R^{1d}$ is halogen.
23. The compound of claim 17, wherein $R^{1d}$ is —Cl.
24. The method of claim 19, wherein the step of oxidizing is carried out in the presence of Dess-Martin periodinane (DMP).
25. The method of claim 24, wherein the step of oxidizing is carried out in $CH_2Cl_2$.
26. The method of claim 24, wherein the step of oxidizing is carried out at room temperature.
27. The method of claim 19 further comprising a step of reducing a compound of the formula:

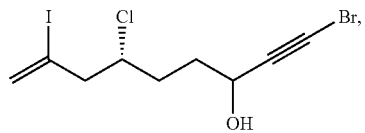

or a salt thereof, to yield a compound of the formula:

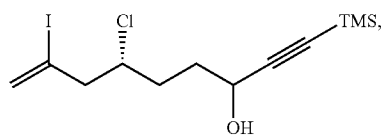 [SMILES: C=C(I)C[C@H](Cl)CCC(O)C#C[Si](C)(C)C]

or a salt thereof.

28. The method of claim 27, wherein the step of reducing is carried out in the presence of diisobutylaluminium hydride (DIBALH) and $AlCl_3$.
29. The method of claim 28, wherein the step of reducing is carried out in $Et_2O$.
30. The method of claim 28, wherein the step of reducing is carried out at a temperature from 0° C. to room temperature.
31. The method of claim 27 further comprising a step of substituting a compound of the formula:

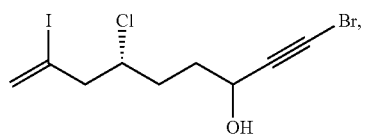

or a salt thereof, to yield a compound of the formula:

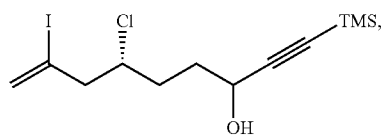 [SMILES: C=C(I)C[C@H](Cl)CCC(O)C#C[Si](C)(C)C]

or a salt thereof.

32. The method of claim 31, wherein the step of substituting is carried out in the presence of N-bromosuccinimide (NBS) and $AgNO_3$.
33. The method of claim 32, wherein the step of substituting is carried out in acetone.
34. The method of claim 32, wherein the step of substituting is carried out at room temperature.
35. The method of claim 31 further comprising a step of adding a compound of the formula:

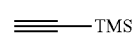

to a compound of the formula:

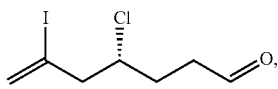

or a salt thereof, to yield a compound of the formula:

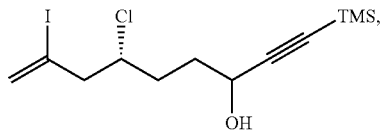

or a salt thereof.

36. The method of claim 35, wherein the step of adding is carried out in the presence of n-BuLi and BF$_3$.Et$_2$O.

37. The method of claim 36, wherein the step of adding is carried out in THF.

38. The method of claim 36, wherein the step of adding is carried out at −78° C.

39. The method of claim 35 further comprising a step of oxidizing a compound of the formula:

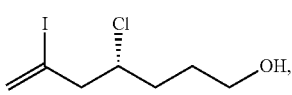

or a salt thereof, to yield a compound of the formula:

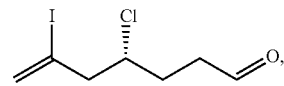

or a salt thereof.

40. The method of claim 39, wherein the step of oxidizing is carried out in the presence of Dess-Martin periodinane (DMP).

41. The method of claim 40, wherein the step of oxidizing is carried out in CH$_2$Cl$_2$.

42. The method of claim 40, wherein the step of oxidizing is carried out at room temperature.

* * * * *